US008329438B2

(12) United States Patent
Savile et al.

(10) Patent No.: US 8,329,438 B2
(45) Date of Patent: Dec. 11, 2012

(54) ENONE REDUCTASES

(75) Inventors: Christopher Savile, Sunnyvale, CA (US); Vesna Mitchell, San Jose, CA (US); Xiyun Zhang, Fremont, CA (US); Gjalt Huisman, San Carlos, CA (US)

(73) Assignee: Codexis, Inc., Redwood City, CA (US)

( * ) Notice: Subject to any disclaimer, the term of this patent is extended or adjusted under 35 U.S.C. 154(b) by 332 days.

(21) Appl. No.: 12/646,907

(22) Filed: Dec. 23, 2009

(65) Prior Publication Data
US 2010/0190218 A1 Jul. 29, 2010

Related U.S. Application Data

(60) Provisional application No. 61/140,879, filed on Dec. 25, 2008.

(51) Int. Cl.
*C12N 9/02* (2006.01)
(52) U.S. Cl. ......................................... 435/189
(58) Field of Classification Search ........................ None
See application file for complete search history.

(56) References Cited

U.S. PATENT DOCUMENTS

| | | | |
|---|---|---|---|
| 5,605,793 | A | 2/1997 | Stemmer |
| 5,811,238 | A | 9/1998 | Stemmer et al. |
| 5,830,721 | A | 11/1998 | Stemmer et al. |
| 5,998,616 | A | 12/1999 | Murthy et al. |
| 6,046,043 | A | 4/2000 | Murthy et al. |
| 6,117,679 | A | 9/2000 | Stemmer |
| 6,376,246 | B1 | 4/2002 | Crameri et al. |
| 6,586,182 | B1 | 7/2003 | Patten et al. |
| 7,202,068 | B2 | 4/2007 | Kataoka et al. |
| 2004/0253695 | A1 | 12/2004 | Yamamoto et al. |
| 2005/0244941 | A1 | 11/2005 | Shimizu et al. |
| 2008/0220990 | A1 | 9/2008 | Fox |
| 2009/0117612 | A1 | 5/2009 | Glieder et al. |
| 2009/0117613 | A1 | 5/2009 | Glieder et al. |
| 2009/0312196 | A1 | 12/2009 | Colbeck et al. |

FOREIGN PATENT DOCUMENTS

| | | |
|---|---|---|
| EP | 0924294 A2 | 6/1999 |
| EP | 1894999 A1 | 3/2008 |
| WO | 03/070959 A2 | 8/2003 |
| WO | 2006/128277 A2 | 12/2006 |
| WO | 2008/137789 A1 | 11/2008 |
| WO | 2008/143956 A1 | 11/2008 |

OTHER PUBLICATIONS

Niino et al JBC 1995, 270, 1983-1191.*
Matsushima, A., et al., "An enone reductase from Nicotiana tabacum: cDNA cloning, expression in *Escherichia coli*, and reduction of enones with the recombinant proteins," Bioorganic Chemistry, 36:23-28, 2008.
Altamirano, M.M., et al., "Directed evolution of new catalytic activity using the α/β-barrel scaffold", Nature, 403:617-622, 2000.
Bougioukou, D., "I. NADPH Regeneration Sources in Non-Growing, Engineered *Escherichia Coli* Cells, II. Evaluation of Old and New Alkene Reductases As Potential Biocatalysts", Dissertation, University of Florida, pp. 1-263, 2006.

Brown, B.J., et al., "The Role of Glutamine 114 in Old Yellow Enzyme", The Journal of Biological Chemistry, 277 (3):2138-2145, 2002.
Brown, B.J., et al., "On the Active Site of Old Yellow Enzyme. Role of Histidine 191 and Asparagine 194", J. Biol. Chem., 273(49):32753-32762, 1998.
Chaparro-Riggers, J.F., et al., "Comparison of Three Enoate Reductases and their Potential Use for Biotransformations", Adv. Synth. Catal., 349:1521-1531, 2007.
Chu, Y., et al., "Hydrogen transfer pathways of the asymmetric reduction of α,β-unsaturated ketone mediated by baker's yeast", Bioorganic Chemistry, 34:158-166, 2006.
Crameri, A., et al., "DNA shuffling of a family of genes from diverse species accelerates directed evolution", Nature, 391:288-291, 1998.
De Wildeman, S.M.A., et al., "Biocatalytic Reductions: From Lab Curiosity to 'First Choice'", Acc. Chem. Res., 40:1260-1266, 2007.
Fauve, A., et al., "Inducibility of an Enone Reductase System in the Fungus Beauveria sulfurescens: Application in Enantioselective Organic Synthesis", J. Org. Chem., 52:4893-4897, 1987.
Fonteneau, L., et al., "Chemoenzymatic synthesis of enantiopure isopropyl (3R)- and (3S)-3-hydroxycyclohex-1-ene-1-carboxylates and their reduction to isomers of isopropyl 3-hydroxy-cyclohexane-1-carboxylate", Tetrhedron: Asymmetry, 13:579-585, 2002.
Fox, K.M., et al., "The Flavin Environment in Old Yellow Enzyme. An Evaluation of Insights From Spectroscopic and Artificial Flavin Studies", J. Biol. Chem., 274(14):9357-9362, 1999.
Fox, K.M., et al., "Old yellow enzyme at 2 Å resolution: overall structure, ligand binding, and comparison with related flavoproteins", Structure, 2(11):1089-1105, 1994.
Hall, M., et al., "Asymmetric Bioreduction of Activated C=C Bonds Using Zymomonas mobilis NCR Enoate Reductase and Old Yellow Enzymes OYE 1-3 from Yeasts", Eur. J. Org. Chem., pp. 1511-1516, 2008.
Hsiao, Y., et al., "Highly Efficient Synthesis of β-Amino Acid Derivatives via Asymmetric Hydrogenation of Unprotected Enamines", J. Am. Chem. Soc., 126:9918-9919, 2004.
Kaluzna, I.A., et al., "Systematic Investigation of Saccharomyces cerevisiae Enzymes Catalyzing Carbonyl Reductions", J. Am. Chem. Soc., 126:12827-12832, 2004.
Kanazawa, Y., et al., "Asymmetric Conjugate Reduction of α,β-Unsaturated Ketones and Esters with Chiral Rhodium(2,6-bisoxazolinylphenyl) Catalysts", Chem. Eur. J., 12:63-71, 2006.
Karplus, P.A., et al., "Structure-function relations for old yellow enzyme", The FASEB Journal, 9:1518-1526, 1995.
Kohli, R.M., et al., "The Oxidative Half-reaction of Old Yellow Enzyme. The Role of Tyrosine 196", The Journal of Biological Chemistry, 273(49):32763-32770, 1998.
Kosjek, B., et al., "Asymmetric bioreduction of α,β-unsaturated nitriles and ketones", Tetrahedron: Asymmetry, 19:1403-1406, 2008.

(Continued)

Primary Examiner — Tekchand Saidha
Assistant Examiner — MD. Younus Meah
(74) Attorney, Agent, or Firm — Codexis, Inc.

(57) ABSTRACT

The disclosure relates to engineered enone reductase polypeptides having improved properties, polynucleotides encoding the engineered polypeptides, related vectors, host cells, and methods for making the engineered enone reductase polypeptides. The disclosure also provides methods of using the engineered enone reductase polypeptides for chemical transformations.

14 Claims, 6 Drawing Sheets

OTHER PUBLICATIONS

Martin, N.J.A., et al., "Highly Enantioselective Transfer Hydrogenation of α,β-Unsaturated Ketones", J. Am. Chem. Soc., 128:13368-13369, 2006.

Massey, V., "The Chemical and Biological Versatility of Riboflavin", Biochemical Society Transactions, 28 (part4):283-296, 2000.

Meah, Y., et al., "Old yellow enzyme: Reduction of nitrate esters, glycerin trinitrate, and propylene 1,2-dinitrate", PNAS, 98(15):8560-8565, 2001.

Meah, Y., et al., "Old Yellow Enzyme: Stepwise reduction of nitro-olefins and catalysis of aci-nitro tautomerization", PNAS, 97(20):10733-10738, 2000.

Müller, A., et al., "Stereospecific Alkyne Reduction: Novel Activity of Old Yellow Enzymes", Angew. Chem. Int. Ed., 46:3316-3318, 2007.

Müller, A., et al., "Asymmetric alkene reduction by yeast old yellow enzymes and by a novel Zymomonas mobilis reductase", Biotechnology and Bioengineering, 98(1):22-29, 2007.

Müller, A., et al., "Enzymatic reduction of the α, β-unsaturated carbon bond in citral", Journal of Molecular Catalysis B: Enzymatic, 38:126-130, 2006.

Murthy, Y.V.S.N., et al., "Conversion of a Flavoprotein Reductase to a Desaturase by Manipulation of the Flavin Redox Potential", J. Am. Chem. Soc., 121(22):5354-5345, 1999.

Niino, Y.S., et al., "A New Old Yellow Enzyme of *Saccharomyces cerevisiae*", The Journal of Biological Chemistry, 270(5):1983-1991, 1995.

Odat, S., et al., "Old Yellow Enzymes, Highly Homologous FMN Oxidoreductases with Modulating Roles in Oxidative Stress and Programmed Cell Death in Yeast", The Journal of Biological Chemistry, 282(49):36010-36023, 2007.

Ostermeier, M., et al., "Combinatorial protein engineering by incremental truncation", Proc. Natl. Acad. Sci. USA, 96:3562-3567, 1999.

Padhi, S.K., et al., "Site-Saturation Mutagenesis of Tryptophan 116 of *Saccharomyces pastorianus* Old Yellow Enzyme Uncovers Stereocomplementary Variants", J. Am. Chem. Soc., 131:3271-3280, 2009.

Riechmann, L., et al., "Novel folded protein domains generated by combinatorial shuffling of polypeptide segments", PNAS, 97(18):10068-10073, 2000.

Robert, F., et al., "Synthesis and Sensorial Properties of 2-Alkylalk-2-enals and 3-(Acetylthio)-2-alkyl Alkanals", J. Agric. Food Chem., 52:3525-3529, 2004.

Rohdich, F., et al., "Enoate Reductases of Clostridia: Cloning, Sequencing, and Expression", The Journal of Biological Chemistry, 276(8):5779-5787, 2001.

Saito, K., et al., "The Cloning and Expression of a Gene Encoding Old Yellow Enzyme from *Saccharomyces carlsbergensis*", The Journal of Biological Chemistry, 266(31):20720-20724, 1991.

Shimoda, K., et al., "Asymmetric reduction of enones with *Synechococcus* sp. PCC 7942", Tetrahedron: Asymmetry, 15:1677-1679, 2004.

Shimoda, K., et al., "Asymmetric reduction of α,β-unsaturated carbonyl compounds with reductases from Nicotiana tabacum", Tetrahedron: Asymmetry, 15:2443-2446, 2004.

Shimoda, K., et al., "Biotransformation of enones with biocatalysts—two enone reductases from Astasia longa", Journal of Molecular Catalysis B: Enzymatic, 8:255-264, 2000.

Shimoda, K., et al., "Stereochemistry in the Reduction of Enones by the Reductase from *Euglena gracilis* Z", Phytochemistry, 49(1):49-53, 1998.

Stemmer, W.P.C., "Rapid evolution of a protein in vitro by DNA shuffling", Nature, 370:389-391, 1994.

Stott, K., et al., "Old Yellow Enzyme—The Discovery of Multiple Isozymes and a Family of Related Proteins", The Journal of Biological Chemistry, 268(9):6097-6106, 1993.

Stueckler, C., et al., "Stereocomplementary Bioreduction of α,β-Unsaturated Dicarboxylic Acids and Dimethyl Esters using Enoate Reductases: Enzyme- and Substrate-Based Stereocontrol", Organic Letters, 9(26):5409-5411, 2007.

Stuermer, R., et al., "Asymmetric bioreduction of activated C=C bonds using enoate reductases from the old yellow enzyme family", Current Opinion in Chemical Biology, 11:203-213, 2007.

Swiderska, M.A., et al., "Asymmetric Bioreductions of β-Nitro Acrylates as a Route to Chiral β2-Amino Acids", Organic Letters, 8(26):6131-6133, 2006.

Swiderska, M.A., et al., "Stereoselective enone reductions by *Saccharomyces carlsbergensis* old yellow enzyme", Journal of Molecular Catalysis B: Enzymatic, 42:52-54, 2006.

Tellers, D.M., et al., "On the Mechanism of an Asymmetric α,β-Unsaturated Carboxylic Acid Hydrogenation: Application to the Synthesis of a PGD2 Receptor Antagonist", J. Am. Chem. Soc., 128:17063-17073, 2006.

Tellers, D.M., et al., "On the Mechanism of an Asymmetric α,β-Unsaturated Carboxylic Acid Hydrogenation: Application to the Synthesis of a PGD2 Receptor Antagonist", J. Am. Chem. Soc., Supplemental:S1-S16, 2006.

Utaka, M., et al., "Asymmetric Reduction of the Prochiral Carbon-Carbon Double Bond of Methyl 2-Chloro-2-alkenoates by Use of Fermenting Bakers' Yeast", J. Org. Chem., 54:4989-4992, 1989.

Wada, M., et al., "Production of a Doubly Chiral Compound, (4R,6R)-4-Hydroxy-2,2,6-Trimethylcyclohexanone, by Two-Step Enzymatic Asymmetric Reduction", Applied and Environmental Microbiology, 69(2):933-937, 2003.

Wanner, P., et al., "Purification and characterization of two enone reductases from *Saccharomyces cerevisiae*", Eur. J. Biochem, 255:271-278, 1998.

Williams, R.E., et al., "'New uses for an Old Enzyme'—the Old Yellow Enzyme family of flavoenzymes", Microbiology, 148(6):1607-1614, 2002.

Xu, D., et al., "The role of threonine 37 in flavin reactivity of the old yellow enzyme", Proc. Natl. Acad. Sci. USA, 96:3556-3561, 1999.

Uniprot Accession No. Q03558, integrated into UniProtKB/Swiss-Prot on Oct. 1, 1993.

Uniprot Accession No. A6ZT86, integrated into UniProtKB/TrEMBL on Sep. 11, 2007.

Uniprot Accession No. B3LSU1, integrated into UniProtKB/TrEMBL on Sep. 2, 2008.

Uniprot Accession No. P41816, integrated into UniProtKB/Swiss-Prot on Nov. 1, 1995.

Uniprot Accession No. A6ZW82, integrated into UniProtKB/TrEMBL on Sep. 11, 2007.

Uniprot Accession No. B3LKQ7, integrated into UniProtKB/TrEMBL on Sep. 2, 2008.

Uniprot Accession No. B5VT01, integrated into UniProtKB/TrEMBL on Nov. 25, 2008.

Extended European Search Report in EP Appl. 09835878.1, Aug. 1, 2012.

\* cited by examiner

```
1                                                                    50
ATGTCTTTCG TTAAGGACTT CAAGCCGCAG GCACTGGGCG ACACCAACCT
(SEQ ID NO:1)
ATGCCTTTCG TTAAGGACTT CAAGCCGCAG GCACTGGGCG ACACCAACCT
(SEQ ID NO:3)
ATGCCTTTCG TTAAGGGCTT CGAGCCGATT TCACTGCGCG ACACCAACCT
(SEQ ID NO:5)

51                                                                  100
GTTCAAACCT ATTAAAATTG GGAACAACGA GCTGCTGCAT CGCGCGGTAA

GTTCAAACCT ATTAAAATTG GGAACAACGA GCTGCTGCAT CGCGCGGTAA

GTTCGAACCT ATTAAAATTG GGAACACACA GCTGGCTCAT CGCGCGGTAA 101                                                                 150
TTCCTCCGCT GACCCGCATG CGCGCTCTGC ATCCGGGCAA CATTCCGAAC

TTCCTCCGCT GACCCGCATG CGCGCTCAGC ATCCGGGCAA CATTCCGAAC

TGCCTCCGCT GACCCGCATG CGCGCTACCC ATCCGGGCAA CATTCCGAAC 151                                                                 200
CGTGATTGGG CTGTGGAATA CTACACCCAG CGTGCACAGC GTCCGGGGAC

CGTGATTGGG CTGTGGAATA CTACGCCCAG CGTGCACAGC GTCCGGGGAC

AAGGAGTGGG CTGCGGTTTA CTACGGCCAG CGTGCACAGC GTCCGGGGAC 201                                                                 250
AATGATTATC ACGGAGGGTG CGTTCATCAG CCCGCAGGCA GGTGGGTACG

ACTGATTATC ACGGAGGGTA CGTTCCCTAG CCCGCAGTCA GGTGGGTACG

AATGATTATC ACGGAGGGTA CGTTCATCAG CCCGCAGGCA GGTGGGTACG
```

FIGURE 2A

```
251                                                             300
ATAACGCGCC  TGGTGTTTGG  TCAGAAGAAC  AGATGGTCGA  ATGGACGAAA

ATAACGCGCC  TGGTATTTGG  TCAGAAGAAC  AGATTAAAGA  ATGGACGAAA

ATAACGCGCC  TGGTATTTGG  TCAGACGAAC  AGGTTGCCGA  ATGGAAGAAC 301                                                             350
ATCTTCAACG  CTATTCATGA  AAAAAAGTCA  TTTGTGTGGG  TGCAACTGTG

ATCTTCAAGG  CTATTCATGA  AAATAAGTCA  TTTGCGTGGG  TGCAACTGTG

ATCTTCCTGG  CTATTCATGA  CTGTCAGTCA  TTTGCGTGGG  TGCAACTGTG 351                                                             400
GGTCCTGGGC  TGGGCCGCCT  TTCCGGATAA  CCTGGCGCGT  GATGGGTTAC

GGTCCTGGGC  TGGGCCGCCT  TTCCGGATAC  GCTGGCGCGT  GATGGGTTAC

GAGCCTGGGC  TGGGCCTCCT  TTCCGGATGT  GCTGGCGCGT  GATGGGTTAC 401                                                             450
GTTACGATTC  TGCCTCCGAT  AATGTGTTTA  TGGATGCGGA  ACAGGAGGCA

GTTACGATTC  TGCCTCCGAT  AATGTGTATA  TGAATGCGGA  ACAGGAGGAA

GTTACGATTG  TGCCTCCGAT  CGTGTGTATA  TGAATGCGAC  ACTGCAGGAA 451                                                             500
AAAGCGAAAA  AAGCTAACAA  TCCGCAACAT  AGCTTGACTA  AAGACGAAAT

AAAGCGAAAA  AAGCTAACAA  TCCGCAACAT  AGCATTACTA  AAGACGAAAT

AAAGCGAAAG  ATGCTAACAA  TCTGGAACAT  AGCTTGACTA  AAGACGATAT
```

FIGURE 2B

```
501                                                              550
TAAACAATAT ATCAAGAAT ATGTTCAGGC AGCTAAGAAC TCGATCGCTG

TAAACAATAT GTCAAAGAAT ATGTTCAGGC AGCTAAGAAC TCGATCGCTG

TAAACAATAT ATCAAAGATT ATATTCATGC AGCTAAGAAC TCGATCGCTG 551                                                              600
CGGGTGCGGA CGGCGTGGAA ATTCACTCAG CCAACGGTTA TCTGTTAAAT

CGGGTGCGGA CGGCGTGGAA ATTCACTCAG CCAACGGTTA TCTGTTAAAT

CGGGTGCGGA CGGCGTGGAA ATTCACTCAG CCAACGGTTA TCTGTTAAAT 601                                                              650
CAGTTCCTGG ATCCGCACAG CAACACACGC ACCGATGAGT ATGGGGGCTC

CAGTTCCTGG ATCCGCACAG CAACAACCGC ACCGATGAGT ATGGGGGCTC

CAGTTCCTGG ATCCGCACAG CAACAAACGC ACCGATGAGT ATGGGGGCAC 651                                                              700
AATTGAAAAT CGTGCACGTT TTACTCTGGA AGTCGTTGAC GCGCTGGTTG

AATTGAAAAT CGTGCACGTT TTACTCTGGA AGTCGTTGAC GCGGTGGTTG

AATTGAAAAT CGTGCACGTT TTACTCTGGA AGTCGTTGAC GCGCTGATTG 701                                                              750
AGGCCATCGG CCATGAAAAA GTGGGTTTAC GTCTGAGTCC GTACGGCGTT

ATGCCATCGG CCCAGAAAAA GTGGGTTTAC GTCTGAGTCC GTACGGCGTT

AGACCATCGG CCCAGAACGC GTGGGTTTAC GTCTGAGTCC GTACGGCACT
```

FIGURE 2C

```
751                                                              800
TTCAACTCTA TGTCGGGCGG CGCGGAAACG GGCATTGTTG CTCAGTATGC

TTCAACTCTA TGTCGGGCGG CGCGGAAACG GCATTGTTG CTCAGTATGC

TTCAACTCTA TGTCGGGCGG CGCGGAACCG GGCATTATTG CTCAGTATAG 801                                                              850
CTATGTCGCG GGTGAGCTGG AGAAACGCGC CAAGGCGGGG AAACGCCTGG

CTATGTCCTG GGTGAGCTGG AGCGTCGCGC CAAGGCGGGG AAACGCCTGG

CTATGTCCTG GGTGAGCTGG AGAAACGCGC CAAGGCGGGG AAACGCCTGG 851                                                              900
CGTTTGTTCA TTTAGTCGAA CCACGCGTGA CAAACCCTTT TCTGACTGAG

CGTTTGTTCA TTTAGTCGAA CCACGCGTGA CAAACCCTTT TCTGACTGAG

CGTTTGTTCA TTTAGTCGAA CCACGCGTGA CAGACCCTTC TCTGGTTGAG 901                                                              950
GGGGAGGGCG AATACGAAGG GGGCAGCAAC GATTTGTTT ATTCCATTTG

GGGGAGGGCG AATACAACGG GGGCAGCAAC AAATTTGCTT ATTCCATTTG

GGGGAGGGCG AATACTCAGA GGGCACCAAC GATTTGCTT ATTCCATTTG 951                                                             1000
GAAAGGTCCG GTTATCCGTG CCGGCAACTT CGCACTGCAC CCTGAAGTTG

GAAAGGTCCG ATTATCCGTG CCGGCAACTT CGCACTGCAC CCTGAAGTTG

GAAAGGTCCG ATTATCCGTG CCGGCAACTA CGCACTGCAC CCTGAAGTTG
```

FIGURE 2D

```
1001                                                1050
TGCGCGAAGA AGTTAAGGAC AAACGCACCC TGATCGGCTA CGGCCGCTTC

TGCGCGAAGA AGTTAAGGAC CCTCGCACCC TGATCGGCTA CGGCCGCTTC

TGCGCGAACA AGTTAAGGAC CCTCGCACCC TGATCGGCTA CGGCCGCTTC 1051                                                1100
TTTATTTCAA ATCCAGACCT GGTTGACCGC TTAGAAAAAG GTCTGCCACT

TTTATTTCAA ATCCAGACCT GGTTGACCGC TTAGAAAAAG GTCTGCCACT

TTTATTTCAA ATCCAGACCT GGTTTACCGC TTAGAAGAAG GTCTGCCACT 1101                                                1150
GAACAAGTAT GACCGTGATA CGTTCTACCA GATGAGCGCG CATGGTTACA

GAACAAGTAT GACCGTGATA CGTTCTACAA AATGAGCGCG GAGGGTTACA

GAACAAGTAT GACCGTTCTA CGTTCTACAC CATGAGCGCG GAGGGTTACA 1151                                                1200
TCGACTACCC GACCTACGAA GAAGCCTTAA AACTGGGCTG GGACAAAAAA

TCGACTACCC GACCTACGAA GAAGCCTTAA AACTGGGCTG GGACAAAAAC

CCGACTACCC GACCTACGAA GAAGCCGTAG ATCTGGGCTG GAACAAAAAC

1201
TAATGA

TAATGA

TAATGA
```

FIGURE 2E

ENONE REDUCTASES

This application claims the benefit, pursuant 35 U.S.C. §119(e), of U.S. Ser. No. 61/140,879, filed Dec. 25, 2008, which is incorporated herein by reference in its entirety.

TECHNICAL FIELD

The present disclosure relates to polypeptides, polynucleotides encoding the polypeptides, and methods of using the polypeptides and polynucleotides.

REFERENCE TO SEQUENCE LISTING, TABLE OR COMPUTER PROGRAM

The Sequence Listing concurrently submitted herewith under 37 C.F.R. §1.821 in a computer readable form (CRF) via EFS-Web as file name 2-026US1 Sequence Listing.txt is herein incorporated by reference. The electronic copy of the Sequence Listing was created on Dec. 22, 2009 with a file size of 530 kilobytes.

BACKGROUND

Enone reductase enzymes of the Old Yellow Enzyme (OYE) family catalyze a range of reductions of $\alpha,\beta$ unsaturated ketones, aldehydes, esters, and nitriles that are of potential industrial importance. One reaction of interest is the hydrogenation of nitroalkenes, which is present in certain industrial explosives and serves as intermediates for the synthesis of a range of compounds, such as alkaloids, antibiotics, and biocides. Accumulation of the nitronate can be enhanced by a Y196F mutation of OYE (Meah and Massey, 2000, *Proc Natl Acad Sci USA* 97(20):10733-8; Meah et al., 2001, *Proc Natl Acad Sci USA* 98(15):8560-5), providing a attractive biocatalytic based production of a nitronate and a useful alternative to the more complex chemical transformation needed to provide the same products.

Another useful reaction carried out by enone reductases is the reduction of 3,5,5-trimethyl-2-cyclohexene-1,4-dione to produce (6R)-2,2,6-trimethylcyclohexane-1,4-dione, also known as levodione, which is a useful chiral building block for synthesis of naturally occurring optically active carotenoid compounds, such as xanthoxin and zeaxanthin. Old Yellow Enzymes OYE1, OYE2 and OYE3 from yeast *Saccharomyces pastorianus* and *Saccharomyces cerevisiae* can also catalyze stereoselective reduction of $\alpha,\beta$-unsaturated carbonyls, esters and nitriles. However, these enzymes can have a narrow substrate recognition profile and/or have stability properties that are not suited for commercial applications. Thus, it is desirable to identify enone reductases having properties that may be advantageous, such as with respect to substrate recognition profile, stereoselectivity, and stability.

SUMMARY OF THE INVENTION

The present disclosure relates to engineered enone reductase polypeptides having altered enzyme properties relative to wildtype enone reductases. These engineered enone reductase polypeptides are capable of reducing an $\alpha,\beta$ unsaturated compound, such as an $\alpha,\beta$ unsaturated ketone, aldehyde, ester or nitrile to the corresponding saturated ketone, aldehyde, ester or nitrile. In one aspect, the enone reductases of the disclosure comprise a chimeric polypeptide of enone reductase 2 (ERED 2) of SEQ ID NO:4 and enone reductase 3 (ERED 3) of SEQ ID NO:6. In some embodiments, the chimeric polypeptide can also comprise a chimeric polypeptide of enone reductase 1 (ERED 1) of SEQ ID NO:2, enone reductase 2 (ERED 2) of SEQ ID NO:4, and enone reductase 3 (ERED 3) of SEQ ID NO:6. The chimeric polypeptides described herein are characterized by improvements in thermal and/or solvent stability. In some embodiments, the chimeric enone reductase polypeptides are stable to treatment conditions of 50% isopropanol at 30° C. and/or 10-20% isopropanol at 40° C. In some embodiments, the chimeric enone reductases are capable of reducing or converting 1-cyclohex-2-enone to cyclohexanone. In some embodiments, the chimeric polypeptides are also capable of reducing or converting methyl(E)-but-2-enoate to methyl butanoate.

The present disclosure provides an enone reductase polypeptide comprising an amino acid sequence that is selected from the group consisting of: (a) an amino acid sequence that is at least 80% identical to a reference sequence selected from the group consisting of SEQ ID NOs: 8, 190, 192, 194, 196, 198, 200, 202, 204, 206, 208, 210, 212, 214, 216 and 217; (b) an amino acid sequence encoded by a nucleic acid sequence that hybridizes under stringent conditions to a reference nucleic acid sequence selected from the group consisting of SEQ ID NOs: 7, 189, 191, 193, 195, 197, 199, 201, 203, 205, 207, 209, 211, 213, and 215, or a complementary sequence thereof.

In some embodiments, the enone reductases of the present invention can have one or more residue differences as compared to a reference enone reductase, such as the chimeric enone reductases characterized by improved thermal and/or solvent stability. In some embodiments, the residue differences can occur at one or more of the following residue positions: X5; X10; X28; X38; X40; X44; X75; X83; X117; X119; X122; X124; X147; X148; X153; X154; X179; X209; X240; X248; X251; X252; X255; X259; X294; X295; X296; X297; X302; X304; X305; X311; X315; X330; X333; X339; X358; X369; X376; X379; X384; X386; X397; X399; and X400. The presence of certain amino acids at these residue positions are associated with altered enzyme properties, including, among others, substrate recognition profile, stereoselectivity, and enzyme activity. Various amino acids that can occupy the specified positions and the associated changes to enzyme properties are described in the detailed description.

In some embodiments, the engineered enone reductase is capable of converting the $\alpha,\beta$ unsaturated ketone of (5S)-2-methyl-5-prop-1-en-2-ylcyclohex-2-en-1-one (S-carvone) to (2R,5S)-2-methyl-5-prop-1-en-2-ylcyclohexan-1-one. In some embodiments, the reductase polypeptide capable of converting (5S)-2-methyl-5-prop-1-en-2-ylcyclohex-2-en-1-one to (2R,5S)-2-methyl-5-prop-1-en-2-ylcyclohexan-1-one comprises an amino acid sequence that corresponds to the sequence of SEQ ID NO: 10, 14, 16, 18, 46, 44, 68, 70, 72, 74, 76, 82, 86, 88, 90, 98, 102, 104, 108, 110, 112, 114, 116, 118, 122, 126, 128, 130, 162 or 172.

In some embodiments, the engineered enone reductase is capable of converting the $\alpha,\beta$ unsaturated ketone of (5S)-2-methyl-5-prop-1-en-2-ylcyclohex-2-en-1-one to (2S,5S)-2-methyl-5-prop-1-en-2-ylcyclohexan-1-one in diastereomeric excess. In some embodiments, the engineered enone reductase capable of converting (5S)-2-methyl-5-prop-1-en-2-ylcyclohex-2-en-1-one to (2S,5S)-2-methyl-5-prop-1-en-2-ylcyclohexan-1-one in diastereomeric excess comprises an amino acid sequence that corresponds to the sequence of SEQ ID NO: 20, 24, 28, 30, 32, 38, 48, 50, 52, 54, 56, 60, 64, 66, 92, 144, 148, 152, 154, 156, or 158.

In some embodiments, the engineered enone reductase is capable of converting the $\alpha,\beta$ unsaturated ketone of (5R)-2-methyl-5-prop-1-en-2-ylcyclohex-2-en-1-one (R-carvone)

to (2R,5R)-2-methyl-5-prop-1-en-2-ylcyclohexan-1-one with at least 90% diastereomeric excess.

In some embodiments, the engineered enone reductase capable of converting (5R)-2-methyl-5-prop-1-en-2-ylcyclohex-2-en-1-one to (2R,5R)-2-methyl-5-prop-1-en-2-ylcyclohexan-1-one with at least 90% diastereomeric excess comprises an amino acid sequence that corresponds to the sequence of SEQ ID NO: 10, 12, 14, 16, 18, 22, 26, 32, 34, 36, 40, 42, 44, 46, 68, 70, 72, 74, 76, 78, 80, 82, 86, 88, 90, 94, 96, 98, 102, 104, 106, 108, 110, 112, 114, 116, 118, 120, 122, 126, 128, 134, 136, 138, 140, 142, 146, 162, 166, 168, 170, 172, 174 or 186.

In some embodiments, the engineered enone reductase is capable of converting the α,β unsaturated ketone of (5R)-2-methyl-5-prop-1-en-2-ylcyclohex-2-en-1-one to (2S,5R)-2-methyl-5-prop-1-en-2-ylcyclohexan-1-one in diastereomeric excess.

In some embodiments, the enone reductase capable of converting (5R)-2-methyl-5-prop-1-en-2-ylcyclohex-2-en-1-one to (2S,5R)-2-methyl-5-prop-1-en-2-ylcyclohexan-1-one in diastereomeric excess comprises an amino acid that corresponds to the sequence of SEQ ID NO: 28, 40, 144 or 148.

In some embodiments, the enone reductase is capable of reducing (Z)-ethyl 2-cyano-3-phenylbut-2-enoate to ethyl 2-cyano-3-phenylbutanoate with at least 5 times the conversion rate of SEQ ID NO:6 or SEQ ID NO:8.

In some embodiments, the enone reductase capable of reducing (Z)-ethyl 2-cyano-3-phenylbut-2-enoate to ethyl 2-cyano-3-phenylbutanoate comprises an amino acid sequence that corresponds to the sequence of SEQ ID NO: 20, 22, 24, 26, 28, 30, 36, 40, 44, 48, 50, 54, 56, 82, 92, 94, 96, 100, 128, 144, 146, 148, 152, 154, 156, 158, 170, 174, 176, 178, 180, 182, or 184.

In some embodiments, the engineered enone reductase is capable of reducing the α,β unsaturated ketone of 8a-methyl-3,4,8,8a-tetrahydronaphthalene-1,6(2H,7H)-dione to 8a-methylhexahydronaphthalene-1,6(2H,7H)-dione with at least 2 times the conversion rate of SEQ ID NO:6 or SEQ ID NO:8.

In some embodiments, the engineered enone reductase capable of reducing 8a-methyl-3,4,8,8a-tetrahydronaphthalene-1,6(2H,7H)-dione to 8a-methylhexahydronaphthalene-1,6(2H,7H)-dione with at least 2 times the conversion rate of SEQ ID NO:6 or SEQ ID NO:8 comprises an amino acid sequence that corresponds to the sequence of SEQ ID NO: 12, 42, 68, 72, 82, 86, 88, 98, 104, 106, 114, 118, 120, 122, 124, 126, 132, 136, 138, 160, 162, 164, 166, 168, 170, 172, 176, 178, 180, 184, or 182.

In some embodiments, the engineered enone reductase is capable of reducing 3-methylcyclohex-2-enone to 3-methylcyclohexanone with at least 1 or 2 times the conversion rate of SEQ ID NO:6 or SEQ ID NO:8.

In some embodiments, the enone reductase capable of reducing 3-methylcyclohex-2-enone to 3-methylcyclohexanone with at least 1 times the conversion rate of SEQ ID NO:6 or SEQ ID NO:8 comprises an amino acid sequence that corresponds to the sequence of SEQ ID NO: 18, 46, 132, 174, 186 or 140.

In some embodiments, the enone reductase is capable of reducing 2-methylcyclopente-2-none to 2-methylcyclopentanone.

In another aspect, the present disclosure provides polynucleotides encoding the engineered enone reductases described herein, and polynucleotides that hybridize to such polynucleotides under highly stringent conditions. The polynucleotide can include promoters and other regulatory elements useful for expression of the encoded engineered enone reductases, and can utilize codons optimized for specific desired expression systems. Exemplary polynucleotides include, but are not limited to, the sequence of SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In another aspect, the present disclosure provides host cells comprising the polynucleotides and/or expression vectors described herein, and methods for culturing or incubating the host cells to produce the engineered enone reductase polypeptides. The host cells may be *E. coli* or they may be a different organism. The host cells can be used for the expression and isolation of the engineered enone reductase enzymes described herein, or, alternatively, they can be used directly for the conversion of an α,β unsaturated substrate to the corresponding saturated product.

In a further aspect, the present disclosure provides methods of using the enone reductase polypeptides described herein to reduce or convert an α,β unsaturated compound selected from the group consisting of a ketone, a nitrile, an ester, and a nitrile to the corresponding saturated ketone, nitrile, ester, or nitrile.

BRIEF DESCRIPTION OF THE FIGURES

FIG. 2 provides an alignment of the nucleic acid sequence encoding ERED 1 (top row: SEQ ID NO:1), ERED 2 (middle row: SEQ ID NO:3), and ERED 3 (bottom row: SEQ ID NO:5), showing regions of nucleic acid sequence homology. The underlined nucleotides represent regions of differences in the sequences.

DETAILED DESCRIPTION

Figure 1:
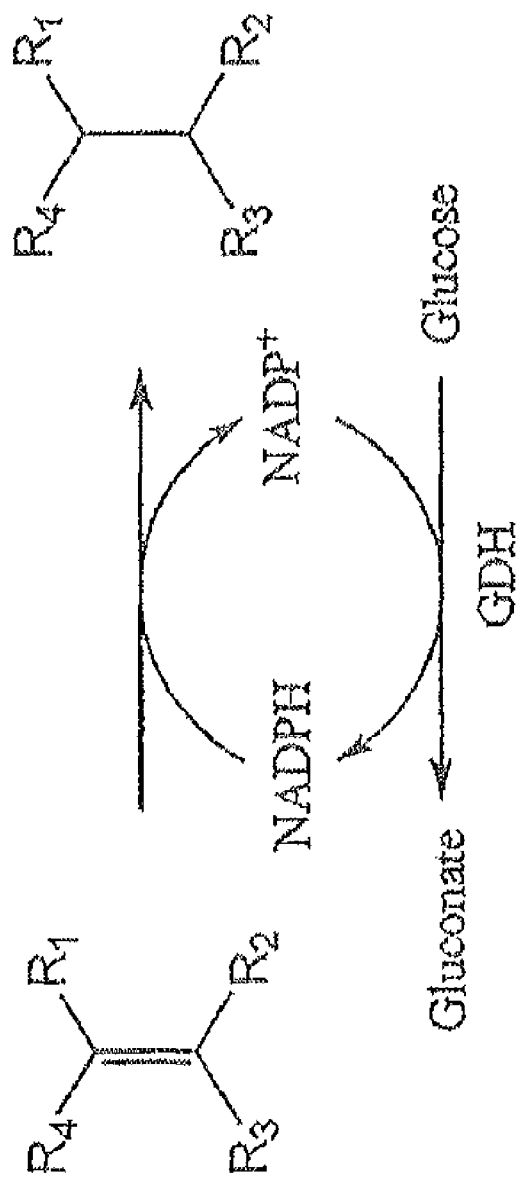
FIG. 1 illustrates a reaction carried out by enone reductases of the present invention.

The present disclosure provides engineered enone reductase polypeptides, polynucleotides encoding the polypeptides and methods of using the polypeptides for the reduction of α,β unsaturated ketones, aldehydes, esters, and nitrile compounds. For the descriptions herein and the appended claims, the singular forms "a", "an" and "the" include plural referents unless the context clearly indicates otherwise. Thus, for example, reference to "a polypeptide" includes more than one polypeptide, and reference to "a compound" refers to more than one compound.

It is to be further understood that where descriptions of various embodiments use the term "comprising," those skilled in the art would understand that in some specific instances, an embodiment can be alternatively described using language "consisting essentially of" or "consisting of".

The foregoing general description, including the drawings, and the following detailed description are exemplary and explanatory only and are not restrictive of this disclosure.

Abbreviations

The abbreviations used for the genetically encoded amino acids are conventional and are as follows:

| Amino Acid | Three-Letter | One-letter abbreviation |
| --- | --- | --- |
| Alanine | Ala | A |
| Arginine | Arg | R |

-continued

| Amino Acid | Three-Letter | One-letter abbreviation |
|---|---|---|
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When peptide sequences are presented as a string of one-letter or three-letter abbreviations (or mixtures thereof), the sequences are presented in the N→C direction in accordance with common convention.

DEFINITIONS

Unless otherwise defined, all technical and scientific terms used herein have the same meaning as commonly understood by one of ordinary skill in the art, unless specifically defined herein. Accordingly, the following terms are intended to have the following meanings.

"Enone reductase" and "ERED" are used interchangeably herein to refer to a polypeptide having a capability of reducing an α,β unsaturated compound to the corresponding saturated compound. More specifically, enone reductases are capable of reducing α, β unsaturated ketones, aldehydes, nitriles and esters. Enone reductases typically utilize a cofactor reduced nicotinamide adenine dinucleotide (NADH) or reduced nicotinamide adenine dinucleotide phosphate (NADPH) as the reducing agent. Enone reductases as used herein include naturally occurring (wild type) enone reductases as well as non-naturally occurring engineered polypeptides generated by human manipulation.

"Chimeric" in the context of a gene or polypeptide refers to any gene or DNA or polypeptide that contains (1) DNA or polypeptide sequences that are not found together in nature, or (2) sequences encoding parts of proteins or proteins not naturally adjoined. Accordingly, a chimeric gene or polypeptide may include sequences that are present in different sources or from the same source rearranged in a manner not found in nature. In some embodiments, the chimeric polypeptides comprise fusion proteins.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristination, ubiquitination, etc.). Included within this definition are D- and L-amino acids, and mixtures of D- and L-amino acids.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)), all of which references are incorporated herein by reference. Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively, both of which references are incorporated herein by reference. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915, which is incorporated herein by reference). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

In some embodiments, a "reference sequence" can be based on a primary amino acid sequence, where the reference sequence is a sequence that can have one or more changes in the primary sequence. For instance, a "reference sequence based on SEQ ID NO:8 having at the residue corresponding to X117 an isoleucine" refers to a reference sequence in which the corresponding residue at X117 in SEQ ID NO:4 has been changed to an isoleucine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered enone reductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diasteromers, commonly alternatively reported as the diastereomeric excess (d.e.). Enantiomeric excess and diastereomeric excess are types of stereomeric excess.

"Highly stereoselective" refers to an enone reductase polypeptide that is capable of converting or reducing the substrate to the corresponding product with at least about 85% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a enone reductase polypeptide that exhibits an improvement in any enzyme property as compared to a reference enone reductase. For the engineered enone reductase polypeptides described herein, the comparison is generally made to the wild-type enone reductase enzyme, although in some embodiments, the reference enone reductase can be another improved engineered enone reductase. Enzyme properties for which improvement is desirable include, but are not limited to, enzymatic activity (which can be expressed in terms of percent conversion of the substrate), thermal stability, solvent stability, pH activity profile, cofactor requirements, refractoriness to inhibitors (e.g., product inhibition), stereospecificity, and stereoselectivity (including enantioselectivity).

"Increased enzymatic activity" refers to an improved property of the engineered enone reductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of ERED) as compared to the reference enone reductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type enone reductase enzyme, to as much as 2 times. 5 times, 10 times, 20 times, 25 times, 50 times, 75 times, 100 times, or more enzymatic activity than the naturally occurring enone reductase or another engineered enone reductase from which the enone reductase polypeptides were derived. In specific embodiments, the engineered enone reductase enzyme exhibits improved enzymatic activity in the range of 1.5 to 50 times, 1.5 to 100 times greater than that of the parent reductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1} s^{-1}$). Hence, any improvements in the enzyme activity of the enone reductase will have an upper limit related to the diffusion rate of the substrates acted on by the enone reductase enzyme. Enone reductase activity can be measured by any one of standard assays used for measuring enone reductases, such as a decrease in absorbance or fluorescence of NADPH due to its oxidation with the concomitant reduction of the unsaturated bond, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic reduction of the substrate to the corresponding product. "Percent conversion" refers to the percent of the substrate that is reduced to the product within a period of time under specified conditions. Thus, the "enzymatic activity" or "activity" of a enone reductase polypeptide can be expressed as "percent conversion" of the substrate to the product.

"Thermostable" refers to a enone reductase polypeptide that maintains similar activity (more than 60% to 80% for example) after exposure to elevated temperatures (e.g., 40-80° C.) for a period of time (e.g., 0.5-24 hrs) compared to the untreated enzyme.

"Solvent stable" refers to a enone reductase polypeptide that maintains similar activity (more than e.g., 60% to 80%) after exposure to varying concentrations (e.g., 5-99%) of solvent, (e.g., isopropyl alcohol, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"pH stable" refers to a enone reductase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a enone reductase polypeptide that are both thermostable and solvent stable.

"Derived from" as used herein in the context of engineered enone reductase enzymes, identifies the originating enone reductase enzyme, and/or the gene encoding such enone reductase enzyme, upon which the engineering was based. For example, the engineered enone reductase enzyme of SEQ ID NO: 8 was obtained by artificially recombining the genes encoding enone reductase 1 (SEQ ID NO:2), enone reductase 2 (SEQ ID NO:4), and enone reductase 3 (SEQ ID NO:6). Thus, this engineered enone reductase enzyme is "derived from" the wild-type polypeptides of SEQ ID NO: 2, 4, and 6.

"Hydrophilic amino acid or residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

"Non-polar amino acid or aesidue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. The table below shows exemplary conservative substitutions.

TABLE 1

| Residue | Possible Conservative Mutations |
|---------|--------------------------------|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered enone reductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids to the reference polypeptide. In some embodiments, the improved engineered enone reductase enzymes comprise insertions of one or more amino acids to the naturally occurring enone reductase polypeptide as well as insertions of one or more amino acids to other improved enone reductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length enone reductase polypeptide, for example the polypeptide of SEQ ID NO:8.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved enone reductase enzymes may be present within a cell, present in the cellular medium, or prepared in various forms, such as lysates or isolated preparations. As such, in some embodiments, the improved enone reductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure enone reductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved enone reductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci. USA* 83:8893-8897; Freier et al., 1986, *Proc. Natl. Acad. Sci. USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit. Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered enone reductase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the enone reductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, *Bioinformatics* 14:372-73; Stenico et al., 1994, *Nucleic Acids Res.* 222437-46; Wright, F., 1990, Gene 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinfor-* matics: *Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" is a nucleic acid sequence that is recognized by a host cell for expression of a polynucleotide of interest, such as a coding sequence. The control sequence may comprise an appropriate promoter sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., $NADP^+$ to NADPH). Cofactors oxidized by the enone reductase-catalyzed reduction of the $\alpha,\beta$ unsaturated substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant.

"Optionally substituted" refers to the replacement of hydrogen with a monovalent or divalent radical. Suitable substitution groups include, for example, hydroxyl, nitro, amino, imino, cyano, halo, thio, thioamido, aminidino, imidino, oxo, oxamidino, methoxamidino, imidino, guanidine, sulfonamide, carboxyl, formyl, lower alkyl, lower alkoxy, and the like.

"Lower alkyl" refers to branched or straight chain alkyl groups comprising one to ten carbon atoms that are unsubstituted or substituted, e.g., with one or more halogen, hydroxyl, and the like.

"Lower alkoxy" refers to RO—, wherein R is lower alkyl. Representative examples of lower alkoxy groups include methoxy, ethoxy, t-butoxy, trifluoromethoxy, and the like.

"Aryl" refers to monocyclic and polycyclic aromatic groups and include both carbocyclic aryl groups and heterocylic aryl groups. Aryl substituents of the present invention typically have from 3 to 14 backbone carbon or hetero atoms.

"Aralkyl" refers to an aryl moiety substituted with an alkyl substituent.

Engineered Enone Reductase Polypeptides

The present disclosure provides engineered (or recombinant) enone reductase (ERED) polypeptides useful for reducing an $\alpha,\beta$ unsaturated substrate compound to the corresponding saturated product compound. More specifically, the engineered enone reductase polypeptides are capable of reducing $\alpha,\beta$ unsaturated ketones, aldehydes, nitriles and esters, as further discussed below. The engineered enone reductase polypeptides described herein may also be isolated. In the embodiments herein, the engineered EREDs have an improved property as compared to the naturally occurring enone reductase I enzyme ("ERED 1") obtained from *Saccharomyces pastorianus* (SEQ ID NO: 2); the enone reductase 2 ("ERED 2") obtained from *Saccharomyces cerevisiae* (SEQ ID NO:4); or the enone reductase 3 ("ERED 3") obtained from *Saccharomyces cerevisiae* (SEQ ID NO:6), or improved as compared to another engineered enone reductase, such as the enone reductase of SEQ ID NO:8. The polynucleotide and/or amino acid sequence of the naturally occurring enone reductases are described in the art as follows: ERED 1, also referred to as Old Yellow Enzyme 1 (OYE1), is available as Genbank Accession No. Q02899.3 GI:417-431, and presented herein as SEQ ID NO:1 (polynucleotide) and SEQ ID NO:2 (amino acid); ERED 2, also referred to as Old Yellow Enzyme 2 (OYE2), is available as Genbank Accession No. NP_012049.1 GI:6321973, presented herein as SEQ ID NO:3 (polynucleotide) and SEQ ID NO:4 (amino acid); and ERED 3, also referred to a Old Yellow Enzyme 3 (OYE3) is available as Genbank Accession No. NP_015154.1 GI:6325086, and is presented herein as SEQ ID NO:5 (polynucleotide) and SEQ ID NO:6 (amino acid). The improved property includes improvements in one or more of the following properties: enzyme activity, stability (e.g., solvent and/or thermo stability), stereoselectivity, stereospecificity, inhibitor resistance, and/or substrate recognition. In some embodiments, the engineered enone reductase polypeptides can have more than one improved property, such as increased stability and substrate recognition.

In the characterizations of the enone reductase polypeptides herein, the polypeptide can be described in reference to a sequence of a naturally occurring enone reductase (e.g., ERED 1, ERED 2, or ERED 3) or another engineered enone reductase, such as the engineered chimeric enone reductase of SEQ ID NO:8, or another invention enone reductase polypeptide described herein. In some embodiments, the amino acid position is determined in the reference polypeptide beginning from the initiating methionine (M) residue, although it will be understood by the skilled artisan that this initiating methionine residue may be removed by biological processing machinery, such as in a host cell or in vitro translation system, to generate the mature protein lacking the initiating methionine. The amino acid residue position at which a particular amino acid is present or an amino acid change occurs in an amino acid sequence is sometimes described herein as "Xn" or "position n", where n refers to the residue position. A substitution mutation, where described, may be denoted by the symbol "→" or by conventional notation used by those skilled in the art, for example "W117V, where W is the amino acid present in the reference sequence, the number 117 is the residue position in the reference sequence, and V is the amino acid substitution.

The present disclosure provides engineered enone reductase polypeptides comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or more identical to the reference sequence selected from the group consisting of SEQ ID NOs: 8, 190, 192, 194, 196, 198, 200, 202, 204, 206, 208, 210, 212, 214, 216, and 217. Engineered enone reductase polypeptides of the present invention do not include polypeptides having the amino acid sequences of SEQ ID NOS: 2, 4, and 6. Typically, the engineered enone reductase polypeptides have one or more differences or modifications relative to the reference sequence as described hereinbelow.

In some embodiments, the engineered enone reductases can have one or more residue differences (i.e., modifications) as compared to a reference sequence, such as the naturally occurring ERED 1, ERED 2, or ERED 3, or an engineered ERED, such as the chimeric enzymes having increased thermo- and solvent stability. In some embodiments, the modifications are with respect to the sequence of SEQ ID NO: 8, 190, 192, 194, 196, 198, 200, 202, 204, 206, 208, 210, 212, 214, or 216. In some embodiments, the modifications can be with respect to SEQ ID NO:2, SEQ ID NO:4 or SEQ ID NO:6, particularly with respect to SEQ ID NO:6. In some embodiments, the enone polypeptides herein can have a number of residue differences as compared to the reference sequence (e.g., naturally occurring polypeptide or an engineered polypeptide) to change the properties of the enzyme, including, among others, enzymatic activity, substrate recognition, inhibitor resistance, stereoselectivity, stereospecificity, and stability enhancements.

Residue differences or modifications include amino acid substitutions, deletions, and insertions. Any one or a combination of modifications can be introduced into the naturally occurring or engineered polypeptide to generate engineered polypeptides. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 15% of the total number of amino acids, up to 20% of the total number of amino acids, or up to 30% of the total number of amino acids of the reference polypeptide sequence. In some embodiments, the number of modifications to the naturally occurring polypeptide or an engineered polypeptide that produces an improved property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35, 40, 45, 50, 55, or 60 amino acid residue positions. The modifications can comprise insertions, deletions, substitutions, or combinations thereof.

In some embodiments, the modifications comprise amino acid substitutions to the reference sequence. Substitutions that can produce an improved property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an altered enone reductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 amino acid substitutions of the reference sequence. In some embodiments, the number of substitutions can be at 1, 2, 3, 4, 5, 6, 7, 8, 9, 10, 11, 12, 14, 15, 16, 18, 20, 22, 24, 26, 30, 35, 40, 45, 50, 55, or 60 amino acid residue positions.

In some embodiments, the engineered enone reductase polypeptides of the disclosure can have residue differences as compared to one of the a reference sequences described herein at one or more of the following residue positions: X5; X10; X28; X38; X40; X44; X75; X83; X117; X119; X122; X124; X147; X148; X153; X154; X179; X209; X240; X248; X251; X252; X255; X259; X294; X295; X296; X297; X302; X304; X305; X311; X315; X330; X333; X339; X358; X369; X376; X379; X384; X386; X397; X399; and X400. The occupation by particular amino acid residues at these residue positions is associated with changes to properties of the enone reductases and described in detail below as features of the enone reductase amino acid sequences.

In some embodiments, the residue differences at the specified residue positions can be with respect to a reference chimeric enone reductase described hereinbelow having the thermo- and/or solvent stability as described herein, such as, for example, SEQ ID NO: 8, 190, 192, 194, 196, 198, 200, 202, 204, 206, 208, 210, 212, 214, or 216. That is, particular amino acid residues at the specified positions can be present in an amino acid sequence encoding the chimeric enone reductase polypeptides described hereinbelow, which exhibit thermo- and/or solvent stability.

In some embodiments, the residue differences at the specified residue positions can be with respect to a reference sequence of a naturally occurring enone reductase, such as the polypeptides of SEQ ID NO:2, 4, or 6. Thus, while the exemplary enone reductases presented herein are based on a chimeric enone reductase, it is to be understood that various residue differences resulting in altered enzyme properties can be applied to naturally occurring enone reductases of SEQ ID NO:2, SEQ ID NO:4 and SEQ ID NO:6. Accordingly, in some embodiments, the engineered enone reductases can also comprise an amino acid sequence that is at least 80%, 85%, 86%, 87%, 88%, 89%, 90%, 91%, 92%, 93%, 94%, 95%, 96%, 97%, 98%, 99% or more identical to a reference sequence of SEQ ID NO:2, SEQ ID NO:4 or SEQ ID NO:6 having any one or more of the features or residue differences described in detail herein.

In some embodiments, the choice of amino acid residues for the specified residue positions can be based on the following features: residue corresponding to X5 is a basic or acidic residue, particularly an acidic residue; residue corresponding to X10 is a polar or constrained residue, particularly a polar residue; residue corresponding to X28 is an aliphatic or constrained residue, particularly a constrained residue; residue corresponding to X38 is a polar or basic residue; residue corresponding to X40 is a non-polar, aliphatic, aromatic, acidic or polar residue, particularly an aliphatic, aromatic, acidic or polar residue; residue corresponding to X44 is a constrained or aromatic residue, particularly an aromatic residue; residue corresponding to X75 is an aromatic, aliphatic or polar residue, particularly an aliphatic or polar residue; residue corresponding to X83 is an aromatic, aliphatic, acidic, or basic residue, particularly an aliphatic, acidic, or basic residue; residue corresponding to X117 is a cysteine or nonpolar, aliphatic, basic, acidic, polar, or aromatic residue; residue corresponding to X119 is a constrained or aliphatic residue; residue corresponding to X122 is an aliphatic or polar residue, particularly a polar residue; residue corresponding to X124 is an aromatic, non-polar or a constrained residue, particularly a non-polar or a constrained residue; residue corresponding to X147 is an acidic or non-polar residue, particularly a non-polar residue; residue corresponding to X148 is a polar or basic residue, particularly a basic residue; residue corresponding to X153 is a basic or acidic residue, particularly a basic residue; residue corresponding to X154 is a basic residue; residue corresponding to X179 is a basic residue; residue corresponding to X209 is a polar or acidic residue, particularly an acidic residue; residue corresponding to X240 is a basic residue; residue corresponding to X248 is an aromatic residue or cysteine, particularly cysteine; residue corresponding to X251 is a cysteine, or aromatic, non-polar, aliphatic, acidic, basic, or polar residue; residue corresponding to X252 is a polar, aromatic or constrained residue, particularly an aromatic or constrained residue; residue corresponding to X255 is a polar or constrained residue, particularly a constrained residue; residue corresponding to X259 is an acidic or non-polar residue, particularly a non-polar residue; residue corresponding to X294 is a polar or aliphatic residue, particularly an aliphatic residue; residue corresponding to X295 is an acidic, polar, basic, or non-polar residue, particularly polar, basic, or non-polar residue; residue corresponding to X296 is a constrained, aromatic, non-polar, aliphatic, basic, acidic, or polar residue, particularly an aromatic, non-polar, aliphatic, basic, acidic, or polar residue; residue corresponding to X297 is a polar, aromatic, non-polar, aliphatic, or basic residue, particularly aromatic, non-polar, aliphatic, or basic residue; residue corresponding to X302 is an acidic or non-polar residue, particularly a non-polar residue; residue corresponding to X304 is an acidic or basic residue, particularly a basic residue; residue corresponding to X305 is an aromatic or polar residue, particularly a polar residue; residue corresponding to X311 is an acidic residue; residue corresponding to X315 is a constrained residue; residue corresponding to X330 is a constrained, aromatic or basic residue, particularly an aromatic or basic residue; residue corresponding to X333 is an aliphatic residue; residue corresponding to X339 is a basic or polar residue, particularly a polar residue; residue corresponding to X358 is an aliphatic residue; residue corresponding to X369 is a basic or acidic residue, particularly an acidic residue; residue corresponding to X376 is an aromatic, non-polar, aliphatic, basic or acidic residue, particularly a non-polar, aliphatic, basic or acidic residue; residue corresponding to X379 is a polar or nonpolar residue, particularly a non-polar residue; residue corresponding to X384 is a polar or aliphatic residue, particularly an aliphatic residue; residue corresponding to X386 is an aromatic or acidic residue, particularly an acidic residue; residue corresponding to X397 is an aromatic or basic residue, particularly a basic residue; residue corresponding to X399 is a basic or acidic residue, particularly an acidic residue; and residue corresponding to X400 is a polar residue. In some embodiments, the amino acid sequence can have at least two, three, four, five, six, seven, eight, nine, ten, or more of the features. The sequence formula described herein as SEQ ID NO:217 presents these features in the context of the chimeric enone reductase of SEQ ID NO:8. In some embodiments, the enone reductase polypeptides can have additionally one or more residue differences at residue positions not specified by an X above as compared to a reference sequence, for example SEQ ID NO:8. In some embodiments, the differences can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions not defined by X above. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at other amino acid residue positions. In some embodiments, the differences comprise conservative mutations.

In some embodiments, the amino acid residues at the specified positions can be selected from one or more of the following features: residue corresponding to X5 is E; residue corresponding to X10 is P; residue corresponding to X28 is P; residue corresponding to X38 is N or S; residue corresponding to X40 is L, Y, E or S; residue corresponding to X44 is Y; residue corresponding to X75 is L or S; residue corresponding to X83 is L, R, V, I, K, E, or M; residue corresponding to X117 is C, L, A, M, V, I, N, Q, E, F, or S; residue corresponding to X119 is P or V; residue corresponding to X122 is T; residue corresponding to X124 is G or P; residue corresponding to X147 is G; residue corresponding to X148 is R; residue corresponding to X153 is E; residue corresponding to X154 is R; residue corresponding to X179 is R; residue corresponding to X209 is D; residue corresponding to X240 is R; residue corresponding to X248 is C; residue corresponding to X251 is A; C, R, E, D, W, Y, R, S, V, G, L, or I; residue corresponding to X252 is H; residue corresponding to X255 is P; residue corresponding to X259 is G; residue corresponding to X294 is A; residue corresponding to X295 is T, N, or G; residue corresponding to X296 is G, F, A, S, R, E, Q, K, or I; residue corresponding to X297 is F; K; Y, W, G, A, or I; residue corresponding to X302 is G; residue corresponding to X304 is K; residue corresponding to X305 is S; residue corresponding to X311 is E; residue corresponding to X315 is P; residue corresponding to X330 is Y or R; residue corresponding to X333 is A; residue corresponding to X339 is Q; residue corresponding to X358 is A; residue corresponding to X369 is E; residue corresponding to X376 is T, K, I, A, or E; residue corresponding to X379 is G; residue corresponding to X384 is I; residue corresponding to X386 is D; residue corresponding to X397 is R; residue corresponding to X399 is E; and residue corresponding to X400 is T. In some embodiments, the enone reductase polypeptides can have additionally one or more residue differences at residue positions not specified by an X above as compared to the reference sequence (e.g., SEQ ID NO:8). In some embodiments, the differences can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions not defined by X above. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at other amino acid residue positions. In some embodiments, the differences comprise conservative mutations.

In some embodiments, the engineered enone reductase amino acid sequence has at least one or more of the following features: residue corresponding to X40 is L, Y, E or S; residue corresponding to X83 is L, R, V, I, K, E, or M; residue corresponding to X117 is C; L; A; M; V; I; N; Q; E, F, or S; residue corresponding to X124 is G or P; residue corresponding to X251 is A; C, R, E, D, W, Y, R, S, V, G, L, or I; residue corresponding to X296 is G, F, A, S, R, E, Q, K, or I; residue corresponding to X297 is F; K; Y, W, G, A, or I; and residue corresponding to X376 is T, K, I, A, or E.

In some embodiments, the engineered enone reductase amino acid sequence has at least one of the following features: residue corresponding to X38 is S and X117 is A; residue corresponding to X40 is L and X294 is A; residue corresponding to X75 is L and X297 is A; residue corresponding to X83 is I and X124 is P; residue corresponding to X83 is I and X251 is R; residue corresponding to X83 is I and X251 is A; residue corresponding to X83 is I and X251 is V; residue corresponding to X83 is I and X251 is S; residue corresponding to X83 is K and X117 is I; residue corresponding to X83 is I and X117 is I; residue corresponding to X117 is A and X122 is T; residue corresponding to X117 is E and X386 is D; residue corresponding to X148 is R and X251 is G; residue corresponding to X248 is C and 5297 is G; residue corresponding to X251 is L and X379 is G; residue corresponding to X294 is A and X295 is G; residue corresponding to X296 is R and X330 is Y; residue corresponding to X296 is A and X297 is F; residue corresponding to X305 is S and X376 is I; residue corresponding to X315 is P and X376 is T; residue corresponding to X296 is K and X376 is A; residue corresponding to X10 is P, X297 is G and X379 is G; residue corresponding to X38 is S, X83 is I and X117 is L; residue corresponding to X40 is S, X302 is G and X330 is Y; residue corresponding to X83 is I, X251 is V and X295 is N; residue corresponding to X38 is S, X75 is L, X83 is I, X117 is I and X255 is P; residue corresponding to X38 is S, X83 is I, X117 is I and X119 is V; residue corresponding to X38 is S, X40 is Y, X83 is I and X117 is A; residue corresponding to X38 is S, X83 is I, X117 is A and X251 is D; residue corresponding to X38 is S, X83 is I, X117 is A and X251 is A; residue corresponding to X83 is I, X251 is A and X330 is Y; residue corresponding to X83 is I, X124 is G and X304 is K; residue corresponding to X251 is E, X330 is R and X376 is I; residue corresponding to X38 is S, X83 is I, X117 is I, X153 is E, X251 is W, X295 is T, X296 is F and X297 is Y; residue corresponding to X38 is S, X83 is I, X117 is I, X251 is A, X295 is N, X296 is F and X297 is W; residue corresponding to X38 is S, X83 is I, X117 is A, X251 is Y, X295 is T, X296 is F and X297 is W; residue corresponding to X38 is S, X83 is I, X117 is I, X295 is T and X296 is A; residue corresponding to X5 is E, X44 is Y, X83 is I, X251 is A, X295 is N and X297 is G; residue corresponding to X83 is I, X179 is R, X251 is C and X339 is Q; residue corresponding to X38 is S, X83 is I, X117 is F and X251 is S; residue corresponding to X38 is S, X83 is I, X117 is L, X209 is D, X251 is S, X376 is K and X400 is T; residue corresponding to X38 is S, X83 is I, X251 is S and X296 is G; residue corresponding to X38 is S, X83 is I, X117 is F, X251 is V and X376 is I; residue corresponding to X38 is S, X83 is I, X117 is F, X251 is S, X295 is N, X296 is G and X297 is F; residue corresponding to X38 is S, X83 is I, X251 is S, X295 is T, X296 is S, X297 is F and X384 is I; residue corresponding to X28 is P, X83 is I, X117 is A and X251 is V; residue corresponding to X83 is I, X117 is N, X295 is T, X296 is G and X297 is F; residue corresponding to X83 is I, X117 is S, X251 is V, X296 is R and X297 is F; residue corresponding to X83 is I, X296 is S, X297 is F, X376 is I and X397 is R; residue corresponding to X38 is S, X83 is I, X117 is N and X251 is V; residue corresponding to X38 is S, X83 is I, X251 is S, X295 is T, X296 is G and X297 is F; residue corresponding to X38 is S, X83 is I, X154 is R, X251 is V, X295 is T and X297 is F; residue corresponding to X38 is S, X83 is I, X117 is A and X330 is Y; residue corresponding to X38 is S, X83 is I and X297 is Y; residue corresponding to X38 is S, X40 is E, X75 is S, X83 is I and X117 is I; residue corresponding to X38 is S, X83 is I and X117 is I; residue corresponding to X83 is E, X117 is I and X333 is A; residue corresponding to X251 is S, X296 is E, X297 is A and X311 is E; residue corresponding to X240 is R, X251 is S, X259 is G, X296 is Q and X297 is A; residue corresponding to X251 is I, X296 is S and X297 is F; residue corresponding to X251 is S, X297 is I and X358 is A; residue corresponding to X251 is A, X296 is A; X297 is K and X399 is E; residue corresponding to X251 is I, X296 is E, X297 is A and X376 is I; residue corresponding to X296 is I; X297 is A, X333 is A and X376 is A; residue corresponding to X296 is A, X297 is A; X330 is R and X376 is I; residue corresponding to X147 is G, X296 is A, X297 is F, X330 is R and X376 is E; or residue corresponding to X297 is F, X369 is E and X376 is K. In some embodiments, the enone reductase polypeptides can have additionally one or more residue differences at other residue positions as compared to the reference sequence (e.g., SEQ ID NO:8). In some embodiments, the differences can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at other amino acid residue positions. In some embodiments, the differences comprise conservative mutations.

In some embodiments, exemplary engineered enone reductase polypeptides comprising an amino acid sequence with various features described herein can be a sequence corresponding to SEQ ID NO: 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, or 188.

The present invention also provides an engineered enone reductase polypeptide comprising an amino acid sequence encoded by a nucleic acid that hybridizes under stringent hybridization conditions over substantially the entire length of a nucleic acid corresponding to a reference polynucleotide sequence selected from the group consisting of SEQ ID NOs: 7, 189, 191, 193, 195, 197, 199, 201, 203, 205, 207, 209, 211, 213, and 215 and a complementary sequence thereof, where the amino acid sequence is not SEQ ID NOS: 2, 4 or 6. The amino acid sequence of the encoded polypeptide may have one or more residue differences relative to the amino acid sequence encoded by the reference polynucleotide sequences (i.e., SEQ ID NOs: 8, 190, 192, 194, 196, 198, 200, 202, 204, 206, 208, 210, 212, 214, and 216, respectively) that are described herein.

Typically, the encoded amino acid sequences comprise one or more of the following features residue corresponding to X5 is E; residue corresponding to X10 is P; residue corresponding to X28 is P; residue corresponding to X38 is N or S; residue corresponding to X40 is L, Y, E or S; residue corresponding to X44 is Y; residue corresponding to X75 is L or S; residue corresponding to X83 is L, R, V, I, K, E, or M; residue corresponding to X117 is C, L, A, M, V, I, N, Q, E, F, or S; residue corresponding to X119 is P or V; residue corresponding to X122 is T; residue corresponding to X124 is G or P; residue corresponding to X147 is G; residue corresponding to X148 is R; residue corresponding to X153 is E; residue corresponding to X154 is R; residue corresponding to X179 is R; residue corresponding to X209 is D; residue corresponding to X240 is R; residue corresponding to X248 is C; residue corresponding to X251 is A; C, R, E, D, W, Y, R, S, V, G, L, or I; residue corresponding to X252 is H; residue corresponding to X255 is P; residue corresponding to X259 is G; residue corresponding to X294 is A; residue corresponding to X295 is T, N, or G; residue corresponding to X296 is G, F, A, S, R, E, Q, K, or I; residue corresponding to X297 is F; K; Y, W, G, A, or I; residue corresponding to X302 is G; residue corresponding to X304 is K; residue corresponding to X305 is S; residue corresponding to X311 is E; residue corresponding to X315 is P; residue corresponding to X330 is Y or R; residue corresponding to X333 is A; residue corresponding to X339 is Q; residue corresponding to X358 is A; residue corresponding to X369 is E; residue corresponding to X376 is T, K, I, A, or E; residue corresponding to X379 is G; residue corresponding to X384 is I; residue corresponding to X386 is D; residue corresponding to X397 is R; residue corresponding to X399 is E; and residue corresponding to X400 is T.

In some embodiments, the enone reductases of the disclosure are characterized by increased stability as compared to the naturally occurring enone reductases ERED 1, ERED 2 or ERED 3. In some embodiments, the enone reductases are characterized by increased thermostability and/or solvent stability, particularly with respect to the ERED of SEQ ID NO:6. Thermostability can be readily assessed by subjecting the polypeptide to a defined temperature under a set of solution conditions and measuring the enzyme activity remaining (i.e., residual activity) following exposure to the defined temperature. Likewise, solvent stability can be readily assessed by subjecting the polypeptide to a defined solvent under a defined condition and measuring the enzyme activity remaining following exposure to the solvent. Thermal stability is advantageous where reaction with substrates are carried out at elevated temperatures and/or the enzymatic reaction carried out for long time periods. Because certain substrates acted on by the engineered enone reductases are prepared in organic solvents and the reaction carried out in such solvents, solvent stability is also an advantageous enzyme property. Solvent stability can include stability in, among others, methanol (MeOH), isopropanol (IPA), tetrahydrofuran (THF), acetone (ACTN), acetonitrile (ACN), dimethylsulfoxide (DMSO), dimethylformamide (DMF), methyl tert butyl ether (MTBE), and n-butylacetate (nBuOAc). While the properties of thermal stability and solvent stability can be separate, for example, an enone reductase that is stable to elevated temperatures but not stable to isopropanol, in some embodiments, the enone reductases herein display both thermal stability and solvent stability.

In some embodiments, the engineered enone reductase polypeptides are characterized by increased stability under conditions of 50% isopropanol at 30° C. and/or 10-20% isopropanol at 40° C. as compared to the naturally occurring enone reductase 3. In some embodiments, the enone reductases are characterized by increased stability in 50% isopropanol at 30° C. In some embodiments, the enone reductases are characterized by increased stability in 10% isopropanol at 40° C. In some embodiments, the enone reductases are characterized by increased stability in 20% isopropanol at 40° C. The enone reductases are generally exposed to such conditions for about 18 to 24 hrs to assess their stability under the specified conditions.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:8.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:190.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:192.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:194.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:196.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:198.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:200.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:202.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:204.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:206.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:208.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:210.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:212.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:214.

In some embodiments, the engineered enone reductase with increased stability comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:216.

In some embodiments, the enone reductases with increased thermal and/or solvent stability can comprise a chimeric polypeptide of enone reductase 2 (ERED 2) of SEQ ID NO:4, and enone reductase 3 (ERED 3) of SEQ ID NO:6. In some embodiments, the chimera can also include sequences from enone reductase 1 (ERED 1) of SEQ ID NO:2 such that the polypeptide with increased thermal and/or solvent stability comprises a fusion polypeptide of amino acid sequences derived from ERED 1, ERED 2, and ERED 3. These chimeric enzymes can be obtained based on in vitro recombination at regions of nucleic acid sequence homology between the different enone reductase genes. Techniques to obtain chimeric enzymes are described in the art, such as that disclosed in Riechmann and Winter, 2000, *Proc Natl Acad Sci USA* 97(18):10068-10073; Crameri et al., 1998, *Nature* (London)

391:288-291; Ostermeier et al., 1999, *Proc Natl Acad Sci USA* 96:3562-3567; and Altamirano et al., 2000, *Nature* (London) 403:617-622; Stemmer, W. P. C., 1994, *Nature* 370:389-391; Stemmer, W. P. C., 1994, *Proc Natl Acad. Sci. USA* 91:10751; U.S. Pat. No. 5,605,793; U.S. Pat. No. 5,811,238; and U.S. Pat. No. 5,830,721; all of which references are incorporated herein by reference. The regions of polynucleotide sequence identity between ERED 1, ERED 2, and ERED 3 are shown in FIG. 2. Once chimeras with the desired properties are obtained, general recombinant DNA methodology can be used to generate additional chimeric polypeptides with varying recombination points in the polypeptide sequence.

In some embodiments, the chimera can have the following basic structure $$S^A \sim S^B$$

wherein $S^A$ comprises a segment initiating from residues of about 1 and terminating at residues of about 120 to 150 and is derived from ERED 1, ERED 2, ERED 3, or combinations thereof and $S^B$ comprises a segment initiating from residues of about 121 to 151 and terminating at residue of about 400 and is derived from ERED 2, ERED 3, or combinations thereof. The chimera with segments $S^A$ and $S^B$ can be further subdivided into sub-segments, where the sub-segments can be derived from the specified enone reductases and combinations thereof. It is also to be understood that the chimeric structure does not exclude a fusion polypeptide where a contiguous portion of a specific enone reductase beginning in segment $S^A$ extends to segment $S^B$, thereby forming a continuous sequence across the segments as found in the naturally occurring enone reductase. The same applies to any of the chimeric structures described herein.

In some embodiments, the enone reductase comprises the structure:

$$S^1 \sim S^2 \sim S^3 \sim S^4$$

wherein $S^1$ comprises a segment initiating from residue of about 1 and terminating at residues of about 14 to 20 and is derived from ERED 1;

$S^2$ comprises a segment initiating from residues of about 15 to 21 and terminating at residues of about 124 to 130 and is derived from ERED 3;

$S^3$ comprises a segment initiating from residues of about 125 to 131 and terminating at residues of about 272 to 278 and is derived from ERED 2; and $S^4$ comprises a segment initiating from residues of about 273 to 279 and terminating at residue of about 400 and is derived from ERED 3.

In some embodiments, the enone reductase comprises the structure:

$$S^1 \sim S^2 \sim S^3 \sim S^4 \sim S^5 \sim S^6$$

wherein $S^1$ comprises a segment initiating from residue of about 1 and terminating at residues of about 16 to 22 and is derived from ERED 1;

$S^2$ comprises a segment initiating from residues of about 17 to 23 and terminating at residues of about 56 to 62 and is derived from ERED 3;

$S^3$ comprises a segment initiating from residues of about 57 to 63 and terminating at residues of about 106 to 112 and is derived from ERED 2;

$S^4$ comprises a segment initiating from residues of about 107 to 113 and terminating at residues of about 138 to 144 and is derived from ERED 3;

$S^5$ comprises a segment initiating from residues of about 139 to 145 and terminating at residues of about 296 to 302 and is derived from ERED 2; and $S^6$ comprises a segment initiating from residues of about 297 to 303 and terminating at residue of about 400 and is derived from ERED 3.

In some embodiments, the enone reductase comprises the structure:

$$S^1 \sim S^2 \sim S^3$$

wherein $S^1$ comprises a segment initiating from residue of about 1 and terminating at residues of about 56 to 62 and is derived from ERED 3;

$S^2$ comprises a segment initiating from residues of about 57 to 63 and terminating at residues of about 272 to 278 and is derived from ERED 2; and $S^3$ comprises a segment initiating from residues of about 273 to 279 and terminating at residue of about 400 and is derived from ERED 3.

In some embodiments, the enone reductase comprises the structure:

$$S^1 \sim S^2 \sim S^3$$

wherein $S^1$ comprises a segment initiating from residue of about 1 and terminating at residues of about 106 to 112 and is derived from ERED 3;

$S^2$ comprises a segment initiating from residues of about 107 to 113 and terminating at residue of about 247 to 253 and is derived from ERED 2; and $S^3$ comprises a segment initiating from residues of about 248 to 254 and terminating at residue of about 400 and is derived from ERED 3.

In some embodiments, the enone reductase comprises the structure:

$$S^1 \sim S^2 \sim S^3 \sim S^4$$

wherein $S^1$ comprises a segment initiating from residue of about 1 and terminating at residues of about 77 to 83 and is derived from ERED 3;

$S^2$ comprises a segment initiating from residues of about 78 to 84 and terminating at residues of about 173 to 179 and is derived from ERED 2;

$S^3$ comprises a segment initiating from residues of about 174 to 180 and terminating at residues of about 334-340 and is derived from ERED 3:

$S^4$ comprises a segment initiating from residues of about 335 to 341 and terminating at residue of about 400 and is derived from ERED 2.

In some embodiments, the enone reductase comprises the structure:

$$S^1 \sim S^2 \sim S^3 \sim S^4$$

wherein $S^1$ comprises a segment initiating from residue of about 1 and terminating at residues of about 26 to 32 and is derived from ERED 2;

$S^2$ comprises a segment initiating from residues of about 27 to 33 and terminating at residues of about 100 to 106 and is derived from ERED 3;

$S^3$ comprises a segment initiating from residues of about 101 to 107 and terminating at residues of about 120-126 and is derived from ERED 1; and S⁴ comprises a segment initiating from residues of about 121 to 127 and terminating at residue of about 400 and is derived from ERED 2.

In some embodiments, the enone reductase comprises the structure:

$$S^1\text{~}S^2\text{~}S^3\text{~}S^4\text{~}S^5\text{~}S^6$$

wherein

S¹ comprises a segment initiating from residue of about 1 and terminating at residues of about 16 to 22 and is derived from ERED 2;

S² comprises a segment initiating from residue of about 17 to 23 and terminating at residues of about 65 to 71 and is derived from ERED 3;

S³ comprises a segment initiating from residues of about 66 to 73 and terminating at about residues 100 to 106 and is derived from ERED 2:

S⁴ comprises a segment initiating from residues of about 101 to 107 and terminating at residues of about 138 to 144 and is derived from ERED 3;

S⁵ comprises a segment initiating from residues of about 139 to 145 and terminating at residues of about 173 to 179 and is derived from ERED 2; and S⁶ comprises a segment initiating from residues of about 173 to 180 and terminating at residue of about 400 and is derived from ERED 3.

In some embodiments, the enone reductase comprises the structure:

$$S^1\text{~}S^2\text{~}S^3\text{~}S^4$$

wherein

S¹ comprises a segment initiating from residue of about 1 and terminating at residues of about 16 to 22 and is derived from ERED 2;

S² comprises a segment initiating from residues of about 17 to 23 and terminating at residues of about 247 to 253 and is derived from ERED 3;

S³ comprises a segment initiating from residues of about 248 to 254 and terminating at residues of about 296 to 302 and is derived from ERED 2; and S⁴ comprises a segment initiating from residues of about 297 to 303 and terminating at residue of about 400 and is derived from ERED 3.

In some embodiments, the enone reductase comprises the structure:

$$S^1\text{~}S^2\text{~}S^3\text{~}S^4\text{~}S^5$$

wherein

S¹ comprises a segment initiating from residue of about 1 and terminating at residues of about 65 to 71 and is derived from ERED 3;

S² comprises a segment initiating from residues of about 66 to 72 and terminating at residues of about 173 to 179 and is derived from ERED 2;

S³ comprises a segment initiating from residues of about 174 to 180 and terminating at residues of about 237 to 243 and is derived from ERED 3:

S⁴ comprises a segment initiating from residues of about 238 to 244 and terminating at residues of about 294 to 300 and is derived from ERED 2; and S⁵ comprises a segment initiating from residues of about 295 to 301 and terminating at residues of about 400 and is derived from ERED 3.

In some embodiments, the enone reductase comprises the structure:

$$S^1\text{~}S^2$$

wherein

S¹ comprises a segment initiating from residue of about 1 and terminating at residues of about 308 to 314 and is derived from ERED 3; and S² comprises a segment initiating from residues of about 309 to 315 and terminating at residue of about 400 and is derived from ERED 2.

In some embodiments, the enone reductase comprises the structure:

$$S^1\text{~}S^2\text{~}S^3\text{~}S^4\text{~}S^5$$

wherein

S¹ comprises a segment initiating from residue of about 1 and terminating at residues of about 40 to 46 and is derived from ERED 2;

S² comprises a segment initiating from residue of about 41 to 47 and terminating at residues of about 53 to 59 and is derived from ERED 3;

S³ comprises a segment initiating from residues of about 54 to 60 and terminating residues of about 206 to 212 and is derived from ERED 2:

S⁴ comprises a segment initiating from residues of about 207 to 213 and terminating at residues of about 257 to 263 and is derived from ERED 3; and S⁵ comprises a segment initiating from residues of about 258 to 264 and terminating at residue of about 400 and is derived from ERED 2.

In some embodiments, the enone reductase comprises the structure:

$$S^1\text{~}S^2\text{~}S^3$$

wherein

S¹ comprises a segment initiating from residue of about 1 and terminating at residues of about 16 to 24 and is derived from ERED 2;

S² comprises a segment initiating from residues of about 17 to 25 and terminating at residues of about 124 to 130 and is derived from ERED 3; and S³ comprises a segment initiating from residues of about 125 to 131 and terminating at residue of about 400 and is derived from ERED 2.

In some embodiments, the enone reductase comprises the structure:

$$S^1\text{~}S^2\text{~}S^3\text{~}S^4$$

wherein

S¹ comprises a segment initiating from residue of about 1 and terminating at residues of about 53 to 59 and is derived from ERED 3;

S² comprises a segment initiating from residues of about 54 to 60 and terminating at residues of about 71 to 77 and is derived from ERED 1;

S³ comprises a segment initiating from residues of about 72 to 78 and terminating at residues of about 115 to 121 and is derived from ERED 3; and S⁴ comprises a segment initiating from residues of about 116 to 120 and terminating at residue of about 400 and is derived from ERED 2.

In some embodiments, the enone reductase comprises the structure:

$$S^1\text{~}S^2\text{~}S^3$$

wherein

S¹ comprises a segment initiating from residue of about 1 and terminating at residues of about 40 to 46 and is derived from ERED 3;

$S^2$ comprises a segment initiating from residues of about 41 to 47 and terminating at residues of about 109 to 115 and is derived from ERED 1; and $S^3$ comprises a segment initiating from residues of about 110 to 116 and terminating at residue of about 400 and is derived from ERED 2.

In some embodiments, the enone reductase comprises the structure:

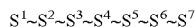

wherein $S^1$ comprises a segment initiating from residue of about 1 and terminating at residues of about 16 to 22 and is derived from ERED 2;

$S^2$ comprises a segment initiating from residues of about 17 to 23 and terminating at residues of about 31 to 36 and is derived from ERED 3;

$S^3$ comprises a segment initiating from residues of about 32 to 37 and terminating at residues of about 69 to 75 and is derived from ERED 1:

$S^4$ comprises a segment initiating from residues of about 70 to 76 and terminating at residues of about 77 to 83 and is derived from ERED 2;

$S^5$ comprises a segment initiating from residues of about 78 to 84 and terminating at residues of about 106 to 112 and is derived from ERED 3:

$S^6$ comprises a segment initiating from residues of about 107 to 113 and terminating at about residues of about 173 to 179 and is derived from ERED 2; and $S^7$ comprises a segment initiating from residues of about 174 to 180 and terminating at residue of about 400 and is derived from ERED 3.

In some embodiments, the engineered enone reductase is characterized by increased stability in 50% isopropanol at 30° C. as compared to the polypeptide of SEQ ID NO:6 and comprises an amino acid sequence corresponding to SEQ ID NO: 8, 192, 194, 200, 204, or 216.

In some embodiments, the engineered enone reductase is characterized by increased stability in 10% isopropanol at 40° C. as compared to the polypeptide of SEQ ID NO:6 and comprises an amino acid sequence corresponding to SEQ ID NO: 8, 192, 194, 196, 198, 200, 202, 204, 206, 208, 210, or 216.

In some embodiments, the enone reductase is characterized by increased stability in 20% isopropanol at 40° C. and comprises an amino acid sequence corresponding to SEQ ID NO: 8, 192, 194, 196, 198, 200, 202, or 210.

In some embodiments, the enone reductase is characterized by increased stability under conditions of 50% isopropanol at 30° C. and 10% isopropanol at 40° C. as compared to the polypeptide of SEQ ID NO:6. In some embodiments, the enone reductase stable to elevated temperature and isopropanol comprises a sequence corresponding to SEQ ID NO: 8, 192, 194, 200, 204, or 216.

In some embodiments, the engineered enone reductases are capable of reducing an optionally substituted cyclohexenone to the corresponding cyclohexanone. For example, these embodiments include engineered reductases that are capable of reducing 1-cyclohex-2-enone of formula (III) to the cyclohexanone of formula (IV):

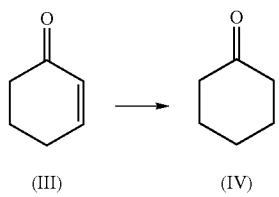

The naturally occurring ERED 1 is capable of acting on the 1-cyclohex-2-enone while the naturally occurring ERED 2 and ERED 3 show minimal activity towards this substrate. Given that the naturally occurring ERED 1 is not stable to temperature and organic solvents, none of the naturally occurring enone reductases display significant temperature and/or solvent stability and activity towards the substrate of formula (III). In some embodiments, the engineered enone reductases described herein are thermo and solvent stable, and have the capability of reducing 1-cyclohex-2-enone to the cyclohexanone. The latter is used in the production of adipic acid for the synthesis of nylon and caprolactam, as well serving as a solvent in various organic synthesis processes, such as the synthesis of polymers.

In some embodiments, the engineered enone reductases are also capable of reducing an optionally alkenoate to the corresponding alkanoate. For example, these embodiments include engineered reductases that are capable of reducing methyl(E)-but-2-enoate of formula (V) to methyl butanoate of formula (VI):

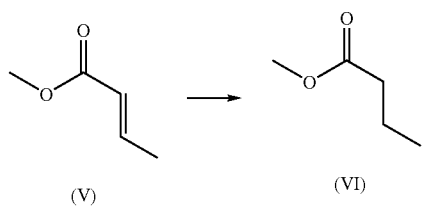

and have improved properties of thermal stability and/or solvent stability as compared to the naturally occurring enone reductases of SEQ ID NO:2, SEQ ID NO:4, or SEQ ID NO:6, particularly the polypeptide of SEQ ID NO:6. Enone reductases capable of reducing both 1-cyclohex-2-enone and methyl(E)-but-2-enoate have expanded substrate specificity and are good starting points for generation of other engineered enone reductases with improved properties. As will be apparent to the skilled artisan, various chimeric enone reductases characterized by thermal and/or solvent stability, and capable of converting 1-cyclohex-2-enone to cyclohexanone and/or methyl(E)-but-2-enoate to methyl butanoate can be screened and obtained using the guidance provided in the present disclosure.

In some embodiments, the engineered enone reductase is capable of reducing an optionally substituted cyclohexenone to the corresponding cyclohexanone. For example, these embodiments include engineered enone reductase polypeptides that are capable of converting the α,β unsaturated ketone of (5S)-2-methyl-5-prop-1-en-2-ylcyclohex-2-en-1-one (VII) to (2R,5S)-2-methyl-5-prop-1-en-2-ylcyclohexan-1-one (VIII) as follows:

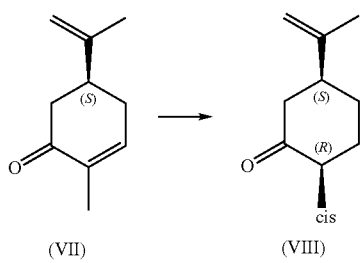

(VII)  (VIII)

In some embodiments, the engineered enone reductase is capable of converting (5S)-2-methyl-5-prop-1-en-2-ylcyclohex-2-en-1-one to (2R,5S)-2-methyl-5-prop-1-en-2-ylcyclohexan-1-one. In some embodiments, the engineered enone reductase is capable of converting (5S)-2-methyl-5-prop-1-en-2-ylcyclohex-2-en-1-one to (2R,5S)-2-methyl-5-prop-1-en-2-ylcyclohexan-1-one the with at least 1.5 times the conversion rate of SEQ ID NO:6 or SEQ ID NO:8.

In some embodiments, the engineered enone reductase capable of converting (5S)-2-methyl-5-prop-1-en-2-ylcyclohex-2-en-1-one to (2R,5S)-2-methyl-5-prop-1-en-2-ylcyclohexan-1-one comprises an amino acid sequence with at least one of the following features: residue corresponding to X83 is V; residue corresponding to X83 is L; residue corresponding to X83 is R; residue corresponding to X119 is P; residue corresponding to X251 is C; residue corresponding to X251 is A; residue corresponding to X251 is R; residue corresponding to X296 is G; residue corresponding to X83 is I and X124 is P; residue corresponding to X40 is L and X294 is A; residue corresponding to X83 is I, X124 is G, X304 is K; residue corresponding to X296 is A and X297 is F; residue corresponding to X251 is L and X379 is G; residue corresponding to X296 is R and X330 is Y; residue corresponding to X294 is A and X295 is G; residue corresponding to X83 is I and X251 is R; residue corresponding to X83 is I and X251 is A; residue corresponding to X148 is R and X251 is G; residue corresponding to X83 is I and X251 is V; residue corresponding to X83 is I and X251 is S; residue corresponding to X83 is I, X251 is A and X330 is Y; residue corresponding to X83 is I, X251 is V and X295 is N; residue corresponding to X83 is I, X179 is R, X251 is C and X339 is Q; residue corresponding to X251 is A, X296 is A, X297 is K and X399 is E; residue corresponding to X38 is S, X83 is I, X251 is S and X296 is G; residue corresponding to X5 is E, X44 is Y, X83 is I, X251 is A, X295 is N and X297 is G; residue corresponding to X38 is S, X83 is I, X251 is S, X295 is T, X296 is G and X297 is F; residue corresponding to X38 is S, X83 is I, X251 is S, X295 is T, X296 is S, X297 is F and X384 is I; residue corresponding to X38 is S, X83 is I, X117 is F, X251 is S, X295 is N, X296 is G and X297 is F; or residue corresponding to X38 is S, X83 is I, X117 is N and X251 is V.

In some embodiments, the reductase polypeptide capable of converting (5S)-2-methyl-5-prop-1-en-2-ylcyclohex-2-en-1-one to (2R,5S)-2-methyl-5-prop-1-en-2-ylcyclohexan-1-one comprises an amino acid sequence that corresponds to the sequence of SEQ ID NO: 10, 14, 16, 18, 46, 44, 68, 70, 72, 74, 76, 82, 86, 88, 90, 98, 102, 104, 108, 110, 112, 114, 116, 118, 122, 126, 128, 130, 162 or 172.

In some embodiments, the enone reductase is capable of converting (5S)-2-methyl-5-prop-1-en-2-ylcyclohex-2-en-1-one to the (2R,5S)-2-methyl-5-prop-1-en-2-ylcyclohexan-1-one with at least 2 times the conversion rate of SEQ ID NO:6 or SEQ ID NO:8. In some embodiments, the enone reductase comprises an amino acid sequence that corresponds to the sequence of SEQ ID NO: 16, 44, 46, 68, 70, 72, 74, 76, 82, 90, 98, 108, 112, 114, 116, 118, 130 or 172.

In some embodiments, the enone reductase is capable of converting the (5S)-2-methyl-5-prop-1-en-2-ylcyclohex-2-en-1-one to the (2R,5S)-2-methyl-5-prop-1-en-2-ylcyclohexan-1-one with at least 2.5 times the conversion rate of SEQ ID NO:6 or SEQ ID NO:8. In some embodiments, the enone reductase comprises an amino acid sequence that corresponds to the sequence of SEQ ID NO: 68, 72, 76, 90, 98, 130 or 172.

In some embodiments, the engineered enone reductase is capable of converting (5S)-2-methyl-5-prop-1-en-2-ylcyclohex-2-en-1-one to (2R,5S)-2-methyl-5-prop-1-en-2-ylcyclohexan-1-one with at least 90% diastereomeric excess and 1.5 times the conversion rate of SEQ ID NO:6. In these embodiments, the enone reductase can comprise an amino acid sequence having at least one of the following features: residue corresponding to X83 is L; residue corresponding to X83 is R; residue corresponding to X119 is P; residue corresponding to X251 is C; residue corresponding to X251 is A; residue corresponding to X251 is L and X379 is G; residue corresponding to X83 is I and X124 is P; residue corresponding to X83 is I and X251 is R; residue corresponding to X83 is I and X251 is A; residue corresponding to X148 is R and X251 is G; residue corresponding to X83 is I and X251 is V; residue corresponding to X83 is I and X251 is S; residue corresponding to X83 is I, X251 is A and X330 is Y; residue corresponding to X83 is I, X251 is V and X295 is N; residue corresponding to X38 is S, X83 is I, X251 is S and X296 is G; residue corresponding to X251 is A, X296 is A, X297 is K and X399 is E; residue corresponding to X83 is I, X179 is R, X251 is C and X339 is Q; residue corresponding to X5 is E, X44 is Y, X83 is I, X251 is A, X295 is N and X297 is G; residue corresponding to X38 is S, X83 is I, X251 is S, X295 is T, X296 is G and X297 is F; or residue corresponding to X38 is S, X83 is I, X117 is F, X251 is S, X295 is N, X296 is G and X297 is F.

In some embodiments, the engineered enone reductase capable of converting (5S)-2-methyl-5-prop-1-en-2-ylcyclohex-2-en-1-one to (2R,5S)-2-methyl-5-prop-1-en-2-ylcyclohexan-1-one with at least 90% diastereomeric excess and 1.5 times the conversion rate of SEQ ID NO:6 comprises an amino acid sequence that corresponds to the sequence of SEQ ID NO: 16, 14, 46, 68, 70, 72, 74, 76, 82, 86, 90, 98, 104, 108, 110, 112, 114, 116, 130 or 172.

In some embodiments, the engineered enone reductase is capable of converting the α,β unsaturated ketone of (5S)-2-methyl-5-prop-1-en-2-ylcyclohex-2-en-1-one (VII) to (2S,5S)-2-methyl-5-prop-1-en-2-ylcyclohexan-1-one (VIIIb) in diastereomeric excess, as illustrated in the following reaction:

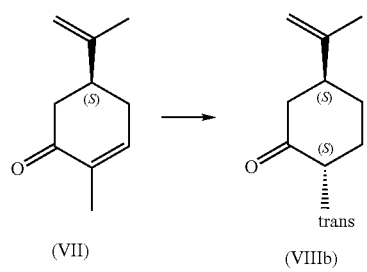

(VII)  (VIIIb)

In some embodiments, the engineered enone reductase capable of converting (5S)-2-methyl-5-prop-1-en-2-ylcyclohex-2-en-1-one to (2S,5S)-2-methyl-5-prop-1-en-2-ylcyclohexan-1-one in diastereomeric excess comprises an amino acid sequence with at least one of the following features: residue corresponding to X117 is Q; residue corresponding to X117 is A; residue corresponding to X117 is I; residue corresponding to X117 is C; residue corresponding to X117 is V; residue corresponding to X83 is I and X117 is I; residue corresponding to X117 is A and X122 is T; residue corresponding to X38 is S and X117 is A; residue corresponding to X38 is S, X83 is I, and X117 is I; residue corresponding to X38 is S, X83 is I, and X117 is L; residue corresponding to X28 is P, X83 is I, X117 is A, and X251 is V; residue corresponding to X38 is S, X83 is I, X117 is A and X251 is D; residue corresponding to X38 is S, X83 is I, X117 is A and X251 is A; residue corresponding to X38 is S, X40 is Y, X83 is I and X117 is A; residue corresponding to X38 is S, X83 is I, X117 is A and X330 is Y; residue corresponding to X38 is S, X83 is I, X117 is I and X119 is V; residue corresponding to X38 is S, X40 is E, X75 is S, X83 is I and X117 is I; residue corresponding to X38 is S, X83 is I, X117 is I, D295 is T and X296 is A; residue corresponding to X38 is S, X75 is L, X83 is I, X117 is I and X255 is P; or residue corresponding to X38 is S, X83 is I, X117 is I, X251 is A, X295 is N, X296 is F and X297 is W.

In some embodiments, the engineered enone reductase capable of converting (5S)-2-methyl-5-prop-1-en-2-ylcyclohex-2-en-1-one to (2S,5S)-2-methyl-5-prop-1-en-2-ylcyclohexan-1-one in diastereomeric excess comprises an amino acid sequence that corresponds to the sequence of SEQ ID NO: 20, 24, 28, 30, 32, 38, 48, 50, 52, 54, 56, 60, 64, 66, 92, 144, 148, 152, 154, 156, or 158.

In some embodiments, the engineered enone reductase is capable of converting (5S)-2-methyl-5-prop-1-en-2-ylcyclohex-2-en-1-one to (2S,5S)-2-methyl-5-prop-1-en-2-ylcyclohexan-1-one with at least 80% diastereomeric excess and comprises an amino acid sequence that corresponds to the sequence of SEQ ID NO: 20, 24, 28, 30, 48, 50, 52, 54, 64, 144, 148, 152, 154, or 158.

In some embodiments, the engineered enone reductase is capable of converting (5S)-2-methyl-5-prop-1-en-2-ylcyclohex-2-en-1-one to (2S,5S)-2-methyl-5-prop-1-en-2-ylcyclohexan-1-one with at least 90% diastereomeric excess and comprises an amino acid sequence that corresponds to the sequence of SEQ ID NO: 24, 28, 30, 48, 50, 54, 144, 148, 152, or 154.

In some embodiments, the engineered enone reductase is capable of converting (5S)-2-methyl-5-prop-1-en-2-ylcyclohex-2-en-1-one to (2S,5S)-2-methyl-5-prop-1-en-2-ylcyclohexan-1-one with greater than 95% diastereomeric excess and comprises an amino acid sequence that corresponds to the sequence of SEQ ID NO: 24, 48, 50, 144, 148, 152, or 154.

In some embodiments, the engineered enone reductase is capable of converting the α,β unsaturated ketone of (5R)-2-methyl-5-prop-1-en-2-ylcyclohex-2-en-1-one (R-carvone) (IX) to (2R,5R)-2-methyl-5-prop-1-en-2-ylcyclohexan-1-one (X) with at least 90% diastereomeric excess, as illustrated below:

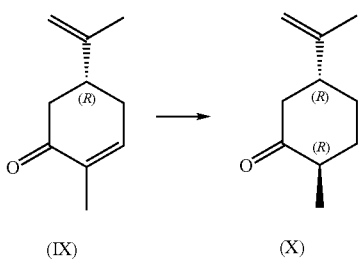

In some embodiments, the enone reductase polypeptides capable of converting (5R)-2-methyl-5-prop-1-en-2-ylcyclohex-2-en-1-one to (2R,5R)-2-methyl-5-prop-1-en-2-ylcyclohexan-1-one comprises an amino acid sequence with at least one of the following features: residue corresponding to X38 is N; residue corresponding to X83 is V; residue corresponding to X83 is L; residue corresponding to X83 is R residue corresponding to X117 is M; residue corresponding to X117 is N; residue corresponding to X117 is L; residue corresponding to X117 is I; residue corresponding to X251 is A; residue corresponding to X251 is C; residue corresponding to X251 is R; residue corresponding to X252 is H; residue corresponding to X296 is G; residue corresponding to X297 is K; residue corresponding to X297 is Y; residue corresponding to X297 is F; residue corresponding to X83 is I and X124 is P; residue corresponding to X83 is I and X251 is R; residue corresponding to X83 is I and X251 is S; residue corresponding to X305 is S and X376 is I; residue corresponding to X40 is L and X294 is A; residue corresponding to X315 is P and X376 is T; residue corresponding to X75 is L and X297 is A; residue corresponding to X296 is A and X297 is F; residue corresponding to X248 is C and X297 is G; residue corresponding to X251 is L and X379 is G; residue corresponding to X296 is K and X376 is A; residue corresponding to X296 is R and X330 is Y; residue corresponding to X294 is A and X295 is G; residue corresponding to X83 is I and X251 is A; residue corresponding to X148 is R and X251 is G; residue corresponding to X83 is I and X251 is V; residue corresponding to X117 is E and X386 is D; residue corresponding to X297 is F, X369 is E and X376 is K; residue corresponding to X83 is I, X124 is G and X304 is K; residue corresponding to X40 is S, X302 is G and X330 is Y; residue corresponding to X251 is I, X296 is S and X297 is F; residue corresponding to X38 is S, X83 is I and X297 is Y; residue corresponding to X251 is S, X297 is I and X358 is A; residue corresponding to X83 is I, X251 is A and X330 is Y; residue corresponding to X83 is I, X251 is V, and X295 is N; residue corresponding to X83 is I, X179 is R, X251 is C and X339 is Q; residue corresponding to X251 is A, X296 is A, X297 is K and X399 is E; residue corresponding to X5 is E, X44 is Y, X83 is I, X251 is A, X295 is N and X297 is G; residue corresponding to X38 is S, X83 is I, X154 is R, X251 is V, X295 is T and X297 is F; residue corresponding to X38 is S, X83 is I, X251 is S, X295 is T, X296 is S, X297 is F and X384 is I; residue corresponding to X83 is I, X117 is S, X251 is V, X296 is R and X297 is F; residue corresponding to X38 is S, X83 is I, X251 is S and X296 is G; residue corresponding to X38 is S, X83 is I, X117 is F and X251 is S; residue corresponding to X38 is S, X83 is I, X251 is S, X295 is T, X296 is G and X297 is F; residue corresponding to X38 is S, X83 is I, X117 is F, X251 is S, X295 is N, X296 is G and X297 is F; residue corresponding to X38 is S, X83 is I, X117 is L, X209 is D, X251 is S, X376 is K, and 400 is T; residue corresponding to X38 is S, X83 is I, X117 is N and X251 is V; or residue corresponding to X83 is I, X117 is N, X295 is T, X296 is G and X297 is F.

In some embodiments, the engineered enone reductase capable of converting the α, β unsaturated ketone of (5R)-2-methyl-5-prop-1-en-2-ylcyclohex-2-en-1-one to (2R,5R)-2-methyl-5-prop-1-en-2-ylcyclohexan-1-one with at least 90% diastereomeric excess comprises an amino acid sequence that corresponds to the sequence of SEQ ID NO: 10, 12, 14, 16, 18, 22, 26, 32, 34, 36, 40, 42, 44, 46, 68, 70, 72, 74, 76, 78, 80, 82, 86, 88, 90, 94, 96, 98, 102, 104, 106, 108, 110, 112, 114, 116, 118, 120, 122, 126, 128, 134, 136, 138, 140, 142, 146, 162, 166, 168, 170, 172, 174 or 186.

In some embodiments, the engineered enone reductase is capable of converting the α, β unsaturated ketone of (5R)-2-methyl-5-prop-1-en-2-ylcyclohex-2-en-1-one to (2R,5R)-2-methyl-5-prop-1-en-2-ylcyclohexan-1-one with greater than 95% diastereomeric excess.

In some embodiments, the engineered enone reductase polypeptide capable of converting (5R)-2-methyl-5-prop-1-en-2-ylcyclohex-2-en-1-one to (2R,5R)-2-methyl-5-prop-1-en-2-ylcyclohexan-1-one with greater than 95% diastereomeric excess comprises an amino acid sequence that corresponds to the sequence of SEQ ID NO: 34 or 186.

In some embodiments, the engineered enone reductase is capable of converting the α,β unsaturated ketone of (5R)-2-methyl-5-prop-1-en-2-ylcyclohex-2-en-1-one (R-carvone) (IX) to (2S,5R)-2-methyl-5-prop-1-en-2-ylcyclohexan-1-one (Xb) in diastereomeric excess, as illustrated in the following reaction:

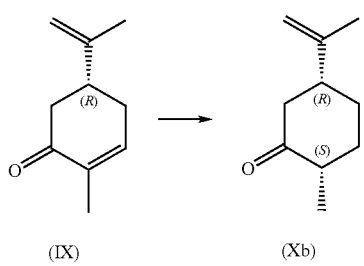

In some embodiments, the enone reductase polypeptides capable of converting (5R)-2-methyl-5-prop-1-en-2-ylcyclohex-2-en-1-one to (2S,5R)-2-methyl-5-prop-1-en-2-ylcyclohexan-1-one comprises an amino acid sequence with at least one of the following features: residue corresponding to X117 is A and X122 is T; residue corresponding to X315 is P and X376 is T; residue corresponding to X38 is S and X117 is A; residue corresponding to X38 is S, X83 is I, X117 is A and X330 is Y.

In some embodiments, the enone reductase polypeptides capable of converting (5R)-2-methyl-5-prop-1-en-2-ylcyclohex-2-en-1-one to (2S,5R)-2-methyl-5-prop-1-en-2-ylcyclohexan-1-one in diastereomeric excess comprises an amino acid that corresponds to the sequence of SEQ ID NO:28, 40, 144 or 148.

In some embodiments, the enone reductase polypeptide of the present invention is capable of reducing an optionally substituted arylalkenone to an optionally substituted arylalkanone. For example, the present invention provides engineered enone reductase polypeptides that are capable of reducing the arylalkenone of Formula XI to the arylalkanone of Formula XII:

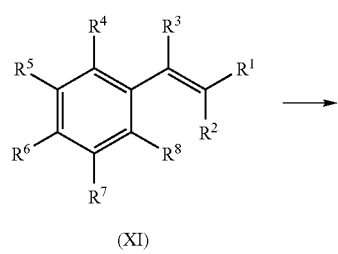

(XI)

-continued

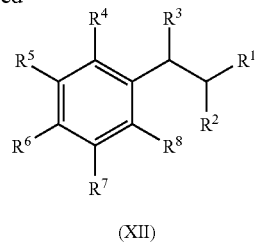

(XII)

wherein for (XI) and (XII), $R^1$ and $R^2$ are each independently selected from the group consisting of CN, $C(O)R^{11}$, $C(O)OR^{11}$, an alkyl (such as, for example, a lower alkyl), and H, wherein $R^{11}$ is selected from the group consisting of H and an alkyl (such as, for example, a lower alkyl), and wherein $R^3$, $R^4$, $R^5$, $R^6$, $R^7$, and $R^8$ are each independently selected from H, an alkyl (such as, for example, a lower alkyl), an alkoxy (such as, for example, a lower alkoxy), a hydroxyl, and a halide. Typically, only one of $R^1$ and $R^2$ is CN and only one of $R^1$ and $R^2$ is $C(O)R^{11}$ or $C(O)OR^{11}$. Usually, at least one of $R^1$ and $R^2$ is $C(O)R^{11}$ or $C(O)OR^{11}$. In some embodiments, $R^2$ is an alkyl, such as, for example, a lower alkyl (i.e., methyl, propyl, isopropyl, and the like).

In some embodiments, the engineered enone reductase is capable of reducing the α,β unsaturated nitrile (Z)-ethyl 2-cyano-3-phenylbut-2-enoate (XIII) to ethyl 2-cyano-3-phenylbutanoate (XIV) as follows:

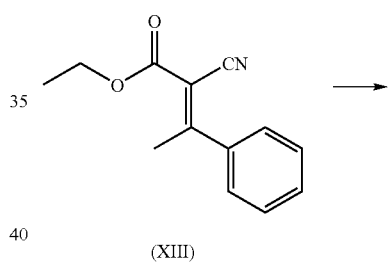

(XIII)

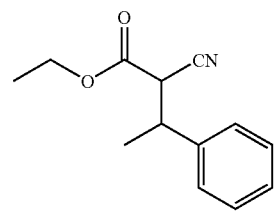

(XIV)

In some embodiments, the enone reductase is capable of reducing (Z)-ethyl 2-cyano-3-phenylbut-2-enoate to ethyl 2-cyano-3-phenylbutanoate with at least 5 times the conversion rate of SEQ ID NO:6 or SEQ ID NO:8.

In some embodiments, the enone reductase capable of reducing (Z)-ethyl 2-cyano-3-phenylbut-2-enoate to ethyl 2-cyano-3-phenylbutanoate comprises an amino acid sequence with at least one of the following features: residue corresponding to X117 is N; residue corresponding to X117 is L; residue corresponding to X117 is A; residue corresponding to X117 is M; residue corresponding to X117 is C; residue corresponding to X117 is V; residue corresponding to X296 is G; residue corresponding to X38 is S and X117 is A; residue corresponding to X83 is I and X117 is I; residue corresponding to X117 is A and X122 is T; residue corresponding to X305 is S and X376 is I; residue corresponding to X315 is P and X376 is T; residue corresponding to X296 is K and X376 is A; residue corresponding to X38 is S, X83 is I and X297 is Y; residue corresponding to X38 is S, X83 is I and X117 is I; residue corresponding to X83 is I, X124 is G and X304 is K; residue corresponding to X83 is E, X117 is I and X333 is A; residue corresponding to X251 is E, X330 is R and X376 is I; residue corresponding to X38 is S, X83 is I, X117 is A and X251 is D; residue corresponding to X38 is S, X83 is I, X117 is A, X251 is A; residue corresponding to X296 is I, X297 is A, X333 is A and X376 is A; residue corresponding to X296 is A, X297 is A, X330 is R and X376 is I; residue corresponding to X83 is I, X296 is S, X297 is F, X376 is I and X397 is R; residue corresponding to X147 is G, X296 is A, X297 is F, X330 is R and X376 is E; residue corresponding to X251 is I, X296 is E, X297 is A, X376 is I; residue corresponding to X38 is S, X75 is L, X83 is I, X117 is I and X255 is P; residue corresponding to X38 is S, X83 is I, X117 is I and X119 is V; residue corresponding to X83 is I, X117 is S, X251 is V, X296 is R, X297 is F; residue corresponding to X38 is S, X83 is I, X251 is S and X296 is G; residue corresponding to X38 is S, X83 is I, X117 is A, X330 is Y; residue corresponding to X38 is S, X40 is E, X75 is S, X83 is I and X117 is I; residue corresponding to X83 is I, X117 is N, X295 is T, X296 is G and X297 is F; or residue corresponding to X28 is P, X83 is I, X117 is A and X251 is V.

In some embodiments, the enone reductase capable of reducing (Z)-ethyl 2-cyano-3-phenylbut-2-enoate to ethyl 2-cyano-3-phenylbutanoate comprises an amino acid sequence that corresponds to the sequence of SEQ ID NO: 20, 22, 24, 26, 28, 30, 36, 40, 44, 48, 50, 54, 56, 82, 92, 94, 96, 100, 128, 144, 146, 148, 152, 154, 156, 158, 170, 174, 176, 178, 180, 182, or 184.

In some embodiments, the enone reductase is capable of reducing (Z)-ethyl 2-cyano-3-phenylbut-2-enoate to ethyl 2-cyano-3-phenylbutanoate with at least 10 times the conversion rate of SEQ ID NO:6 or SEQ ID NO:8. In some embodiments, the enone reductase capable of reducing the α,β unsaturated nitrile of (Z)-ethyl 2-cyano-3-phenylbut-2-enoate to ethyl 2-cyano-3-phenylbutanoate with at least 10 times the conversion rate of SEQ ID NO:6 comprises an amino acid sequence that corresponds to the sequence of SEQ ID NO: 20, 24, 28, 30, 44, 48, 50, 54, 92, 94, 100, 144, 146, 148, 170, 174, 176, 180, or 184.

In some embodiments, the enone reductase is capable of reducing (Z)-ethyl 2-cyano-3-phenylbut-2-enoate to ethyl 2-cyano-3-phenylbutanoate with greater than 20 times the conversion rate of SEQ ID NO:6 or SEQ ID NO:8. In some embodiments, the enone reductase capable of reducing (Z)-ethyl 2-cyano-3-phenylbut-2-enoate to ethyl 2-cyano-3-phenylbutanoate with greater than 20 times the conversion rate of SEQ ID NO:6 comprises an amino acid sequence that corresponds to the sequence of SEQ ID NO: 24, 28, 30, 54, 92, 100, 144, 148, 170, 180 or 184.

In some embodiments, the engineered enone reductases can be used in a method for converting/reducing (E)-2-(3,4-dimethyoxybenzylidene)-3-methylbutanal to 2-(3,4-dimethyoxybenzyl)-3-methylbutanal, as illustrated below:

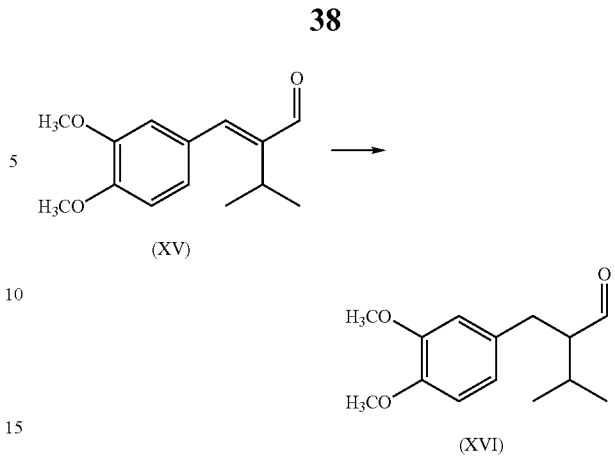

In some embodiments, the engineered enone reductase capable of reducing/converting (E)-2-(3,4-dimethyoxybenzylidene)-3-methylbutanal to 2-(3,4-dimethyoxybenzyl)-3-methylbutanal comprises an amino acid sequence with at least one of the following features: residue corresponding to X5 is E; residue corresponding to X10 is P; residue at X28 is P; residue at X38 is S; residue at X40 is S or Y; residue at X44 is Y; residue at X75 is L; residue at X83 is L, R, V, or I; residue at X117 is A, I, F, or S; residue at X124 is G or P; residue at X147 is G; residue at X154 is R; residue at X179 is R; residue at X248 is C; residue at X251 is A, C, E, L, R, S, V, I, or D; residue at X252 is H; residue at X294 is A; residue at X295 is T, G, or N; residue at X296 is G, R, A, S, E, K, I, or F; residue at X297 is G, F, K, Y, A, or G; residue at X302 is G; residue at X304 is K; residue at X305 is S; residue at X315 is P; residue at X330 is Y or R; residue at X333 is Q; residue at X369 is E; residue at X376 is I, T, A, or E; residue at X379 is G; and/or residue at X397 is R. Certain of these engineered enone reductases are capable of converting greater than 90% of substrate (XVIII).

These engineered enone reductases include those comprising an amino acid sequence with at least one of the following features: residue corresponding to X5 is E; residue corresponding to X28 is P; residue corresponding to X44 is Y; residue corresponding to X83 is R, V, or I; residue corresponding to X147 is G; residue corresponding to X154 is R; residue corresponding to X179 is R; residue corresponding to X251 is A, E, V, or I; residue corresponding to X295 is T or N; residue corresponding to X296 is A, S, E, K, or I; residue corresponding to X297 is G, F, or A; residue corresponding to X305 is S; residue corresponding to X315 is P; residue corresponding to X330 is R; residue corresponding to X333 is A; residue corresponding to X339 is Q; residue corresponding to X369 is E; residue corresponding to X376 is I, I, A, or E; and/or residue corresponding to X397 is R. Exemplary engineered reductases include those corresponding to SEQ ID NOs: 138, 174, 40, 16, 18, 68, 76, 96, 100, 106, 170, 176, 178, 182, 184, and 186.

In some embodiments, these engineered enone reductases comprise an amino acid sequence with at least one of the following features: residue corresponding to X10 is P; residue corresponding to X38 is S; residue corresponding to X83 os R, V, or I; residue corresponding to X117 is F; residue corresponding to X147 is G; residue corresponding to X251 is V; residue corresponding to X296 is A; residue corresponding to X297 is F, Y, A, or G; residue corresponding to X315 is P; residue corresponding to X330 is R; residue corresponding to X333 is A; residue corresponding to X376 is I, K, A, or E; and/or residue corresponding to X379 is G. Exemplary engineered reductases include those corresponding to SEQ ID NOs: 142, 16, 18, 146, 178, 184, and 186. Certain of these engineered enone reductases include those comprising an amino acid sequence with at elast one of the following features: residue corresponding to X83 is V; residue corresponding to X251 is V; residue corresponding to X297 is F or A; residue corresponding to X333 is A; residue corresponding to X369 is E; and/or residue corresponding to X376 is I, K, or A. Engineered enone reductases of the present invention include those that are capable of converting 90% or more, 95% or more, and 99% or more of substrate XV to product XVI, and also include those capable of catalyzing the conversion to the R-enantiomer of XVI at a % ee of 80% or more, 90% or more, 95%, or more, and 99% or more. In one embodiment, the engineered enone reductase comprises an amino acid sequence comprising the features: residue corresponding to X297 is F; residue corresponding to X369 is E; and residue corresponding to X376 is K. An exemplary engineered enone reductase is illustrated by SEQ ID NO: 186.

Where the reference sequence is SEQ ID NO: 8, mutations that provide improved activity and selectivity in one enantiomer of product (XVI) include Y83I or V, P296 A or I, S297 A or F, K369E, and Y376 A, I, or K. Mutations that provide improved properties activity and selectivity in the other enantiomer of product (XVI) include T38S, W117A, N, or S, F251 A, G, E, or V, S297F, and H330Y.

In some embodiments, the engineered enone reductase polypeptide is capable of reducing the α,β unsaturated ketone that is an optionally substituted tetrahydronaphthaledione to the corresponding hexahydronaphthalendione. For example, the present invention provides engineered enone reductases that are capable of reducing 8a-methyl-3,4,8,8a-tetrahydronaphthalene-1,6(2H,7H)-dione (XVIII) to 8a-methylhexahydronaphthalene-1,6(2H,7H)-dione (XIX) as follows:

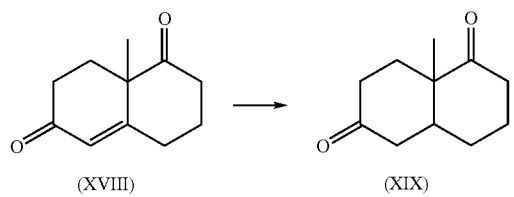

(XVIII)      (XIX)

In some embodiments, the engineered enone reductase is capable of reducing 8a-methyl-3,4,8,8a-tetrahydronaphthalene-1,6(2H,7H)-dione to 8a-methylhexahydronaphthalene-1,6(2H,7H)-dione with at least 2 times the conversion rate of SEQ ID NO:6 or SEQ ID NO:8.

In some embodiments, the engineered enone reductase capable of reducing 8a-methyl-3,4,8,8a-tetrahydronaphthalene-1,6(2H,7H)-dione to 8a-methylhexahydronaphthalene-1,6(2H,7H)-dione comprises an amino acid sequence with at least one of the following features: residue corresponding to X38 is N; residue corresponding to X295 is T; residue corresponding to X297 is F; residue corresponding to X251 is R; residue corresponding to X252 is H; residue corresponding to X296 is A and X297 is F; residue corresponding to X248 is C and X297 is G; residue corresponding to X251 is L and X379 is G; residue corresponding to X296 is K and X376 is A; residue corresponding to X296 is R and X330 is Y; residue corresponding to X83 is I and X251 is R; residue corresponding to X294 is A and X295 is G; residue corresponding to X10 is P, X297 is G and X379 is G; residue corresponding to X40 is S, X302 is G and X330 is Y; residue corresponding to X251 is I, X296 is S, and X297 is F; residue corresponding to X251 is S, X297 is I and X358 is A; residue corresponding to X83 is I, X251 is V and X295 is N; residue corresponding to X251 is E, X330 is R and X376 is I; residue corresponding to X38 is S, X83 is I, X251 is S and X296 is G; residue corresponding to X296 is A, X297 is A, X330 is R and X376 is I; residue corresponding to X296 is I, X297 is A, X333 is A and X376 is A; residue corresponding to X251 is S, X296 is E, X297 is A and X311 is E; residue corresponding to X251 is I, X296 is E, X297 is A and X376 is I; residue corresponding to X251 is A, X296 is A, X297 is K and X399 is E; residue corresponding to X147 is G, X296 is A, X297 is F, X330 is R and X376 is E; residue corresponding to X5 is E, X44 is Y, X83 is I, X251 is A, X295 is N and X297 is G; residue corresponding to X240 is R, X251 is S, X259 is G, X296 is Q and X297 is A; residue corresponding to X38 is S, X83 is I, X154 is R, X251 is V, X295 is T and X297 is F; residue corresponding to X38 is S, X83 is I, X251 is S, X295 is T, X296 is S, X297 is F and X384 is I; residue corresponding to X38 is S, X83 is I, X251 is S, X295 is T, X296 is G and X297 is F; or residue corresponding to X38 is S, X83 is I, X117 is F, X251 is S, X295 is N, X296 is G and X297 is F.

In some embodiments, the engineered enone reductase capable of reducing 8a-methyl-3,4,8,8a-tetrahydronaphthalene-1,6(2H,7H)-dione to 8a-methylhexahydronaphthalene-1,6(2H,7H)-dione with at least 2 times the conversion rate of SEQ ID NO:6 or SEQ ID NO:8 comprises an amino acid sequence that corresponds to the sequence of SEQ ID NO: 12, 42, 68, 72, 82, 86, 88, 98, 104, 106, 114, 118, 120, 122, 124, 126, 132, 136, 138, 160, 162, 164, 166, 168, 170, 172, 176, 178, 180, 184, or 182.

In some embodiments, the engineered enone reductase is capable of reducing 8a-methyl-3,4,8,8a-tetrahydronaphthalene-1,6(2H,7H)-dione to 8a-methylhexahydronaphthalene-1,6(2H,7H)-dione with at least 5 times the conversion rate of SEQ ID NO:6 or SEQ ID NO:8. In some embodiments, the engineered enone reductase capable of reducing 8a-methyl-3,4,8,8a-tetrahydronaphthalene-1,6(2H,7H)-dione to 8a-methylhexahydronaphthalene-1,6(2H,7H)-dione with at least 5 times the conversion rate of SEQ ID NO:6 or SEQ ID NO:8 comprises an amino acid sequence that corresponds to the sequence of SEQ ID NO: 82, 88, 104, 114, 160, 164, 166 or 172.

In some embodiments, the engineered enone reductase is capable of reducing 8a-methyl-3,4,8,8a-tetrahydronaphthalene-1,6(2H,7H)-dione to 8a-methylhexahydronaphthalene-1,6(2H,7H)-dione with greater than 10 times the conversion rate of SEQ ID NO:6 or SEQ ID NO:8. In some embodiments, the engineered enone reductase capable of reducing 8a-methyl-3,4,8,8a-tetrahydronaphthalene-1,6(2H,7H)-dione to 8a-methylhexahydronaphthalene-1,6(2H,7H)-dione with at least 10 times the conversion rate of SEQ ID NO:6 or SEQ ID NO:8 comprises an amino acid sequence that corresponds to the sequence of SEQ ID NO: 164 or 172.

In some embodiments, the engineered enone reductase is capable of reducing an optionally substituted cyclopentenone to an optionally substituted cyclopentanone. For example, the present invention provides engineered enone reductases of the present invention that are capable of reducing 3-methyl-cyclohex-2-enone to 3-methylcyclohexanone, as illustrated below, with at least for 2 times the conversion rate of SEQ ID NO:6 or SEQ ID NO:8

In some embodiments, the enone reductase capable of reducing an optionally substituted cyclohexenone to the corresponding cyclohexanone. For example, in some embodiments the engineered enone reductase polypeptide is capable of reducing 3-methylcyclohex-2-enone to 3-methylcyclohexanone, as illustrated below, with at least 1 times the conversion rate of SEQ ID NO:6 or SEQ ID NO:8:

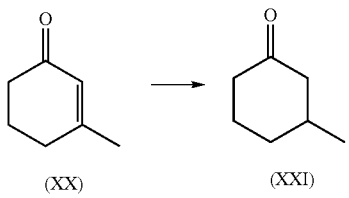

(XX)    (XXI)

In some embodiments, the enone reductase capable of reducing 3-methylcyclohex-2-enone to 3-methylcyclohexanone with at elast 1 times the conversion rate of SEQ ID NO: 6 or SEQ ID NO: 8 comprises an amino acid sequence with at least one of the following features: residue corresponding to X83 is V; residue corresponding to X297 is K; residue corresponding to X83 is I and X124 is P; residue corresponding to X305 is S and X376 is I; residue corresponding to X297 is F, X369 is E and X376 is K; or residue corresponding to X10 is P, X297 is G and X379 is G.

In some embodiments, the enone reductase capable of reducing 3-methylcyclohex-2-enone to 3-methylcyclohexanone with at least 1 times the conversion rate of SEQ ID NO:6 or SEQ ID NO:8 comprises an amino acid sequence that corresponds to the sequence of SEQ ID NO: 18, 46, 132, 174, 186 or 140.

In some embodiments, the enone reductase is capable of reducing 3-methylcyclohex-2-enone to 3-methylcyclohexanone with greater than 1.5 times the conversion rate of SEQ ID NO:6 or SEQ ID NO:8. In some embodiments, the enone reductase capable of reducing 3-methylcyclohex-2-enone to 3-methylcyclohexanone with greater than 1.5 times the conversion rate of SEQ ID NO:6 or SEQ ID NO:8 comprises an amino acid sequence that corresponds to the sequence of SEQ ID NO: 186 or 132.

In some embodiments, the enone reductase is capable of reducing an optionally substituted cyclopentenone to the corresponding cyclopentanone. For example, in some embodiments, the engineered enone reductase polypeptides of the present invention are capable of reducing 2-methylcyclopente-2-none to 2-methylcyclopentanone as follows:

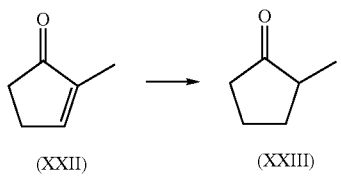

(XXII)    (XXIII)

In certain embodiments, the engineered enone reductase polypeptide is capable of reducing substrate (X) to a product that is enantiomerically enriched for either the (R) or (S) enantiomer of product (XOH). In some embodiments, the engineered enone reductase polypeptide capable of reducing 2-methylcyclopente-2-none to 2-methylcyclopentanone comprises an amino acid sequence with one of the following features: residue corresponding to X38 is S, X83 is I, X117 is A, X251 is Y, X295 is T, X296 is F, and X297 is W; or residue corresponding to X38 is S, X83 is I, X117 is I. X251 is A, X295 is N, X296 is F and X297 is W.

In some embodiments, the enone reductase capable of reducing 2-methylcyclopente-2-none to 2-methylcyclopentanone comprises an amino acid sequence that corresponds to the sequence of SEQ ID NO: 60 or 62.

Table 2 below provides exemplary chimeric enone reductase polypeptides, unless specified otherwise. In Table 2 below, each row lists two SEQ ID NOs, where the odd number refers to the nucleotide sequence that codes for the amino acid sequence provided by the even number. In the description of the chimeric structure, the number preceding the parenthesis is the source of the segment and the numbers in parenthesis refers to the segment from the first residue to the terminal residue position. The chimeric structure is presented, from left to right, the amino to the carboxy terminus.

TABLE 2

| SEQ ID NO. | CHIMERIC STRUCTURE OF POLYPEPTIDE |
|---|---|
| 1/2 | Old Yellow Enzyme 1 *Saccharomyces pastorianus* (ERED 1) |
| 3/4 | Old Yellow Enzyme 2 *Saccharomyces cerevisiae* (ERED 2) |
| 5/6 | Old Yellow Enzyme 3 *Saccharomyces cerevisiae* (ERED 3) |
| 189/190 | 1(1-19)-3(20-59)-2(60-109)-3(110-141)-2(142-299)-3(300-400) |
| 191/192 | 3(1-59)-2(60-275)-3(276-400) |
| 193/194 | 3(1-109)-2(110-250)-3-(251-400) |
| 195/196 | 3(1-80)-2(81-176)-3(177-337)-2(338-400) |
| 197/198 | 2(1-29)-3(30-103)-1(104-123)-2(124-400) |
| 199/200 | 2(1-19)-3(20-68)-2(69-103)-3(104-141)-2(142-176)-3(177-400) |
| 201/202 | 2(1-19)-3(20-250)-2(251-299)-3(300-400) |
| 203/204 | 3(1-68)-2(69-176)-3(177-240)-2(241-297)-3(298-400) |
| 205/206 | 3(1-311)-2(312-400) |
| 207/208 | 2(1-43)-3(44-56)-2(57-209)-3(210-260)-2(261-400) |
| 209/210 | 2(1-19)-3(20-127)-2(128-400) |
| 211/212 | 3(1-56)-1(57-74)-3(75-118)-2(119-400) |
| 213/214 | 3(1-43)-1(44-112)-2(113-400) |
| 215/216 | 2(1-19)-3(20-34)-1(35-72)-2(73-80)-3(81-109)-2(110-176)-3(177-400) |
| 7/8 | 1(1-17)-3(18-127)-2(128-275)-3(276-400) |

The stabilities of the chimeric enone reductases with respect to temperature and/or isopropanol are presented in Table 3, where the polypeptides were assayed for reduction of cyclohex-2-enone to cyclohexanone. Activity of the exemplary chimeric enone reductases on methyl crotonate (methyl (E)-but-2-enoate) and 3-methyl-cyclohexanone are also shown.

TABLE 3

| SEQ ID NO. | 50% IPA ON 30° C.[1] | 10% IPA at 40° C.[1] | 20% IPA at 40° C.[1] | ACTIVITY ON METHYL CROTONATE[2] | ACTIVITY ON 3-METHYL CYCLOHEXENONE[2] |
|---|---|---|---|---|---|
| 5/6 | | | | | |
| 189/190 | | | | + | + |
| 191/192 | + | | + | | |
| 193/194 | + | | + | | + |
| 195/196 | | | + | | |
| 197/198 | | | + | | |
| 199/200 | + | | + | | |

TABLE 3-continued

| SEQ ID NO. | 50% IPA ON 30° C.[1] | 10% IPA at 40° C.[1] | 20% IPA at 40° C.[1] | ACTIVITY ON METHYL CROTONATE[2] | ACTIVITY ON 3-METHYL CYCLOHEXENONE[2] |
|---|---|---|---|---|---|
| 201/202 |   | + | + |   | + |
| 203/204 | + | + |   |   | + |
| 205/206 |   | + |   |   |   |
| 207/208 |   | + |   |   | + |
| 209/210 |   | + | + | + |   |
| 211/212 |   |   |   | + | + |
| 213/214 |   |   |   |   | + |
| 215/216 | + | + |   |   |   |
| 7/8 | + | + | + |   | + |

[1]Residual activity = (activity after incubation with IPA/activity after incubation without IPA) * 100
+ = Higher residual activity than OYE3
[2]Relative activity calculated based on that of OYE3
+ = Higher conversion than OYE3

Table 4 below provides exemplary engineered enone reductase polypeptides and, unless specified otherwise, the residue differences as compared to the reference sequence of SEQ ID NO:8. As with Table 2, each row in Table 4 lists two SEQ ID NOs, where the odd number refers to the nucleotide sequence that codes for the amino acid sequence provided by the even number. The column listing the residue differences is with respect to the number of amino acid substitutions as compared to the chimeric ERED of SEQ ID NO:8.

TABLE 4

| SEQ ID NO. | RESIDUE DIFFERENCES FROM SEQ ID NO: 8 |
|---|---|
| 53/54 | T38S; Y83I; W117A; F251D |
| 55/56 | T38S; Y83I; W117A; F251A |
| 51/52 | T38S; M40Y; Y83I; W117A |
| 57/58 | T38S; Y83I; W117I; K153E; F251W; D295T; P296F; S297Y |
| 61/62 | T38S; Y83I; W117A; F251Y; D295T; P296F; S297W |
| 59/60 | T38S; Y83I; W117I; F251A; D295N; P296F; S297W |
| 185/186 | S297F; K369E; Y376K |
| 131/132 | Q10P; S297G; S379G |
| 173/174 | Y305S; Y376I |
| 17/18 | Y83V |
| 139/140 | S297K |
| 45/46 | Y83I; F124P |
| 41/42 | T38N |
| 9/10 | M40L; T294A |
| 39/40 | S315P; Y376T |
| 123/124 | D295T |
| 133/134 | F75L; S297A |
| 13/14 | Y83L |
| 137/138 | S297F |
| 119/120 | N252H |
| 129/130 | L119P |
| 43/44 | Y83I; F124G; E304K |
| 177/178 | P296I; S297A; V333A; Y376A |
| 11/12 | M40S; E302G; H330Y |
| 141/142 | S297Y |
| 161/162 | P296A; S297F |
| 135/136 | Y248C; S297G |
| 127/128 | P296G |
| 113/114 | F251L; S379G |
| 169/170 | P296K; Y376A |
| 125/126 | P296R; H330Y |
| 179/180 | P296A; S297A; H330R; Y376I |
| 121/122 | T294A; D295G |
| 99/100 | Y83I; P296S; S297F; Y376I; W397R |
| 115/116 | F251C |
| 165/166 | F251I; P296S; S297F |
| 111/112 | F251A |
| 25/26 | W117M |
| 145/146 | T38S; Y83I; S297Y |
| 183/184 | E147G; P296A; S297F; H330R; Y376E |
| 67/68 | K5E; H44Y; Y83I; F251A; D295N; S297G |
| 155/156 | Y83E; W117I; V333A |
| 167/168 | F251S; S297I; V358A |
| 71/72 | Y83I; F251R |
| 105/106 | T38S; Y83I; K154R; F251V; D295T; S297F |
| 73/74 | Y83I; F251A |
| 109/110 | Q148R; F251G |
| 89/90 | Y83I; F251V |
| 75/76 | Y83I; K179R; F251C; K339Q |
| 159/160 | F251S; P296E; S297A; D311E |
| 35/36 | W117N |
| 21/22 | W117L |
| 107/108 | Y83I; F251S |
| 175/176 | F251I; P296E; S297A; Y376I |
| 37/38 | W117Q |
| 69/70 | Y83I; F251A; H330Y |
| 117/118 | F251R |
| 171/172 | F251A; P296A; S297K; K399E |
| 33/34 | W117E; Y386D |
| 47/48 | T38S; F75L; Y83I; W117I; S255P |
| 163/164 | K240R; F251S; E259G; P296Q; S297A |
| 157/158 | Y83I; W117I |
| 149/150 | Y83K; W117I |
| 187/188 | F251E |
| 153/154 | T38S; Y83I; W117I |
| 63/64 | T38S; Y83I; W117L |
| 23/24 | W117A |
| 87/88 | T38S; Y83I; F251S; D295T; P296S; S297F; T384I |
| 49/50 | T38S; Y83I; W117I; L119V |
| 97/98 | Y83I; F251V; D295N |
| 95/96 | Y83I; W117S; F251V; P296R; S297F |
| 181/182 | F251E; H330R; Y376I |
| 81/82 | T38S; Y83I; F251S; P296G |
| 77/78 | T38S; Y83I; W117F; F251S |
| 103/104 | T38S; Y83I; F251S; D295T; P296G; S297F |
| 27/28 | W117A; A122T |
| 19/20 | W117C |
| 143/144 | T38S; Y83I; W117A; H330Y |
| 151/152 | T38S; M40E; F75S; Y83I; W117I |
| 147/148 | T38S; W117A |
| 83/84 | T38S; Y83I; W117F; F251V; Y376I |
| 85/86 | T38S; Y83I; W117F; F251S; D295N; P296G; S297F |
| 31/32 | W117I |
| 65/66 | T38S; Y83I; W117I; D295T; P296A |
| 79/80 | T38S; Y83I; W117L; N209D; F251S; Y376K; N400T |
| 101/102 | T38S; Y83I; W117N; F251V |
| 29/30 | W117V |
| 93/94 | Y83I; W117N; D295T; P296G; S297F |
| 91/92 | L28P; Y83I; W117A; F251V |
| 15/16 | Y83R |

In some embodiments, an engineered enone reductase can comprise an amino acid sequence that is at least about 80%, 85%, 86%, 87%, 88%, 89%, 90%, 91%, 92%, 93%, 94%, 95%, 96%, 97%, 98%, 99% or more identical to a reference sequence listed in Table 3, with the proviso that the enone reductase has the thermal and/or solvent stability characteristics described herein. In some embodiments, the enone reductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences, such as those described hereinabove, as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences. In some embodiments, the differences comprise conservative mutations.

In some embodiments, an engineered enone reductase can comprise an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO: 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, or 188, with the proviso that the enone reductase amino acid sequence comprises any one of the set of mutations contained in any one of the polypeptide sequences listed in Table 4. In some embodiments, the enone reductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at other amino acid residues. In some embodiments, the differences comprise conservative mutations.

In some embodiments, the engineered enone reductase polypeptide can comprise deletions of the naturally occurring enone reductase polypeptides or deletions of the engineered enone reductase polypeptides. In some embodiments, the engineered enone reductase polypeptides can comprise deletions of the engineered enone reductase polypeptides described herein. Thus, for each and every embodiment of the enone reductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the enone reductase polypeptides, as long as the functional activity of the enone reductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 amino acid residues. In some embodiments, the number of deletions can be 1, 2, 3, 4, 5, 6, 7, 8, 9, 10, 11, 12, 14, 15, 16, 18, 20, 22, 24, 26, 30, 35, 40, 45, 50, 55, or 60 amino acids. In some embodiments, the deletions can comprise deletions of 1, 2, 3, 4, 5, 6, 7, 8, 9, 10, 11, 12, 13, 14, 15, 16, 18, 20, 22, 24, 26, 28, or 30 amino acid residues.

As described herein, the enone reductase polypeptides of the disclosure can be in the form of fusion polypeptides in which the enone reductase polypeptides are fused to other polypeptides, such as, by way of example and not limitation, antibody tags (e.g., myc epitope), purifications sequences (e.g., His tags), and cell localization signals (e.g., secretion signals). Thus, the engineered enone reductase polypeptides can be used with or without fusions to other polypeptides.

In some embodiments, the engineered enone reductases may be prepared and used in the form of cells expressing the enzymes, as crude extracts, or as isolated or purified preparations. The enone reductases may be prepared as lyophilizates, in powder form (e.g., acetone powders), or prepared as enzyme solutions. In some embodiments, the enone reductases can be in the form of substantially pure preparations.

In some embodiments, the enone reductase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylanine (2pAla); pyrid-3-ylanine (3pAla); pyrid-4-ylanine (4pAla); naphth-1-ylanine (1nAla); naphth-2-ylanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys(nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr(O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered enone reductase enzyme can be targeted to a specific property of the enzyme.

Polynucleotides Encoding Enone Reductase Polypeptides

In another aspect, the present disclosure provides polynucleotides encoding the engineered enone reductase polypeptides. The polynucleotides may be operatively linked to one or more heterologous regulatory sequences that control gene expression to create a recombinant polynucleotide capable of expressing the polypeptide. Expression constructs containing a heterologous polynucleotide encoding the engineered enone reductases can be introduced into appropriate host cells to express the corresponding enone reductase polypeptide.

Polynucleotides encoding engineered enone reductase polypeptides of the present invention include polynucleotides that hybridize under stringent conditions to a reference nucleic acid sequence selected from the group consisting of SEQ ID NOs: 7, 189, 191, 193, 195, 197, 199, 201, 203, 205, 207, 209, 211, 213, and 215.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the engineered enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Tables 3 and 4.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In certain embodiments, all codons need not be replaced to optimize the codon usage of the enone reductases since the natural sequence will comprise preferred codons and because use of preferred codons may not be required for all amino acid residues. Consequently, codon optimized polynucleotides encoding the enone reductase enzymes may contain preferred codons at about 40%, 50%, 60%, 70%, 80%, or greater than 90% of codon positions of the full length coding region.

In some embodiments, the polynucleotide comprises a nucleotide sequence encoding a enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to any of the reference engineered enone reductase polypeptides described herein. Accordingly, in some embodiments, the polynucleotide encodes an amino acid sequence that is at least about 80%, 85%, 86%, 87%, 88%, 89%, 90%, 91%, 92%, 93%, 94%, 95%, 96%, 97%, 98%, 99% or more identical to SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

In some embodiments, the polynucleotide comprises a nucleotide sequence encoding a enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 8.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 190.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 192.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 194.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 196.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 198.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 200.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 202.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 204.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 206.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 208.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 210.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 212.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 214.

In some embodiments, the polynucleotide comprises a nucleotide sequence encoding an enone reductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO: 216.

In some embodiments, the polynucleotides encoding the enone reductases are selected from SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In some embodiments, the polynucleotides are capable of hybridizing under highly stringent conditions to a polynucleotide comprising SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered enone reductases. In some embodiments, the reference polynucleotide is selected from SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

An isolated polynucleotide encoding the enone reductases herein may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual*, 3$^{rd}$ Ed., Cold Spring Harbor Laboratory Press; and *Current Protocols in Molecular Biology*, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *E. coli* trp operon, bacteriophage λ, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, *Mol Cell Bio* 15:5983-5990, which is incorporated herein by reference.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137, which is incorporated herein by reference.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra, which is incorporated herein by reference.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus* subtilis neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the ERED polypeptide of the present invention would be operably linked with the regulatory sequence.

Thus, in another embodiment, the present disclosure is also directed to a recombinant expression vector comprising a polynucleotide encoding an engineered enone reductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, *Proc Natl Acad. Sci. USA* 75:1433, which is incorporated herein by reference).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3xFLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, *Gene* 57:193-201).

Host Cells for Expression of Enone Reductases

In another aspect, the present disclosure provides a host cell comprising a polynucleotide encoding an improved enone reductase polypeptide of the present disclosure, the polynucleotide being operatively linked to one or more control sequences for expression of the enone reductase enzyme in the host cell. Host cells for use in expressing the ERED polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the enone reductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved enone reductase into the plasmid pCK110900 operatively linked to the lac promoter under control of the lad repressor. The expression vector also contained the P15a origin of replication and the chloramphenicol resistance gene. Cells containing the subject polynucleotide in *Escherichia coli* W3110 were isolated by subjecting the cells to chloramphenicol selection.

Methods of Generating Engineered Enone Reductase Polypeptides

In some embodiments, to make the engineered ERED polynucleotides and polypeptides of the present disclosure, the naturally-occurring enone reductase enzyme that catalyzes the reduction reaction is obtained (or derived) from *Saccharomyces pastorianis*. In some embodiments, the parent polynucleotide sequence is codon optimized to enhance expression of the enone reductase in a specified host cell.

The engineered enone reductases can be obtained by subjecting the polynucleoticde encoding the naturally occurring enone reductases to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767; U.S. Pat. No. 6,537,746; Stemmer, W. P. C., 1994, *Nature* 370:389-391; Crameri, A. et al., 1998, *Nature* 391:288-291; U.S. Pat. No. 5,605,793; U.S. Pat. No. 5,811,238; and U.S. Pat. No. 5,830,721. All references are incorporated herein by reference. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529).

The clones obtained following mutagenesis treatment are screened for engineered enone reductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. In this reaction, the NADH or NADPH is consumed (oxidized) by the enone reductase as the reductase reduces an $\alpha,\beta$ unsaturated substrate to the corresponding saturated compound. The rate of decrease of NADH or NADPH concentration, as measured by the decrease in absorbance or fluorescence, per unit time indicates the relative (enzymatic) activity of the ERED polypeptide in a fixed amount of the lysate (or a lyophilized powder made therefrom). Where the improved enzyme property desired is thermal or solvent stability, enzyme activity may be measured after subjecting the enzyme preparations to a defined temperature and/or solvent and measuring the amount of enzyme activity remaining after heat treatments. Clones containing a polynucleotide encoding a enone reductase are then isolated, sequenced to identify the nucleotide sequence changes (if any), and used to express the enzyme in a host cell.

Where the sequence of the engineered enone reductase polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Great American Gene Company, Ramona, Calif., ExpressGen Inc. Chicago, Ill., Operon Technologies Inc., Alameda, Calif., and many others.

The present invention provides a method of producing an engineered enone reductase polypeptide, the method comprising culturing a host cell transformed with a polynucleotide encoding an engineered enone reductase polypeptide of the present invention under conditions suitable for the expression of the engineered enone reductase polypeptide. The engineered enone reductase enzyme can optionally be recovered from the culture medium or from the transformed and cultured cells. For example, engineered enone reductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the enone reductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the engineered enone reductase enzymes. For affinity chromatography purification, any antibody which specifically binds the enone reductase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Methods of Using the Engineered Enone Reductase Enzymes and Compounds Prepared Therewith The present disclosure provides a method of reducing or converting an α,β unsaturated compound comprising (a) providing an α,β unsaturated compound selected from the group consisting of an α,β unsaturated ketone, and α,β unsaturated aldehyde, an α,β unsaturated nitrile, and an α,β unsaturated ester; and (b) contacting the α,β unsaturated compound with an engineered enone reductase polypeptide of the present invention under reaction conditions suitable for conversion of the α,β unsaturated compound to the corresponding saturated product compound (i.e., saturated ketone, aldehyde, nitrile, or ester). Further illustrative embodiments of this method are described hereinbelow.

In some embodiments, the enone reductases of the disclosure are capable of reducing the α,β unsaturated compound of formula (I) to the saturated compound of formula (II):

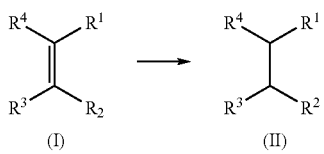

where
$R^1$ is H, OH, alkyl, CN, or halide;
$R^2$ is H, alkyl, aryl, aralkyl, or alkoxy;
$R^3$ is H, alkyl, aryl, or C(O)$R^7$, wherein $R^7$ is H or alkyl;

$R^4$ is CN, an aryl, C(O)$R^5$, or C(O)O$R^6$, wherein $R^5$ is H or alkyl and $R^6$ is H or alkyl; and wherein $R^3$ and $R^5$ can form a ring, including a fused ring. In some embodiments, the ring can be substituted or unsubstituted. In the above, the alkyl group can be substituted or unsubstituted, branched or straight chain, and the aryl group substituted or unsubstituted. In some embodiments, the halide is Cl. Various substrates known to be recognized by Old Yellow Enzymes are known in the art, such as those described in Vas et al., 1995, *Biochemistry* 34:4246-4256, which is incorporated herein by reference.

Accordingly, the engineered reductases can be used in a method for converting the compound of formula (I) ("the substrate") to the compound of formula (II) ("the product), which method comprises incubating or contacting the compound of formula (I) with an engineered enone reductase of the present disclosure under reaction conditions suitable for the conversion of the substrate to the product of formula (II).

In some embodiments, the engineered enone reductases can be used to reduce the α,β unsaturated carbonyl compound of formula (V) to the saturated carbonyl compound of formula (VI):

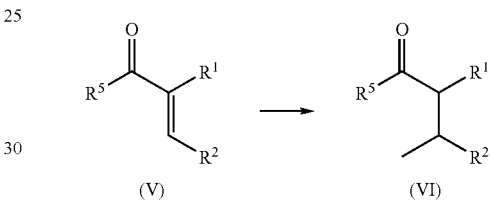

where,
$R^1$ is H, substituted or unsubstituted lower alkyl (e.g., C1-C4);
$R^2$ is substituted or unsubstituted alkyl, aryl, aralkyl, or alkoxy; and
$R^5$ is substituted or unsubstituted alkyl.

The method can comprise incubating or contacting a compound of formula (V) with an enone reductase of the present disclosure under reaction conditions suitable for the conversion of compound (V) to the product of formula (VI).

In some embodiments, the enone reductases of the disclosure are capable of reducing the α,β unsaturated compound of formula (I) to the saturated compound of formula (II):

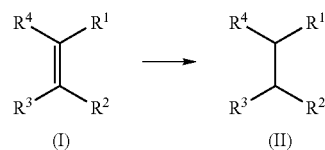

where
$R^1$ is H, OH, alkyl, CN, or halide;
$R^2$ is H or alkyl;
$R^4$ is C(O)$R^5$, and
$R^3$ and $R^5$ form a ring. In some embodiments, the ring comprises a substituted or unsubstituted cycloalkyl. Exemplary cycloalkyl rings include, cyclobutenyl, cyclopentenyl, cyclohexenyl; and the like, wherein the ring can be substituted or unsubstituted. In some embodiments, the ring comprises a fused ring. In the above, the alkyl group can be substituted or unsubstituted, branched or straight chain. In some embodiments, the halide is Cl. In these embodiments, the method can comprise incubating or contacting the ring compound described in the foregoing with an enone reductase of the present disclosure under suitable conditions to reduce the ring compound to the corresponding reduced ring product.

In some embodiments, the engineered enone reductases can be used in a method for converting/reducing an optionally substituted cycloxenone to the corresponding cyclohexanone, where the method comprises incubating or contacting the cyclohexenone with an enone reductase of the present invention under reaction conditions suitable for converting or reducing the optionally substituted cyclohexenone to the corresponding cyclohexanone. For example, the present invention provides a method for converting/reducing 1-cyclohex-2-enone of formula (III) to the cyclohexanone of formula (IV):

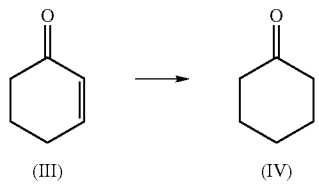

(III)    (IV)

In these embodiments, the method can comprise incubating or contacting a compound of formula (III) with an enone reductase of the present disclosure under reaction conditions suitable for the conversion of compound (III) to the product of formula (IV).

In some embodiments, the engineered enone reductases can be used in a method for converting (5S)-2-methyl-5-prop-1-en-2-ylcyclohex-2-en-1-one (VII) to (2R,5S)-2-methyl-5-prop-1-en-2-ylcyclohexan-1-one (VIII) as follows:

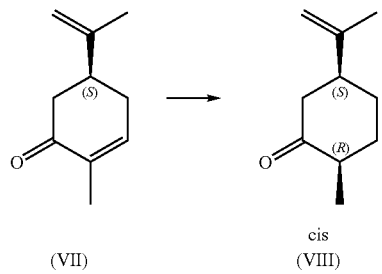

cis
(VII)    (VIII)

In these embodiments, the method can comprise incubating or contacting a compound of formula (VII) with an enone reductase of the present disclosure under reaction conditions suitable for the conversion of compound (VII) to the product of formula (VIII).

In some embodiments, the engineered enone reductase can be used in a method for converting (5S)-2-methyl-5-prop-1-en-2-ylcyclohex-2-en-1-one (VII) to (2S,5S)-2-methyl-5-prop-1-en-2-ylcyclohexan-1-one (VIIIb) in diastereomeric excess, as illustrated in the following reaction:

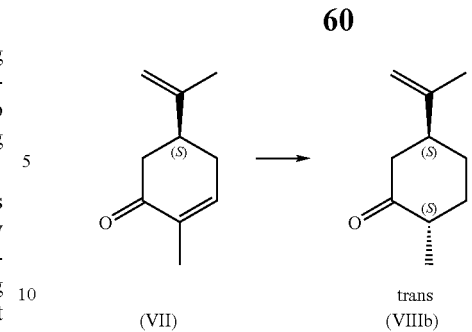

trans
(VII)    (VIIIb)

In these embodiments, the method can comprise incubating or contacting a compound of formula (VII) with an enone reductase of the present disclosure under reaction conditions suitable for the conversion of compound (VII) to the product of formula (VIIIb) in diastereomeric excess.

In some embodiments, the engineered enone reductase can be used in a method for converting (5R)-2-methyl-5-prop-1-en-2-ylcyclohex-2-en-1-one (R-carvone) (IX) to (2R,5R)-2-methyl-5-prop-1-en-2-ylcyclohexan-1-one (X) with at least 90% diastereomeric excess, as illustrated below:

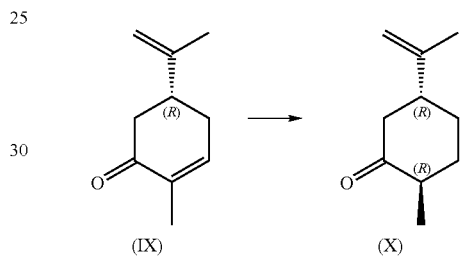

(IX)    (X)

In these embodiments, the method can comprise incubating or contacting a compound of formula (IX) with an enone reductase of the present disclosure under reaction conditions suitable for the conversion of compound (IX) to the product of formula (X) in diastereomeric excess.

In some embodiments, the engineered enone reductases can be used in a method for converting (5R)-2-methyl-5-prop-1-en-2-ylcyclohex-2-en-1-one (R-carvone) (IX) to (2S,5R)-2-methyl-5-prop-1-en-2-ylcyclohexan-1-one (Xb) in diastereomeric excess, as illustrated in the following reaction:

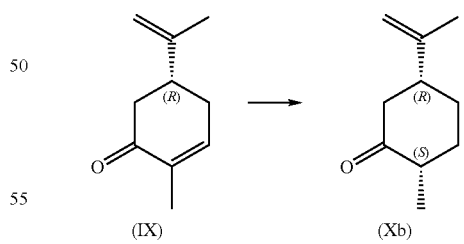

(IX)    (Xb)

In these embodiments, the method can comprise incubating or contacting a compound of formula (IX) with an enone reductase of the present disclosure under reaction conditions suitable for the conversion of compound (IX) to the product of formula (Xb) in diastereomeric excess.

The present invention also provides a method for reducing an optionally substituted arylalkenone to an optionally substituted arylalkanone. In some embodiments, the method comprises incubating or contacting a compound of formula (XI) with an enone reductase of the present disclosure under reaction conditions suitable for the conversion of compound (XI) to (XII):

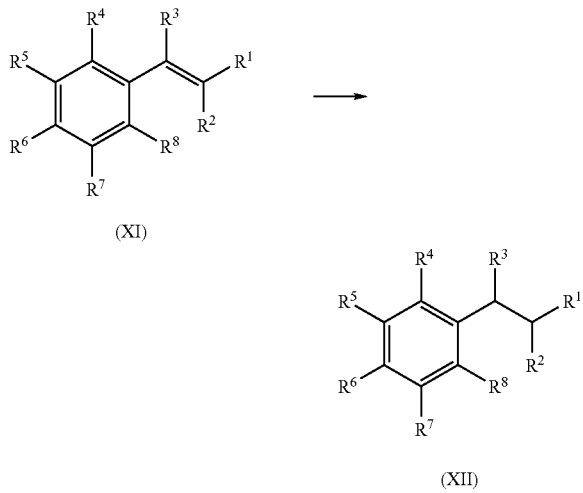

(XI)

(XII)

wherein for (XI) and (XII), $R^1$ and $R^2$ are each independently selected from the group consisting of CN, $C(O)R^{11}$, $C(O)OR^{11}$, an alkyl (such as, for example, a lower alkyl), and H, wherein $R^{11}$ is selected from the group consisting of H and an alkyl (such as, for example, a lower alkyl), and wherein $R^3$, $R^4$, $R^5$, $R^6$, $R^7$, and $R^8$ are each independently selected from the group consisting of H, an alkyl (such as, for example, a lower alkyl), an alkoxy (such as, for example, a lower alkoxy), a hydroxyl, and a halide. Typically, only one of $R^1$ and $R^2$ is CN and only one of $R^1$ and $R^2$ is $C(O)R^{11}$ or $C(O)OR^{11}$. Usually, at least one of $R^1$ and $R^2$ is $C(O)R^{11}$ or $C(O)OR^{11}$. In some embodiments, $R^2$ is an alkyl, such as, for example, a lower alkyl (i.e., methyl, propyl, isopropyl, and the like).

In some embodiments, the engineered enone reductases can be used in a method for converting (Z)-ethyl 2-cyano-3-phenylbut-2-enoate (XIII) to ethyl 2-cyano-3-phenylbutanoate (XIV) as follows:

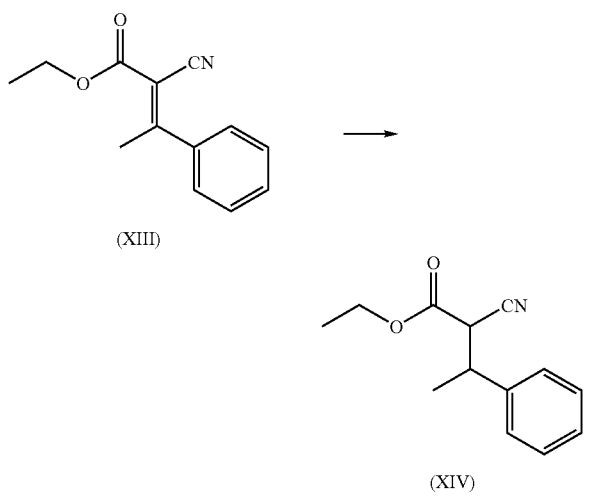

(XIII)

(XIV)

In these embodiments, the method can comprise incubating or contacting a compound of formula (XIII) with an enone reductase of the present disclosure under reaction conditions suitable for the conversion of compound (XIII) to the product of formula (XIV) at a rate that is greater conversion rate than the polypeptide of SEQ ID NO:6 or SEQ ID NO:8.

In some embodiments, the engineered enone reductases can be used in a method for converting/reducing (E)-2-(3,4-dimethyoxybenzylidene)-3-methylbutanal (XV) to 2-(3,4-dimethyoxybenzyl)-3-methylbutanal (XVI), as illustrated below:

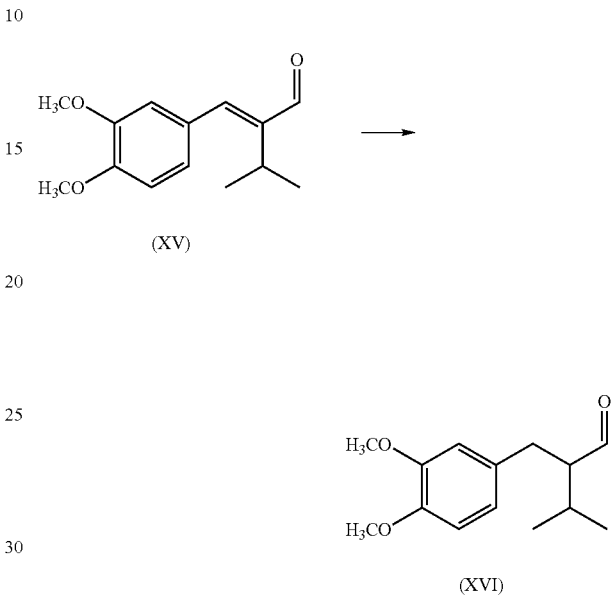

(XV)

(XVI)

In these embodiments, the method can comprise incubating or contacting a compound of formula (XV) with an enone reductase of the present disclosure under reaction conditions suitable for the conversion of compound (XV) to the product of formula (XVI).

In some embodiments, the engineered enone reductases can be used in a method for converting 8a-methyl-3,4,8,8a-tetrahydronaphthalene-1,6(2H,7H)-dione (XVIII) to 8a-methylhexahydronaphthalene-1,6(2H,7H)-dione (XIX) as follows:

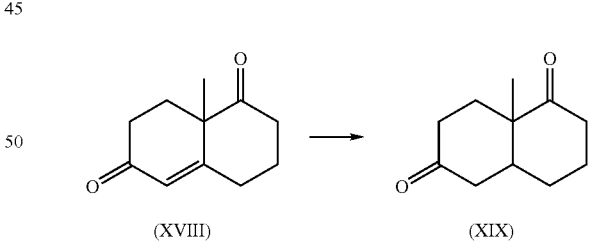

(XVIII)        (XIX)

In these embodiments, the method can comprise incubating or contacting a compound of formula (XVIII) with an enone reductase of the present disclosure under reaction conditions suitable for the conversion of compound (XVIII) to the product of formula (XIX) at a conversion rate that is greater than the polypeptide of SEQ ID NO:6 or SEQ ID NO:8.

In some embodiments, the engineered enone reductases can be used in a method for converting 3-methylcyclohex-2-enone (XX) to 3-methylcyclohexanone (XXI), as illustrated below:

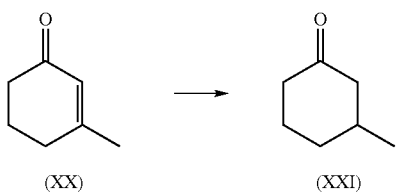

(XX)   (XXI)

In these embodiments, the method can comprise incubating or contacting a compound of formula (XX) with an enone reductase of the present disclosure under reaction conditions suitable for the conversion of compound (XX) to the product of formula (XXI).

In some embodiments, the engineered enone reductases can be used in a method for converting or reducing an optionally substituted cyclopentenone to the corresponding cyclopentanone. For example, the engineered enone reductase polypeptides can be used in a method for converting/reducing 2-methylcyclopente-2-none (XXII) to 2-methylcyclopentanone (XXIII) as illustrated below:

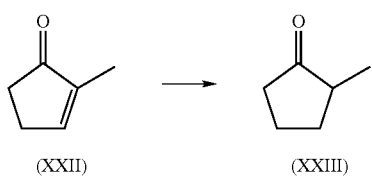

(XXII)   (XXIII)

In these embodiments, the method can comprise incubating or contacting a compound of formula (XXII) with an enone reductase of the present disclosure under reaction conditions suitable for the conversion of compound (XXII) to the product of formula (XXIII).

Since enone reductases use a cofactor, the engineered enone reductases can be used in combination with a cofactor regenerating system in the methods for reducing the α,β unsaturated compounds. In some embodiments, the reduction by enone reductases results in the generation of NADP+ from NADPH, and therefore any system capable of regenerating NADPH can be used.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP+/NADPH or NAD+/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

Glucose dehydrogenase (GDH) are NAD+ or NADP+-dependent enzymes that catalyzes the conversion of D-glucose and NAD+ or NADP+ to gluconic acid and NADH or NADPH, respectively. Equation (1), below, describes the glucose dehydrogenase-catalyzed reduction of NAD+ or NADP+ by glucose.

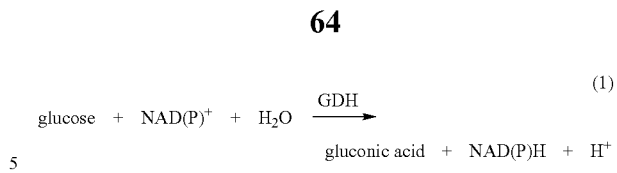

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (*Nature*, 2003, 423:87-91; Genbank Acc. No. AE017013) and *B. megaterium* (Eur. J. Biochem., 1988, 174:485-490, Genbank Acc. No. X12370; J. Ferment. Bioeng., 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring are well known in the art and may also be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the enone reductase-catalyzed reduction reactions disclosed herein are provided in U.S. application publication Nos. 2005/0095619 and 2005/0153417, the disclosures of which are incorporated herein by reference.

Glucose dehydrogenases employed in the enone reductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The enone reductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the enone reductase enzyme. Appropriate co-solvent systems can be readily identified by measuring the enzymatic activity of the specified engineered enone reductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (3) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a enone reductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD$^+$ or NADP$^+$-dependent enzyme that catalyzes the conversion of formate and NAD$^+$ or NADP$^+$ to carbon dioxide and NADH or NADPH, respectively. Formate dehydrogenases that are suitable for use as cofactor regenerating systems in the enone reductase-catalyzed reduction reactions described herein are well known in the art and include both naturally occurring formate dehydrogenases, as well as non-naturally occurring formate dehydrogenases. Suitable formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher, and can be readily screened for activity in the assay described in Example 4 of PCT publication WO 2005/018579.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2^-$ and HCO$_2$H in equilibrium concentrations. At pH values above about pH 4, formate is predominantly present as HCO$_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2^-$, Equation (2) below, describes the formate dehydrogenase-catalyzed reduction of NAD$^+$ or NADP$^+$ by formate.

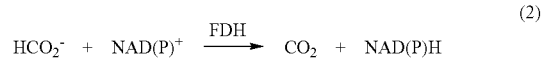

(2)

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., $KH_2PO_4$), bisulfate salts (e.g., $NaHSO_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an $NAD^+$ or $NADP^+$-dependent enzyme that catalyzes the conversion of a secondary alcohol and $NAD^+$ or $NADP^+$ to a ketone and NADH or NADPH, respectively. Equation (3), below, describes the reduction of $NAD^+$ or $NADP^+$ by a secondary alcohol, illustrated by isopropanol.

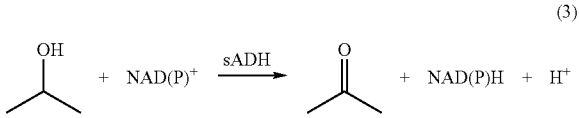

(3)

Secondary alcohol dehydrogenases that are suitable for use as cofactor regenerating systems in the enone reductase-catalyzed reduction reactions described herein are well known in the art and include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanerobium brockii, Rhodococcus etythropolis, Lactobacillus kefir,* and *Lactobacillus brevis*, and non-naturally occurring secondary alcohol dehydrogenases include engineered alcohol dehydrogenases derived therefrom. Secondary alcohol dehydrogenases employed in the methods described herein, whether naturally occurring or non-naturally occurring, may exhibit an activity of at least about 1 μmol/min/mg, sometimes at least about 10 μmol/min/mg, or at least about $10^2$ μmol/min/mg, up to about $10^3$ μmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-alkyl carbinols include unsubstituted and substituted 1-arylethanols.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant.

In carrying out embodiments of the enone reductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the enone reductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the reduction reactions described herein, the engineered enone reductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered enone reductase enzyme and the optional cofactor regeneration enzymes can be transformed into host cells separately or together into the same host cell. For example, in some embodiments one set of host cells can be transformed with gene(s) encoding the engineered enone reductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered enone reductase enzyme and the cofactor regeneration enzymes.

Whole cells transformed with gene(s) encoding the engineered enone reductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of enone reductase substrate employed. The following guidelines can be used to determine the amounts of enone reductase, cofactor, and optional cofactor regeneration system to use. Generally, substrates can be employed at a concentration of about 5 to 300 grams/liter using from about 50 mg to about 5 g of enone reductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or enone reductase utilized.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, enone reductase, and enone reductase substrate may be added first to the solvent.

For improved mixing efficiency when an aqueous co-solvent system is used, the cofactor regeneration system, enone reductase, and cofactor may be added and mixed into the aqueous phase first. The organic phase may then be added and mixed in, followed by addition of the enone reductase substrate. Alternatively, the enone reductase substrate may be premixed in the organic phase, prior to addition to the aqueous phase Suitable conditions for carrying out the enone reductase-catalyzed reduction reactions described herein include a wide variety of conditions which can be readily optimized by routine experimentation that includes, but is not limited to, contacting the engineered enone reductase enzyme and substrate at an experimental pH and temperature and detecting product, for example, using the methods described in the Examples provided herein.

The enone reductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the reduction product generated in the reaction mixture are generally greater than about 50%, may also be greater than about 60%, may also be greater than about 70%, may also be greater than about 80%, may also be greater than about 90%, and are often greater than about 97%.

EXAMPLES

Various features and embodiments of the disclosure are illustrated in the following representative examples, which are intended to be illustrative, and not limiting.

Generation of Chimeric Enone Reductases

The chimeric enone reductases were generated by standard domain shuffling methods as described in Stemmer, W. P. C., 1994, "Rapid evolution of a protein in vitro by DNA shuffling," Nature 370:389-391; Stemmer, W. P. C., 1994, "DNA Shuffling by random fragmentation and reassembly: In vitro recombination for molecular evolution," Proc Natl Acad. Sci. USA 91:10751; Crameri, A. et al., 1998, "DNA shuffling of a family of genes from diverse species accelerates directed evolution." Nature 391:288-291; U.S. Pat. No. 5,605,793 (Stemmer); U.S. Pat. No. 5,811,238 (Stemmer and Crameri); and U.S. Pat. No. 5,830,721 (Stemmer and Crameri). All references are incorporated herein by reference. The enone reductases polynucleotides used to generate the chimeras were the genes encoding Old Yellow Enzyme 1 from *Saccharomyces pastorianus*, Old Yellow Enzyme 2 from *Saccharomyces cerevisiae*, and Old Yellow Enzyme 3 from *Saccharomyces cerevisiae*, and presented herein as SEQ ID NO:1, SEQ ID NO:3, and SEQ ID NO:5, respectively.

As noted above, polynucleotides encoding engineered enone reductases of the present invention may also be cloned into any suitable vector, such as vector pCK110900 (depicted in FIG. 3 in U.S. Patent Application Publication 20060195947, which is incorporated herein by reference) for expression in *E. coli* W3110.

Production of Enone reductase Powders—Shake Flask Procedure

A single microbial colony of *E. coli* containing a plasmid encoding an enone reductase of interest is inoculated into 50 ml Luria-Bertani broth containing 30 µg/ml chloramphenicol and 1% glucose. Cells are grown overnight (at least 16 hrs) in an incubator at 30° C. with shaking at 250 rpm. The culture is diluted into 250 ml Terrific Broth (12 g/L bacto-tryptone, 24 g/L yeast extract, 4 ml/L glycerol, 65 mM potassium phosphate, pH 7.0, 1 mM $MgSO_4$) containing 30 µg/ml chloramphenicol, in a 1 liter flask to an optical density at 600 nm ($OD_{600}$) of 0.2 and allowed to grow at 30° C. Expression of the enone reductase gene is induced by addition of iso-propyl-β-D-thiogalactoside (IPTG) to a final concentration of 1 mM when the $OD_{600}$ of the culture is 0.6 to 0.8 and incubation is then continued overnight (at least 16 hrs). Cells are harvested by centrifugation (5000 rpm, 15 min, 4° C.) and the supernatant discarded. The cell pellet is resuspended with an equal volume of cold (4° C.) 100 mM triethanolamine (chloride) buffer, pH 7.5, and harvested by centrifugation as above. The washed cells are resuspended in two volumes of the cold triethanolamine (chloride) buffer and passed through a French Press twice at 12,000 psi while maintained at 4° C. Cell debris is removed by centrifugation (9000 rpm, 45 min, 4° C.). The clear lysate supernatant is collected and stored at −20° C. Lyophilization of frozen clear lysate provides a dry powder of crude enone reductase enzyme. Alternatively, the cell pellet (before or after washing) may be stored at 4° C. or −80° C.

Production of Enone Reductases—Fermentation Procedure

Bench-scale fermentations are carried out at 30° C. in an aerated, agitated 15 L fermentor using 6.0 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate). The fermentor is inoculated with a late exponential culture of *E. coli* W3110 containing a plasmid encoding the enone reductase gene of interest (grown in a shake flask as described in Example 2) to a starting $OD_{600}$ of 0.5 to 2.0. The fermentor is agitated at 500-1500 rpm and air is supplied to the fermentation vessel at 1.0-15.0 L/min to maintain a dissolved oxygen level of 30% saturation or greater. The pH of the culture is maintained at 7.0 by addition of 20% v/v ammonium hydroxide. Growth of the culture is maintained by addition of a feed solution containing 500 g/L cerelose, 12 g/L ammonium chloride and 10.4 g/L magnesium sulfate heptahydrate. After the culture reaches an OD600 of 50, expression of enone reductase is induced by addition of isopropyl-β-D-thiogalactoside (IPTG) to a final concentration of 1 mM and fermentation continued for another 14 hours. The culture is then chilled to 4° C. and maintained at that temperature until harvested. Cells are collected by centrifugation at 5000 G for 40 minutes in a Sorval RC12BP centrifuge at 4° C. Harvested cells are used directly in the following downstream recovery process or they may be stored at 4° C. or frozen at −80° C. until such use.

The cell pellet is resuspended in 2 volumes of 100 mM triethanolamine (chloride) buffer, pH 6.8, at 4° C. to each volume of wet cell paste. The intracellular enone reductase is released from the cells by passing the suspension through a homogenizer fitted with a two-stage homogenizing valve assembly using a pressure of 12000 psig. The cell homogenate is cooled to 4° C. immediately after disruption. A solution of 10% w/v polyethyleneimine, pH 7.2, is added to the lysate to a final concentration of 0.5% w/v and stirred for 30 minutes. The resulting suspension is clarified by centrifugation at 5000G in a standard laboratory centrifuge for 30 minutes. The clear supernatant is decanted and concentrated tenfold using a cellulose ultrafiltration membrane with a molecular weight cut off of 30 kD. The final concentrate is dispensed into shallow containers, frozen at −20° C. and lyophilized to powder. The enone reductase powder is stored at −80° C.

Analytical Methods: Conversion of Unsaturated Enone Substrate to Saturated Ketone Product and Stereopurity of Product Achiral GC method to determine conversion of methyl crotonate to methyl butanoate: Reduction of methyl crotonate to methyl butanoate is determined using an Agilent 6890 GC-FID equipped with a 30 m×0.32 mm (0.25 μm film) Agilent HP-5 column using He as carrier gas with the following temperature program: 20 psi, 60° C. for 3 min. Retention times: methyl butanoate: 3.1 min; methyl crotonate: 3.6 min.

Achiral GC method to determine conversion of (S)-2-methyl-5-(prop-1-en-2-yl)cyclohex-2-enone to (2R or 2S, 5S)-2-methyl-5-(prop-1-en-2-yl)cyclohexanone and diastereomeric purity of 2-methyl-5-(prop-1-en-2-yl)cyclohexanone: Reduction of (S)-2-methyl-5-(prop-1-en-2-yl)cyclohex-2-enone to (2R or 2S, 5S)-2-methyl-5-(prop-1-en-2-yl)cyclohexanone is determined using an Agilent 6890 GC-FID equipped with a 30 m×0.32 mm (0.25 μm film) Agilent HP-5 column using He as carrier gas with the following temperature program: 25 psi, 125° C. for 3.25 min. Retention times: (2S,5S)-2-methyl-5-(prop-1-en-2-yl)cyclohexanone: 2.6 min; (2R,5S)-2-methyl-5-(prop-1-en-2-yl)cyclohexanone: 2.7 min; (S)-2-methyl-5-(prop-1-en-2-yl)cyclohex-2-enone: 3.1 min.

Achiral GC method to determine conversion of (R)-2-methyl-5-(prop-1-en-2-yl)cyclohex-2-enone to (2R or 2S, 5R)-2-methyl-5-(prop-1-en-2-yl)cyclohexanone and diastereomeric purity of 2-methyl-5-(prop-1-en-2-yl)cyclohexanone: Reduction of (R)-2-methyl-5-(prop-1-en-2-yl)cyclohex-2-enone to (2R or 2S, 5S)-2-methyl-5-(prop-1-en-2-yl)cyclohexanone is determined using an Agilent 6890 GC-FID equipped with a 30 m×0.32 mm (0.25 μm film) Agilent HP-5 column using He as carrier gas with the following temperature program: 25 psi, 125° C. for 3.25 min. Retention times: (2R,5R)-2-methyl-5-(prop-1-en-2-yl)cyclohexanone: 2.5 min; (2S,5R)-2-methyl-5-(prop-1-en-2-yl)cyclohexanone: 2.6 min; (S)-2-methyl-5-(prop-1-en-2-yl)cyclohex-2-enone: 2.9 min.

Achiral GC method to determine conversion of (E/Z)-ethyl 2-cyano-3-phenylbut-2-enoate to ethyl 2-cyano-3-phenylbutanoate and the diastereomeric purity of ethyl 2-cyano-3-phenylbutanoate: Reduction of ethyl 2-cyano-3-phenylbut-2-enoate to ethyl 2-cyano-3-phenylbutanoate is determined using an Agilent 6890 GC-FID equipped with a 30 m×0.32 mm (0.25 μm film) Agilent HP-5 column using He as carrier gas with the following temperature program: 20 psi, 170° C. for 5 min. Retention times: diastereomer-1 of ethyl 2-cyano-3-phenylbutanoate: 3.3; diastereomer-2 of ethyl 2-cyano-3-phenylbutanoate: 3.4 min; (E or Z)-ethyl 2-cyano-3-phenylbut-2-enoate: 4.1 min; (E or Z)-ethyl 2-cyano-3-phenylbut-2-enoate: 4.9 min.

Achiral GC method to determine conversion of 8a-methyl-3,4,8,8a-tetrahydronaphthalene-1,6(2H,7H)-dione to 8a-methylhexahydronaphthalene-1,6(2H,7H)-dione and the diastereomeric purity of 8a-methylhexahydronaphthalene-1,6(2H,7H)-dione: Reduction of 8a-methyl-3,4,8,8a-tetrahydronaphthalene-1,6(2H,7H)-dione to 8a-methylhexahydronaphthalene-1,6(2H,7H)-dione is determined using an Agilent 6890 GC-FID equipped with a 30 m×0.32 mm (0.25 μm film) Agilent HP-5 column using He as carrier gas with the following temperature program: 20 psi, 165° C. for 4 min. Retention times: diastereomer-1 of 8a-methylhexahydronaphthalene-1,6(2H,7H)-dione: 3.2 min; diastereomer-2 of 8a-methylhexahydronaphthalene-1,6(2H,7H)-dione: 3.5 min; 8a-methyl-3,4,8,8a-tetrahydronaphthalene-1,6(2H,7H)-dione: 3.8 min.

Chiral GC method to determine conversion of 3-methylcyclohexenone to 3-methylcyclohexanone and the enantiopurity of 3-methylcyclohexanone: Reduction of 3-methylcyclohexenone to 3-methylcyclohexanone is determined using an Agilent 6890 GC-FID equipped with a 30 m×0.25 mm (0.25 μm film) Restek chiral Rt-βDex$_{sm}$ column using He as carrier gas with the following temperature program: 18 psi, 110° C. for 8 min; 25° C. min$^{-1}$, 150° C. for 1.4 min. Retention times: (R)-3-methylcyclohexanone: 7.1 min; (S)-3-methylcyclohexanone: 7.3 min; 3-methylcyclohexenone: 10.4 min.

Chiral GC method to determine conversion of 2-methyl-2-pentenal to 2-methylpentanol and the enantiopurity of 2-methylpentanol: Reduction of 2-methyl-2-pentenal to 2-methylpentanol is determined using an Agilent 6890 GC-FID equipped with a 30 m×0.25 mm (0.25 μm film) Supelco Betadex-225 column using He as carrier gas with the following temperature program: 12 psi, 80° C. for 9.5 min; 70° C. min$^{-1}$, 150° C. for 2 min. Retention times: (R)-2-methylpentanol: 8.0 min; (S)-2-methylpentanol: 8.1 min; 2-methyl-2-pentenal: 11.9 min.

Chiral GC method to determine conversion of 2-methyl-2-pentenal to 2-methylpentanol and the enantiopurity of 2-methylpentanol: Reduction of 2-methyl-2-pentenal to 2-methylpentanol is determined using an Agilent 6890 GC-FID equipped with a 30 m×0.25 mm (0.25 μm film) Supelco Betadex-225 column using He as carrier gas with the following temperature program: 12 psi, 80° C. for 9.5 min; 70° C. min$^{-1}$, 150° C. for 2 min. Retention times: (R)-2-methylpentanol: 8.0 min; (S)-2-methylpentanol: 8.1 min; 2-methyl-2-pentenal: 11.9 min.

Chiral HPLC method to determine conversion of (E)-2-(3,4-dimethoxybenzylidene)-3-methylbutanal to give (R or S)-2-(3,4-dimethoxybenzyl)-3-methylbutanal and the enantiomeric purity of (R or S)-2-(3,4-dimethoxybenzyl)-3-methylbutanal: Reduction of (E)-2-(3,4-dimethoxybenzylidene)-3-methylbutanal to give (R or S)-2-(3,4-dimethoxybenzyl)-3-methylbutanal is determined using an Agilent 1100 HPLC equipped with a Chiralcel OJ-H column (15 cm length, 4.6 mm diameter) using 85:15 heptane/isopropanol as eluent at a flow rate of 1 ml/min; and at a column temperature of 30° C.; UV=225 nm. Retention times: enantiomer-1 of 2-(3,4-dimethoxybenzyl)-3-methylbutanal: 3.7 min; enantiomer-2 of 2-(3,4-dimethoxybenzyl)-3-methylbutanal: 4.7 min; (E)-2-(3,4-dimethoxybenzylidene)-3-methylbutanal: 5.6 min.

Cell Selection, Growth, and Induced Expression of Enone Reductase Polypeptides (Variant Enzymes)

Individual colonies are robotically picked with a Q-Bot™ instrument (Genetix, USA Inc., Boston, Mass.) to 180 µL Luria-Bertani (LB) broth containing 1% glucose and 30 µg/mL chloramphenicol (CAM) in a 96 well NUNC® plate (Nalge Nunc International, Rochester N.Y.). The plate (the "masterplate") is sealed with AirPore tape (Qiagen, Valencia Calif.) and a lid, and incubated overnight at 30° C. at 250 rpm (2 inch throw) at 85% relative humidity. Masterplates are subcultured by inoculating a 10 µL, aliquot from each well into a well of a Costar® deep well plate (Corning®, Acton Mass.) containing 390 µL Terrific Broth, pH 7.0, supplemented with 30 µg/ml chloramphenicol (CAM). The inoculated Costar® deep well plates are incubated for 2.5 hours at 30° C., 85% relative humidity, at 250 rpm on a shaker with a 2 inch throw. The inducer IPTG is then added to each well to a final concentration of 1 mM and incubation continued for an additional 18 hours. Cells are harvested by centrifuging the Costar® deep well plates at 4000 rpm for 10 minutes, discarding the supernatant. Generally, the pellets are frozen for one hour before lysis.

Glycerol is added to the wells of the masterplate to a final concentration of 20%. Masterplates are then stored at −80° C.

Screen for Enone Reductases Capable of Reducing Cyclohexenone in the Presence of NADPH yielding NADP+ and Cyclohexanone Recombinant *E. coli* colonies carrying a gene encoding enone reductase are picked using a Q-Bot® robotic colony picker (Genetix USA, Inc., Boston, Mass.) into 96-well shallow well microtiter plates containing 180 µL Luria-Bertani (LB), 1% glucose and 30 µg/mL chloramphenicol (CAM). Cells are grown overnight at 30° C. with shaking at 200 rpm. A 10 µL aliquot of this culture is then transferred into 96-deep well plates containing 390 µL Terrific Broth (TB) and 30 µg/mL CAM. After incubation of the deep-well plates at 30° C. with shaking at 250 rpm for 2.5 hours, recombinant gene expression within the cultured cells is induced by addition of IPTG to a final concentration of 1 mM. The plates are then incubated at 30° C. with shaking at 250 rpm for 18 hrs.

Cells are pelleted by centrifugation (4000 RPM, 10 min, 4° C.), resuspended in 200 µL lysis buffer and lysed by shaking at room temperature for 2 hours. The lysis buffer contains 100 mM triethylamine (chloride) buffer or 100 mM sodium phosphate buffer, pH 7.5, 1 mg/mL lysozyme, and 500 µg/mL polymixin B sulfate (PMBS). After sealing the plates with aluminum/polypropylene laminate heat seal tape (Velocity 11 (Menlo Park, Calif.), Cat# 06643-001), they are shaken vigorously for 2 hours at room temperature. Cell debris is collected by centrifugation (4000 RPM, 10 min., 4° C.) and the clear supernatant is assayed directly or stored at 4° C. until use.

In this assay, 20 µl of sample (diluted in 100 mM triethanolamine(chloride) buffer or 100 mM sodium phosphate buffer, at the same pH as the lysis buffer) is added to 180 µl of an assay mixture in a well of 96-well black microtiter plates. Assay buffer consists of 100 mM triethanolamine (chloride) buffer or 100 mM sodium phosphate buffer, pH 7.5, 0.1 mg/ml cyclohexenone and 0.1 mg/ml NADPH. The reaction is followed by measuring the reduction in fluorescence of NADPH as it is converted to NADP+ using a Flexstation® instrument (Molecular Devices, Sunnyvale, Calif.). NADPH fluorescence is measured at 445 nm upon excitation at 330 nm. For residual activity determination, samples of lysates were preincubated at 30° C. or 40° C. in the presence of 10, 20 or 50% IPA or additional co-solvents prior to addition to the assay mixture and compared to the corresponding lysate diluted with buffer only. Activity measurement of lysate preincubated in co-solvent divided by activity measurement of lysate preincubated in buffer yields the residual activity.

Assay of Enone Reductase Activity: Stereoselective Reduction of Enones or Enoates to corresponding products Cell lysis: Cell pellets (collected in the wells of a microtiter plate) are lysed by addition of 200 µL lysis buffer (0.5 mg/ml PMBS, 1 mg/ml lysozyme, 100 mM triethylamine (chloride) or 100 mM sodium phosphate, pH 7.5, to each well. The plates are sealed, shaken vigorously for two hours at room temperature, and then centrifuged at 4000 rpm for 20 minutes at 4° C. The supernatants are recovered and stored at 4° C. until assayed.

Enzymatic reduction reaction using glucose dehydrogenase (GDH), glucose for cofactor recycling: For substrates with ketone or aldehyde functionality (e.g., 3-methyl cyclohexenone), 100 µl of cell lysate is transferred to a deep well plate (Costar #3960) (Corning®, Acton Mass.) containing 150 µl of assay mix (per 100 ml: 83 ml 100 mM sodium phosphate (pH 7.5), 83 mg Na-NADP (Oriental Yeast, Andover, Mass.), 835 mg enone substrate, 334 mg appropriate glucose dehydrogenase, 2 g glucose, and 17 ml tetrahydrofuran). After sealing the plates with aluminum/polypropylene laminate heat seal tape (Velocity 11 (Menlo Park, Calif.), Cat# 06643-001), reactions are run for 18-24 hrs at temperatures ranging from ambient to 30° C. Reactions are quenched by the addition of 1 ml MTBE. Plates are resealed, shaken for 5 min, and the organic and aqueous layer separated by centrifugation (4000 rpm, 5 min, at ambient temperature). 200 µl of the organic layer of each well is transferred into the wells of a new shallow-well polypropylene plate (Costar #3365) (Corning®, Acton Mass.). After resealing the plates, samples are subjected to GC analysis as described in example 4.

Enzymatic reduction reaction using ketoreductase, isopropanol for cofactor recycling: For substrates without ketone or aldehyde functionality (e.g., methyl crotonate), 100 µl of cell lysate is transferred to a deep well plate (Costar #3960) (Corning®, Acton Mass.) containing 150 µl of assay mix (per 100 ml: 67 ml 100 mM triethanolamine(chloride) (pH 7.5), 83 mg Na-NADP (Oriental Yeast, Andover, Mass.), 835 mg enoate substrate, 167 mg of appropriate ketoreductase and 33 ml isopropyl alcohol). After sealing the plates with aluminum/polypropylene laminate heat seal tape (Velocity 11 (Menlo Park, Calif.), Cat# 06643-001), reactions are run for 18-24 hrs at temperatures ranging from ambient to 30° C.

Reactions are quenched by the addition of 1 ml MTBE. Plates are resealed, shaken for 5 min, and the organic and aqueous layer separated by centrifugation (4000 rpm, 5 min, at ambient temperature). 200 μl of the organic layer of each well is transferred into the wells of a new shallow-well polypropylene plate (Costar #3365) (Corning, Acton Mass.). After resealing the plates, samples are subjected to GC analysis as described in example 4.

Table 5 provides the activities of exemplary enone reductases for (5S)-2-methyl-5-prop-1-en-2-ylcyclohex-2-en-1-one (S-carvone) and (5R)-2-methyl-5-prop-1-en-2-ylcyclohex-2-en-1-one (R-carvone) and the products generated by the enone reductases.

TABLE 5

| SEQ ID NO: | S-CARVONE % CONV$^A$ | S-CARVONE % DE$^B$ | R-CARVONE % CONV.$^C$ | R-CARVONE % DE$^D$ |
|---|---|---|---|---|
| 53/54 | + | S++ | N.D. | |
| 55/56 | | S | N.D. | |
| 51/52 | | S+ | N.D. | |
| 57/58 | | RACEMIC | N.D. | |
| 61/62 | | RACEMIC | N.D. | |
| 59/60 | | S | N.D. | |
| 185/186 | | | | ++++ |
| 131/132 | + | R+ | | ++ |
| 173/174 | | R | | +++ |
| 17/18 | ++ | R+ | + | +++ |
| 139/140 | + | R+ | | +++ |
| 45/46 | +++ | R++ | + | +++ |
| 7/8 | + | R+ | + | +++ |
| 41/42 | | R+ | | +++ |
| 9/10 | ++ | R+ | + | +++ |
| 39/40 | | R | | S+++ |
| 123/124 | + | R | | ++ |
| 133/134 | + | R+ | + | +++ |
| 13/14 | ++ | R++ | + | +++ |
| 137/138 | | R+ | | +++ |
| 119/120 | + | R+ | | +++ |
| 129/130 | ++++ | R++ | + | ++ |
| 43/44 | +++ | R+ | + | +++ |
| 177/178 | | R | | ++ |
| 11/12 | + | R | | +++ |
| 141/142 | | R+ | + | +++ |
| 161/162 | ++ | R+ | + | +++ |
| 135/136 | + | R | | +++ |
| 127/128 | ++ | R+ | + | +++ |
| 113/114 | +++ | R++ | | +++ |
| 169/170 | | R | | +++ |
| 125/126 | ++ | R+ | | +++ |
| 179/180 | | R | | ++ |
| 121/122 | ++ | R+ | + | +++ |
| 99/100 | | R | | ++ |
| 115/116 | +++ | R++ | + | +++ |
| 165/166 | + | R+ | | +++ |
| 111/112 | +++ | R++ | | +++ |
| 25/26 | | RACEMIC | | +++ |
| 145/146 | | R+ | + | +++ |
| 183/184 | | R | | ++ |
| 67/68 | ++++ | R++ | + | +++ |
| 155/156 | +++ | S | | RACEMIC |
| 167/168 | + | R+ | | +++ |
| 71/72 | ++++ | R++ | + | +++ |
| 105/106 | + | R++ | | +++ |
| 73/74 | +++ | R++ | + | +++ |
| 109/110 | ++ | R++ | | +++ |
| 89/90 | ++++ | R++ | + | +++ |
| 75/76 | ++++ | R++ | + | +++ |
| 159/160 | | R+ | | ++ |
| 35/36 | | RACEMIC | | +++ |
| 21/22 | + | R+ | + | +++ |
| 107/108 | +++ | R+ | + | +++ |
| 175/176 | | R | | ++ |
| 37/38 | | S | | ++ |
| 69/70 | +++ | R++ | + | +++ |
| 117/118 | +++ | R+ | + | +++ |
| 171/172 | ++++ | R++ | + | +++ |
| 33/34 | | RACEMIC | | ++++ |
| 47/48 | ++++ | S+++ | | RACEMIC |
| 163/164 | + | R+ | | ++ |
| 157/158 | +++ | S+ | | + |
| 149/150 | + | Racemic | | ++ |
| 187/188 | | R | | ++ |
| 153/154 | ++++ | S+++ | | racemic |
| 63/64 | ++++ | S+ | + | + |
| 23/24 | | S+++ | | racemic |
| 87/88 | ++ | R+ | | +++ |
| 49/50 | ++++ | S+++ | | + |
| 97/98 | ++++ | R++ | + | +++ |
| 95/96 | + | R++ | + | +++ |
| 181/182 | | R | | ++ |
| 81/82 | +++ | R++ | + | +++ |
| 77/78 | + | R+ | | +++ |
| 103/104 | ++ | R++ | | +++ |
| 27/28 | | S++ | | + |
| 19/20 | | S+ | | S+ |
| 143/144 | +++ | S+++ | | S+ |
| 151/152 | ++++ | S+++ | | + |
| 147/148 | +++ | S+++ | | S+ |
| 83/84 | | | | + |
| 85/86 | ++ | R++ | + | +++ |
| 31/32 | + | S | | +++ |
| 65/66 | + | S | | ++ |
| 79/80 | | Racemic | | +++ |
| 101/102 | ++ | R+ | | +++ |
| 29/30 | | S++ | | + |
| 93/94 | | R | | +++ |
| 91/92 | | S | | + |
| 15/16 | +++ | R++ | + | +++ |

$^A$ + = 100-149% of parent (SEQ ID NO: 8) ++ = 150-199% of parent +++ = 200-250% of parent ++++ = >250% of parent
$^B$ +++ = >95% ee ++ = 90-95% ee + = 80-90% ee None = 30-80% ee Racemic = <30% ee S = (2S,5S) product R = (2R,5S) product
$^C$ + = >100% of parent (SEQ ID NO: 8)
$^D$ +++ = >95% ee ++ = 90-95% EE + = 80-90% EE None = 30-80% ee Racemic = <30% ee S = (2S,5R) Product Table 6 provides the activities of exemplary enone reductases on conversion of (Z)-ethyl 2-cyano-3-phenylbut-2-enoate to ethyl 2-cyano-3-phenylbutanoate.

TABLE 6

| SEQ ID NO: | ethyl 2-cyano-3-phenylbut-2-enoate % conv.$^a$ |
|---|---|
| 53/54 | ++++ |
| 55/56 | ++ |
| 51/52 | + |
| 57/58 | + |
| 61/62 | + |
| 185/186 | + |
| 131/132 | + |
| 173/174 | +++ |
| 17/18 | + |
| 139/140 | + |
| 45/46 | + |
| 7/8 | + |
| 9/10 | + |
| 39/40 | ++ |
| 123/124 | + |
| 133/134 | + |
| 13/14 | + |
| 137/138 | + |
| 129/130 | + |
| 43/44 | +++ |
| 177/178 | ++ |
| 11/12 | + |
| 141/142 | + |
| 161/162 | + |

TABLE 6-continued ethyl 2-cyano-3-phenylbut-2-enoate

| SEQ ID NO: | % conv.[a] |
|---|---|
| 135/136 | + |
| 127/128 | ++ |
| 113/114 | + |
| 169/170 | ++++ |
| 125/126 | + |
| 179/180 | ++++ |
| 121/122 | + |
| 99/100 | ++++ |
| 115/116 | + |
| 165/166 | + |
| 25/26 | ++ |
| 145/146 | +++ |
| 183/183 | ++++ |
| 67/68 | + |
| 155/156 | ++ |
| 71/72 | + |
| 105/106 | + |
| 73/74 | + |
| 109/110 | + |
| 89/90 |  |
| 75/76 | + |
| 159/160 | + |
| 35/36 | ++ |
| 21/22 | ++ |
| 107/108 | + |
| 175/176 | +++ |
| 37/38 | + |
| 69/70 | + |
| 117/118 | + |
| 171/172 | + |
| 33/34 | + |
| 47/48 | +++ |
| 163/164 | + |
| 157/158 | ++ |
| 149/150 | + |
| 153/154 | ++ |
| 63/64 | + |
| 23/24 | ++++ |
| 87/88 | + |
| 49/50 | +++ |
| 97/98 | + |
| 95/96 | ++ |
| 181/182 | ++ |
| 81/82 | ++ |
| 77/78 | + |
| 103/104 | + |
| 27/28 | ++++ |
| 19/20 | +++ |
| 143/144 | ++++ |
| 151/152 | ++ |
| 147/148 | ++++ |
| 83/84 | + |
| 85/86 | + |
| 31/32 | + |
| 65/66 | + |
| 101/102 | + |
| 29/30 | ++++ |
| 93/94 | +++ |
| 91/92 | ++++ |
| 15/16 | + |

[a] + = 100-500% of parent (SEQ ID NO: 8) ++ = 500-1000% of parent +++ = 1000-2000% of parent ++++ = >2000% of parent Table 7 shows the activities of exemplary enone reductases on the conversion of 8a-methyl-3,4,8,8a-tetrahydronaphthalene-1,6(2H,7H)-dione to 8a-methylhexahydronaphthalene-1,6(2H,7H)-dione.

TABLE 7

8a-methyl-3,4,8,8a-tetrahydronaphthalene-1,6(2H,7H)-dione

| SEQ ID NO: | % conv.[a] |
|---|---|
| 185/186 | + |
| 131/132 | ++ |
| 173/174 | + |
| 139/140 | + |
| 7/8 | + |
| 41/42 | +++ |
| 9/10 | + |
| 39/40 | + |
| 123/124 | ++ |
| 133/134 | + |
| 137/138 | ++ |
| 119/120 | ++ |
| 129/130 |  |
| 43/44 | + |
| 177/178 | ++ |
| 11/12 | ++ |
| 141/142 | + |
| 161/162 | ++ |
| 135/136 | ++ |
| 127/128 | + |
| 113/114 | +++ |
| 169/170 | ++ |
| 125/126 | ++ |
| 179/180 | ++ |
| 121/122 | ++ |
| 99/100 | + |
| 115/116 | + |
| 165/166 | +++ |
| 111/112 | + |
| 145/146 | + |
| 183/183 | ++ |
| 67/68 | ++ |
| 167/168 | ++ |
| 71/72 | ++ |
| 105/106 | ++ |
| 75/76 | + |
| 159/160 | +++ |
| 107/108 | + |
| 175/176 | ++ |
| 117/118 | ++ |
| 171/172 | ++++ |
| 33/34 | + |
| 163/164 | ++++ |
| 187/188 | + |
| 87/88 | +++ |
| 97/98 | ++ |
| 181/182 | ++ |
| 81/82 | +++ |
| 77/78 | + |
| 103/104 | +++ |
| 143/144 | + |
| 85/86 | ++ |

[a] + = 100-200% of parent (SEQ ID NO: 8) ++ = 200-500% of parent +++ = 500-1000% of parent ++++ = >1000% of parent All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

That which is claimed is:

1. An isolated enone reductase polypeptide comprising an amino acid sequence that is at least 80% identical to a reference sequence set forth in SEQ ID: 8, wherein the amino acid sequence comprises one or more residue differences as compared to the reference sequence, wherein the residue corresponding to X117 is a cysteine or nonpolar, aliphatic, basic, acidic, polar, or aromatic residue, selected from C, L, A, M, V, I, N, Q, E, F, and S, wherein said enone reductase polypeptide has enone reductase activity.

2. The enone reductase polypeptide of claim 1, wherein the polypeptide comprises a substitution set selected from:
   the residue corresponding to X38 is S and X117 is A;
   the residue corresponding to X83 is K and X117 is I;

the residue corresponding to X83 is I and X117 is I;
the residue corresponding to X117 is A and X122 is T;
the residue corresponding to X117 is E and X386 is D;
the residue corresponding to X38 is S, X83 is I and X117 is L;
the residue corresponding to X38 is S, X75 is L, X83 is I, X117 is I and X255 is P;
the residue corresponding to X38 is S, X83 is I, X117 is I and X119 is V;
the residue corresponding to X38 is S, X40 is Y, X83 is I and X117 is A;
the residue corresponding to X38 is S, X83 is I, X117 is A and X251 is D;
the residue corresponding to X38 is S, X83 is I, X117 is A and X251 is A;
the residue corresponding to X38 is S, X83 is I, X117 is I, X153 is E, X251 is W, X295 is T, X296 is F and X297 is Y;
the residue corresponding to X38 is S, X83 is I, X117 is I, X251 is A, X295 is N, X296 is F and X297 is W;
the residue corresponding to X38 is S, X83 is I, X117 is A, X251 is Y, X295 is T, X296 is F and X297 is W;
the residue corresponding to X38 is S, X83 is I, X117 is I, X295 is T and X296 is A;
the residue corresponding to X38 is S, X83 is I, X117 is F and X251 is S;
the residue corresponding to X38 is S, X83 is I, X117 is L, X209 is D, X251 is S, X376 is K and X400 is T;
the residue corresponding to X38 is S, X83 is I, X117 is F, X251 is V and X376 is I;
the residue corresponding to X38 is S, X83 is I, X117 is F, X251 is S, X295 is N, X296 is G and X297 is F;
the residue corresponding to X28 is P, X83 is I, X117 is A and X251 is V;
the residue corresponding to X83 is I, X117 is N, X295 is T, X296 is G and X297 is F;
the residue corresponding to X83 is I, X117 is S, X251 is V, X296 is R and X297 is F;
the residue corresponding to X38 is S, X83 is I, X117 is N and X251 is V;
the residue corresponding to X38 is S, X83 is I, X117 is A and X330 is Y;
the residue corresponding to X38 is S, X40 is E, X75 is S, X83 is I and X117 is I;
the residue corresponding to X38 is S, X83 is I and X117 is I; and
the residue corresponding to X83 is E, X117 is I and X333 is A.

3. The enone reductase polypeptide of claim 1, wherein the amino acid sequence comprises the following substitutions from X38 is S, X83 is I, X117 is F, X251 is S, X295 is N, X296 is G and X297 is F; or the residue corresponding to X38 is S, X83 is I, X117 is N and X251 is V.

4. The enone reductase polypeptide of claim 1, wherein the amino acid sequence comprises the following substitutions X38 is S, X83 is I, X117 is F, X251 is S, X295 is N, X296 is G and X297 is F.

5. The enone reductase of claim 1, wherein the amino acid sequence comprises a substitution at X117 is selected from Q, A, I, C, V, or L and further comprising a substitution or substitution set selected from:
the residue corresponding to X83 is I;
the residue corresponding to X122 is T;
the residue corresponding to X38 is S;
the residue corresponding to X38 is S, and X83 is I;
the residue corresponding to X38 is S, and X83 is I;
the residue corresponding to X28 is P, X83 is I, and X251 is V;
the residue corresponding to X38 is S, X83 is I, and X251 is D;
the residue corresponding to X38 is S, X83 is I, and X251 is A;
the residue corresponding to X38 is S, X40 is Y, and X83 is I;
the residue corresponding to X38 is S, X83 is I, and X330 is Y;
the residue corresponding to X38 is S, X83 is I, and X119 is V;
the residue corresponding to X38 is S, X40 is E, X75 is S, and X83 is I;
the residue corresponding to X38 is S, X83 is I, D295 is T and X296 is A;
the residue corresponding to X38 is S, X75 is L, X83 is I, and X255 is P; and
the residue corresponding to X38 is S, X83 is I, 251 is A, X295 is N, X296 is F and X297 is W.

6. The enone reductase of claim 1, wherein the amino acid sequence comprises a substitution at the residue corresponding to X117, wherein the substitution is selected from M, N, L, S, F, or I, and a further substitution selected from:
the residue corresponding to X386 is D;
the residue corresponding to X83 is I, X251 is V, X296 is R and X297 is F;
the residue corresponding to X38 is S, X83 is I, X251 is S;
the residue corresponding to X38 is S, X83 is I, X251 is S, X295 is N, X296 is G and X297 is F;
the residue corresponding to X38 is S, X83 is I, X209 is D, X251 is S, X376 is K, and 400 is T;
the residue corresponding to X38 is S, X83 is I, and X251 is V; and
the residue corresponding to X83 is I, X295 is T, X296 is G and X297 is F.

7. The enone reductase of claim 1, wherein the amino acid sequence comprises a substitution at the residue corresponding to X117, wherein the substitution is selected from A, M, N, L, S, F, C, V, or I, and a further substitution selected from:
the residue corresponding to X38 is S;
the residue corresponding to X83 is I;
the residue corresponding to X122 is T;
the residue corresponding to X38 is S, and X83 is I;
the residue corresponding to X83 is E, and X333 is A;
the residue corresponding to X38 is S, X83 is I, and X251 is D;
the residue corresponding to X38 is S, X83 is I, X251 is A;
the residue corresponding to X38 is S, X75 is L, X83 is I, and X255 is P;
the residue corresponding to X38 is S, X83 is I, X119 is V;
the residue corresponding to X83 is I, X251 is V, X296 is R, X297 is F;
the residue corresponding to X38 is S, X83 is I, and X330 is Y;
the residue corresponding to X38 is S, X40 is E, X75 is S, X83 is I;
the residue corresponding to X83 is I, X295 is T, X296 is G and X297 is F; and
the residue corresponding to X28 is P, X83 is I, and X251 is V.

8. The enone reductase polypeptide of claim 1, wherein the amino acid sequence comprises residue corresponding to X38 is S, X83 is I, X117 is F, X251 is S, X295 is N, X296 is G and X297 is F.

9. The enone reductase of claim 1, wherein the amino acid sequence comprises a a substitution set selected from:

the residue corresponding to X117 is E and X386 is D;
the residue corresponding to X28 is P, X83 is I, X117 is A and X251 is V;
the residue corresponding to X38 is S, X83 is I, X117 is A and X330 is Y; and
the residue corresponding to X38 is S, X83 is I, X117 is F and X251 is S.

10. The enone reductase polypeptide of claim 1, wherein the amino acid sequence comprises a substitution set selected from:
X38 is S, X83 is I, X117 is A, X251 is Y, X295 is T, X296 is F, X297 is W; and
X38 is S, X83 is I, X117 is I, X251 is A, X295 is N, X296 is F, and X297 is W.

11. The enone reductase polypeptide of claim 1, wherein the amino acid sequence comprises a substitution at position W117, relative to SEQ ID NO:8.

12. The enone reductase polypeptide of claim 11, wherein the amino acid sequence comprises one of the following substitutions W117A/C/E/I/L/M/N/Q/V/F/X relative to SEQ ID NO: 8.

13. The enone reductase polypeptide of claim 1, wherein said enone reductase is an Old Yellow Enzyme (OYE).

14. The enone reductase polypeptide of claim 13, wherein said enone reductase polypeptide is a chimeric Old Yellow Enzyme (OYE) polypeptide.

* * * * *

SEQUENCE LISTING

<160> NUMBER OF SEQ ID NOS: 217

<210> SEQ ID NO 1
<211> LENGTH: 1203
<212> TYPE: DNA
<213> ORGANISM: Artificial Sequence
<220> FEATURE:
<223> OTHER INFORMATION: Old Yellow Enzyme 1 from Saccharomyces
      pastorianus

<400> SEQUENCE: 1

```
atgtctttcg ttaaggactt caagccgcag gcactgggcg acaccaacct gttcaaacct      60
attaaaattg ggaacaacga gctgctgcat cgcgcggtaa ttcctccgct gacccgcatg     120
cgcgctctgc atccgggcaa cattccgaac cgtgattggg ctgtggaata ctacacccag     180
cgtgcacagc gtccggggac aatgattatc acggagggtg cgttcatcag cccgcaggca     240
ggtgggtacg ataacgcgcc tggtgtttgg tcagaagaac agatggtcga atggacgaaa     300
atcttcaacg ctattcatga aaaaagtca tttgtgtggg tgcaactgtg ggtcctgggc     360
tgggccgcct ttccggataa cctggcgcgt gatgggttac gttacgattc tgcctccgat     420
aatgtgttta tggatgcgga acaggaggca aaagcgaaaa agctaacaa tccgcaacat     480 agcttgacta aagacgaaat taacaatat atcaaagaat atgttcaggc agctaagaac     540
tcgatcgctg cgggtgcgga cggcgtggaa attcactcag ccaacggtta tctgttaaat     600
cagttcctgg atccgcacag caacacacgc accgatgagt atggggggctc aattgaaaat     660 cgtgcacgtt ttactctgga agtcgttgac gcgctggttg aggccatcgg ccatgaaaaa     720
gtgggtttac gtctgagtcc gtacggcgtt ttcaactcta tgtcgggcgg cgcggaaacg     780
ggcattgttg ctcagtatgc ctatgtcgcg ggtgagctgg agaaacgcgc caaggcgggg     840
aaacgcctgg cgtttgttca tttagtcgaa ccacgcgtga caaacccttt tctgactgag     900
ggggagggcg aatacgaagg gggcagcaac gattttgttt attccatttg gaaaggtccg     960
gttatccgtg ccggcaactt cgcactgcac cctgaagttg tgcgcgaaga agttaaggac    1020
aaacgcaccc tgatcggcta cggccgcttc tttatttcaa atccagacct ggttgaccgc    1080
ttagaaaaag tctgccact gaacaagtat gaccgtgata cgttctacca gatgagcgcg    1140
catggttaca tcgactaccc gacctacgaa gaagccttaa aactgggctg ggacaaaaaa    1200
taa                                                                  1203
```

<210> SEQ ID NO 2
<211> LENGTH: 400
<212> TYPE: PRT
<213> ORGANISM: Artificial Sequence
<220> FEATURE:
<223> OTHER INFORMATION: Old Yellow Enzyme 1 from Saccharomyces
      pastorianus

<400> SEQUENCE: 2

```
Met Ser Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
    50                  55                  60
```

| | | | | | | | | | | | | | | |
|---|---|---|---|---|---|---|---|---|---|---|---|---|---|---|
| Pro | Gly | Thr | Met | Ile | Ile | Thr | Glu | Gly | Ala | Phe | Ile | Ser | Pro | Gln | Ala |
| 65 | | | | 70 | | | | | 75 | | | | | 80 | |
| Gly | Gly | Tyr | Asp | Asn | Ala | Pro | Gly | Val | Trp | Ser | Glu | Glu | Gln | Met | Val |
| | | | | 85 | | | | | 90 | | | | | 95 | |
| Glu | Trp | Thr | Lys | Ile | Phe | Asn | Ala | Ile | His | Glu | Lys | Lys | Ser | Phe | Val |
| | | | 100 | | | | | 105 | | | | | 110 | | |
| Trp | Val | Gln | Leu | Trp | Val | Leu | Gly | Trp | Ala | Ala | Phe | Pro | Asp | Asn | Leu |
| | | 115 | | | | | 120 | | | | | 125 | | | |
| Ala | Arg | Asp | Gly | Leu | Arg | Tyr | Asp | Ser | Ala | Ser | Asp | Asn | Val | Phe | Met |
| | 130 | | | | | 135 | | | | | 140 | | | | |
| Asp | Ala | Glu | Gln | Glu | Ala | Lys | Ala | Lys | Lys | Ala | Asn | Asn | Pro | Gln | His |
| 145 | | | | | 150 | | | | | 155 | | | | | 160 |
| Ser | Leu | Thr | Lys | Asp | Glu | Ile | Lys | Gln | Tyr | Ile | Lys | Glu | Tyr | Val | Gln |
| | | | | 165 | | | | | 170 | | | | | 175 | |
| Ala | Ala | Lys | Asn | Ser | Ile | Ala | Ala | Gly | Ala | Asp | Gly | Val | Glu | Ile | His |
| | | | 180 | | | | | 185 | | | | | 190 | | |
| Ser | Ala | Asn | Gly | Tyr | Leu | Leu | Asn | Gln | Phe | Leu | Asp | Pro | His | Ser | Asn |
| | | 195 | | | | | 200 | | | | | 205 | | | |
| Thr | Arg | Thr | Asp | Glu | Tyr | Gly | Gly | Ser | Ile | Glu | Asn | Arg | Ala | Arg | Phe |
| 210 | | | | | 215 | | | | | 220 | | | | | |
| Thr | Leu | Glu | Val | Val | Asp | Ala | Leu | Val | Glu | Ala | Ile | Gly | His | Glu | Lys |
| 225 | | | | | 230 | | | | | 235 | | | | | 240 |
| Val | Gly | Leu | Arg | Leu | Ser | Pro | Tyr | Gly | Val | Phe | Asn | Ser | Met | Ser | Gly |
| | | | | 245 | | | | | 250 | | | | | 255 | |
| Gly | Ala | Glu | Thr | Gly | Ile | Val | Ala | Gln | Tyr | Ala | Tyr | Val | Ala | Gly | Glu |
| | | | 260 | | | | | 265 | | | | | 270 | | |
| Leu | Glu | Lys | Arg | Ala | Lys | Ala | Gly | Lys | Arg | Leu | Ala | Phe | Val | His | Leu |
| | | 275 | | | | | 280 | | | | | 285 | | | |
| Val | Glu | Pro | Arg | Val | Thr | Asn | Pro | Phe | Leu | Thr | Glu | Gly | Glu | Gly | Glu |
| 290 | | | | | 295 | | | | | 300 | | | | | |
| Tyr | Glu | Gly | Gly | Ser | Asn | Asp | Phe | Val | Tyr | Ser | Ile | Trp | Lys | Gly | Pro |
| 305 | | | | | 310 | | | | | 315 | | | | | 320 |
| Val | Ile | Arg | Ala | Gly | Asn | Phe | Ala | Leu | His | Pro | Glu | Val | Val | Arg | Glu |
| | | | | 325 | | | | | 330 | | | | | 335 | |
| Glu | Val | Lys | Asp | Lys | Arg | Thr | Leu | Ile | Gly | Tyr | Gly | Arg | Phe | Phe | Ile |
| | | | 340 | | | | | 345 | | | | | 350 | | |
| Ser | Asn | Pro | Asp | Leu | Val | Asp | Arg | Leu | Glu | Lys | Gly | Leu | Pro | Leu | Asn |
| | | 355 | | | | | 360 | | | | | 365 | | | |
| Lys | Tyr | Asp | Arg | Asp | Thr | Phe | Tyr | Gln | Met | Ser | Ala | His | Gly | Tyr | Ile |
| | 370 | | | | | 375 | | | | | 380 | | | | |
| Asp | Tyr | Pro | Thr | Tyr | Glu | Glu | Ala | Leu | Lys | Leu | Gly | Trp | Asp | Lys | Lys |
| 385 | | | | | 390 | | | | | 395 | | | | | 400 |

<210> SEQ ID NO 3
<211> LENGTH: 1203
<212> TYPE: DNA
<213> ORGANISM: Artificial Sequence
<220> FEATURE:
<223> OTHER INFORMATION: Old Yellow Enzyme 2 from Saccharomyces
      cerevisiae

<400> SEQUENCE: 3

| | | |
|---|---|---|
| atgcctttcg ttaaggactt caagccgcag gcactgggcg acaccaacct gttcaaacct | 60 |
| attaaaattg ggaacaacga gctgctgcat cgcgcggtaa ttcctccgct gacccgcatg | 120 |
| cgcgctcagc atccgggcaa cattccgaac cgtgattggg ctgtggaata ctacgcccag | 180 |

-continued

```
cgtgcacagc gtccggggac actgattatc acggagggta cgttccctag cccgcagtca    240
ggtgggtacg ataacgcgcc tggtatttgg tcagaagaac agattaaaga atggacgaaa    300
atcttcaagg ctattcatga aaataagtca tttgcgtggg tgcaactgtg ggtcctgggc    360
tgggccgcct ttccggatac gctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaacccttt tctgactgag    900
ggggagggcg aatacaacgg gggcagcaac aaatttgctt attccatttg gaaaggtccg    960
attatccgtg ccggcaactt cgcactgcac cctgaagttg tgcgcgaaga agttaaggac   1020
cctcgcaccc tgatcggcta cggccgcttc tttatttcaa atccagacct ggttgaccgc   1080
ttagaaaaag gtctgccact gaacaagtat gaccgtgata cgttctacaa aatgagcgcg   1140
gagggttaca tcgactaccc gacctacgaa gaagccttaa aactgggctg ggacaaaaac   1200
taa                                                                 1203
```

<210> SEQ ID NO 4
<211> LENGTH: 400
<212> TYPE: PRT
<213> ORGANISM: Artificial Sequence
<220> FEATURE:
<223> OTHER INFORMATION: Old Yellow Enzyme 2 from Saccharomyces cerevisiae

<400> SEQUENCE: 4

```
Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Arg Asp Trp Ala Val Glu Tyr Tyr Ala Gln Arg Ala Gln Arg
    50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175
```

```
Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
370                 375                 380

Asp Tyr Pro Thr Tyr Glu Glu Ala Leu Lys Leu Gly Trp Asp Lys Asn
385                 390                 395                 400

<210> SEQ ID NO 5
<211> LENGTH: 1203
<212> TYPE: DNA
<213> ORGANISM: Artificial Sequence
<220> FEATURE:
<223> OTHER INFORMATION: Old Yellow Enzyme 3 from Saccharomyces
      cerevisiae

<400> SEQUENCE: 5
atgcctttcg ttaagggctt cgagccgatt tcactgcgcg acaccaacct gttcgaacct      60
attaaaattg gaacacacac gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtatttgg tcagacgaac aggttgccga atggaagaac     300
atcttcctgg ctattcatga ctgtcagtca tttgcgtggg tgcaactgtg agcctgggc     360 tgggcctcct ttccggatgt gctggcgcgt gatgggttac gttacgattg tgcctccgat     420
cgtgtgtata tgaatgcgac actgcaggaa aaagcgaaag atgctaacaa tctggaacat     480
agcttgacta agacgatat taaacaatat atcaaagatt atattcatgc agctaagaac     540
tcgatcgctg cgggtgcgga cggcgtggaa attcactcag ccaacggtta tctgttaaat     600
cagttcctgg atccgcacag caacaaacgc accgatgagt atgggggcac aattgaaaat     660
cgtgcacgtt ttactctgga agtcgttgac gcgctgattg agaccatcgg cccagaacgc     720
gtgggtttac gtctgagtcc gtacggcact ttcaactcta tgtcgggcgg cgcggaaccg     780
ggcattattg ctcagtatag ctatgtcctg ggtgagctgg agaaacgcgc caaggcgggg     840
```

```
aaacgcctgg cgtttgttca tttagtcgaa ccacgcgtga cagacccttc tctggttgag    900
ggggagggcg aatactcaga gggcaccaac gatttttgctt attccatttg gaaaggtccg    960
```

```
aaacgcctgg cgtttgttca tttagtcgaa ccacgcgtga cagacccttc tctggttgag    900
ggggagggcg aatactcaga gggcaccaac gatttgtgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200
taa                                                                1203

<210> SEQ ID NO 6
<211> LENGTH: 400
<212> TYPE: PRT
<213> ORGANISM: Artificial Sequence
<220> FEATURE:
<223> OTHER INFORMATION: Old Yellow Enzyme 3 from Saccharomyces
      cerevisiae

<400> SEQUENCE: 6

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
        115                 120                 125

Ala Arg Asp Gly Leu Arg Tyr Asp Cys Ala Ser Asp Arg Val Tyr Met
    130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Lys Arg Thr Asp Glu Tyr Gly Gly Thr Ile Glu Asn Arg Ala Arg Phe
    210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
            260                 265                 270

Leu Glu Lys Arg Ala Lys Ala Gly Lys Arg Leu Ala Phe Val His Leu
        275                 280                 285
```

-continued

| | | | | | | | | | | | | |
|---|---|---|---|---|---|---|---|---|---|---|---|---|
|Val|Glu|Pro|Arg|Val|Thr|Asp|Pro|Ser|Leu|Val|Glu|Gly Glu Gly Glu|
| |290| | | |295| | | |300| | | |

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 7
<211> LENGTH: 1200
<212> TYPE: DNA
<213> ORGANISM: Artificial Sequence
<220> FEATURE:
<223> OTHER INFORMATION: ERED chimera of Old Yellow Enzyme

<400> SEQUENCE: 7

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 8
<211> LENGTH: 400
<212> TYPE: PRT
<213> ORGANISM: Artificial Sequence
<220> FEATURE:
<223> OTHER INFORMATION: ERED chimera of Old Yellow Enzyme

<400> SEQUENCE: 8

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
    195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
    355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 9
<211> LENGTH: 1200
<212> TYPE: DNA

<213> ORGANISM: Artificial Sequence
<220> FEATURE:
<223> OTHER INFORMATION: ERED variant

<400> SEQUENCE: 9

```
atgtctttcg ttaaggactt caagccgcag gcactgcgcg acaccaacct gttcgaacct      60
attaaaattg ggaacacaca gctggctcat cgcgcggtaa tgcctccgct gacccgcctg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg cccagtatgc ctatgtcctg ggtgagctgg agcgtcgcgc caaggcgggg     840
aaacgcctgg cgtttgttca tttagtcgaa ccacgcgtgg cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 10
<211> LENGTH: 400
<212> TYPE: PRT
<213> ORGANISM: Artificial Sequence
<220> FEATURE:
<223> OTHER INFORMATION: ERED variant

<400> SEQUENCE: 10

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Leu Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
                195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
                275                 280                 285

Val Glu Pro Arg Val Ala Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
                370                 375                 380

Asp Tyr Pro Thr Tyr Glu Glu Ala Val Asp Leu Gly Trp Asn Lys Asn
385                 390                 395                 400

<210> SEQ ID NO 11
<211> LENGTH: 1200
<212> TYPE: DNA
<213> ORGANISM: Artificial Sequence
<220> FEATURE:
<223> OTHER INFORMATION: ERED variant

<400> SEQUENCE: 11
atgtctttcg ttaaggactt caagccgcag gcactgcgcg acaccaacct gttcgaacct     60
attaaaattg gaacacaca gctggctcat cgcgcggtaa tgcctccgct gacccgctcg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480 agcattacta aagacgaaat taacaatat gtcaaagaat atgttcaggc agctaagaac    540
tcgatcgctg cgggtgcgga cggcgtggaa attcactcag ccaacggtta tctgttaaat    600

| | | |
|---|---|---|
| cagttcctgg atccgcacag caacaaccgc accgatgagt atgggggctc aattgaaaat | 660 | |
| cgtgcacgtt ttactctgga agtcgttgac gcggtggttg atgccatcgg cccagaaaaa | 720 | |
| gtgggtttac gtctgagtcc gtacggcgtt ttcaactcta tgtcgggcgg cgcggaaacg | 780 | |
| ggcattgttg ctcagtatgc ctatgtcctg ggtgagctgg agcgtcgcgc caaggcgggg | 840 | |
| aaacgcctgg cgtttgttca tttagtcgaa ccacgcgtga cagacccttc tctggttgag | 900 | |
| ggggggggcg aatactcaga gggcaccaac gattttgctt attccatttg aaaggtccg | 960 | |
| attatccgtg ccggcaacta cgcactgtac cctgaagttg tgcgcgaaca agttaaggac | 1020 | |
| cctcgcaccc tgatcggcta cggccgcttc tttatttcaa atccagacct ggtttaccgc | 1080 | |
| ttagaagaag gtctgccact gaacaagtat gaccgttcta cgttctacac catgagcgcg | 1140 | |
| gagggttaca ccgactaccc gacctacgaa gaagccgtag atctgggctg aacaaaaac | 1200 | |

<210> SEQ ID NO 12
<211> LENGTH: 400
<212> TYPE: PRT
<213> ORGANISM: Artificial Sequence
<220> FEATURE:
<223> OTHER INFORMATION: ERED variant

<400> SEQUENCE: 12

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Ser Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
```

```
                260                 265                 270
Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Gly Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu Tyr Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 13
<211> LENGTH: 1200
<212> TYPE: DNA
<213> ORGANISM: Artificial Sequence
<220> FEATURE:
<223> OTHER INFORMATION: ERED variant

<400> SEQUENCE: 13
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggttgg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660 cgtgcacgtt ttactctgga agtcgttgac gcggtggttg atgccatcgg cccagaaaaa     720
gtgggtttac gtctgagtcc gtacggcgtt tcaactctca tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 14
<211> LENGTH: 400
<212> TYPE: PRT
```

<213> ORGANISM: Artificial Sequence
<220> FEATURE:
<223> OTHER INFORMATION: ERED variant

<400> SEQUENCE: 14

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Leu Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 15
<211> LENGTH: 1200
<212> TYPE: DNA
<213> ORGANISM: Artificial Sequence
<220> FEATURE:
<223> OTHER INFORMATION: ERED variant

<400> SEQUENCE: 15

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggaggta cgttcatcag cccgcaggca      240
ggtgggcggg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag tctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 16
<211> LENGTH: 400
<212> TYPE: PRT
<213> ORGANISM: Artificial Sequence
<220> FEATURE:
<223> OTHER INFORMATION: ERED variant

<400> SEQUENCE: 16

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Arg Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala

```
                    100                 105                 110
Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
    195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
    275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
    355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 17
<211> LENGTH: 1200
<212> TYPE: DNA
<213> ORGANISM: Artificial Sequence
<220> FEATURE:
<223> OTHER INFORMATION: ERED variant

<400> SEQUENCE: 17
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240 ggtgggggtgg ataacgcgcc tggtgtttgg tcagacgaac aggttgccga atggaagaac    300
atcttcctgg ctattcatga ctgtcagtca tttgcgtggg tgcaactgtg gtcctgggc     360 tgggccgcct tccggataaa cctggcgcgt gatgggttac gttacgattc tgcctccgat    420
```

-continued

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gatttttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200
```

<210> SEQ ID NO 18
<211> LENGTH: 400
<212> TYPE: PRT
<213> ORGANISM: Artificial Sequence
<220> FEATURE:
<223> OTHER INFORMATION: ERED variant

<400> SEQUENCE: 18

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Val Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 19
<211> LENGTH: 1200
<212> TYPE: DNA
<213> ORGANISM: Artificial Sequence
<220> FEATURE:
<223> OTHER INFORMATION: ERED variant

<400> SEQUENCE: 19
atgtctttcg ttaaggactt caagccgcag gcactgcgcg acaccaacct gttcgaacct     60
attaaaattg gaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgtg tgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta agacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200

<210> SEQ ID NO 20
<211> LENGTH: 400
<212> TYPE: PRT
<213> ORGANISM: Artificial Sequence
<220> FEATURE:
<223> OTHER INFORMATION: ERED variant

<400> SEQUENCE: 20

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Cys Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

-continued

| Lys | Tyr | Asp | Arg | Ser | Thr | Phe | Tyr | Thr | Met | Ser | Ala | Glu | Gly | Tyr | Thr |
|     |     |     |     | 370 |     |     |     | 375 |     |     |     | 380 |     |     |     |

| Asp | Tyr | Pro | Thr | Tyr | Glu | Glu | Ala | Val | Asp | Leu | Gly | Trp | Asn | Lys | Asn |
| 385 |     |     |     |     | 390 |     |     |     |     | 395 |     |     |     |     | 400 |

<210> SEQ ID NO 21
<211> LENGTH: 1200
<212> TYPE: DNA
<213> ORGANISM: Artificial Sequence
<220> FEATURE:
<223> OTHER INFORMATION: ERED variant

<400> SEQUENCE: 21

```
atgtctttcg ttaaggactt caagccgcag gcactgcgcg acaccaacct gttcgaacct    60
attaaaattg gaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgct tgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta agacgaaat taacaatat gtcaaagaat atgttcaggc agctaagaac    540
tcgatcgctg cgggtgcgga cggcgtgaa attcactcag ccaacggtta tctgttaaat    600
cagttcctgg atccgcacag caacaaccgc accgatgagt atggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
gggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200
```

<210> SEQ ID NO 22
<211> LENGTH: 400
<212> TYPE: PRT
<213> ORGANISM: Artificial Sequence
<220> FEATURE:
<223> OTHER INFORMATION: ERED variant

<400> SEQUENCE: 22

| Met | Ser | Phe | Val | Lys | Asp | Phe | Lys | Pro | Gln | Ala | Leu | Arg | Asp | Thr | Asn |
| 1   |     |     |     | 5   |     |     |     |     | 10  |     |     |     |     | 15  |     |

| Leu | Phe | Glu | Pro | Ile | Lys | Ile | Gly | Asn | Thr | Gln | Leu | Ala | His | Arg | Ala |
|     |     |     | 20  |     |     |     |     | 25  |     |     |     |     | 30  |     |     |

| Val | Met | Pro | Pro | Leu | Thr | Arg | Met | Arg | Ala | Thr | His | Pro | Gly | Asn | Ile |
|     |     |     | 35  |     |     |     | 40  |     |     |     |     | 45  |     |     |     |

| Pro | Asn | Lys | Glu | Trp | Ala | Ala | Val | Tyr | Tyr | Gly | Gln | Arg | Ala | Gln | Arg |
|     |     | 50  |     |     |     |     | 55  |     |     |     |     | 60  |     |     |     |

| Pro | Gly | Thr | Met | Ile | Ile | Thr | Glu | Gly | Thr | Phe | Ile | Ser | Pro | Gln | Ala |
| 65  |     |     |     |     | 70  |     |     |     |     | 75  |     |     |     |     | 80  |

Gly Gly Tyr Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
            100                 105                 110
Trp Val Gln Leu Leu Val Leu Gly Trp Ala Ala Phe Pro Asp Asn Leu
        115                 120                 125
Ala Arg Asp Gly Leu Arg Tyr Asp Ser Ala Ser Asp Asn Val Tyr Met
    130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
        195                 200                 205
Asn Arg Thr Asp Glu Tyr Gly Gly Ser Ile Glu Asn Arg Ala Arg Phe
    210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Phe Asn Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
    290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Tyr Pro Thr Tyr Glu Glu Ala Val Asp Leu Gly Trp Asn Lys Asn
385                 390                 395                 400

<210> SEQ ID NO 23
<211> LENGTH: 1200
<212> TYPE: DNA
<213> ORGANISM: Artificial Sequence
<220> FEATURE:
<223> OTHER INFORMATION: ERED variant

<400> SEQUENCE: 23
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300

```
atcttcctgg ctattcatga ctgtcagtca tttgcgtggg tgcaactggc tgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat     480 agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggctc aattgaaaat     660 cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg aaaggtccg    960 attatccgtg ccggcaacta cgcactacac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 24
<211> LENGTH: 400
<212> TYPE: PRT
<213> ORGANISM: Artificial Sequence
<220> FEATURE:
<223> OTHER INFORMATION: ERED variant

<400> SEQUENCE: 24

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Asn Arg Thr Asp Glu Tyr Gly Gly Ser Ile Glu Asn Arg Ala Arg Phe
        210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 25
<211> LENGTH: 1200
<212> TYPE: DNA
<213> ORGANISM: Artificial Sequence
<220> FEATURE:
<223> OTHER INFORMATION: ERED variant

<400> SEQUENCE: 25
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgat ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480 agcattacta agacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atggggggctc aattgaaaat      660 cgtgcacgtt ttactctgga agtcgttgac gcggtggttg atgccatcgg cccagaaaaa      720
gtgggtttac gtctgagtcc gtacggcgtt ttcaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga cagaccctc tctggtgag      900 ggggagggcg aatactcaga gggcaccaac gattttgctt attccatttg gaaaggtccg      960
attatccgtg ccggcaacta cgcactgcac cctgaagttg tgcgcgaaca agttaaggac     1020
```

```
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 26
<211> LENGTH: 400
<212> TYPE: PRT
<213> ORGANISM: Artificial Sequence
<220> FEATURE:
<223> OTHER INFORMATION: ERED variant

<400> SEQUENCE: 26

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Met Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

```
                340             345             350
Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 27
<211> LENGTH: 1200
<212> TYPE: DNA
<213> ORGANISM: Artificial Sequence
<220> FEATURE:
<223> OTHER INFORMATION: ERED variant

<400> SEQUENCE: 27
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgttttgg tcagacgaac aggttgccga atggaagaac     300
atcttcctgg ctattcatga ctgtcagtca tttgcgtggg tgcaactggc ggtcctgggc     360
tggaccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta agacgaaat taaacaatat gtcaaagaat atgttcaggc agctaagaac     540
tcgatcgctg cgggtgcgga cggcgtgaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg aaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200

<210> SEQ ID NO 28
<211> LENGTH: 400
<212> TYPE: PRT
<213> ORGANISM: Artificial Sequence
<220> FEATURE:
<223> OTHER INFORMATION: ERED variant

<400> SEQUENCE: 28

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Thr Arg Met Arg Ala Thr His Pro Gly Asn Ile
            35                  40                  45
```

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Thr Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 29
<211> LENGTH: 1200
<212> TYPE: DNA
<213> ORGANISM: Artificial Sequence
<220> FEATURE:
<223> OTHER INFORMATION: ERED variant

<400> SEQUENCE: 29
atgtctttcg ttaaggactt caagccgcag gcactgcgcg acaccaacct gttcgaacct      60
attaaaattg gaacacacag ctggctcat cgcgcggtaa tgcctccgct gacccgcatg     120

```
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactggt ggtcctgggc    360
tgggccgcct ttccggataa cctggcgcgt gatgggttac gttacgattc tgcctccgat    420
aatgtgtata tgaatgcgga acaggaggaa aagcgaaaa aagctaacaa tccgcaacat     480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gatttttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 30
<211> LENGTH: 400
<212> TYPE: PRT
<213> ORGANISM: Artificial Sequence
<220> FEATURE:
<223> OTHER INFORMATION: ERED variant

<400> SEQUENCE: 30

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Val Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

```
                    180               185               190
Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 31
<211> LENGTH: 1200
<212> TYPE: DNA
<213> ORGANISM: Artificial Sequence
<220> FEATURE:
<223> OTHER INFORMATION: ERED variant

<400> SEQUENCE: 31
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgat tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
```

-continued

```
ggggagggcg aatactcaga gggcaccaac gattttgctt attccatttg gaaaggtccg      960
attatccgtg ccggcaacta cgcactgcac cctgaagttg tgcgcgaaca agttaaggac     1020
cctcgcaccc tgatcggcta cggccgcttc tttatttcaa atccagacct ggtttaccgc     1080
ttagaagaag gtctgccact gaacaagtat gaccgttcta cgttctacac catgagcgcg     1140
gagggttaca ccgactaccc gacctacgaa gaagccgtag atctgggctg aacaaaaac      1200
```

<210> SEQ ID NO 32
<211> LENGTH: 400
<212> TYPE: PRT
<213> ORGANISM: Artificial Sequence
<220> FEATURE:
<223> OTHER INFORMATION: ERED variant

<400> SEQUENCE: 32

```
Met Ser Phe Val Lys Asp Phe Lys Pro Gln Ala Leu Arg Asp Thr Asn
1               5                  10                 15

Leu Phe Glu Pro Ile Lys Ile Gly Asn Thr Gln Leu Ala His Arg Ala
            20                 25                 30

Val Met Pro Pro Leu Thr Arg Met Arg Ala Thr His Pro Gly Asn Ile
        35                 40                 45

Pro Asn Lys Glu Trp Ala Ala Val Tyr Tyr Gly Gln Arg Ala Gln Arg
    50                 55                 60

Pro Gly Thr Met Ile Ile Thr Glu Gly Thr Phe Ile Ser Pro Gln Ala
65                 70                 75                 80

Gly Gly Tyr Asp Asn Ala Pro Gly Val Trp Ser Asp Glu Gln Val Ala
                85                 90                 95

Glu Trp Lys Asn Ile Phe Leu Ala Ile His Asp Cys Gln Ser Phe Ala
           100                105                110

Trp Val Gln Leu Ile Val Leu Gly Trp Ala Ala Phe Pro Asp Asn Leu
       115                120                125

Ala Arg Asp Gly Leu Arg Tyr Asp Ser Ala Ser Asp Asn Val Tyr Met
   130                135                140

Asn Ala Glu Gln Glu Glu Lys Ala Lys Lys Ala Asn Asn Pro Gln His
145                150                155                160

Ser Ile Thr Lys Asp Glu Ile Lys Gln Tyr Val Lys Glu Tyr Val Gln
               165                170                175

Ala Ala Lys Asn Ser Ile Ala Ala Gly Ala Asp Gly Val Glu Ile His
           180                185                190

Ser Ala Asn Gly Tyr Leu Leu Asn Gln Phe Leu Asp Pro His Ser Asn
       195                200                205

Asn Arg Thr Asp Glu Tyr Gly Gly Ser Ile Glu Asn Arg Ala Arg Phe
   210                215                220

Thr Leu Glu Val Val Asp Ala Val Val Asp Ala Ile Gly Pro Glu Lys
225                230                235                240

Val Gly Leu Arg Leu Ser Pro Tyr Gly Val Phe Asn Ser Met Ser Gly
               245                250                255

Gly Ala Glu Thr Gly Ile Val Ala Gln Tyr Ala Tyr Val Leu Gly Glu
           260                265                270

Leu Glu Arg Arg Ala Lys Ala Gly Lys Arg Leu Ala Phe Val His Leu
       275                280                285

Val Glu Pro Arg Val Thr Asp Pro Ser Leu Val Glu Gly Glu Gly Glu
   290                295                300

Tyr Ser Glu Gly Thr Asn Asp Phe Ala Tyr Ser Ile Trp Lys Gly Pro
305                310                315                320
```

```
Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 33
<211> LENGTH: 1200
<212> TYPE: DNA
<213> ORGANISM: Artificial Sequence
<220> FEATURE:
<223> OTHER INFORMATION: ERED variant

<400> SEQUENCE: 33

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgga ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta agacgaaat taaacaatat gtcaaagaat atgttcaggc agctaagaac      540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg aaaggtccg      960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgacgaccc gacctacgaa gaagccgtag atctgggctg aacaaaaac     1200
```

<210> SEQ ID NO 34
<211> LENGTH: 400
<212> TYPE: PRT
<213> ORGANISM: Artificial Sequence
<220> FEATURE:
<223> OTHER INFORMATION: ERED variant

<400> SEQUENCE: 34

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
```

```
                    20                  25                  30
Val Met Pro Leu Thr Arg Met Arg Ala Thr His Pro Gly Asn Ile
        35                  40                  45
Pro Asn Lys Glu Trp Ala Ala Val Tyr Tyr Gly Gln Arg Ala Gln Arg
 50                  55                  60
Pro Gly Thr Met Ile Ile Thr Glu Gly Thr Phe Ile Ser Pro Gln Ala
 65                  70                  75                  80
Gly Gly Tyr Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
            100                 105                 110
Trp Val Gln Leu Glu Val Leu Gly Trp Ala Ala Phe Pro Asp Asn Leu
        115                 120                 125
Ala Arg Asp Gly Leu Arg Tyr Asp Ser Ala Ser Asp Asn Val Tyr Met
    130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
        195                 200                 205
Asn Arg Thr Asp Glu Tyr Gly Gly Ser Ile Glu Asn Arg Ala Arg Phe
    210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Phe Asn Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
    290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Asp Pro Thr Tyr Glu Glu Ala Val Asp Leu Gly Trp Asn Lys Asn
385                 390                 395                 400

<210> SEQ ID NO 35
<211> LENGTH: 1200
<212> TYPE: DNA
<213> ORGANISM: Artificial Sequence
<220> FEATURE:
<223> OTHER INFORMATION: ERED variant

<400> SEQUENCE: 35
```

-continued

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgaa tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat    660 cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg aaaggtccg      960 attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 36
<211> LENGTH: 400
<212> TYPE: PRT
<213> ORGANISM: Artificial Sequence
<220> FEATURE:
<223> OTHER INFORMATION: ERED variant

<400> SEQUENCE: 36

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Asn Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160
```

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 37
<211> LENGTH: 1200
<212> TYPE: DNA
<213> ORGANISM: Artificial Sequence
<220> FEATURE:
<223> OTHER INFORMATION: ERED variant

<400> SEQUENCE: 37
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgca ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660 cgtgcacgtt ttactctgga agtcgttgac gcggtggttg atgccatcgg cccagaaaaa     720

```
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 38
<211> LENGTH: 400
<212> TYPE: PRT
<213> ORGANISM: Artificial Sequence
<220> FEATURE:
<223> OTHER INFORMATION: ERED variant

<400> SEQUENCE: 38

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Gln Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

```
Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400
```

<210> SEQ ID NO 39
<211> LENGTH: 1200
<212> TYPE: DNA
<213> ORGANISM: Artificial Sequence
<220> FEATURE:
<223> OTHER INFORMATION: ERED variant

<400> SEQUENCE: 39

| | | | | | |
|---|---|---|---|---|---|
| atgtctttcg | ttaaggactt | caagccgcag | gcactgcgcg | acaccaacct | gttcgaacct | 60 |
| attaaaattg | ggaacacaca | gctggctcat | cgcgcggtaa | tgcctccgct | gacccgcatg | 120 |
| cgcgctaccc | atccgggcaa | cattccgaac | aaggagtggg | ctgcggttta | ctacggccag | 180 |
| cgtgcacagc | gtccggggac | aatgattatc | acggagggta | cgttcatcag | cccgcaggca | 240 |
| ggtgggtacg | ataacgcgcc | tggtgtttgg | tcagacgaac | aggttgccga | atggaagaac | 300 |
| atcttcctgg | ctattcatga | ctgtcagtca | tttgcgtggg | tgcaactgtg | ggtcctgggc | 360 |
| tgggccgcct | ttccggataa | cctggcgcgt | gatgggttac | gttacgattc | tgcctccgat | 420 |
| aatgtgtata | tgaatgcgga | acaggaggaa | aaagcgaaaa | agctaacaa | tccgcaacat | 480 |
| agcattacta | aagacgaaat | taaacaatat | gtcaaagaat | atgttcaggc | agctaagaac | 540 |
| tcgatcgctg | cgggtgcgga | cggcgtggaa | attcactcag | ccaacggtta | tctgttaaat | 600 |
| cagttcctgg | atccgcacag | caacaaccgc | accgatgagt | atgggggctc | aattgaaaat | 660 |
| cgtgcacgtt | ttactctgga | agtcgttgac | gcggtggttg | atgccatcgg | cccagaaaaa | 720 |
| gtgggtttac | gtctgagtcc | gtacggcgtt | ttcaactcta | tgtcgggcgg | cgcggaaacg | 780 |
| ggcattgttg | ctcagtatgc | ctatgtcctg | ggtgagctgg | agcgtcgcgc | caaggcgggg | 840 |
| aaacgcctgg | cgtttgttca | tttagtcgaa | ccacgcgtga | cagacccttc | tctggttgag | 900 |
| ggggagggcg | aatactcaga | gggcaccaac | gattttgctt | atcccatttg | gaaaggtccg | 960 |
| attatccgtg | ccggcaacta | cgcactgcac | cctgaagttg | tgcgcgaaca | agttaaggac | 1020 |
| cctcgcaccc | tgatcggcta | cggccgcttc | tttatttcaa | atccagacct | ggtttaccgc | 1080 |
| ttagaagaag | gtctgccact | gaacaagtat | gaccgttcta | cgttcacgac | catgagcgcg | 1140 |
| gagggttaca | ccgactaccc | gacctacgaa | gaagccgtag | atctgggctg | gaacaaaaac | 1200 |

<210> SEQ ID NO 40
<211> LENGTH: 400
<212> TYPE: PRT
<213> ORGANISM: Artificial Sequence
<220> FEATURE:
<223> OTHER INFORMATION: ERED variant

<400> SEQUENCE: 40

```
Met Ser Phe Val Lys Asp Phe Lys Pro Gln Ala Leu Arg Asp Thr Asn
1               5                   10                  15
Leu Phe Glu Pro Ile Lys Ile Gly Asn Thr Gln Leu Ala His Arg Ala
            20                  25                  30
Val Met Pro Pro Leu Thr Arg Met Arg Ala Thr His Pro Gly Asn Ile
        35                  40                  45
Pro Asn Lys Glu Trp Ala Ala Val Tyr Tyr Gly Gln Arg Ala Gln Arg
    50                  55                  60
Pro Gly Thr Met Ile Ile Thr Glu Gly Thr Phe Ile Ser Pro Gln Ala
65                  70                  75                  80
Gly Gly Tyr Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
            100                 105                 110
Trp Val Gln Leu Trp Val Leu Gly Trp Ala Ala Phe Pro Asp Asn Leu
        115                 120                 125
Ala Arg Asp Gly Leu Arg Tyr Asp Ser Ala Ser Asp Asn Val Tyr Met
    130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
        195                 200                 205
Asn Arg Thr Asp Glu Tyr Gly Gly Ser Ile Glu Asn Arg Ala Arg Phe
    210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Phe Asn Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
    290                 295                 300
Tyr Ser Glu Gly Thr Asn Asp Phe Ala Tyr Pro Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Thr Thr Met Ser Ala Glu Gly Tyr Thr
    370                 375                 380
Asp Tyr Pro Thr Tyr Glu Glu Ala Val Asp Leu Gly Trp Asn Lys Asn
385                 390                 395                 400

<210> SEQ ID NO 41
<211> LENGTH: 1200
<212> TYPE: DNA
```

<213> ORGANISM: Artificial Sequence
<220> FEATURE:
<223> OTHER INFORMATION: ERED variant

<400> SEQUENCE: 41

```
atgtctttcg ttaaggactt caagccgcag gcactgcgcg acaccaacct gttcgaacct        60
attaaaattg ggaacacaca gctggctcat cgcgcggtaa tgcctccgct gaatcgcatg       120
cgcgctaccc atccgggcaa cattccgaac aaggagtggg ctgcggttta ctacggccag       180
cgtgcacagc gtccggggac aatgattatc acggagggta cgttcatcag cccgcaggca       240
ggtgggtacg ataacgcgcc tggtgtttgg tcagacgaac aggttgccga atggaagaac       300
atcttcctgg ctattcatga ctgtcagtca tttgcgtggg tgcaactgtg ggtcctgggc       360
tgggccgcct ttccggataa cctggcgcgt gatgggttac gttacgattc tgcctccgat       420
aatgtgtata tgaatgcgga acaggaggaa aaagcgaaaa agctaacaa tccgcaacat        480
agcattacta aagacgaaat taaacaatat gtcaaagaat atgttcaggc agctaagaac       540
tcgatcgctg cgggtgcgga cggcgtggaa attcactcag ccaacggtta tctgttaaat       600
cagttcctgg atccgcacag caacaaccgc accgatgagt atggggggctc aattgaaaat       660
cgtgcacgtt ttactctgga agtcgttgac gcggtggttg atgccatcgg cccagaaaaa       720
gtgggtttac gtctgagtcc gtacggcgtt ttcaactcta tgtcgggcgg cgcggaaacg       780
ggcattgttg ctcagtatgc ctatgtcctg ggtgagctgg agcgtcgcgc caaggcgggg       840
aaacgcctgg cgtttgttca tttagtcgaa ccacgcgtga cagacccttc tctggttgag       900
ggggagggcg aatactcaga gggcaccaac gattttgctt attccatttg gaaaggtccg       960
attatccgtg ccggcaacta cgcactgcac cctgaagttg tgcgcgaaca agttaaggac      1020
cctcgcaccc tgatcggcta cggccgcttc tttatttcaa atccagacct ggtttaccgc      1080
ttagaagaag gtctgccact gaacaagtat gaccgttcta cgttctacac catgagcgcg      1140
gagggttaca ccgactaccc gacctacgaa gaagccgtag atctgggctg aacaaaaac       1200
```

<210> SEQ ID NO 42
<211> LENGTH: 400
<212> TYPE: PRT
<213> ORGANISM: Artificial Sequence
<220> FEATURE:
<223> OTHER INFORMATION: ERED variant

<400> SEQUENCE: 42

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Asn Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125
```

```
Ala Arg Asp Gly Leu Arg Tyr Asp Ser Ala Ser Asp Asn Val Tyr Met
        130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
        180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 43
<211> LENGTH: 1200
<212> TYPE: DNA
<213> ORGANISM: Artificial Sequence
<220> FEATURE:
<223> OTHER INFORMATION: ERED variant

<400> SEQUENCE: 43
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgccg gtccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taacaatat gtcaaagaat atgttcaggc agctaagaac     540
tcgatcgctg cgggtgcgga cggcgtggaa attcactcag ccaacggtta tctgttaaat     600
```

```
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggca atactcaga gggcaccaac gattttgctt attccatttg gaaaggtccg    960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 44
<211> LENGTH: 400
<212> TYPE: PRT
<213> ORGANISM: Artificial Sequence
<220> FEATURE:
<223> OTHER INFORMATION: ERED variant

<400> SEQUENCE: 44

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Gly Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
```

```
                260                 265                 270
Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Glu Gly Lys
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 45
<211> LENGTH: 1200
<212> TYPE: DNA
<213> ORGANISM: Artificial Sequence
<220> FEATURE:
<223> OTHER INFORMATION: ERED variant

<400> SEQUENCE: 45
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtg gtcctgggc      360 tgggccgccc cgccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaat      660 cgtgcacgtt ttactctgga agtcgttgac gcggtggttg atgccatcgg cccagaaaaa     720
gtgggtttac gtctgagtcc gtacggcgtt tcaactcta tgtcgggcgg cgcggaaacg      780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 46
<211> LENGTH: 400
<212> TYPE: PRT
```

<213> ORGANISM: Artificial Sequence
<220> FEATURE:
<223> OTHER INFORMATION: ERED variant

<400> SEQUENCE: 46

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Pro Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 47
<211> LENGTH: 1200
<212> TYPE: DNA
<213> ORGANISM: Artificial Sequence
<220> FEATURE:
<223> OTHER INFORMATION: ERED variant

<400> SEQUENCE: 47

```
atgtctttcg ttaaggactt caagccgcag gcactgcgcg acaccaacct gttcgaacct      60
attaaaattg ggaacacaca gctggctcat cgcgcggtaa tgcctccgct gagccgcatg     120
cgcgctaccc atccgggcaa cattccgaac aaggagtggg ctgcggttta ctacggccag     180
cgtgcacagc gtccggggac aatgattatc acggagggta cgttgatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgat cgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgccgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gatttgcctt attccatttg gaaaggtccg     960
attatccgtg ccggcaacta cgcactgcac cctgaagtcg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 48
<211> LENGTH: 400
<212> TYPE: PRT
<213> ORGANISM: Artificial Sequence
<220> FEATURE:
<223> OTHER INFORMATION: ERED variant

<400> SEQUENCE: 48

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Ser Arg Met Arg Ala Thr His Pro Gly Asn Ile
            35                  40                  45

Pro Asn Lys Glu Trp Ala Ala Val Tyr Tyr Gly Gln Arg Ala Gln Arg
        50                  55                  60

Pro Gly Thr Met Ile Ile Thr Glu Gly Thr Leu Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala

```
                    100                 105                 110
Trp Val Gln Leu Ile Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
    195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Pro Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
    275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
    355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 49
<211> LENGTH: 1200
<212> TYPE: DNA
<213> ORGANISM: Artificial Sequence
<220> FEATURE:
<223> OTHER INFORMATION: ERED variant

<400> SEQUENCE: 49
atgtctttcg ttaaggactt caagccgcag gcactgcgcg acaccaacct gttcgaacct      60
attaaaattg gaacacaca gctggctcat cgcgcggtaa tgcctccgct gagccgcatg     120
cgcgctaccc atccgggcaa cattccgaac aaggagtggg ctgcggttta ctacggccag     180
cgtgcacagc gtccggggac aatgattatc acgagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgat cgtcgttggc     360
tgggccgcct ttccggataa cctggcgcgt gatgggttac gttacgattc tgcctccgat     420
```

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 50
<211> LENGTH: 400
<212> TYPE: PRT
<213> ORGANISM: Artificial Sequence
<220> FEATURE:
<223> OTHER INFORMATION: ERED variant

<400> SEQUENCE: 50

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ile Val Val Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
                275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 51
<211> LENGTH: 1200
<212> TYPE: DNA
<213> ORGANISM: Artificial Sequence
<220> FEATURE:
<223> OTHER INFORMATION: ERED variant

<400> SEQUENCE: 51

| | | |
|---|---|---|
| atgtctttcg ttaaggactt caagccgcag gcactgcgcg acaccaacct gttcgaacct | 60 |
| attaaaattg gaacacaca gctggctcat cgcgcggtaa tgcctccgct gagccgctac | 120 |
| cgcgctaccc atccgggcaa cattccgaac aaggagtggg ctgcggttta ctacggccag | 180 |
| cgtgcacagc gtccggggac aatgattatc acggagggta cgttcatcag cccgcaggca | 240 |
| ggtgggatcg ataacgcgcc tggtgtttgg tcagacgaac aggttgccga atggaagaac | 300 |
| atcttcctgg ctattcatga ctgtcagtca tttgcgtggg tgcaactggc cgtcctgggc | 360 |
| tgggccgcct ttccggataa cctggcgcgt gatgggttac gttacgattc tgcctccgat | 420 |
| aatgtgtata tgaatgcgga acaggaggaa aaagcgaaaa aagctaacaa tccgcaacat | 480 |
| agcattacta aagacgaaat taaacaatat gtcaaagaat atgttcaggc agctaagaac | 540 |
| tcgatcgctg cgggtgcgga cggcgtggaa attcactcag ccaacggtta tctgttaaat | 600 |
| cagttcctgg atccgcacag caacaaccgc accgatgagt atgggggctc aattgaaaat | 660 |
| cgtgcacgtt ttactctgga agtcgttgac gcggtggttg atgccatcgg cccagaaaaa | 720 |
| gtgggtttac gtctgagtcc gtacggtgtt ttcaactcta tgtcgggcgg cgcggaaacg | 780 |
| ggcattgttg ctcagtatgc ctatgtcctg ggtgagctgg agcgtcgcgc caaggcgggg | 840 |
| aaacgcctgg cgtttgttca tttagtcgaa ccacgcgtga cagacccttc tctggttgag | 900 |
| ggggagggcg aatactcaga gggcaccaac gattttgctt attccatttg gaaaggtccg | 960 |
| attatccgtg ccggcaacta cgcactgcac cctgaagttg tgcgcgaaca agttaaggac | 1020 |
| cctcgcaccc tgatcggcta cggccgcttc tttatttcaa atccagacct ggtttaccgc | 1080 |
| ttagaagaag gtctgccact gaacaagtat gaccgttcta cgttctacac catgagcgcg | 1140 |
| gagggttaca ccgactaccc gacctacgaa gaagccgtag atctgggctg gaacaaaaac | 1200 |

<210> SEQ ID NO 52
<211> LENGTH: 400
<212> TYPE: PRT
<213> ORGANISM: Artificial Sequence
<220> FEATURE:
<223> OTHER INFORMATION: ERED variant

<400> SEQUENCE: 52

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Tyr Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

```
Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400
```

<210> SEQ ID NO 53
<211> LENGTH: 1200
<212> TYPE: DNA
<213> ORGANISM: Artificial Sequence
<220> FEATURE:
<223> OTHER INFORMATION: ERED variant

<400> SEQUENCE: 53

```
atgtctttcg ttaaggactt caagccgcag gcactgcgcg acaccaacct gttcgaacct      60
attaaaattg ggaacacaca gctggctcat cgcgcggtaa tgcctccgct gagccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactggc cgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt gataactcca tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gatttggctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtac gaccgttcta cgttctacac catgagcgcg    1140
gagggttaca ccgactaccc gacctacgaa gaagccgtag atctgggctg gaacaaaaac    1200
```

<210> SEQ ID NO 54
<211> LENGTH: 400
<212> TYPE: PRT
<213> ORGANISM: Artificial Sequence
<220> FEATURE:
<223> OTHER INFORMATION: ERED variant

<400> SEQUENCE: 54

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80
```

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Asp Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 55
<211> LENGTH: 1200
<212> TYPE: DNA
<213> ORGANISM: Artificial Sequence
<220> FEATURE:
<223> OTHER INFORMATION: ERED variant

<400> SEQUENCE: 55
atgtctttcg ttaaggactt caagccgcag gcactgcgcg acaccaacct gttcgaacct      60
attaaaattg gaacacaca gctggctcat cgcgcggtaa tgcctccgct gagccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggatcg ataacgcgcc tggtgtttgg tcagacgaac aggttgccga atggaagaac      300

```
atcttcctgg ctattcatga ctgtcagtca tttgcgtggg tgcaactggc cgtcctgggc    360
tgggccgcct ttccggataa cctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat    660 cgtgcacgtt ttactctgga agtcgttgac gcggtggttg atgccatcgg cccagaaaaa    720
gtgggtttac gtctgagtcc gtacggcgtt gcgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 56
<211> LENGTH: 400
<212> TYPE: PRT
<213> ORGANISM: Artificial Sequence
<220> FEATURE:
<223> OTHER INFORMATION: ERED variant

<400> SEQUENCE: 56

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Asn Arg Thr Asp Glu Tyr Gly Gly Ser Ile Glu Asn Arg Ala Arg Phe
        210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ala Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 57
<211> LENGTH: 1200
<212> TYPE: DNA
<213> ORGANISM: Artificial Sequence
<220> FEATURE:
<223> OTHER INFORMATION: ERED variant

<400> SEQUENCE: 57

```
atgtctttcg ttaaggactt caagccgcag gcactgcgcg acaccaacct gttcgaacct      60
attaaaattg gaacacaca gctggctcat cgcgcggtaa tgcctccgct gagccgcatg     120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat     480
agcattacta agacgaaat taaacaatat gtcaaagaat atgttcaggc agctaagaac    540
tcgatcgctg cgggtgcgga cggcgtgaaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt tggaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaccttta cctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
```

```
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 58
<211> LENGTH: 400
<212> TYPE: PRT
<213> ORGANISM: Artificial Sequence
<220> FEATURE:
<223> OTHER INFORMATION: ERED variant

<400> SEQUENCE: 58

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Glu Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Trp Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Thr Phe Tyr Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

```
                    340                 345                 350
Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 59
<211> LENGTH: 1200
<212> TYPE: DNA
<213> ORGANISM: Artificial Sequence
<220> FEATURE:
<223> OTHER INFORMATION: ERED variant

<400> SEQUENCE: 59
atgtctttcg ttaaggactt caagccgcag gcactgcgcg acaccaacct gttcgaacct     60
attaaaattg gaacacaca gctggctcat cgcgcggtaa tgcctccgct gagccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aagcgaaaa agctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggctc aattgaaaat    660
cgtgcacgtt ttactctgga agtcgttgac gcggtggttg atgccatcgg cccagaaaaa    720
gtgggtttac gtctgagtcc gtacggcgtt gcgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaactttg gctggttgag    900
ggggagggcg aatactcaga gggcaccaac gattttgctt attccatttg aaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200

<210> SEQ ID NO 60
<211> LENGTH: 400
<212> TYPE: PRT
<213> ORGANISM: Artificial Sequence
<220> FEATURE:
<223> OTHER INFORMATION: ERED variant

<400> SEQUENCE: 60

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Ser Arg Met Arg Ala Thr His Pro Gly Asn Ile
            35                  40                  45
```

| | | | | | | | | | | | | |
|---|---|---|---|---|---|---|---|---|---|---|---|---|
|Pro|Asn|Lys|Glu|Trp|Ala|Ala|Val|Tyr|Tyr|Gly|Gln|Arg|Ala|Gln|Arg|
|   50|   |   |   |   55|   |   |   |   |   60|   |   |   |   |   |   |

Pro Asn Lys Glu Trp Ala Ala Val Tyr Tyr Gly Gln Arg Ala Gln Arg
 50              55              60

Pro Gly Thr Met Ile Ile Thr Glu Gly Thr Phe Ile Ser Pro Gln Ala
 65              70              75              80

Gly Gly Ile Asp Asn Ala Pro Gly Val Trp Ser Asp Glu Gln Val Ala
             85              90              95

Glu Trp Lys Asn Ile Phe Leu Ala Ile His Asp Cys Gln Ser Phe Ala
            100             105             110

Trp Val Gln Leu Ile Val Leu Gly Trp Ala Ala Phe Pro Asp Asn Leu
            115             120             125

Ala Arg Asp Gly Leu Arg Tyr Asp Ser Ala Ser Asp Asn Val Tyr Met
130             135             140

Asn Ala Glu Gln Glu Glu Lys Ala Lys Lys Ala Asn Asn Pro Gln His
145             150             155             160

Ser Ile Thr Lys Asp Glu Ile Lys Gln Tyr Val Lys Glu Tyr Val Gln
            165             170             175

Ala Ala Lys Asn Ser Ile Ala Ala Gly Ala Asp Gly Val Glu Ile His
            180             185             190

Ser Ala Asn Gly Tyr Leu Leu Asn Gln Phe Leu Asp Pro His Ser Asn
            195             200             205

Asn Arg Thr Asp Glu Tyr Gly Gly Ser Ile Glu Asn Arg Ala Arg Phe
210             215             220

Thr Leu Glu Val Val Asp Ala Val Val Asp Ala Ile Gly Pro Glu Lys
225             230             235             240

Val Gly Leu Arg Leu Ser Pro Tyr Gly Val Ala Asn Ser Met Ser Gly
            245             250             255

Gly Ala Glu Thr Gly Ile Val Ala Gln Tyr Ala Tyr Val Leu Gly Glu
            260             265             270

Leu Glu Arg Arg Ala Lys Ala Gly Lys Arg Leu Ala Phe Val His Leu
            275             280             285

Val Glu Pro Arg Val Thr Asn Phe Trp Leu Val Glu Gly Glu Gly Glu
            290             295             300

Tyr Ser Glu Gly Thr Asn Asp Phe Ala Tyr Ser Ile Trp Lys Gly Pro
305             310             315             320

Ile Ile Arg Ala Gly Asn Tyr Ala Leu His Pro Glu Val Val Arg Glu
            325             330             335

Gln Val Lys Asp Pro Arg Thr Leu Ile Gly Tyr Gly Arg Phe Phe Ile
            340             345             350

Ser Asn Pro Asp Leu Val Tyr Arg Leu Glu Glu Gly Leu Pro Leu Asn
            355             360             365

Lys Tyr Asp Arg Ser Thr Phe Tyr Thr Met Ser Ala Glu Gly Tyr Thr
            370             375             380

Asp Tyr Pro Thr Tyr Glu Glu Ala Val Asp Leu Gly Trp Asn Lys Asn
385             390             395             400

<210> SEQ ID NO 61
<211> LENGTH: 1200
<212> TYPE: DNA
<213> ORGANISM: Artificial Sequence
<220> FEATURE:
<223> OTHER INFORMATION: ERED variant

<400> SEQUENCE: 61
atgtctttcg ttaaggactt caagccgcag gcactgcgcg acaccaacct gttcgaacct      60
attaaaattg ggaacacaca gctggctcat cgcgcggtaa tgcctccgct gagccgcatg     120

```
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactggc cgtcctgggc    360
tgggccgcct ttccggataa cctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt tataactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caacctttg gctggttgag    900 ggggagggcg aatactcaga gggcaccaac gatttgctt attccatttg gaaaggtccg    960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 62
<211> LENGTH: 400
<212> TYPE: PRT
<213> ORGANISM: Artificial Sequence
<220> FEATURE:
<223> OTHER INFORMATION: ERED variant

<400> SEQUENCE: 62

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

|     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- |
| Ser | Ala | Asn | Gly | Tyr | Leu | Leu | Asn | Gln | Phe | Leu | Asp | Pro | His | Ser | Asn |     |
|     |     |     | 195 |     |     |     |     | 200 |     |     |     |     | 205 |     |     |     |
| Asn | Arg | Thr | Asp | Glu | Tyr | Gly | Gly | Ser | Ile | Glu | Asn | Arg | Ala | Arg | Phe |     |
|     | 210 |     |     |     |     | 215 |     |     |     |     | 220 |     |     |     |     |     |
| Thr | Leu | Glu | Val | Val | Asp | Ala | Val | Val | Asp | Ala | Ile | Gly | Pro | Glu | Lys |     |
| 225 |     |     |     |     | 230 |     |     |     |     | 235 |     |     |     |     | 240 |     |
| Val | Gly | Leu | Arg | Leu | Ser | Pro | Tyr | Gly | Val | Tyr | Asn | Ser | Met | Ser | Gly |     |
|     |     |     |     | 245 |     |     |     |     | 250 |     |     |     |     | 255 |     |     |
| Gly | Ala | Glu | Thr | Gly | Ile | Val | Ala | Gln | Tyr | Ala | Tyr | Val | Leu | Gly | Glu |     |
|     |     |     | 260 |     |     |     |     | 265 |     |     |     |     | 270 |     |     |     |
| Leu | Glu | Arg | Arg | Ala | Lys | Ala | Gly | Lys | Arg | Leu | Ala | Phe | Val | His | Leu |     |
|     |     | 275 |     |     |     |     | 280 |     |     |     |     | 285 |     |     |     |     |
| Val | Glu | Pro | Arg | Val | Thr | Thr | Phe | Trp | Leu | Val | Glu | Gly | Glu | Gly | Glu |     |
|     | 290 |     |     |     |     | 295 |     |     |     |     | 300 |     |     |     |     |     |
| Tyr | Ser | Glu | Gly | Thr | Asn | Asp | Phe | Ala | Tyr | Ser | Ile | Trp | Lys | Gly | Pro |     |
| 305 |     |     |     |     | 310 |     |     |     |     | 315 |     |     |     |     | 320 |     |
| Ile | Ile | Arg | Ala | Gly | Asn | Tyr | Ala | Leu | His | Pro | Glu | Val | Val | Arg | Glu |     |
|     |     |     |     | 325 |     |     |     |     | 330 |     |     |     |     | 335 |     |     |
| Gln | Val | Lys | Asp | Pro | Arg | Thr | Leu | Ile | Gly | Tyr | Gly | Arg | Phe | Phe | Ile |     |
|     |     |     | 340 |     |     |     |     | 345 |     |     |     |     | 350 |     |     |     |
| Ser | Asn | Pro | Asp | Leu | Val | Tyr | Arg | Leu | Glu | Glu | Gly | Leu | Pro | Leu | Asn |     |
|     |     | 355 |     |     |     |     | 360 |     |     |     |     | 365 |     |     |     |     |
| Lys | Tyr | Asp | Arg | Ser | Thr | Phe | Tyr | Thr | Met | Ser | Ala | Glu | Gly | Tyr | Thr |     |
|     | 370 |     |     |     |     | 375 |     |     |     |     | 380 |     |     |     |     |     |
| Asp | Tyr | Pro | Thr | Tyr | Glu | Glu | Ala | Val | Asp | Leu | Gly | Trp | Asn | Lys | Asn |     |
| 385 |     |     |     |     | 390 |     |     |     |     | 395 |     |     |     |     | 400 |     |

<210> SEQ ID NO 63
<211> LENGTH: 1200
<212> TYPE: DNA
<213> ORGANISM: Artificial Sequence
<220> FEATURE:
<223> OTHER INFORMATION: ERED variant

<400> SEQUENCE: 63

| atgtctttcg | ttaaggactt | caagccgcag | gcactgcgcg | acaccaacct | gttcgaacct | 60   |
| ---------- | ---------- | ---------- | ---------- | ---------- | ---------- | ---- |
| attaaaattg | ggaacacaca | gctggctcat | cgcgcggtaa | tgcctccgct | gagccgcatg | 120  |
| cgcgctaccc | atccgggcaa | cattccgaac | aaggagtggg | ctgcggttta | ctacggccag | 180  |
| cgtgcacagc | gtccggggac | aatgattatc | acggagggta | cgttcatcag | cccgcaggca | 240  |
| ggtgggatcg | ataacgcgcc | tggtgtttgg | tcagacgaac | aggttgccga | atggaagaac | 300  |
| atcttcctgg | ctattcatga | ctgtcagtca | tttgcgtggg | tgcaactgct | ggtcctgggc | 360  |
| tgggccgcct | ttccggataa | cctggcgcgt | gatgggttac | gttacgattc | tgcctccgat | 420  |
| aatgtgtata | tgaatgcgga | acaggaggaa | aaagcgaaaa | agctaacaa | tccgcaacat | 480  |
| agcattacta | aagacgaaat | taaacaatat | gtcaaagaat | atgttcaggc | agctaagaac | 540  |
| tcgatcgctg | cgggtgcgga | cggcgtggaa | attcactcag | ccaacggtta | tctgttaaat | 600  |
| cagttcctgg | atccgcacag | caacaaccgc | accgatgagt | atgggggctc | aattgaaaat | 660  |
| cgtgcacgtt | ttactctgga | agtcgttgac | gcggtggttg | atgccatcgg | cccagaaaaa | 720  |
| gtgggtttac | gtctgagtcc | gtacggcgtt | tcaactcta | tgtcgggcgg | cgcggaaacg | 780  |
| ggcattgttg | ctcagtatgc | ctatgtcctg | ggtgagctgg | agcgtcgcgc | caaggcgggg | 840  |
| aaacgcctgg | cgtttgttca | tttagtcgaa | ccacgcgtga | cagacccttc | tctggttgag | 900  |

```
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gcctgccact gaacaagtat gaccgttcta cgttctacac catgagcgcg    1140
gagggttaca ccgactaccc gacctacgaa gaagccgtag atctgggctg aacaaaaac    1200
```

```
<210> SEQ ID NO 64
<211> LENGTH: 400
<212> TYPE: PRT
<213> ORGANISM: Artificial Sequence
<220> FEATURE:
<223> OTHER INFORMATION: ERED variant

<400> SEQUENCE: 64

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Ser Arg Met Arg Ala Thr His Pro Gly Asn Ile
            35                  40                  45

Pro Asn Lys Glu Trp Ala Ala Val Tyr Tyr Gly Gln Arg Ala Gln Arg
        50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Leu Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320
```

```
Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 65
<211> LENGTH: 1200
<212> TYPE: DNA
<213> ORGANISM: Artificial Sequence
<220> FEATURE:
<223> OTHER INFORMATION: ERED variant

<400> SEQUENCE: 65

```
atgtctttcg ttaaggactt caagccgcag gcactgcgcg acaccaacct gttcgaacct      60
attaaaattg gaacacaca gttggctcat cgcgcggtaa tgcctccgct gagccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgat cgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt tcaactctca tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caactgcttc tctggttgag     900
ggggaggggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 66
<211> LENGTH: 400
<212> TYPE: PRT
<213> ORGANISM: Artificial Sequence
<220> FEATURE:
<223> OTHER INFORMATION: ERED variant

<400> SEQUENCE: 66

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
```

```
                20                  25                  30
Val Met Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
 50                  55                  60

Pro Gly Thr Met Ile Ile Thr Glu Gly Thr Phe Ile Ser Pro Gln Ala
 65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
                100                 105                 110

Trp Val Gln Leu Ile Val Leu Gly Trp Ala Ala Phe Pro Asp Asn Leu
                115                 120                 125

Ala Arg Asp Gly Leu Arg Tyr Asp Ser Ala Ser Asp Asn Val Tyr Met
            130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
        210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
            275                 280                 285

Val Glu Pro Arg Val Thr Thr Ala Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 67
<211> LENGTH: 1200
<212> TYPE: DNA
<213> ORGANISM: Artificial Sequence
<220> FEATURE:
<223> OTHER INFORMATION: ERED variant

<400> SEQUENCE: 67
```

```
atgtctttcg ttgaggactt caagccgcag gcactgcgcg acaccaacct gttcgaacct    60
attaaaattg ggaacacaca gctggctcat cgcgcggtaa tgcctccgct gacccgcatg   120
cgcgctacct atccgggcaa cattccgaac aaggagtggg ctgcggttta ctacggccag   180
cgtgcacagc gtccggggac aatgattatc acggagggta cgttcatcag cccgcaggca   240
ggtgggatcg ataacgcgcc tggtgtttgg tcagacgaac aggttgccga atggaagaac   300
atcttcctgg ctattcatga ctgtcagtca tttgcgtggg tgcaactgtg ggtcctgggc   360
tgggccgcct ttccggataa cctggcgcgt gatgggttac gttacgattc tgcctccgat   420
aatgtgtata tgaatgcgga acaggaggaa aaagcgaaaa agctaacaa tccgcaacat    480 agcattacta aagacgaaat taaacaatat gtcaaagaat atgttcaggc agctaagaac   540
tcgatcgctg cgggtgcgga cggcgtggaa attcactcag ccaacggtta tctgttaaat   600
cagttcctgg acccgcacag caacaaccgc accgatgagt atgggggctc aattgaaaat   660
cgtgcacgtt ttactctgga agtcgttgac gcggtggttg atgccatcgg cccagaaaaa   720
gtgggtttac gtctgagtcc gtacggcgtt gcgaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga caaatccggg cctggttgag   900
ggggagggcg aatactcaga gggcaccaac gattttgctt attccatttg aaaggtccg    960 attatccgtg ccggcaacta cgcactgcac cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttctacac catgagcgcg  1140
gagggttaca ccgactaccc gacctacgaa gaagccgtag atctgggctg aacaaaaac   1200
```

<210> SEQ ID NO 68
<211> LENGTH: 400
<212> TYPE: PRT
<213> ORGANISM: Artificial Sequence
<220> FEATURE:
<223> OTHER INFORMATION: ERED variant

<400> SEQUENCE: 68

```
Met Ser Phe Val Glu Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr Tyr Pro Gly Asn Ile
        35                  40                  45

Pro Asn Lys Glu Trp Ala Ala Val Tyr Tyr Gly Gln Arg Ala Gln Arg
50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Trp Val Leu Gly Trp Ala Ala Phe Pro Asp Asn Leu
    115                 120                 125

Ala Arg Asp Gly Leu Arg Tyr Asp Ser Ala Ser Asp Asn Val Tyr Met
130                 135                 140

Asn Ala Glu Gln Glu Glu Lys Ala Lys Lys Ala Asn Asn Pro Gln His
145                 150                 155                 160
```

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Ala Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Gly Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 69
<211> LENGTH: 1200
<212> TYPE: DNA
<213> ORGANISM: Artificial Sequence
<220> FEATURE:
<223> OTHER INFORMATION: ERED variant

<400> SEQUENCE: 69
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggca cgttcatcag cccgcaggca      240
ggtgggatcg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480 agcattacta aagacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atgggggctc aattgaaaat      660
cgtgcacgtt ttactctgga agtcgttgac gcggtggttg atgccatcgg cccagaaaaa      720

```
gtgggtttac gtctgagtcc gtacggcgtt gcgaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga cagacccttc tctggttgag   900
ggggagggcg aatactcaga gggcaccaac gattttgctt attccatttg aaaggtccg    960 attatccgtg ccggcaacta cgcactgtac cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttctacac catgagcgcg  1140
gagggttaca ccgactaccc gacctacgaa gaagccgtag atctgggctg aacaaaaac   1200
```

<210> SEQ ID NO 70
<211> LENGTH: 400
<212> TYPE: PRT
<213> ORGANISM: Artificial Sequence
<220> FEATURE:
<223> OTHER INFORMATION: ERED variant

<400> SEQUENCE: 70

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ala Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

-continued

```
Val Glu Pro Arg Val Thr Asp Pro Ser Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu Tyr Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400
```

<210> SEQ ID NO 71
<211> LENGTH: 1200
<212> TYPE: DNA
<213> ORGANISM: Artificial Sequence
<220> FEATURE:
<223> OTHER INFORMATION: ERED variant

<400> SEQUENCE: 71

```
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtg gtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt cgcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
gggagggcg aatactcaga gggcaccaac gattttgctt attccatttg gaaaggtccg     960
attatccgtg ccggcaacta cgcactgcac cccgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 72
<211> LENGTH: 400
<212> TYPE: PRT
<213> ORGANISM: Artificial Sequence
<220> FEATURE:
<223> OTHER INFORMATION: ERED variant

<400> SEQUENCE: 72

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Thr Arg Met Arg Ala Thr His Pro Gly Asn Ile
            35                  40                  45

Pro Asn Lys Glu Trp Ala Ala Val Tyr Tyr Gly Gln Arg Ala Gln Arg
        50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
                100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Arg Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 73
<211> LENGTH: 1200
<212> TYPE: DNA
```

<213> ORGANISM: Artificial Sequence
<220> FEATURE:
<223> OTHER INFORMATION: ERED variant

<400> SEQUENCE: 73

```
atgtctttcg ttaaggactt caagccgcag gcactgcgcg acaccaacct gttcgaacct     60
attaaaattg ggaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggctc aattgaaaat    660
cgtgcacgtt ttactctgga agtcgttgac gcggtggttg atgccatcgg cccagaaaaa    720
gtgggtttac gtctgagtcc gtacggcgtt gcgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccgag cctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200
```

<210> SEQ ID NO 74
<211> LENGTH: 400
<212> TYPE: PRT
<213> ORGANISM: Artificial Sequence
<220> FEATURE:
<223> OTHER INFORMATION: ERED variant

<400> SEQUENCE: 74

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125
```

```
Ala Arg Asp Gly Leu Arg Tyr Asp Ser Ala Ser Asp Asn Val Tyr Met
        130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ala Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 75
<211> LENGTH: 1200
<212> TYPE: DNA
<213> ORGANISM: Artificial Sequence
<220> FEATURE:
<223> OTHER INFORMATION: ERED variant

<400> SEQUENCE: 75
atgtctttcg ttaaggactt caaaccgcag gcactgcgcg acaccaacct gttcgaacct        60
attaaaattg gaacacaca gctggctcat cgcgcggtaa tgcctccgct gacccgcatg        120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggatcg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480 agcattacta aagacgaaat taacaatat gtcaaagaat atgttcaggc agctaggaac      540
tcgatcgctg cgggtgcgga cggcgtggaa attcactcag ccaacggtta tctgttaaat      600
```

```
cagttcctgg atccgcacag caacaaccgc accgatgagt atgggggctc aattgaaaat      660
cgtgcacgtt ttactctgga agtcgttgac gcggtggttg atgccatcgg cccagaaaaa      720
gtgggtttac gtctgagtcc gtacggcgtt tgcaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga cagacccttc tctggttgag      900
ggggagggcg aatactcaga gggcaccaac gattttgctt attccatttg gaaaggtccg      960
attatccgtg ccggcaacta cgcactgcac cctgaagttg tgcgcgaaca agttcaggac     1020
cctcgcaccc tgatcggcta cggccgcttc tttatttcaa atccagacct ggtttaccgc     1080
ttagaagaag gtctgccact gaacaagtat gaccgttcta cgttctacac catgagcgcg     1140
gagggttaca ccgactaccc gacctacgaa gaagccgtag atctgggctg aacaaaaac     1200
```

<210> SEQ ID NO 76
<211> LENGTH: 400
<212> TYPE: PRT
<213> ORGANISM: Artificial Sequence
<220> FEATURE:
<223> OTHER INFORMATION: ERED variant

<400> SEQUENCE: 76

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Arg Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Cys Asn Ser Met Ser Gly
                245                 250                 255

Gly Ala Glu Thr Gly Ile Val Ala Gln Tyr Ala Tyr Val Leu Gly Glu
```

```
                    260                 265                 270
Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Gln Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 77
<211> LENGTH: 1200
<212> TYPE: DNA
<213> ORGANISM: Artificial Sequence
<220> FEATURE:
<223> OTHER INFORMATION: ERED variant

<400> SEQUENCE: 77
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtt tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat      660 cgtgcacgtt ttactctgga agtcgttgac gcggtggttg atgccatcgg cccagaaaaa     720
gtgggtttac gtctgagtcc gtacggcgtt tcgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 78
<211> LENGTH: 400
<212> TYPE: PRT
```

<213> ORGANISM: Artificial Sequence
<220> FEATURE:
<223> OTHER INFORMATION: ERED variant

<400> SEQUENCE: 78

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Phe Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 79
<211> LENGTH: 1200
<212> TYPE: DNA
<213> ORGANISM: Artificial Sequence
<220> FEATURE:
<223> OTHER INFORMATION: ERED variant

<400> SEQUENCE: 79

```
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtt ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggag attcactcag ccaacggtta tctgttaaat     600
cagttcctgg atccgcacag caacgaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt tcgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttcaagac catgagcgcg    1140
gagggttaca ccgactaccc gacctacgaa gaagccgtag atctgggctg gaacaaaact    1200
```

<210> SEQ ID NO 80
<211> LENGTH: 400
<212> TYPE: PRT
<213> ORGANISM: Artificial Sequence
<220> FEATURE:
<223> OTHER INFORMATION: ERED variant

<400> SEQUENCE: 80

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
```

|     |     |     |     | 100 |     |     |     | 105 |     |     |     | 110 |     |     |
| --- | --- | --- | --- | --- | --- | --- | --- | --- | --- | --- | --- | --- | --- | --- |

Trp Val Gln Leu Leu Val Leu Gly Trp Ala Ala Phe Pro Asp Asn Leu
          115          120          125

Ala Arg Asp Gly Leu Arg Tyr Asp Ser Ala Ser Asp Asn Val Tyr Met
 130          135          140

Asn Ala Glu Gln Glu Glu Lys Ala Lys Lys Ala Asn Asn Pro Gln His
145          150          155          160

Ser Ile Thr Lys Asp Glu Ile Lys Gln Tyr Val Lys Glu Tyr Val Gln
          165          170          175

Ala Ala Lys Asn Ser Ile Ala Ala Gly Ala Asp Gly Val Glu Ile His
        180          185          190

Ser Ala Asn Gly Tyr Leu Leu Asn Gln Phe Leu Asp Pro His Ser Asn
        195          200          205

Asp Arg Thr Asp Glu Tyr Gly Gly Ser Ile Glu Asn Arg Ala Arg Phe
 210          215          220

Thr Leu Glu Val Val Asp Ala Val Val Asp Ala Ile Gly Pro Glu Lys
225          230          235          240

Val Gly Leu Arg Leu Ser Pro Tyr Gly Val Ser Asn Ser Met Ser Gly
          245          250          255

Gly Ala Glu Thr Gly Ile Val Ala Gln Tyr Ala Tyr Val Leu Gly Glu
        260          265          270

Leu Glu Arg Arg Ala Lys Ala Gly Lys Arg Leu Ala Phe Val His Leu
        275          280          285

Val Glu Pro Arg Val Thr Asp Pro Ser Leu Val Glu Gly Glu Gly Glu
 290          295          300

Tyr Ser Glu Gly Thr Asn Asp Phe Ala Tyr Ser Ile Trp Lys Gly Pro
305          310          315          320

Ile Ile Arg Ala Gly Asn Tyr Ala Leu His Pro Glu Val Val Arg Glu
          325          330          335

Gln Val Lys Asp Pro Arg Thr Leu Ile Gly Tyr Gly Arg Phe Phe Ile
        340          345          350

Ser Asn Pro Asp Leu Val Tyr Arg Leu Glu Glu Gly Leu Pro Leu Asn
        355          360          365

Lys Tyr Asp Arg Ser Thr Phe Lys Thr Met Ser Ala Glu Gly Tyr Thr
 370          375          380

Asp Tyr Pro Thr Tyr Glu Glu Ala Val Asp Leu Gly Trp Asn Lys Thr
385          390          395          400

<210> SEQ ID NO 81
<211> LENGTH: 1200
<212> TYPE: DNA
<213> ORGANISM: Artificial Sequence
<220> FEATURE:
<223> OTHER INFORMATION: ERED variant

<400> SEQUENCE: 81

| | | |
|---|---|---|
| atgtctttcg ttaaggactt caagccgcag gcactgcgcg acaccaacct gttcgaacct | 60 |
| attaaaattg gaacacaca gctggctcat cgcgcggtaa tgcctccgct gtcacgcatg | 120 |
| cgcgctaccc atccgggcaa cattccgaac aaggagtggg ctgcggttta ctacggccag | 180 |
| cgtgcacagc gtccggggac aatgattatc acgagggta cgttcatcag cccgcaggca | 240 |
| ggtgggatcg ataacgcgcc tggtgtttgg tcagacgaac aggttgccga atggaagaac | 300 |
| atcttcctgg ctattcatga ctgtcagtca tttgcgtggg tgcaactgtg gtcctgggc | 360 |
| tgggccgcct ttccggataa cctggcgcgt gatgggttac gttacgattc tgcctccgat | 420 |

-continued

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt tcgaactcta tgtcgggcgg cgcggagacg    780
ggcattgttg ctcagtatgc ctatgtcctg ggtgagctgg agcgtcgcgc caaggcgggg    840
aaacgcctgg cgtttgttca tttagtcgaa ccacgcgtga cagatgggtc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 82
<211> LENGTH: 400
<212> TYPE: PRT
<213> ORGANISM: Artificial Sequence
<220> FEATURE:
<223> OTHER INFORMATION: ERED variant

<400> SEQUENCE: 82

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Ser Asn Ser Met Ser Gly
            245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
            275                 280                 285

Val Glu Pro Arg Val Thr Asp Gly Ser Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 83
<211> LENGTH: 1200
<212> TYPE: DNA
<213> ORGANISM: Artificial Sequence
<220> FEATURE:
<223> OTHER INFORMATION: ERED variant

<400> SEQUENCE: 83
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtt tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660 cgtgcacgtt ttactctgga agtcgttgac gcggtggttg atgccatcgg cccagaaaaa     720
gtgggtttac gtctgagtcc gtacggcgtt gtgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttcattac catgagcgcg    1140
gagggttaca ccgactaccc gacctacgaa gaagccgtag atctgggctg gaacaaaaac    1200

<210> SEQ ID NO 84
<211> LENGTH: 400
<212> TYPE: PRT
<213> ORGANISM: Artificial Sequence
<220> FEATURE:
<223> OTHER INFORMATION: ERED variant

<400> SEQUENCE: 84

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Phe Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

```
Lys Tyr Asp Arg Ser Thr Phe Ile Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400
```

<210> SEQ ID NO 85
<211> LENGTH: 1200
<212> TYPE: DNA
<213> ORGANISM: Artificial Sequence
<220> FEATURE:
<223> OTHER INFORMATION: ERED variant

<400> SEQUENCE: 85

```
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtt tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taacaatat gtcaaagaat atgttcaggc agctaagaac     540
tcgatcgctg cgggtgcgga cggcgtgaa attcactcag ccaacggtta tctgttaaat     600
cagttcctgg atccgcacag caacaaccgc accgatgagt atggggctc aattgaaaat     660
cgtgcacgtt ttactctgga agtcgttgac gcggtggttg atgccatcgg cccagaaaaa     720
gtgggtttac gtctgagtcc gtacggcgtt tcgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caaatgggtt tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 86
<211> LENGTH: 400
<212> TYPE: PRT
<213> ORGANISM: Artificial Sequence
<220> FEATURE:
<223> OTHER INFORMATION: ERED variant

<400> SEQUENCE: 86

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80
```

Gly Gly Ile Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Phe Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Gly Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 87
<211> LENGTH: 1200
<212> TYPE: DNA
<213> ORGANISM: Artificial Sequence
<220> FEATURE:
<223> OTHER INFORMATION: ERED variant

<400> SEQUENCE: 87
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgttttgg tcagacgaac aggttgccga atggaagaac     300

```
atcttcctgg ctattcacga ctgtcagtca tttgcgtggg tgcaactgtg ggtcctgggc      360
tgggccgcct ttccggataa cctggcgcgt gatgggctac gttacgattc tgcctccgat      420
aatgtgtata tgaatgcgga acaggaggaa aaagcgaaaa agctaacaa tccgcaacat       480
agcattacta aagacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atgggggctc aattgaaaat      660
cgtgcacgtt ttactctgga agtcgttgac gcggtggttg atgccatcgg cccagaaaaa      720
gtgggtttac gtctgagtcc gtacggcgtt tcgaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga caacgtcgtt tctggttgag      900
ggggagggcg aatactcaga gggcaccaac gattttgctt attccatttg gaaaggtccg      960
attatccgtg ccggcaacta cgcactgcac cctgaagttg tgcgcgaaca agttaaggac     1020
cctcgcaccc tgatcggcta cggccgcttc tttatttcaa atccagacct ggtttaccgc     1080
ttagaagaag gtctgccact gaacaagtat gaccgttcta cgttctacac catgagcgcg     1140
gagggttaca tcgactaccc gacctacgaa gaagccgtag atctgggctg gaacaaaaac     1200
```

<210> SEQ ID NO 88  
<211> LENGTH: 400  
<212> TYPE: PRT  
<213> ORGANISM: Artificial Sequence  
<220> FEATURE:  
<223> OTHER INFORMATION: ERED variant

<400> SEQUENCE: 88

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Asn Arg Thr Asp Glu Tyr Gly Gly Ser Ile Glu Asn Arg Ala Arg Phe
        210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
            275                 280                 285

Val Glu Pro Arg Val Thr Thr Ser Phe Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Ile
370                 375                 380

Asp Tyr Pro Thr Tyr Glu Glu Ala Val Asp Leu Gly Trp Asn Lys Asn
385                 390                 395                 400
```

<210> SEQ ID NO 89
<211> LENGTH: 1200
<212> TYPE: DNA
<213> ORGANISM: Artificial Sequence
<220> FEATURE:
<223> OTHER INFORMATION: ERED variant

<400> SEQUENCE: 89

```
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgtg gtcctgggc     360
tgggccgcct ttccggataa cctggcgcgt gatgggttac gttacgattc tgcctccgat    420
aatgtgtata tgaatgcgga acaggaggaa aaagcgaaaa agctaacaa tccgcaacat     480
agcattacta agacgaaat taaacaatat gtcaaagaat atgttcaggc agctaagaac    540
tcgatcgctg cgggtgcgga cggcgtgaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt gtgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
```

```
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 90
<211> LENGTH: 400
<212> TYPE: PRT
<213> ORGANISM: Artificial Sequence
<220> FEATURE:
<223> OTHER INFORMATION: ERED variant

<400> SEQUENCE: 90

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Val Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

```
                340             345              350
Ser Asn Pro Asp Leu Val Tyr Arg Leu Glu Glu Gly Leu Pro Leu Asn
                    355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400
```

<210> SEQ ID NO 91
<211> LENGTH: 1200
<212> TYPE: DNA
<213> ORGANISM: Artificial Sequence
<220> FEATURE:
<223> OTHER INFORMATION: ERED variant

<400> SEQUENCE: 91

```
atgtctttcg ttaaggactt caagccgcag gcactgcgcg acaccaacct gttcgaacct    60
attaaaattg gaacacaca gccggctcat cgcgcggtaa tgcctccgct gacccgcatg    120
cgcgctaccc atccgggcaa cattccgaac aaggagtggg ctgcggttta ctacggccag   180
cgtgcacagc gtccggggac aatgattatc acggagggta cgttcatcag cccgcaggca   240
ggtgggatcg ataacgcgcc tggtgtttgg tcagacgaac aggttgccga atggaagaac   300
atcttcctgg ctattcatga ctgtcagtca tttgcgtggg tgcaactggc agtcctgggc   360
tgggccgcct ttccggataa cctggcgcgt gatgggttac gttacgattc tgcctccgat   420
aatgtgtata tgaatgcgga acaggaggaa aaagcgaaaa agctaacaa tccgcaacat    480
agcattacta aagacgaaat taaacaatat gtcaagaat atgttcaggc agctaagaac   540
tcgatcgctg cgggtgcgga cggcgtgaa attcactcag ccaacggtta tctgttaaat    600
cagttcctgg atccgcacag caacaaccgc accgatgagt atggggctc aattgaaaat   660
cgtgcacgtt ttactctgga agtcgttgac gcggtggttg atgccatcgg cccagaaaaa   720
gtgggtttac gtctgagtcc gtacggcgtt gtgaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga cagatccgtc tctggttgag   900
ggggagggcg aatactcaga gggcaccaac gatttgctt attccatttg aaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200
```

<210> SEQ ID NO 92
<211> LENGTH: 400
<212> TYPE: PRT
<213> ORGANISM: Artificial Sequence
<220> FEATURE:
<223> OTHER INFORMATION: ERED variant

<400> SEQUENCE: 92

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Pro Ala His Arg Ala
            20                  25                  30

Val Met Pro Pro Leu Thr Arg Met Arg Ala Thr His Pro Gly Asn Ile
        35                  40                  45
```

```
Pro Asn Lys Glu Trp Ala Ala Val Tyr Tyr Gly Gln Arg Ala Gln Arg
 50                  55                  60
Pro Gly Thr Met Ile Ile Thr Glu Gly Thr Phe Ile Ser Pro Gln Ala
 65                  70                  75                  80
Gly Gly Ile Asp Asn Ala Pro Gly Val Trp Ser Asp Glu Gln Val Ala
                 85                  90                  95
Glu Trp Lys Asn Ile Phe Leu Ala Ile His Asp Cys Gln Ser Phe Ala
                100                 105                 110
Trp Val Gln Leu Ala Val Leu Gly Trp Ala Ala Phe Pro Asp Asn Leu
            115                 120                 125
Ala Arg Asp Gly Leu Arg Tyr Asp Ser Ala Ser Asp Asn Val Tyr Met
130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
        195                 200                 205
Asn Arg Thr Asp Glu Tyr Gly Gly Ser Ile Glu Asn Arg Ala Arg Phe
210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Val Asn Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
370                 375                 380
Asp Tyr Pro Thr Tyr Glu Glu Ala Val Asp Leu Gly Trp Asn Lys Asn
385                 390                 395                 400

<210> SEQ ID NO 93
<211> LENGTH: 1200
<212> TYPE: DNA
<213> ORGANISM: Artificial Sequence
<220> FEATURE:
<223> OTHER INFORMATION: ERED variant

<400> SEQUENCE: 93
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
```

```
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgaa tgtcctgggc    360
tgggccgcct ttccggataa cctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caacgggggtt tctggttgag    900 ggggagggcg aatactcaga gggcaccaac gatttttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200

<210> SEQ ID NO 94
<211> LENGTH: 400
<212> TYPE: PRT
<213> ORGANISM: Artificial Sequence
<220> FEATURE:
<223> OTHER INFORMATION: ERED variant

<400> SEQUENCE: 94

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Asn Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

```
                180              185              190
Ser Ala Asn Gly Tyr Leu Leu Asn Gln Phe Leu Asp Pro His Ser Asn
        195                  200                  205
Asn Arg Thr Asp Glu Tyr Gly Gly Ser Ile Glu Asn Arg Ala Arg Phe
    210                  215                  220
Thr Leu Glu Val Val Asp Ala Val Asp Ala Ile Gly Pro Glu Lys
225                  230                  235                  240
Val Gly Leu Arg Leu Ser Pro Tyr Gly Val Phe Asn Ser Met Ser Gly
                245                  250                  255
Gly Ala Glu Thr Gly Ile Val Ala Gln Tyr Ala Tyr Val Leu Gly Glu
            260                  265                  270
Leu Glu Arg Arg Ala Lys Ala Gly Lys Arg Leu Ala Phe Val His Leu
            275                  280                  285
Val Glu Pro Arg Val Thr Thr Gly Phe Leu Val Glu Gly Glu Gly Glu
            290                  295                  300
Tyr Ser Glu Gly Thr Asn Asp Phe Ala Tyr Ser Ile Trp Lys Gly Pro
305                  310                  315                  320
Ile Ile Arg Ala Gly Asn Tyr Ala Leu His Pro Glu Val Val Arg Glu
                325                  330                  335
Gln Val Lys Asp Pro Arg Thr Leu Ile Gly Tyr Gly Arg Phe Phe Ile
            340                  345                  350
Ser Asn Pro Asp Leu Val Tyr Arg Leu Glu Glu Gly Leu Pro Leu Asn
            355                  360                  365
Lys Tyr Asp Arg Ser Thr Phe Tyr Thr Met Ser Ala Glu Gly Tyr Thr
    370                  375                  380
Asp Tyr Pro Thr Tyr Glu Glu Ala Val Asp Leu Gly Trp Asn Lys Asn
385                  390                  395                  400

<210> SEQ ID NO 95
<211> LENGTH: 1200
<212> TYPE: DNA
<213> ORGANISM: Artificial Sequence
<220> FEATURE:
<223> OTHER INFORMATION: ERED variant

<400> SEQUENCE: 95
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgag tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt gtgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagatcgttt tctggttgag     900
```

-continued

```
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 96
<211> LENGTH: 400
<212> TYPE: PRT
<213> ORGANISM: Artificial Sequence
<220> FEATURE:
<223> OTHER INFORMATION: ERED variant

<400> SEQUENCE: 96

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ser Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Val Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Arg Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320
```

```
Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 97
<211> LENGTH: 1200
<212> TYPE: DNA
<213> ORGANISM: Artificial Sequence
<220> FEATURE:
<223> OTHER INFORMATION: ERED variant

<400> SEQUENCE: 97
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggatcg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480 agcattacta aagacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atgggggctc aattgaaaat      660
cgtgcacgtt ttactctgga agtcgttgac gcggtggttg atgccatcgg cccagaaaaa      720
gtgggtttac gtctgagtcc gtacggcgtt gtgaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga caaacccttc tctggttgag      900
ggggagggcg aatactcaga gggcaccaac gattttgctt attccatttg aaaggtccg      960 attatccgtg ccggcaacta cgcactgcac cctgaagttg tgcgcgaaca agttaaggac     1020
cctcgcaccc tgatcggcta cggccgcttc tttatttcaa atccagacct ggtttaccgc     1080
ttagaagaag gtctgccact gaacaagtat gaccgttcta cgttctacac catgagcgcg     1140
gagggttaca ccgactaccc gacctacgaa gaagccgtag atctgggctg gaacaaaaac     1200

<210> SEQ ID NO 98
<211> LENGTH: 400
<212> TYPE: PRT
<213> ORGANISM: Artificial Sequence
<220> FEATURE:
<223> OTHER INFORMATION: ERED variant

<400> SEQUENCE: 98

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
```

```
            20                  25                  30
Val Met Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
 50                  55                  60

Pro Gly Thr Met Ile Ile Thr Glu Gly Thr Phe Ile Ser Pro Gln Ala
 65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
                100                 105                 110

Trp Val Gln Leu Trp Val Leu Gly Trp Ala Ala Phe Pro Asp Asn Leu
                115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
                195                 200                 205

Asn Arg Thr Asp Glu Tyr Gly Gly Ser Ile Glu Asn Arg Ala Arg Phe
        210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Val Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
        275                 280                 285

Val Glu Pro Arg Val Thr Asn Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 99
<211> LENGTH: 1200
<212> TYPE: DNA
<213> ORGANISM: Artificial Sequence
<220> FEATURE:
<223> OTHER INFORMATION: ERED variant

<400> SEQUENCE: 99
```

```
atgtctttcg ttaaggactt caagccgcag gcactgcgcg acaccaacct gttcgaacct    60
attaaaattg ggaacacaca gctggctcat cgcgcggtaa tgcctccgct gacccgcatg   120
cgcgctaccc atccgggcaa cattccgaac aaggagtggg ctgcggttta ctacggccag   180
cgtgcacagc gtccggggac aatgattatc acggagggta cgttcatcag cccgcaggca   240
ggtgggatcg ataacgcgcc tggtgtttgg tcagacgaac aggttgccga atggaagaac   300
atcttcctgg ctattcatga ctgtcagtca tttgcgtggg tgcaactgtg ggtcctgggc   360
tgggccgcct ttccggataa cctggcgcgt gatgggttac gttacgattc tgcctccgat   420
aatgtgtata tgaatgcgga acaggaggaa aaagcgaaaa agctaacaa tccgcaacat   480 agcattacta aagacgaaat taaacaatat gtcaaagaat atgttcaggc agctaagaac   540
tcgatcgctg cgggtgcgga cggcgtggaa attcactcag ccaacggtta tctgttaaat   600
cagttcctgg atccgcacag caacaaccgc accgatgagt atgggggctc aattgaaaat   660
cgtgcacgtt ttactctgga agtcgttgac gcggtggttg atgccatcgg tccagaaaaa   720
gtgggtttac gtctgagtcc gtacggcgtt ttcaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga cagattcgtt tctggttgag   900
ggggagggcg aatactcaga gggcaccaac gattttgctt attccatttg aaaggtccg   960 attatccgtg ccggcaacta cgcactgcac cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttcattac catgagcgcg  1140
gagggttaca ccgactaccc gacctacgaa gaagccgtag atctgggccg gaacaaaaac  1200
```

<210> SEQ ID NO 100
<211> LENGTH: 400
<212> TYPE: PRT
<213> ORGANISM: Artificial Sequence
<220> FEATURE:
<223> OTHER INFORMATION: ERED variant

<400> SEQUENCE: 100

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160
```

```
Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Ser Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Ile Thr Met Ser Ala Glu Gly Tyr Thr
    370                 375                 380

Asp Tyr Pro Thr Tyr Glu Glu Ala Val Asp Leu Gly Arg Asn Lys Asn
385                 390                 395                 400

<210> SEQ ID NO 101
<211> LENGTH: 1200
<212> TYPE: DNA
<213> ORGANISM: Artificial Sequence
<220> FEATURE:
<223> OTHER INFORMATION: ERED variant

<400> SEQUENCE: 101
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tgtgtttggt tcagacgaac aggttgccga atggaagaac     300
atcttcctgg ctattcatga ctgtcagtca tttgcgtggg tgcaactgaa tgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
```

```
gtgggtttac gtctgagtcc gtacggcgtt gtgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg aaaggtccg     960 attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 102
<211> LENGTH: 400
<212> TYPE: PRT
<213> ORGANISM: Artificial Sequence
<220> FEATURE:
<223> OTHER INFORMATION: ERED variant

<400> SEQUENCE: 102

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Asn Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Val Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

```
Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 103
<211> LENGTH: 1200
<212> TYPE: DNA
<213> ORGANISM: Artificial Sequence
<220> FEATURE:
<223> OTHER INFORMATION: ERED variant

<400> SEQUENCE: 103
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtg gtcctgggc     360 tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt tcgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caacgggggtt tctggttgag     900 ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 104
<211> LENGTH: 400
<212> TYPE: PRT
<213> ORGANISM: Artificial Sequence
<220> FEATURE:
<223> OTHER INFORMATION: ERED variant

<400> SEQUENCE: 104
```

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Thr Gly Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 105
<211> LENGTH: 1200
<212> TYPE: DNA

<213> ORGANISM: Artificial Sequence
<220> FEATURE:
<223> OTHER INFORMATION: ERED variant

<400> SEQUENCE: 105

```
atgtctttcg ttaaggactt caagccgcag gcactgcgcg acaccaacct gttcgaacct      60
attaaaattg ggaacacaca gctggctcat cgcgcggtaa tgcctccgct gtcacgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa gagctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt gtgaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caacgccgtt tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 106
<211> LENGTH: 400
<212> TYPE: PRT
<213> ORGANISM: Artificial Sequence
<220> FEATURE:
<223> OTHER INFORMATION: ERED variant

<400> SEQUENCE: 106

```
Met Ser Phe Val Lys Asp Phe Lys Pro Gln Ala Leu Arg Asp Thr Asn
1               5                   10                  15
Leu Phe Glu Pro Ile Lys Ile Gly Asn Thr Gln Leu Ala His Arg Ala
            20                  25                  30
Val Met Pro Pro Leu Ser Arg Met Arg Ala Thr His Pro Gly Asn Ile
        35                  40                  45
Pro Asn Lys Glu Trp Ala Ala Val Tyr Tyr Gly Gln Arg Ala Gln Arg
    50                  55                  60
Pro Gly Thr Met Ile Ile Thr Glu Gly Thr Phe Ile Ser Pro Gln Ala
65                  70                  75                  80
Gly Gly Ile Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
            100                 105                 110
Trp Val Gln Leu Trp Val Leu Gly Trp Ala Ala Phe Pro Asp Asn Leu
        115                 120                 125
```

```
Ala Arg Asp Gly Leu Arg Tyr Asp Ser Ala Ser Asp Asn Val Tyr Met
    130                 135                 140

Asn Ala Glu Gln Glu Lys Ala Lys Arg Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Val Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Thr Pro Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 107
<211> LENGTH: 1200
<212> TYPE: DNA
<213> ORGANISM: Artificial Sequence
<220> FEATURE:
<223> OTHER INFORMATION: ERED variant

<400> SEQUENCE: 107
atgtctttcg ttaaggactt caagccgcag gcactgcgcg acaccaacct gttcgaacct    60
attaaaattg gaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc cggtgtttgg tcagacgaac aggttgccga atggaagaac    300
atcttcctgg ctattcatga ctgtcagtca tttgcgtggg tgcaactgtg gtcctgggc    360 tgggccgcct tccggataa cctggcgcgt gatgggttac gttacgattc tgcctccgat    420
aatgtgtata tgaatgcgga acaggaggaa aaagcgaaaa agctaacaa tccgcaacat    480 agcattacta aagacgaaat taaacaatat gtcaaagaat atgttcaggc agctaagaac    540
tcgatcgctg cgggtgcgga cggcgtggaa attcactcag ccaacggtta tctgttaaat    600
```

```
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt tcgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 108
<211> LENGTH: 400
<212> TYPE: PRT
<213> ORGANISM: Artificial Sequence
<220> FEATURE:
<223> OTHER INFORMATION: ERED variant

<400> SEQUENCE: 108

```
Met Ser Phe Val Lys Asp Phe Lys Pro Gln Ala Leu Arg Asp Thr Asn
 1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
```

```
                260              265              270
Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Arg Glu
                325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 109
<211> LENGTH: 1200
<212> TYPE: DNA
<213> ORGANISM: Artificial Sequence
<220> FEATURE:
<223> OTHER INFORMATION: ERED variant

<400> SEQUENCE: 109
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acgggaggaa aaagcgaaaa agctaacaa tccgcaacat      480 agcattacta aagacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atgggggctc aattgaaaat      660
cgtgcacgtt ttactctgga agtcgttgac gcggtggttg atgccatcgg cccagaaaaa      720
gtgggtttac gtctgagtcc gtacggcgtt ggtaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga cagacccttc tctggttgag      900
ggggagggcg aatactcaga gggcaccaac gattttgctt attccatttg gaaaggtccg      960
attatccgtg ccggcaacta cgcactgcac cctgaagttg tgcgcgaaca agttaaggac     1020
cctcgcaccc tgatcggcta cggccgcttc tttatttcaa atccagacct ggtttaccgc     1080
ttagaagaag gtctgccact gaacaagtat gaccgttcta cgttctacac catgagcgcg     1140
gagggttaca ccgactaccc gacctacgaa gaagccgtag atctgggctg gaacaaaaac     1200

<210> SEQ ID NO 110
<211> LENGTH: 400
<212> TYPE: PRT
```

<213> ORGANISM: Artificial Sequence
<220> FEATURE:
<223> OTHER INFORMATION: ERED variant

<400> SEQUENCE: 110

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
130                 135                 140

Asn Ala Glu Arg Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Gly Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 111
<211> LENGTH: 1200
<212> TYPE: DNA
<213> ORGANISM: Artificial Sequence
<220> FEATURE:
<223> OTHER INFORMATION: ERED variant

<400> SEQUENCE: 111

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat     660
cgtgcacgtt ttactctgga agtcgttgac gcggtggttg atgccatcgg cccagaaaaa     720
gtgggtttac gtctgagtcc gtacggcgtt gctaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 112
<211> LENGTH: 400
<212> TYPE: PRT
<213> ORGANISM: Artificial Sequence
<220> FEATURE:
<223> OTHER INFORMATION: ERED variant

<400> SEQUENCE: 112

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
```

```
                100             105              110
Trp Val Gln Leu Trp Val Leu Gly Trp Ala Ala Phe Pro Asp Asn Leu
            115                 120                 125
Ala Arg Asp Gly Leu Arg Tyr Asp Ser Ala Ser Asp Asn Val Tyr Met
130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
            165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
            195                 200                 205
Asn Arg Thr Asp Glu Tyr Gly Gly Ser Ile Glu Asn Arg Ala Arg Phe
210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Ala Asn Ser Met Ser Gly
            245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
            275                 280                 285
Val Glu Pro Arg Val Thr Asp Pro Ser Leu Val Glu Gly Glu Gly Glu
            290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
            325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
            355                 360                 365
Lys Tyr Asp Arg Ser Thr Phe Tyr Thr Met Ser Ala Glu Gly Tyr Thr
            370                 375                 380
Asp Tyr Pro Thr Tyr Glu Glu Ala Val Asp Leu Gly Trp Asn Lys Asn
385                 390                 395                 400

<210> SEQ ID NO 113
<211> LENGTH: 1200
<212> TYPE: DNA
<213> ORGANISM: Artificial Sequence
<220> FEATURE:
<223> OTHER INFORMATION: ERED variant

<400> SEQUENCE: 113
atgtctttcg ttaaggactt caagccgcag gcactgcgcg acaccaacct gttcgaacct    60
attaaaattg gaacacaca gctggctcat cgcgcggtaa tgcctccgct gacccgcatg   120
cgcgctaccc atccgggcaa cattccgaac aaggagtggg ctgcggttta ctacggccag   180
cgtgcacagc gtccggggac aatgattatc acgagggta cgttcatcag cccgcaggca   240
ggtgggtacg ataacgcgcc tggtgtttgg tcagacgaac aggttgccga atggaagaac   300
atcttcctgg ctattcatga ctgtcagtca tttgcgtggg tgcaactgtg gtcctgggc   360 tgggccgcct tccggataa cctggcgcgt gatgggttac gttacgattc tgcctccgat   420
```

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttgaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgggcgcg   1140
gagggttaca ccgactaccc gacctacgaa gaagccgtag atctgggctg gaacaaaaac   1200
```

<210> SEQ ID NO 114
<211> LENGTH: 400
<212> TYPE: PRT
<213> ORGANISM: Artificial Sequence
<220> FEATURE:
<223> OTHER INFORMATION: ERED variant

<400> SEQUENCE: 114

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Leu Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Gly Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 115
<211> LENGTH: 1200
<212> TYPE: DNA
<213> ORGANISM: Artificial Sequence
<220> FEATURE:
<223> OTHER INFORMATION: ERED variant

<400> SEQUENCE: 115
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg gtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt tgtaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 116
<211> LENGTH: 400
<212> TYPE: PRT
<213> ORGANISM: Artificial Sequence
<220> FEATURE:
<223> OTHER INFORMATION: ERED variant

<400> SEQUENCE: 116

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Cys Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

```
Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 117
<211> LENGTH: 1200
<212> TYPE: DNA
<213> ORGANISM: Artificial Sequence
<220> FEATURE:
<223> OTHER INFORMATION: ERED variant

<400> SEQUENCE: 117
atgtctttcg ttaaggactt caagccgcag gcactgcgcg acaccaacct gttcgaacct    60
attaaaattg ggaacacaca gctggctcat cgcgcggtaa tgcctccgct gacccgcatg   120
cgcgctaccc atccgggcaa cattccgaac aaggagtggg ctgcggttta ctacggccag   180
cgtgcacagc gtccggggac aatgattatc acggagggta cgttcatcag cccgcaggca   240
ggtgggtacg ataacgcgcc tggtgtttgg tcagacgaac aggttgccga atggaagaac   300
atcttcctgg ctattcatga ctgtcagtca tttgcgtggg tgcaactgtg ggtcctgggc   360
tgggccgcct ttccggataa cctggcgcgt gatgggttac gttacgattc tgcctccgat   420
aatgtgtata tgaatgcgga acaggaggaa aaagcgaaaa agctaacaa tccgcaacat   480 agcattacta aagacgaaat taaacaatat gtcaagaat atgttcaggc agctaagaac   540
tcgatcgctg cgggtgcgga cggcgtggaa attcactcag ccaacggtta tctgttaaat   600
cagttcctgg atccgcacag caacaaccgc accgatgagt atggggggctc aattgaaaat   660 cgtgcacgtt ttactctgga agtcgttgac gcggtggttg atgccatcgg cccagaaaaa   720
gtgggtttac gtctgagtcc gtacggcgtt cggaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga cagacccttc tctggttgag   900
ggggagggcg aatactcaga gggcaccaac gatttgctt attccatttg aaaggtccg    960 attatccgtg ccggcaacta cgcactacac cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttctacac catgagcgcg  1140
gagggttaca ccgactaccc gacctacgaa gaagccgtag atctgggctg gaacaaaaac  1200

<210> SEQ ID NO 118
<211> LENGTH: 400
<212> TYPE: PRT
<213> ORGANISM: Artificial Sequence
<220> FEATURE:
<223> OTHER INFORMATION: ERED variant

<400> SEQUENCE: 118

Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80
```

Gly Gly Tyr Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Arg Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 119
<211> LENGTH: 1200
<212> TYPE: DNA
<213> ORGANISM: Artificial Sequence
<220> FEATURE:
<223> OTHER INFORMATION: ERED variant

<400> SEQUENCE: 119
atgtctttcg ttaaggactt caagccgcag gcactgcgcg acaccaacct gttcgaacct      60
attaaaattg gaacacaca gctggctcat cgcgcggtaa tgcctccgct gacccgcatg       120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgttttgg tcagacgaac aggttgccga atggaagaac    300

```
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat     480 agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat   660 cgtgcacgtt ttactctgga agtcgttgac gcggtggttg atgccatcgg cccagaaaaa    720
gtgggtttac gtctgagtcc gtacggcgtt ttccattcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gatttttgctt attccatttg gaaaggtccg    960
attatccgtc ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200

<210> SEQ ID NO 120
<211> LENGTH: 400
<212> TYPE: PRT
<213> ORGANISM: Artificial Sequence
<220> FEATURE:
<223> OTHER INFORMATION: ERED variant

<400> SEQUENCE: 120

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Asn Arg Thr Asp Glu Tyr Gly Gly Ser Ile Glu Asn Arg Ala Arg Phe
        210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Phe His Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
    290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Tyr Pro Thr Tyr Glu Glu Ala Val Asp Leu Gly Trp Asn Lys Asn
385                 390                 395                 400
```

<210> SEQ ID NO 121
<211> LENGTH: 1200
<212> TYPE: DNA
<213> ORGANISM: Artificial Sequence
<220> FEATURE:
<223> OTHER INFORMATION: ERED variant

<400> SEQUENCE: 121

```
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480
agcattacta agacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atggggctc aattgaaaat      660
cgtgcacgtt ttactctgga agtcgttgac gcggtggttg atgccatcgg cccagaaaaa      720
gtgggtttac gtctgagtcc gtacggcgtt ttcaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtgg cagggccttc tctggttgag      900
ggggagggcg aatactcaga gggcaccaac gattttgctt attccatttg gaaaggtccg      960
attatccgtg ccggcaacta cgcactgcac cctgaagttg tgcgcgaaca agttaaggac     1020
```

```
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 122
<211> LENGTH: 400
<212> TYPE: PRT
<213> ORGANISM: Artificial Sequence
<220> FEATURE:
<223> OTHER INFORMATION: ERED variant

<400> SEQUENCE: 122

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Ala Gly Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

```
                340             345             350
Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400
```

<210> SEQ ID NO 123
<211> LENGTH: 1200
<212> TYPE: DNA
<213> ORGANISM: Artificial Sequence
<220> FEATURE:
<223> OTHER INFORMATION: ERED variant

<400> SEQUENCE: 123

```
atgtctttcg ttaaggactt caagccgcag gcactgcgcg acaccaacct gttcgaacct      60
attaaaattg gaacacaca  gctggctcat cgcgcggtaa tgcctccgct gacccgcatg     120
cgcgctaccc atccgggcaa cattccgaac aaggagtggg ctgcggttta ctacggccag    180
cgtgcacagc gtccggggac aatgattatc acggaggta  cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgtg gtcctgggc    360
tgggccgcct ttccggataa cctggcgcgt gatgggttac gttacgattc tgcctccgat    420
aatgtgtata tgaatgcgga acaggaggaa aagcgaaaa  agctaacaa  tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggttac  gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caacgccttc tctggttgag    900
ggggagggcg aatactcaga gggcaccaac gattttgctt attccatttg aaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200
```

<210> SEQ ID NO 124
<211> LENGTH: 400
<212> TYPE: PRT
<213> ORGANISM: Artificial Sequence
<220> FEATURE:
<223> OTHER INFORMATION: ERED variant

<400> SEQUENCE: 124

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45
```

-continued

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
 65                  70                  75                  80

Gly Gly Tyr Asp Asn Ala Pro Gly Val Trp Ser Asp Glu Gln Val Ala
                 85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Thr Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 125
<211> LENGTH: 1200
<212> TYPE: DNA
<213> ORGANISM: Artificial Sequence
<220> FEATURE:
<223> OTHER INFORMATION: ERED variant

<400> SEQUENCE: 125
atgtctttcg ttaaggactt caagccgcag gcactgcgcg acaccaacct gttcgaacct     60
attaaaattg ggaacacaca gctggctcat cgcgcggtaa tgcctccgct gacccgcatg    120

```
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacaggtc tctggttgag    900
ggggagggcg aatactcaga gggcaccaac gatttttgctt attccatttg gaaaggtccg    960
attatccgtg ccggcaacta cgcactgtac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 126
<211> LENGTH: 400
<212> TYPE: PRT
<213> ORGANISM: Artificial Sequence
<220> FEATURE:
<223> OTHER INFORMATION: ERED variant

<400> SEQUENCE: 126

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

|     |     |     |     |     |     |     |     |     |     |     |     |
| --- | --- | --- | --- | --- | --- | --- | --- | --- | --- | --- | --- |
|     |     |     | 180 |     |     | 185 |     |     | 190 |     |     |
| Ser | Ala | Asn | Gly | Tyr | Leu | Leu | Asn | Gln | Phe | Leu | Asp | Pro | His | Ser | Asn |
|     |     |     | 195 |     |     | 200 |     |     |     | 205 |     |
| Asn | Arg | Thr | Asp | Glu | Tyr | Gly | Gly | Ser | Ile | Glu | Asn | Arg | Ala | Arg | Phe |
|     |     | 210 |     |     |     | 215 |     |     |     | 220 |     |
| Thr | Leu | Glu | Val | Val | Asp | Ala | Val | Val | Asp | Ala | Ile | Gly | Pro | Glu | Lys |
| 225 |     |     |     | 230 |     |     |     | 235 |     |     |     | 240 |
| Val | Gly | Leu | Arg | Leu | Ser | Pro | Tyr | Gly | Val | Phe | Asn | Ser | Met | Ser | Gly |
|     |     |     | 245 |     |     |     | 250 |     |     |     | 255 |
| Gly | Ala | Glu | Thr | Gly | Ile | Val | Ala | Gln | Tyr | Ala | Tyr | Val | Leu | Gly | Glu |
|     |     | 260 |     |     |     | 265 |     |     |     | 270 |     |
| Leu | Glu | Arg | Arg | Ala | Lys | Ala | Gly | Lys | Arg | Leu | Ala | Phe | Val | His | Leu |
|     | 275 |     |     |     | 280 |     |     |     | 285 |     |     |
| Val | Glu | Pro | Arg | Val | Thr | Asp | Arg | Ser | Leu | Val | Glu | Gly | Glu | Gly | Glu |
|     | 290 |     |     |     | 295 |     |     |     | 300 |     |     |
| Tyr | Ser | Glu | Gly | Thr | Asn | Asp | Phe | Ala | Tyr | Ser | Ile | Trp | Lys | Gly | Pro |
| 305 |     |     |     | 310 |     |     |     | 315 |     |     |     | 320 |
| Ile | Ile | Arg | Ala | Gly | Asn | Tyr | Ala | Leu | Tyr | Pro | Glu | Val | Val | Arg | Glu |
|     |     |     | 325 |     |     |     | 330 |     |     |     | 335 |
| Gln | Val | Lys | Asp | Pro | Arg | Thr | Leu | Ile | Gly | Tyr | Gly | Arg | Phe | Phe | Ile |
|     |     | 340 |     |     |     | 345 |     |     |     | 350 |     |
| Ser | Asn | Pro | Asp | Leu | Val | Tyr | Arg | Leu | Glu | Glu | Gly | Leu | Pro | Leu | Asn |
|     | 355 |     |     |     | 360 |     |     |     | 365 |     |     |
| Lys | Tyr | Asp | Arg | Ser | Thr | Phe | Tyr | Thr | Met | Ser | Ala | Glu | Gly | Tyr | Thr |
| 370 |     |     |     | 375 |     |     |     | 380 |     |     |
| Asp | Tyr | Pro | Thr | Tyr | Glu | Glu | Ala | Val | Asp | Leu | Gly | Trp | Asn | Lys | Asn |
| 385 |     |     |     | 390 |     |     |     | 395 |     |     |     | 400 |

<210> SEQ ID NO 127
<211> LENGTH: 1200
<212> TYPE: DNA
<213> ORGANISM: Artificial Sequence
<220> FEATURE:
<223> OTHER INFORMATION: ERED variant

<400> SEQUENCE: 127

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta agacgaaat taaacaatat gtcaaagaat atgttcaggc agctaagaac      540
tcgatcgctg cgggtgcgga cggcgtggaa attcactcag ccaacggtta tctgttaaat     600
cagttcctgg atccgcacag caacaaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacgggtc tctggttgag     900
```

```
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 128
<211> LENGTH: 400
<212> TYPE: PRT
<213> ORGANISM: Artificial Sequence
<220> FEATURE:
<223> OTHER INFORMATION: ERED variant

<400> SEQUENCE: 128

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Gly Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320
```

```
Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 129
<211> LENGTH: 1200
<212> TYPE: DNA
<213> ORGANISM: Artificial Sequence
<220> FEATURE:
<223> OTHER INFORMATION: ERED variant

<400> SEQUENCE: 129
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcccgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta agacgaaat taaacaatat gtcaaagaat atgttcaggc agctaagaac      540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg aaaggtccg     960
attatccgtg ccggcaacta cgcactgcac cctgaagttg tgcgcgaaca agttaaggac    1020
cctcgcaccc tgatcggcta cggccgcttc tttatttcaa atccagacct agtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200

<210> SEQ ID NO 130
<211> LENGTH: 400
<212> TYPE: PRT
<213> ORGANISM: Artificial Sequence
<220> FEATURE:
<223> OTHER INFORMATION: ERED variant

<400> SEQUENCE: 130

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
```

```
                    20                  25                  30
Val Met Pro Pro Leu Thr Arg Met Arg Ala Thr His Pro Gly Asn Ile
                35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
                100                 105                 110

Trp Val Gln Leu Trp Val Pro Gly Trp Ala Ala Phe Pro Asp Asn Leu
                115                 120                 125

Ala Arg Asp Gly Leu Arg Tyr Asp Ser Ala Ser Asp Asn Val Tyr Met
    130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
                195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
    275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
    355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 131
<211> LENGTH: 1200
<212> TYPE: DNA
<213> ORGANISM: Artificial Sequence
<220> FEATURE:
<223> OTHER INFORMATION: ERED variant

<400> SEQUENCE: 131
```

```
atgtctttcg ttaaggactt caagccgccg gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagaccctgg gctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgggcgcg    1140
gagggttaca ccgactaccc gacctacgaa gaagccgtag atctgggctg aacaaaaac     1200
```

<210> SEQ ID NO 132  
<211> LENGTH: 400  
<212> TYPE: PRT  
<213> ORGANISM: Artificial Sequence  
<220> FEATURE:  
<223> OTHER INFORMATION: ERED variant

<400> SEQUENCE: 132

```
Met Ser Phe Val Lys Asp Phe Lys Pro Pro Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160
```

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Gly Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Gly Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 133
<211> LENGTH: 1200
<212> TYPE: DNA
<213> ORGANISM: Artificial Sequence
<220> FEATURE:
<223> OTHER INFORMATION: ERED variant

<400> SEQUENCE: 133
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgctcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720

```
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagaccctgc gctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 134
<211> LENGTH: 400
<212> TYPE: PRT
<213> ORGANISM: Artificial Sequence
<220> FEATURE:
<223> OTHER INFORMATION: ERED variant

<400> SEQUENCE: 134

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Leu Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

```
Val Glu Pro Arg Val Thr Asp Pro Ala Leu Val Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 135
<211> LENGTH: 1200
<212> TYPE: DNA
<213> ORGANISM: Artificial Sequence
<220> FEATURE:
<223> OTHER INFORMATION: ERED variant

<400> SEQUENCE: 135
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg gtcctgggc      360 tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtgcggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagaccctgg ctggttgag      900 ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 136
<211> LENGTH: 400
<212> TYPE: PRT
<213> ORGANISM: Artificial Sequence
<220> FEATURE:
<223> OTHER INFORMATION: ERED variant

<400> SEQUENCE: 136
```

```
Met Ser Phe Val Lys Asp Phe Lys Pro Gln Ala Leu Arg Asp Thr Asn
1               5                   10                  15
Leu Phe Glu Pro Ile Lys Ile Gly Asn Thr Gln Leu Ala His Arg Ala
                20                  25                  30
Val Met Pro Pro Leu Thr Arg Met Arg Ala Thr His Pro Gly Asn Ile
            35                  40                  45
Pro Asn Lys Glu Trp Ala Ala Val Tyr Tyr Gly Gln Arg Ala Gln Arg
        50                  55                  60
Pro Gly Thr Met Ile Ile Thr Glu Gly Thr Phe Ile Ser Pro Gln Ala
65                  70                  75                  80
Gly Gly Tyr Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
                100                 105                 110
Trp Val Gln Leu Trp Val Leu Gly Trp Ala Ala Phe Pro Asp Asn Leu
            115                 120                 125
Ala Arg Asp Gly Leu Arg Tyr Asp Ser Ala Ser Asp Asn Val Tyr Met
        130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Lys Asn Ser Ile Ala Ala Gly Ala Asp Gly Val Glu Ile His
            180                 185                 190
Ser Ala Asn Gly Tyr Leu Leu Asn Gln Phe Leu Asp Pro His Ser Asn
        195                 200                 205
Asn Arg Thr Asp Glu Tyr Gly Gly Ser Ile Glu Asn Arg Ala Arg Phe
210                 215                 220
Thr Leu Glu Val Val Asp Ala Val Val Asp Ala Ile Gly Pro Glu Lys
225                 230                 235                 240
Val Gly Leu Arg Leu Ser Pro Cys Gly Val Phe Asn Ser Met Ser Gly
                245                 250                 255
Gly Ala Glu Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
        275                 280                 285
Val Glu Pro Arg Val Thr Asp Pro Gly Leu Val Glu Gly Glu Gly Glu
    290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Tyr Pro Thr Tyr Glu Glu Ala Val Asp Leu Gly Trp Asn Lys Asn
385                 390                 395                 400

<210> SEQ ID NO 137
<211> LENGTH: 1200
<212> TYPE: DNA
```

<213> ORGANISM: Artificial Sequence
<220> FEATURE:
<223> OTHER INFORMATION: ERED variant

<400> SEQUENCE: 137

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg gtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttt tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 138
<211> LENGTH: 400
<212> TYPE: PRT
<213> ORGANISM: Artificial Sequence
<220> FEATURE:
<223> OTHER INFORMATION: ERED variant

<400> SEQUENCE: 138

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125
```

| | | | | | | | | | | | | |
|---|---|---|---|---|---|---|---|---|---|---|---|---|
|Ala|Arg|Asp|Gly|Leu|Arg|Tyr|Asp|Ser|Ala|Ser|Asp|Asn|Val|Tyr|Met|
| |130| | | |135| | | |140| | | | | | |

Ala Arg Asp Gly Leu Arg Tyr Asp Ser Ala Ser Asp Asn Val Tyr Met
    130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
                275                 280                 285

Val Glu Pro Arg Val Thr Asp Pro Phe Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 139
<211> LENGTH: 1200
<212> TYPE: DNA
<213> ORGANISM: Artificial Sequence
<220> FEATURE:
<223> OTHER INFORMATION: ERED variant

<400> SEQUENCE: 139

```
atgtctttcg ttaaggactt caagccgcag gcactgcgcg acaccaacct gttcgaacct      60
attaaaattg gaacacaca gctggctcat cgcgcggtaa tgcctccgct gacccgcatg       120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat       480 agcattacta aagacgaaat taaacaatat gtcaaagaat atgttcaggc agctaagaac      540
tcgatcgctg cgggtgcgga cggcgtggaa attcactcag ccaacggtta tctgttaaat      600
```

```
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccta a gctggttgag    900 ggggagggcg aatactcaga gggcaccaac gattttgctt attccatttg aaaggtccg     960 attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 140
<211> LENGTH: 400
<212> TYPE: PRT
<213> ORGANISM: Artificial Sequence
<220> FEATURE:
<223> OTHER INFORMATION: ERED variant

<400> SEQUENCE: 140

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
```

```
                260                 265                 270
Leu Glu Arg Arg Ala Lys Ala Gly Lys Arg Leu Ala Phe Val His Leu
                275                 280                 285

Val Glu Pro Arg Val Thr Asp Pro Lys Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
                370                 375                 380

Asp Tyr Pro Thr Tyr Glu Glu Ala Val Asp Leu Gly Trp Asn Lys Asn
385                 390                 395                 400

<210> SEQ ID NO 141
<211> LENGTH: 1200
<212> TYPE: DNA
<213> ORGANISM: Artificial Sequence
<220> FEATURE:
<223> OTHER INFORMATION: ERED variant

<400> SEQUENCE: 141
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaggcgaaaa agctaacaa tccgcaacat      480 agcattacta aagacgaaat taacaatat gtcaaagaat atgttcaggc agctaagaac      540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccta tctggttgag     900 ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 142
<211> LENGTH: 400
<212> TYPE: PRT
```

<213> ORGANISM: Artificial Sequence
<220> FEATURE:
<223> OTHER INFORMATION: ERED variant

<400> SEQUENCE: 142

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Tyr Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400
```

<210> SEQ ID NO 143
<211> LENGTH: 1200
<212> TYPE: DNA
<213> ORGANISM: Artificial Sequence
<220> FEATURE:
<223> OTHER INFORMATION: ERED variant

<400> SEQUENCE: 143

```
atgtctttcg ttaaggactt caagccgcag gcactgcgcg acaccaacct gttcgaacct      60
attaaaattg gaacacaca gctggctcat cgcgcggtaa tgcctccgct gagccgcatg     120
cgcgctaccc atccgggcaa cattccgaac aaggagtggg ctgcggttta ctacggccag     180
cgcgcacagc gtccggggac aatgattatc acggaggta cgttcatcag cccgcaggca     240
ggtgggatcg ataacgcgcc tggtgtttgg tcagacgaac aggttgccga atggaagaac     300
atcttcctgg ctattcatga ctgtcagtca tttgcgtggg tgcaactggc ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gatttgctt attccatttg gaaaggtccg     960
attatccgtg ccggcaacta cgcactgtac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 144
<211> LENGTH: 400
<212> TYPE: PRT
<213> ORGANISM: Artificial Sequence
<220> FEATURE:
<223> OTHER INFORMATION: ERED variant

<400> SEQUENCE: 144

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala

|     |     |     |     |     | 100 |     |     |     | 105 |     |     |     |     | 110 |
| --- | --- | --- | --- | --- | --- | --- | --- | --- | --- | --- | --- | --- | --- | --- |

Trp Val Gln Leu Ala Val Leu Gly Trp Ala Ala Phe Pro Asp Asn Leu
          115                   120                   125

Ala Arg Asp Gly Leu Arg Tyr Asp Ser Ala Ser Asp Asn Val Tyr Met
130                  135                   140

Asn Ala Glu Gln Glu Glu Lys Ala Lys Lys Ala Asn Asn Pro Gln His
145                  150                   155                   160

Ser Ile Thr Lys Asp Glu Ile Lys Gln Tyr Val Lys Glu Tyr Val Gln
                  165                   170                   175

Ala Ala Lys Asn Ser Ile Ala Ala Gly Ala Asp Gly Val Glu Ile His
                  180                   185                   190

Ser Ala Asn Gly Tyr Leu Leu Asn Gln Phe Leu Asp Pro His Ser Asn
                  195                   200                   205

Asn Arg Thr Asp Glu Tyr Gly Gly Ser Ile Glu Asn Arg Ala Arg Phe
          210                   215                   220

Thr Leu Glu Val Val Asp Ala Val Val Asp Ala Ile Gly Pro Glu Lys
225                  230                   235                   240

Val Gly Leu Arg Leu Ser Pro Tyr Gly Val Phe Asn Ser Met Ser Gly
                  245                   250                   255

Gly Ala Glu Thr Gly Ile Val Ala Gln Tyr Ala Tyr Val Leu Gly Glu
                  260                   265                   270

Leu Glu Arg Arg Ala Lys Ala Gly Lys Arg Leu Ala Phe Val His Leu
          275                   280                   285

Val Glu Pro Arg Val Thr Asp Pro Ser Leu Val Glu Gly Glu Gly Glu
          290                   295                   300

Tyr Ser Glu Gly Thr Asn Asp Phe Ala Tyr Ser Ile Trp Lys Gly Pro
305                  310                   315                   320

Ile Ile Arg Ala Gly Asn Tyr Ala Leu Tyr Pro Glu Val Val Arg Glu
                  325                   330                   335

Gln Val Lys Asp Pro Arg Thr Leu Ile Gly Tyr Gly Arg Phe Phe Ile
                  340                   345                   350

Ser Asn Pro Asp Leu Val Tyr Arg Leu Glu Glu Gly Leu Pro Leu Asn
          355                   360                   365

Lys Tyr Asp Arg Ser Thr Phe Tyr Thr Met Ser Ala Glu Gly Tyr Thr
          370                   375                   380

Asp Tyr Pro Thr Tyr Glu Glu Ala Val Asp Leu Gly Trp Asn Lys Asn
385                  390                   395                   400

<210> SEQ ID NO 145
<211> LENGTH: 1200
<212> TYPE: DNA
<213> ORGANISM: Artificial Sequence
<220> FEATURE:
<223> OTHER INFORMATION: ERED variant

<400> SEQUENCE: 145

| atgtctttcg | ttaaggactt | caagccgcag | gcactgcgcg | acaccaacct | gttcgaacct | 60 |
| tattaaaattg | ggaacacaca | gctggctcat | cgcgcggtaa | tgcctccgct | gagccgcatg | 120 |
| cgcgctaccc | atccgggcaa | cattccgaac | aaggagtggg | ctgcggttta | ctacggccag | 180 |
| cgtgcacagc | gtccggggac | aatgattatc | acgagggta | cgttcatcag | cccgcaggca | 240 |
| ggtgggatcg | ataacgcgcc | tggtgtttgg | tcagacgaac | aggttgccga | atggaagaac | 300 |
| atcttcctgg | ctattcatga | ctgtcagtca | tttgcgtggg | tgcaactgtg | gtcctgggc | 360 |
| tgggccgcct | ttccggataa | cctggcgcgt | gatgggttac | gttacgattc | tgcctccgat | 420 |

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag taacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccta tctggttgag     900 ggggagggcg aatactcaga gggcaccaac gatttcgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200
```

<210> SEQ ID NO 146
<211> LENGTH: 400
<212> TYPE: PRT
<213> ORGANISM: Artificial Sequence
<220> FEATURE:
<223> OTHER INFORMATION: ERED variant

<400> SEQUENCE: 146

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Phe Asn Ser Met Ser Gly
        245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Tyr Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 147
<211> LENGTH: 1200
<212> TYPE: DNA
<213> ORGANISM: Artificial Sequence
<220> FEATURE:
<223> OTHER INFORMATION: ERED variant

<400> SEQUENCE: 147
atgtctttcg ttaaggactt caagccgcag gcactgcgcg acaccaacct gttcgaacct    60
attaaaattg gaacacaca gctggctcat cgcgcggtaa tgcctccgct gagccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactggc ggtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta agacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200

<210> SEQ ID NO 148
<211> LENGTH: 400
<212> TYPE: PRT
<213> ORGANISM: Artificial Sequence
<220> FEATURE:
<223> OTHER INFORMATION: ERED variant

<400> SEQUENCE: 148

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ala Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

| Lys | Tyr | Asp | Arg | Ser | Thr | Phe | Tyr | Thr | Met | Ser | Ala | Glu | Gly | Tyr | Thr |
| | 370 | | | | 375 | | | | 380 | | | | | | |

| Asp | Tyr | Pro | Thr | Tyr | Glu | Glu | Ala | Val | Asp | Leu | Gly | Trp | Asn | Lys | Asn |
| 385 | | | | | 390 | | | | | 395 | | | | | 400 |

<210> SEQ ID NO 149
<211> LENGTH: 1200
<212> TYPE: DNA
<213> ORGANISM: Artificial Sequence
<220> FEATURE:
<223> OTHER INFORMATION: ERED variant

<400> SEQUENCE: 149

```
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggaagg ataacgcgcc tggtgtttgg tcagacgaac aggttgccga atggaagaac     300
atcttcctgg ctattcatga ctgtcagtca tttgcgtggg tgcaactgat cgtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta agacgaaat taacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg gaacaaaaac    1200
```

<210> SEQ ID NO 150
<211> LENGTH: 400
<212> TYPE: PRT
<213> ORGANISM: Artificial Sequence
<220> FEATURE:
<223> OTHER INFORMATION: ERED variant

<400> SEQUENCE: 150

| Met | Ser | Phe | Val | Lys | Asp | Phe | Lys | Pro | Gln | Ala | Leu | Arg | Asp | Thr | Asn |
| 1 | | | | 5 | | | | | 10 | | | | | 15 | |

| Leu | Phe | Glu | Pro | Ile | Lys | Ile | Gly | Asn | Thr | Gln | Leu | Ala | His | Arg | Ala |
| | | | 20 | | | | | 25 | | | | | 30 | | |

| Val | Met | Pro | Pro | Leu | Thr | Arg | Met | Arg | Ala | Thr | His | Pro | Gly | Asn | Ile |
| | | 35 | | | | | 40 | | | | | 45 | | | |

| Pro | Asn | Lys | Glu | Trp | Ala | Ala | Val | Tyr | Tyr | Gly | Gln | Arg | Ala | Gln | Arg |
| | 50 | | | | | 55 | | | | | 60 | | | | |

| Pro | Gly | Thr | Met | Ile | Ile | Thr | Glu | Gly | Thr | Phe | Ile | Ser | Pro | Gln | Ala |
| 65 | | | | | 70 | | | | | 75 | | | | | 80 |

Gly Gly Lys Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 151
<211> LENGTH: 1200
<212> TYPE: DNA
<213> ORGANISM: Artificial Sequence
<220> FEATURE:
<223> OTHER INFORMATION: ERED variant

<400> SEQUENCE: 151
atgtctttcg ttaaggactt caagccgcag gcactgcgcg acaccaaccT gttcgaacct     60
attaaaattg gaacacaca gctggctcat cgcgcggtaa tgcctccgct gagccgcgaa    120
cgcgctaccc atccgggcaa cattccgaac aaggagtggg ctgcggttta ctacggccag    180
cgtgcacagc gtccggggac aatgattatc acggagggta cgtccatcag cccgcaggca    240
ggtgggatcg ataacgcgcc tggtgttTgg tcagacgaac aggttgccga atggaagaac    300

-continued

```
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat     480
agcattacta aagacgaaat taaacaatat gtcaaagaat atgttcaggc agctaagaac    540
tcgatcgctg cgggtgcgga tggcgtggaa attcactcag ccaacggtta tctgttaaat    600
cagttcctgg atccgcacag caacaaccgc accgatgagt atggggctc aattgaaaat     660
cgtgcacgtt ttactctgga agtcgttgac gcggtggttg atgccatcgg cccagaaaaa    720
gtgggttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg aaaggtccg     960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 152
<211> LENGTH: 400
<212> TYPE: PRT
<213> ORGANISM: Artificial Sequence
<220> FEATURE:
<223> OTHER INFORMATION: ERED variant

<400> SEQUENCE: 152

```
Met Ser Phe Val Lys Asp Phe Lys Pro Gln Ala Leu Arg Asp Thr Asn
 1               5                  10                  15

Leu Phe Glu Pro Ile Lys Ile Gly Asn Thr Gln Leu Ala His Arg Ala
            20                  25                  30

Val Met Pro Pro Leu Ser Arg Glu Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Ser Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Asn Arg Thr Asp Glu Tyr Gly Gly Ser Ile Glu Asn Arg Ala Arg Phe
        210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400
```

<210> SEQ ID NO 153
<211> LENGTH: 1200
<212> TYPE: DNA
<213> ORGANISM: Artificial Sequence
<220> FEATURE:
<223> OTHER INFORMATION: ERED variant

<400> SEQUENCE: 153

```
atgtctttcg ttaaggactt caagccgcag gcactgcgcg acaccaacct gttcgaacct     60
attaaaattg gaacacaca gctggctcat cgcgcggtaa tgcctccgct gagccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta agacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
```

```
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 154
<211> LENGTH: 400
<212> TYPE: PRT
<213> ORGANISM: Artificial Sequence
<220> FEATURE:
<223> OTHER INFORMATION: ERED variant

<400> SEQUENCE: 154

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Ser Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 155
<211> LENGTH: 1200
<212> TYPE: DNA
<213> ORGANISM: Artificial Sequence
<220> FEATURE:
<223> OTHER INFORMATION: ERED variant

<400> SEQUENCE: 155
atgtctttcg ttaaggactt caagccgcag gcactgcgcg acaccaacct gttcgaacct    60
attaaaattg gaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtggggagg ataacgcgcc tggtgtttgg tcagacgaac aggttgccga atggaagaac    300
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aagcgaaaa aagctaacaa tccgcaacat    480
agcattacta aagacgaaat taaacaatat gtcaaagaat atgttcaggc agctaagaac    540
tcgatcgctg cgggtgcgga cggcgtgaa attcactcag ccaacggtta tctgttaaat    600
cagttcctgg atccgcacag caacaaccgc accgatgagt atggggctc aattgaaaat    660
cgtgcacgtt ttactctgga agtcgttgac gcggtggttg atgccatcgg ccctgaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagaccctc tctggttgag    900
ggggagggcg aatactcaga gggcaccaac gattttgctt attccatttg aagggtccg    960
attatccgtg ccggcaacta cgcactgcac cctgaagctg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200

<210> SEQ ID NO 156
<211> LENGTH: 400
<212> TYPE: PRT
<213> ORGANISM: Artificial Sequence
<220> FEATURE:
<223> OTHER INFORMATION: ERED variant

<400> SEQUENCE: 156

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
 65                  70                  75                  80

Gly Gly Glu Asp Asn Ala Pro Gly Val Trp Ser Asp Glu Gln Val Ala
                 85                  90                  95

Glu Trp Lys Asn Ile Phe Leu Ala Ile His Asp Cys Gln Ser Phe Ala
            100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Ala Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 157
<211> LENGTH: 1200
<212> TYPE: DNA
<213> ORGANISM: Artificial Sequence
<220> FEATURE:
<223> OTHER INFORMATION: ERED variant

<400> SEQUENCE: 157
atgtctttcg ttaaggactt caagccgcag gcactgcgcg acaccaacct gttcgaacct        60
attaaaattg ggaacacaca gctggctcat cgcgcggtaa tgcctccgct gacccgcatg       120

```
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggatcg ataacgcgcc tggtgtttgg tcagacgaac aggttgccga atggaagaac    300
atcttcctgg ctattcatga ctgtcagtca tttgcgtggg tgcaactgat cgtcctgggc    360
tgggccgcct ttccggataa cctggcgcgt gatgggttac gttacgattc tgcctccgat    420
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat    660 cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200
```

<210> SEQ ID NO 158
<211> LENGTH: 400
<212> TYPE: PRT
<213> ORGANISM: Artificial Sequence
<220> FEATURE:
<223> OTHER INFORMATION: ERED variant

<400> SEQUENCE: 158

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Ile Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Ile Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

```
                      180                 185                 190
Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 159
<211> LENGTH: 1200
<212> TYPE: DNA
<213> ORGANISM: Artificial Sequence
<220> FEATURE:
<223> OTHER INFORMATION: ERED variant

<400> SEQUENCE: 159
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta agacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt agcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacgaagc tctggttgag     900
```

```
gggagggcg aatactcaga gggcaccaac gaatttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 160
<211> LENGTH: 400
<212> TYPE: PRT
<213> ORGANISM: Artificial Sequence
<220> FEATURE:
<223> OTHER INFORMATION: ERED variant

<400> SEQUENCE: 160

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Glu Ala Leu Val Glu Gly Glu Gly Glu
    290                 295                 300

Tyr Ser Glu Gly Thr Asn Glu Phe Ala Tyr Ser Ile Trp Lys Gly Pro
305                 310                 315                 320
```

```
Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
                355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 161
<211> LENGTH: 1200
<212> TYPE: DNA
<213> ORGANISM: Artificial Sequence
<220> FEATURE:
<223> OTHER INFORMATION: ERED variant

<400> SEQUENCE: 161
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacgcttt cctggttgag     900
ggggagggcg aatactcaga gggcaccaac gattttgctt attccatttg aaaggtccg      960 attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200

<210> SEQ ID NO 162
<211> LENGTH: 400
<212> TYPE: PRT
<213> ORGANISM: Artificial Sequence
<220> FEATURE:
<223> OTHER INFORMATION: ERED variant

<400> SEQUENCE: 162

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
```

20                  25                  30
Val Met Pro Leu Thr Arg Met Arg Ala Thr His Pro Gly Asn Ile
            35                  40                  45

Pro Asn Lys Glu Trp Ala Ala Val Tyr Tyr Gly Gln Arg Ala Gln Arg
 50                  55                  60

Pro Gly Thr Met Ile Ile Thr Glu Gly Thr Phe Ile Ser Pro Gln Ala
 65                  70                  75                  80

Gly Gly Tyr Asp Asn Ala Pro Gly Val Trp Ser Asp Glu Gln Val Ala
                 85                  90                  95

Glu Trp Lys Asn Ile Phe Leu Ala Ile His Asp Cys Gln Ser Phe Ala
                100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
            130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
            210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
            275                 280                 285

Val Glu Pro Arg Val Thr Asp Ala Phe Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 163
<211> LENGTH: 1200
<212> TYPE: DNA
<213> ORGANISM: Artificial Sequence
<220> FEATURE:
<223> OTHER INFORMATION: ERED variant

<400> SEQUENCE: 163

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaga     720
gtgggtttac gtctgagtcc gtacggcgtt agcaactcta tgtcgggcgg cgcgggaacg     780
ggcattgttg ctcagtatgc ctatgtcctg ggtgagctgg agcgtcgtgc caaggcgggg     840
aaacgcctgg cgtttgttca tttagtcgaa ccacgcgtga cagaccaagc tctggttgag     900
ggggagggcg aatactcaga gggcaccaac gattttgctt attccatttg aaaggtccg      960 attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac     1200
```

<210> SEQ ID NO 164
<211> LENGTH: 400
<212> TYPE: PRT
<213> ORGANISM: Artificial Sequence
<220> FEATURE:
<223> OTHER INFORMATION: ERED variant

<400> SEQUENCE: 164

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160
```

Ser Ile Thr Lys Asp Glu Ile Lys Gln Tyr Val Lys Glu Tyr Val Gln
           165                 170                 175

Ala Ala Lys Asn Ser Ile Ala Ala Gly Ala Asp Gly Val Glu Ile His
           180                 185                 190

Ser Ala Asn Gly Tyr Leu Leu Asn Gln Phe Leu Asp Pro His Ser Asn
           195                 200                 205

Asn Arg Thr Asp Glu Tyr Gly Gly Ser Ile Glu Asn Arg Ala Arg Phe
           210                 215                 220

Thr Leu Glu Val Val Asp Ala Val Asp Ala Ile Gly Pro Glu Arg
225                 230                 235                 240

Val Gly Leu Arg Leu Ser Pro Tyr Gly Val Ser Asn Ser Met Ser Gly
               245                 250                 255

Gly Ala Gly Thr Gly Ile Val Ala Gln Tyr Ala Tyr Val Leu Gly Glu
           260                 265                 270

Leu Glu Arg Arg Ala Lys Ala Gly Lys Arg Leu Ala Phe Val His Leu
           275                 280                 285

Val Glu Pro Arg Val Thr Asp Gln Ala Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
               325                 330                 335

Gln Val Lys Asp Pro Arg Thr Leu Ile Gly Tyr Gly Arg Phe Phe Ile
           340                 345                 350

Ser Asn Pro Asp Leu Val Tyr Arg Leu Glu Glu Gly Leu Pro Leu Asn
           355                 360                 365

Lys Tyr Asp Arg Ser Thr Phe Tyr Thr Met Ser Ala Glu Gly Tyr Thr
           370                 375                 380

Asp Tyr Pro Thr Tyr Glu Glu Ala Val Asp Leu Gly Trp Asn Lys Asn
385                 390                 395                 400

<210> SEQ ID NO 165
<211> LENGTH: 1200
<212> TYPE: DNA
<213> ORGANISM: Artificial Sequence
<220> FEATURE:
<223> OTHER INFORMATION: ERED variant

<400> SEQUENCE: 165
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660 cgtgcacgtt ttactctgga agtcgttgac gcggtggttg atgccatcgg cccagaaaaa     720

```
gtgggtttac gtctgagtcc gtacggcgtt atcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacagttt cctggttgag    900
ggggagggcg aatactcaga gggcaccaac gattttgctt attccatttg aaaggtccg     960 attatccgtg ccggcaacta cgcactgcac cctgaagtcg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 166
<211> LENGTH: 400
<212> TYPE: PRT
<213> ORGANISM: Artificial Sequence
<220> FEATURE:
<223> OTHER INFORMATION: ERED variant

<400> SEQUENCE: 166

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ile Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

-continued

```
Val Glu Pro Arg Val Thr Asp Ser Phe Leu Val Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 167
<211> LENGTH: 1200
<212> TYPE: DNA
<213> ORGANISM: Artificial Sequence
<220> FEATURE:
<223> OTHER INFORMATION: ERED variant

<400> SEQUENCE: 167
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg gtcctgggc     360 tgggccgcct ttccggataa cctggcgcgt gatgggttac gttacgattc tgcctccgat     420
aatgtgtata tgaatgcgga acaggaggaa aaagcgaaaa agctaacaa tccgcaacat     480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt agcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagaccctat tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggcttaccgc    1080
ttagaagaag gtctgccact gaacaagtat gaccgttcta cgttctacac catgagcgcg    1140
gagggttaca ccgactaccc gacctacgaa gaagccgtag atctgggctg aaacaaaaac    1200

<210> SEQ ID NO 168
<211> LENGTH: 400
<212> TYPE: PRT
<213> ORGANISM: Artificial Sequence
<220> FEATURE:
<223> OTHER INFORMATION: ERED variant

<400> SEQUENCE: 168
```

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
            130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
            210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ser Asn Ser Met Ser Gly
            245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
            275                 280                 285

Val Glu Pro Arg Val Thr Asp Pro Ile Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Ala Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400

<210> SEQ ID NO 169
<211> LENGTH: 1200
<212> TYPE: DNA

<213> ORGANISM: Artificial Sequence
<220> FEATURE:
<223> OTHER INFORMATION: ERED variant

<400> SEQUENCE: 169

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg gtcctgggc      360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacaaatc tctggttgag     900
ggggagggcg aatactcaga gggcaccaac gattttgctt attccatttg gaaaggtccg     960
attatccgtg ccggcaacta cgcactacac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttcgccac catgagcgcg    1140
gagggttaca ccgactaccc gacctacgaa gaagccgtag atctgggctg aacaaaaac     1200
```

<210> SEQ ID NO 170
<211> LENGTH: 400
<212> TYPE: PRT
<213> ORGANISM: Artificial Sequence
<220> FEATURE:
<223> OTHER INFORMATION: ERED variant

<400> SEQUENCE: 170

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125
```

```
Ala Arg Asp Gly Leu Arg Tyr Asp Ser Ala Ser Asp Asn Val Tyr Met
        130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
        180                 185                 190

Ser Ala Asn Gly Tyr Leu Leu Asn Gln Phe Leu Asp Pro His Ser Asn
    195                 200                 205

Asn Arg Thr Asp Glu Tyr Gly Gly Ser Ile Glu Asn Arg Ala Arg Phe
210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
    275                 280                 285

Val Glu Pro Arg Val Thr Asp Lys Ser Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
    355                 360                 365

Lys Tyr Asp Arg Ser Thr Phe Ala Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400
```

<210> SEQ ID NO 171
<211> LENGTH: 1200
<212> TYPE: DNA
<213> ORGANISM: Artificial Sequence
<220> FEATURE:
<223> OTHER INFORMATION: ERED variant

<400> SEQUENCE: 171

```
atgtctttcg ttaaggactt caagccgcag gcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggaaggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat      480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
```

```
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt gctaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacgctaa gctggttgag    900
ggggagggcg aatactcaga gggcaccaac gattttgctt attccatttg aaaggtccg    960 attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacgaaaac    1200
```

<210> SEQ ID NO 172
<211> LENGTH: 400
<212> TYPE: PRT
<213> ORGANISM: Artificial Sequence
<220> FEATURE:
<223> OTHER INFORMATION: ERED variant

<400> SEQUENCE: 172

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Ala Asn Ser Met Ser Gly
                245                 250                 255

Gly Ala Glu Thr Gly Ile Val Ala Gln Tyr Ala Tyr Val Leu Gly Glu
```

```
                260             265             270
Leu Glu Arg Arg Ala Lys Ala Gly Lys Arg Leu Ala Phe Val His Leu
            275                 280                 285
Val Glu Pro Arg Val Thr Asp Ala Lys Leu Val Glu Gly Glu Gly Glu
        290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Tyr Pro Thr Tyr Glu Glu Ala Val Asp Leu Gly Trp Asn Glu Asn
385                 390                 395                 400
```

<210> SEQ ID NO 173
<211> LENGTH: 1200
<212> TYPE: DNA
<213> ORGANISM: Artificial Sequence
<220> FEATURE:
<223> OTHER INFORMATION: ERED variant

<400> SEQUENCE: 173

```
atgtctttcg ttaaggactt caagccgcag gcactgcgcg acaccaacct gttcgaacct     60
attaaaattg ggaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttcatcag cccgcaggca    240
ggtgggtacg ataacgcgcc tggtgtttgg tcagacgaac aggttgccga atggaagaac    300
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcgga acaggaggaa aaagcgaaaa agctaacaa tccgcaacat    480
agcattacta aagacgaaat taacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacccttc tctggttgag    900
ggggagggcg aatcctcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttcatcac catgagcgcg   1140
gagggttaca ccgactaccc gacctacgaa gaagccgtag atctgggctg gaacaaaaac   1200
```

<210> SEQ ID NO 174
<211> LENGTH: 400
<212> TYPE: PRT

<213> ORGANISM: Artificial Sequence
<220> FEATURE:
<223> OTHER INFORMATION: ERED variant

<400> SEQUENCE: 174

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Ser Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Ile Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 175
<211> LENGTH: 1200
<212> TYPE: DNA
<213> ORGANISM: Artificial Sequence
<220> FEATURE:
<223> OTHER INFORMATION: ERED variant

<400> SEQUENCE: 175

```
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggaggta cgttcatcag cccgcaggca     240
ggtgggtacg ataacgcgcc tggtgtttgg tcagacgaac aggttgccga atggaagaac     300
atcttcctgg ctattcatga ctgtcagtca tttgcgtggg tgcaactgtg ggtcctgggc     360
tgggccgcct ttccggataa cctggcgcgt gatgggttac gttacgattc tgcctccgat     420
aatgtgtata tgaatgcgga acaggaggaa aaagcgaaaa agctaacaa tccgcaacat     480
agcattacta aagacgaaat taacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660
cgtgcacgtt ttactctgga agtcgttgac gcggtggttg atgccatcgg cccagaaaaa     720
gtgggtttac gtctgagtcc gtacggcgtt atcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacgaagc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttcatcac catgagcgcg    1140
gagggttaca ccgactaccc gacctacgaa gaagccgtag atctgggctg aacaaaaac    1200
```

<210> SEQ ID NO 176
<211> LENGTH: 400
<212> TYPE: PRT
<213> ORGANISM: Artificial Sequence
<220> FEATURE:
<223> OTHER INFORMATION: ERED variant

<400> SEQUENCE: 176

```
Met Ser Phe Val Lys Asp Phe Lys Pro Gln Ala Leu Arg Asp Thr Asn
1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
```

|     |     |     |     |     | 100 |     |     |     |     | 105 |     |     |     |     | 110 |     |     |
| --- | --- | --- | --- | --- | --- | --- | --- | --- | --- | --- | --- | --- | --- | --- | --- | --- | --- |

Trp Val Gln Leu Trp Val Leu Gly Trp Ala Ala Phe Pro Asp Asn Leu
           115                  120                 125

Ala Arg Asp Gly Leu Arg Tyr Asp Ser Ala Ser Asp Asn Val Tyr Met
130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
           165                  170                 175

Ala Ala Lys Asn Ser Ile Ala Ala Gly Ala Asp Gly Val Glu Ile His
               180                  185                 190

Ser Ala Asn Gly Tyr Leu Leu Asn Gln Phe Leu Asp Pro His Ser Asn
           195                  200                 205

Asn Arg Thr Asp Glu Tyr Gly Gly Ser Ile Glu Asn Arg Ala Arg Phe
    210                  215                 220

Thr Leu Glu Val Val Asp Ala Val Asp Ala Ile Gly Pro Glu Lys
225                 230                 235                 240

Val Gly Leu Arg Leu Ser Pro Tyr Gly Val Ile Asn Ser Met Ser Gly
               245                  250                 255

Gly Ala Glu Thr Gly Ile Val Ala Gln Tyr Ala Tyr Val Leu Gly Glu
               260                  265                 270

Leu Glu Arg Arg Ala Lys Ala Gly Lys Arg Leu Ala Phe Val His Leu
           275                  280                 285

Val Glu Pro Arg Val Thr Asp Glu Ala Leu Val Glu Gly Glu Gly Glu
           290                  295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
               325                  330                 335

Gln Val Lys Asp Pro Arg Thr Leu Ile Gly Tyr Gly Arg Phe Phe Ile
           340                  345                 350

Ser Asn Pro Asp Leu Val Tyr Arg Leu Glu Glu Gly Leu Pro Leu Asn
           355                  360                 365

Lys Tyr Asp Arg Ser Thr Phe Ile Thr Met Ser Ala Glu Gly Tyr Thr
    370                  375                 380

Asp Tyr Pro Thr Tyr Glu Glu Ala Val Asp Leu Gly Trp Asn Lys Asn
385                 390                 395                 400

<210> SEQ ID NO 177
<211> LENGTH: 1200
<212> TYPE: DNA
<213> ORGANISM: Artificial Sequence
<220> FEATURE:
<223> OTHER INFORMATION: ERED variant

<400> SEQUENCE: 177

| | | |
|---|---|---|
| atgtctttcg ttaaggactt caagccgcag gcactgcgcg acaccaacct gttcgaacct | 60 |
| attaaaattg gaacacaca gctggctcat cgcgcggtaa tgcctccgct gacccgcatg | 120 |
| cgcgctaccc atccgggcaa cattccgaac aaggagtggg ctgcggttta ctacggccag | 180 |
| cgtgcacagc gtccggggac aatgattatc acggagggta cgttcatcag cccgcaggca | 240 |
| ggtgggtacg ataacgcgcc tggtgttttgg tcagacgaac aggttgccga atggaagaac | 300 |
| atcttcctgg ctattcatga ctgtcagtca tttgcgtggg tgcaactgtg gtcctgggc | 360 |
| tgggccgcct ttccggataa cctggcgcgt gatgggttac gttacgattc tgcctccgat | 420 |

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacattgc tctggttgag    900
ggggagggcg aatactcaga gggcaccaac gattttgctt attccatttg gaaaggtccg    960
attatccgtg ccggcaacta cgcactgcac cctgaagctg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttcgccac catgagcgcg   1140
gagggttaca ccgactaccc gacctacgaa gaagccgtag atctgggctg gaacaaaaac   1200
```

<210> SEQ ID NO 178
<211> LENGTH: 400
<212> TYPE: PRT
<213> ORGANISM: Artificial Sequence
<220> FEATURE:
<223> OTHER INFORMATION: ERED variant

<400> SEQUENCE: 178

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
    275                 280                 285

Val Glu Pro Arg Val Thr Asp Ile Ala Leu Val Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Ala Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Ala Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 179
<211> LENGTH: 1200
<212> TYPE: DNA
<213> ORGANISM: Artificial Sequence
<220> FEATURE:
<223> OTHER INFORMATION: ERED variant

<400> SEQUENCE: 179

```
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgtg gtcctgggc      360
tgggccgcct ttccggataa cctggcgcgt gatgggttac gttacgattc tgcctccgat      420
aatgtgtata tgaatgcgga acaggaggaa aaagcgaaaa agctaacaa tccgcaacat      480
agcattacta aagacgaaat taaacaatat gtcaaagaat atgttcaggc agctaagaac      540
tcgatcgctg cgggtgcgga cggcgtggaa attcactcag ccaacggtta tctgttaaat      600
cagttcctgg atccgcacag caacaaccgc accgatgagt atgggggctc aattgaaaat      660
cgtgcacgtt ttactctgga gtcgttgac gcggtggttg atgccatcgg cccagaaaaa      720
gtgggtttac gtctgagtcc gtacggcgtt ttcaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga cagacgctgc tctggttgag      900
ggggagggcg aatactcaga gggcaccaac gattttgctt attccatttg gaaaggtccg      960
attatccgtg ccggcaacta cgcactgcgc cctgaagttg tgcgcgaaca agttaaggac     1020
cctcgcaccc tgatcggcta cggccgcttc tttatttcaa atccagacct ggtttaccgc     1080
ttagaagaag gtctgccact gaacaagtac gaccgttcta cgttcatcac catgagcgcg     1140
gaggggttaca ccgactaccc gacctacgaa gaagccgtag atctgggctg gaacaaaaac     1200
```

<210> SEQ ID NO 180
<211> LENGTH: 400
<212> TYPE: PRT
<213> ORGANISM: Artificial Sequence
<220> FEATURE:
<223> OTHER INFORMATION: ERED variant

<400> SEQUENCE: 180

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Ala Ala Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu Arg Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365
```

Lys Tyr Asp Arg Ser Thr Phe Ile Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 181
<211> LENGTH: 1200
<212> TYPE: DNA
<213> ORGANISM: Artificial Sequence
<220> FEATURE:
<223> OTHER INFORMATION: ERED variant

<400> SEQUENCE: 181
atgtctttcg ttaaggactt caagccgcag gcactgcgcg acaccaacct gttcgaacct    60
attaaaattg gaacacaca gctggctcat cgcgcggtaa tgcctccgct gacccgcatg   120
cgcgctaccc atccgggcaa cattccgaac aaggagtggg ctgcggttta ctacggccag   180
cgtgcacagc gtccggggac aatgattatc acggagggta cgttcatcag cccgcaggca   240
ggtgggtacg ataacgcgcc tggtgtttgg tcagacgaac aggttgccga atggaagaac   300
atcttcctgg ctattcatga ctgtcagtca tttgcgtggg tgcaactgtg gtcctgggc   360
tgggccgcct ttccggataa cctggcgcgt gatgggttac gttacgattc tgcctccgat   420
aatgtgtata tgaatgcgga acaggaggaa aaagcgaaaa agctaacaa tccgcaacat   480
agcattacta aagacgaaat taaacaatat gtcaaagaat atgttcaggc agctaagaac   540
tcgatcgctg cgggtgcgga cggcgtgaaa attcactcag ccaacggtta tctgttaaat   600
cagttcctgg atccgcacag caacaaccgc accgatgagt atgggggctc aattgaaaat   660
cgtgcacgtt ttactctgga agtcgttgac gcggtggttg atgccatcgg cccagaaaaa   720
gtgggtttac gtctgagtcc gtacggcgtt gaaaactcta tgtcgggcgg cgcggaaacg   780
ggcattgttg ctcagtatgc ctatgtcctg ggtgagctgg agcgtcgcgc caaggcgggg   840
aaacgcctgg cgtttgttca tttagtcgaa ccacgcgtga cagacccttc tctggttgag   900
ggggagggcg aatactcaga gggcaccaac gatttttgctt attccatttg gaaaggtccg   960
attatccgtg ccggcaacta cgcactgcgc cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttcatcac catgagcgcg  1140
gagggttaca ccgactaccc gacctacgaa gaagccgtag atctgggctg gaacaaaaac  1200

<210> SEQ ID NO 182
<211> LENGTH: 400
<212> TYPE: PRT
<213> ORGANISM: Artificial Sequence
<220> FEATURE:
<223> OTHER INFORMATION: ERED variant

<400> SEQUENCE: 182

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
            85                  90                  95

Glu Trp Lys Asn Ile Phe Leu Ala Ile His Asp Cys Gln Ser Phe Ala
        100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Glu Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu Arg Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Ile Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 183
<211> LENGTH: 1200
<212> TYPE: DNA
<213> ORGANISM: Artificial Sequence
<220> FEATURE:
<223> OTHER INFORMATION: ERED variant

<400> SEQUENCE: 183
atgtctttcg ttaaggactt caagccgcag gcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acgagggta cgttcatcag cccgcaggca     240
ggtgggtacg ataatgcgcc tggtgtttgg tcagacgaac aggttgccga atggaagaac     300

```
atcttcctgg ctattcatga ctgtcagtca tttgcgtggg tgcaactgtg ggtcctgggc    360
tgggccgcct ttccggataa cctggcgcgt gatgggttac gttacgattc tgcctccgat    420
aatgtgtata tgaatgcggg acaggaggaa aaagcgaaaa agctaacaa tccgcaacat     480 agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaccgc accgatgagt atggggggctc aattgaaaat   660 cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga cagacgcttt cctggttgag    900
ggggagggcg aatactcaga gggcaccaac gattttgctt attccatttg aaaggtccg     960 attatccgtg ccggcaacta cgcactgcgc cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttcgaaac catgagcgcg   1140
gagggttaca ccgactaccc gacctacgaa gaagccgtag atctgggctg aacaaaaac    1200
```

<210> SEQ ID NO 184
<211> LENGTH: 400
<212> TYPE: PRT
<213> ORGANISM: Artificial Sequence
<220> FEATURE:
<223> OTHER INFORMATION: ERED variant

<400> SEQUENCE: 184

```
Met Ser Phe Val Lys Asp Phe Lys Pro Gln Ala Leu Arg Asp Thr Asn
 1               5                  10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Gly Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

| Asn | Arg | Thr | Asp | Glu | Tyr | Gly | Gly | Ser | Ile | Glu | Asn | Arg | Ala | Arg | Phe |
| | 210 | | | | 215 | | | | 220 | | | | | | |

| Thr | Leu | Glu | Val | Val | Asp | Ala | Val | Val | Asp | Ala | Ile | Gly | Pro | Glu | Lys |
| 225 | | | | | 230 | | | | | 235 | | | | | 240 |

| Val | Gly | Leu | Arg | Leu | Ser | Pro | Tyr | Gly | Val | Phe | Asn | Ser | Met | Ser | Gly |
| | | | | 245 | | | | | 250 | | | | | 255 | |

| Gly | Ala | Glu | Thr | Gly | Ile | Val | Ala | Gln | Tyr | Ala | Tyr | Val | Leu | Gly | Glu |
| | | | 260 | | | | | 265 | | | | | 270 | | |

| Leu | Glu | Arg | Arg | Ala | Lys | Ala | Gly | Lys | Arg | Leu | Ala | Phe | Val | His | Leu |
| | | 275 | | | | | 280 | | | | | 285 | | | |

| Val | Glu | Pro | Arg | Val | Thr | Asp | Ala | Phe | Leu | Val | Glu | Gly | Glu | Gly | Glu |
| | 290 | | | | | 295 | | | | | 300 | | | | |

| Tyr | Ser | Glu | Gly | Thr | Asn | Asp | Phe | Ala | Tyr | Ser | Ile | Trp | Lys | Gly | Pro |
| 305 | | | | | 310 | | | | | 315 | | | | | 320 |

| Ile | Ile | Arg | Ala | Gly | Asn | Tyr | Ala | Leu | Arg | Pro | Glu | Val | Val | Arg | Glu |
| | | | | 325 | | | | | 330 | | | | | 335 | |

| Gln | Val | Lys | Asp | Pro | Arg | Thr | Leu | Ile | Gly | Tyr | Gly | Arg | Phe | Phe | Ile |
| | | | 340 | | | | | 345 | | | | | 350 | | |

| Ser | Asn | Pro | Asp | Leu | Val | Tyr | Arg | Leu | Glu | Glu | Gly | Leu | Pro | Leu | Asn |
| | | 355 | | | | | 360 | | | | | 365 | | | |

| Lys | Tyr | Asp | Arg | Ser | Thr | Phe | Glu | Thr | Met | Ser | Ala | Glu | Gly | Tyr | Thr |
| | 370 | | | | | 375 | | | | | 380 | | | | |

| Asp | Tyr | Pro | Thr | Tyr | Glu | Glu | Ala | Val | Asp | Leu | Gly | Trp | Asn | Lys | Asn |
| 385 | | | | | 390 | | | | | 395 | | | | | 400 |

<210> SEQ ID NO 185
<211> LENGTH: 1200
<212> TYPE: DNA
<213> ORGANISM: Artificial Sequence
<220> FEATURE:
<223> OTHER INFORMATION: ERED variant

<400> SEQUENCE: 185

| atgtctttcg ttaaggactt caagccgcag gcactgcgcg acaccaacct gttcgaacct | 60 |
| attaaaattg gaacacaca gctggctcat cgcgcggtaa tgcctccgct gacccgcatg | 120 |
| cgcgctaccc atccgggcaa cattccgaac aaggagtggg ctgcggttta ctacggccag | 180 |
| cgtgcacagc gtccggggac aatgattatc acggagggta cgttcatcag cccgcaggca | 240 |
| ggtgggtacg ataacgcgcc tggtgttttgg tcagacgaac aggttgccga atggaagaac | 300 |
| atcttcctgg ctattcatga ctgtcagtca tttgcgtggg tgcaactgtg gtcctgggc | 360 |
| tgggccgcct ttccggataa cctggcgcgt gatgggttac gttacgattc tgcctccgat | 420 |
| aatgtgtata tgaatgcgga acaggaggaa aaagcgaaaa agctaacaa tccgcaacat | 480 |
| agcattacta agacgaaat taaacaatat gtcaaagaat atgttcaggc agctaagaac | 540 |
| tcgatcgctg cgggtgcgga cggcgtgaa attcactcag ccaacggtta tctgttaaat | 600 |
| cagttcctgg atccgcacag caacaaccgc accgatgagt atgggggctc aattgaaaat | 660 |
| cgtgcacgtt ttactctgga agtcgttgac gcggtggttg atgccatcgg cccagaaaaa | 720 |
| gtgggtttac gtctgagtcc gtacggcgtt ttcaactcta tgtcgggcgg cgcggaaacg | 780 |
| ggcattgttg ctcagtatgc ctatgtcctg ggtgagctgg agcgtcgcgc caaggcgggg | 840 |
| aaacgcctgg cgtttgttca tttagtcgaa ccacgcgtga cagaccctttt cctggttgag | 900 |
| ggggagggcg aatactcaga gggcaccaac gattttgctt attccatttg gaaaggtccg | 960 |
| attatccgtg ccggcaacta cgcactgcac cctgaagttg tgcgcgaaca agttaaggac | 1020 |

```
cctcgcaccc tgatcggcta cggccgcttc tttatttcaa atccagacct ggtttaccgc    1080
ttagaagaag gtctgccact gaacgagtat gaccgttcta cgttcaaaac catgagcgcg    1140
gagggttaca ccgactaccc gacctacgaa gaagccgtag atctgggctg gaacaaaaac    1200
```

<210> SEQ ID NO 186
<211> LENGTH: 400
<212> TYPE: PRT
<213> ORGANISM: Artificial Sequence
<220> FEATURE:
<223> OTHER INFORMATION: ERED variant

<400> SEQUENCE: 186

```
Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Val Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Asn Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Phe Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
```

```
                    340             345             350
Ser Asn Pro Asp Leu Val Tyr Arg Leu Glu Glu Gly Leu Pro Leu Asn
                355                     360                 365

Glu Tyr Asp Arg Ser Thr Phe Lys Thr Met Ser Ala Glu Gly Tyr Thr
            370                     375                 380

Asp Tyr Pro Thr Tyr Glu Glu Ala Val Asp Leu Gly Trp Asn Lys Asn
385                     390                     395                 400

<210> SEQ ID NO 187
<211> LENGTH: 1200
<212> TYPE: DNA
<213> ORGANISM: Artificial Sequence
<220> FEATURE:
<223> OTHER INFORMATION: ERED variant

<400> SEQUENCE: 187
atgtctttcg ttaaggactt caagccgcag gcactgcgcg acaccaacct gttcgaacct      60
attaaaattg gaacacaca gctggctcat cgcgcggtaa tgcctccgct gacccgcatg      120
cgcgctaccc atccgggcaa cattccgaac aaggagtggg ctgcggttta ctacggccag      180
cgtgcacagc gtccggggac aatgattatc acggagggta cgttcatcag cccgcaggca      240
ggtgggtacg ataacgcgcc tggtgtttgg tcagacgaac aggttgccga atggaagaac      300
atcttcctgg ctattcatga ctgtcagtca tttgcgtggg tgcaactgtg ggtcctgggc      360
tgggccgcct ttccggataa cctggcgcgt gatgggttac gttacgattc tgcctccgat      420
aatgtgtata tgaatgcgga acaggaggaa aagcgaaaa aagctaacaa tccgcaacat      480
agcattacta aagacgaaat taaacaatat gtcaaagaat atgttcaggc agctaagaac      540
tcgatcgctg cggtgcgga cggcgtgaa attcactcag ccaacggtta tctgttaaat      600
cagttcctgg atccgcacag caacaaccgc accgatgagt atgggggctc aattgaaaat      660
cgtgcacgtt ttactctgga agtcgttgac gcggtggttg atgccatcgg cccagaaaaa      720
gtgggtttac gtctgagtcc gtacggcgtt gaaaaactcta tgtcgggcgg cgcggaaacg      780
ggcattgttg ctcagtatgc ctatgtcctg ggtgagctgg agcgtcgcgc caaggcgggg      840
aaacgcctgg cgtttgttca tttagtcgaa ccacgcgtga cagacccttc tctggttgag      900
ggggagggcg aatactcaga gggcaccaac gatttttgctt attccatttg aaaaggtccg      960
attatccgtg ccggcaacta cgcactgcac cctgaagttg tgcgcgaaca agttaaggac      1020
cctcgcaccc tgatcggcta cggccgcttc tttatttcaa atccagacct ggtttaccgc      1080
ttagaagaag gtctgccact gaacaagtat gaccgttcta cgttctacac catgagcgcg      1140
gagggttaca ccgactaccc gacctacgaa gaagccgtag atctgggctg aacaaaaac      1200

<210> SEQ ID NO 188
<211> LENGTH: 400
<212> TYPE: PRT
<213> ORGANISM: Artificial Sequence
<220> FEATURE:
<223> OTHER INFORMATION: ERED variant

<400> SEQUENCE: 188

Met Ser Phe Val Lys Asp Phe Lys Pro Gln Ala Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45
```

```
Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
 65                  70                  75                  80

Gly Gly Tyr Asp Asn Ala Pro Gly Val Trp Ser Asp Glu Gln Val Ala
                 85                  90                  95

Glu Trp Lys Asn Ile Phe Leu Ala Ile His Asp Cys Gln Ser Phe Ala
                100                 105                 110

Trp Val Gln Leu Trp Val Leu Gly Trp Ala Ala Phe Pro Asp Asn Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Asn Arg Thr Asp Glu Tyr Gly Gly Ser Ile Glu Asn Arg Ala Arg Phe
        210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Asn Ser Met Ser Gly
                245                 250                 255

Gly Ala Glu Thr Gly Ile Val Ala Gln Tyr Ala Tyr Val Leu Gly Glu
                260                 265                 270

Leu Glu Arg Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 189
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 189
atgtctttcg ttaaggactt caagccgcag gcactgggcg acaccaacct gttcaaacct    60
attaaaattg ggaacacaca gctggctcat cgcgcggtaa tgcctccgct gacccgcatg   120
```

```
cgcgctaccc atccgggcaa cattccgaac aaggagtggg ctgcggttta ctacggccag    180
cgtgcacagc gtccggggac aatgattatc acggagggtg cgttccctag cccgcagtca    240
ggtgggtacg ataacgcgcc tggtatttgg tcagaagaac agattaaaga atggacgaaa    300
atcttcaagg ctattcatga aaataagtca tttgcgtggg tgcaactgtg gagcctgggc    360
tgggcctcct ttccggatgt gctggcgcgt gatgggttac gttacgattg tgcctccgat    420
cgtgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggtgcgga cggcgtgaaa attcactcag ccaacggtta tctgttaaat    600
cagttcctgg atccgcacag caacaaacgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgaggtgg agggtcgcgc caaggcgggg    840
aaacgcctgg cgtttgttca tttagtcgaa ccacgcgtga caaacccttt tctgactgag    900
ggggagggcg aatactcaga gggcaccaac gatttttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac   1200
```

<210> SEQ ID NO 190
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 190

```
Met Ser Phe Val Lys Asp Phe Lys Pro Gln Ala Leu Gly Asp Thr Asn
1               5                   10                  15

Leu Phe Lys Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Ala Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Ser Leu Gly Trp Ala Ser Phe Pro Asp Val Leu
        115                 120                 125

Ala Arg Asp Gly Leu Arg Tyr Asp Cys Ala Ser Asp Arg Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
```

```
                          180                 185                 190
Ser Ala Asn Gly Tyr Leu Leu Asn Gln Phe Leu Asp Pro His Ser Asn
            195                 200                 205

Lys Arg Thr Asp Glu Tyr Gly Gly Ser Ile Glu Asn Arg Ala Arg Phe
        210                 215                 220

Thr Leu Glu Val Val Asp Ala Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Val Glu Gly Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 191
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 191
atgcctttcg ttaagggctt cgagccgatt tcactgcgcg acaccaacct gttcgaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac actgattatc acggagggta cgttccctag cccgcagtca     240
ggtgggtacg ataacgcgcc tggtatttgg tcagaagaac agattaaaga atggacgaaa     300
atcttcaagg ctattcatga aaataagtca tttgtgtggg tgcaactgtg ggtcctgggc     360
tgggccgcct ttccggatac gctggcgcgt gatgggttac gttacgattc tgcctccgat     420
aatgtgtata tgaatgcgga acaggaggaa aaagcgaaaa agctaacaa tccgcaacat      480 agcattacta agacgaaat taaacaatat gtcaaagaat atgttcaggc agctaagaac     540
tcgatcgctg cgggtgcgga cggcgtggaa attcactcag ccaacggtta ctgttaaat      600 cagttcctgg atccgcacag caacaaccgc accgatgagt atgggggctc aattgaaat      660 cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga cagacccttc tctggttgag     900
```

```
ggggagggcg aatactcaga gggcaccaac gattttgctt attccatttg gaaaggtccg    960
attatccgtg ccggcaacta cgcactacac cctgaagttg tgcgcgaaca agttaaggac   1020
cctcgcaccc tgatcggcta cggccgcttc tttatttcaa atccagatct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 192
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 192

```
Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
                20                  25                  30

Val Met Pro Pro Leu Thr Arg Met Arg Ala Thr His Pro Gly Asn Ile
            35                  40                  45

Pro Asn Lys Glu Trp Ala Ala Val Tyr Tyr Gly Gln Arg Ala Gln Arg
        50                  55                  60

Pro Gly Thr Leu Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Val
                100                 105                 110

Trp Val Gln Leu Trp Val Leu Gly Trp Ala Ala Phe Pro Asp Thr Leu
            115                 120                 125

Ala Arg Asp Gly Leu Arg Tyr Asp Ser Ala Ser Asp Asn Val Tyr Met
        130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320
```

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
        340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
    370                 375                 380

Asp Tyr Pro Thr Tyr Glu Glu Ala Val Asp Leu Gly Trp Asn Lys Asn
385                 390                 395                 400

<210> SEQ ID NO 193
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 193

```
atgcctttcg ttaagggctt cgagccgatt tcactgcgcg acaccaacct gttcgaacct      60
attaaaattg ggaacacaca gctggctcat cgcgcggtaa tgcctccgct gacccgcatg     120
cgcgctctgc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtatttgg tcagacgaac aggttgccga atggaagaac     300
atcttcctgg ctattcatga ctgtcagtca tttgcgtggg tgcaactgtg ggtcctgggc     360
tgggccgcct ttccggatgt gctggcgcgt gatgggttac gttacgattc tgcctccgat     420
aatgtgtata tgaatgcgga acaggaggaa aaagcgaaaa agctaacaa tccgcaacat     480
agcattacta agacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atgggggctc aattgaaaat     660
cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaccg     780
ggcattattg ctcagtatag ctatgtcctg ggtgagctgg agaaacgcgc caaggcgggg     840
aaacgcctgg cgtttgttca tttagtcgaa ccacgcgtga cagacccttc tctggttgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 194
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 194

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala

```
                   20                  25                  30
Val Met Pro Leu Thr Arg Met Arg Ala Leu His Pro Gly Asn Ile
            35                  40                  45
Pro Asn Lys Glu Trp Ala Ala Val Tyr Tyr Gly Gln Arg Ala Gln Arg
 50                  55                  60
Pro Gly Thr Met Ile Ile Thr Glu Gly Thr Phe Ile Ser Pro Gln Ala
 65                  70                  75                  80
Gly Gly Tyr Asp Asn Ala Pro Gly Ile Trp Ser Asp Glu Gln Val Ala
                85                  90                  95
Glu Trp Lys Asn Ile Phe Leu Ala Ile His Asp Cys Gln Ser Phe Ala
               100                 105                 110
Trp Val Gln Leu Trp Val Leu Gly Trp Ala Ala Phe Pro Asp Val Leu
           115                 120                 125
Ala Arg Asp Gly Leu Arg Tyr Asp Ser Ala Ser Asp Asn Val Tyr Met
       130                 135                 140
Asn Ala Glu Gln Glu Glu Lys Ala Lys Lys Ala Asn Asn Pro Gln His
145                 150                 155                 160
Ser Ile Thr Lys Asp Glu Ile Lys Gln Tyr Val Lys Glu Tyr Val Gln
               165                 170                 175
Ala Ala Lys Asn Ser Ile Ala Ala Gly Ala Asp Gly Val Glu Ile His
           180                 185                 190
Ser Ala Asn Gly Tyr Leu Leu Asn Gln Phe Leu Asp Pro His Ser Asn
       195                 200                 205
Asn Arg Thr Asp Glu Tyr Gly Gly Ser Ile Glu Asn Arg Ala Arg Phe
   210                 215                 220
Thr Leu Glu Val Val Asp Ala Val Val Asp Ala Ile Gly Pro Glu Lys
225                 230                 235                 240
Val Gly Leu Arg Leu Ser Pro Tyr Gly Val Phe Asn Ser Met Ser Gly
               245                 250                 255
Gly Ala Glu Pro Gly Ile Ile Ala Gln Tyr Ser Tyr Val Leu Gly Glu
           260                 265                 270
Leu Glu Lys Arg Ala Lys Ala Gly Lys Arg Leu Ala Phe Val His Leu
       275                 280                 285
Val Glu Pro Arg Val Thr Asp Pro Ser Leu Val Glu Gly Glu Gly Glu
   290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
               325                 330                 335
Gln Val Lys Asp Pro Arg Thr Leu Ile Gly Tyr Gly Arg Phe Phe Ile
           340                 345                 350
Ser Asn Pro Asp Leu Val Tyr Arg Leu Glu Glu Gly Leu Pro Leu Asn
       355                 360                 365
Lys Tyr Asp Arg Ser Thr Phe Tyr Thr Met Ser Ala Glu Gly Tyr Thr
   370                 375                 380
Asp Tyr Pro Thr Tyr Glu Glu Ala Val Asp Leu Gly Trp Asn Lys Asn
385                 390                 395                 400
```

<210> SEQ ID NO 195
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 195

```
atgcctttcg ttaagggctt cgagccgatt tcactgcgcg acaccaacct gttcgaacct    60
attaaaattg ggaacacaca gctggctcat cgcgcggtaa tgcctccgct gacccgcatg   120
cgcgctaccc atccgggcaa cattccgaac aaggagtggg ctgcggttta ctacggccag   180
cgtgcacagc gtccggggac aatgattatc acggagggta cgttcatcag cccgcaggca   240
ggtgggtacg ataacgcgcc tggtatttgg tcagaagaac agattaaaga atggacgaaa   300
atcttcaagg ctattcatga aaataagtca tttgcgtggg tgcaactgtg ggccctgggc   360
tgggccgcct ttccggatac gctggcgcgt gatgggttac gttacgattc tgcctccgat   420
aatgtgtata tgaatgcgga acaggaggaa aaagcgaaaa agctaacaa tccgcaacat   480
agcattacta aagacgaaat taaacaatat gtcaaagaat atgttcaggc agctaagaac   540
tcgatcgctg cgggtgcgga cggcgtggaa attcactcag ccaacggtta tctgttaaat   600
cagttcctgg atccgcacag caacaaacgc accgatgagt atggggggcac aattgaaaat   660
cgtgcacgtt ttactctgga agtcgttgac gcgctgattg agaccatcgg cccagaacgc   720
gtgggtttac gtctgagtcc gtacggcact ttcaactcta tgtcgggcgg cgcggaaccg   780
ggcattattg ctcagtatag ctatgtcctg ggtgagctgg agaaacgcgc caaggcgggg   840
aaacgcctgg cgtttgttca tttagtcgaa ccacgcgtga cagacccttc tctggttgag   900
ggggagggcg aatactcaga gggcaccaac gattttgctt attccatttg aaaggtccg   960
attatccgtg ccggcaacta cgcactgcac cctgaagttg tgcgcgaaca agttaaggac  1020
cctcgcaccc tgatcggcta cggccgcttc tttatttcaa atccagacct ggttgaccgc  1080
ttagaaaaag gtctgccact gaacaagtat gaccgtgata cgttctacaa aatgagcgcg  1140
gagggttaca tcgactaccc gacctacgaa gaagccttaa aactgggctg ggacaaaaac  1200
```

<210> SEQ ID NO 196
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 196

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Ala Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

```
Ser Ile Thr Lys Asp Glu Ile Lys Gln Tyr Val Lys Glu Tyr Val Gln
            165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Lys Arg Thr Asp Glu Tyr Gly Gly Thr Ile Glu Asn Arg Ala Arg Phe
210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
            245                 250                 255

Gly Ala Glu Pro Gly Ile Ile Ala Gln Tyr Ser Tyr Val Leu Gly Glu
            260                 265                 270

Leu Glu Lys Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
            325                 330                 335

Gln Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
            355                 360                 365

Lys Tyr Asp Arg Asp Thr Phe Tyr Lys Met Ser Ala Glu Gly Tyr Ile
            370                 375                 380

Asp Tyr Pro Thr Tyr Glu Glu Ala Leu Lys Leu Gly Trp Asp Lys Asn
385                 390                 395                 400

<210> SEQ ID NO 197
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 197
atgcctttcg ttaaggactt caagccgcag gcactgggcg acaccaacct gttcaaacct      60
attaaaattg ggaacaacga gctgctgcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtatttgg tcagacgaac aggttgccga atggaagaac     300
atcttcctgg ctattcatga aaataagtca tttgtgtggg tgcaactgtg ggtcctgggc     360
tgggccgcct ttccggatgt gctggcgcgt gatgggttac gttacgattc tgcctccgat     420
aatgtgtata tgaatgcgga acaggaggaa aaagcgaaaa agctaacaa tccgcaacat      480 agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggggctc aattgaaaat     660 cgtgcacgtt ttactctgga agtcgttgac gcggtggttg atgccatcgg cccagaaaaa     720
```

```
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaacccttt tctgactgag    900
ggggagggcg aatacaacgg gggcagcaac aaatttgctt attccatttg aaaggtccg     960 attatccgtg ccggcaactt cgcactgcac cctgaagttg tgcgcgaaga agttaaggac   1020
cctcgcaccc tgatcggcta cggccgcttc tttatttcaa atccagacct ggttgaccgc   1080
ttagaaaaag gtctgccact gaacaagtat gaccgtgata cgttctacaa aatgagcgcg   1140
gagggttaca tcgactaccc gacctacgaa gaagccttaa aactgggctg ggacaaaaac   1200
```

<210> SEQ ID NO 198
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 198

```
Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Glu Asn Lys Ser Phe Val
            100                 105                 110

Trp Val Gln Leu Trp Val Leu Gly Trp Ala Ala Phe Pro Asp Val Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285
```

```
Val Glu Pro Arg Val Thr Asn Pro Phe Leu Thr Gly Glu Gly Glu
        290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                    325                 330                 335

Glu Val Lys Asp Pro Arg Thr Leu Ile Gly Tyr Gly Arg Phe Phe Ile
                340                 345                 350

Ser Asn Pro Asp Leu Val Asp Arg Leu Glu Lys Gly Leu Pro Leu Asn
                355                 360                 365

Lys Tyr Asp Arg Asp Thr Phe Tyr Lys Met Ser Ala Glu Gly Tyr Ile
370                 375                 380

Asp Tyr Pro Thr Tyr Glu Glu Ala Leu Lys Leu Gly Trp Asp Lys Asn
385                 390                 395                 400

<210> SEQ ID NO 199
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 199
atgcctttcg ttaaggactt caagccgcag gcactgggcg acaccaacct gttcaaacct     60
attaaaattg ggaacacaca gctggctcat cgcgcggtaa tgcctccgct gacccgcatg    120
cgcgctaccc atccgggcaa cattccgaac aaggagtggg ctgcggttta ctacggccag    180
cgtgcacagc gtccggggac aatgattatc acggagggta cgttccctag cccgcagtca    240
ggtgggtacg ataacgcgcc tggtatttgg tcagaagaac agattaaaga atggacgaaa    300
atcttcaagg ctattcatga aaaaagtca tttgcgtggg tgcaactgtg gagcctgggc    360
tgggcctcct ttccggatgt gctggcgcgt gatgggttac gttacgattg tgcctccgat    420
cgtgtgtata tgaatgcgga acaggaggaa aaagcgaaaa agctaacaa tccgcaacat    480
agcattacta aagacgaaat taaacaatat gtcaaagaat atgttcaggc agctaagaac    540
tcgatcgctg cgggtgcgga cggcgtggaa attcactcag ccaacggtta tctgttaaat    600
cagttcctgg atccgcacag caacaaacgc accgatgagt atgggggcac aattgaaaat    660
cgtgcacgtt ttactctgga agtcgttgac gcgctggttg aggccatcgg cccagaacgc    720
gtgggtttac gtctgagtcc gtacggcact ttcaactcta tgtcgggcgg cgcggaaccg    780
ggcattattg ctcagtatag ctatgtcctg ggtgagctgg agaaacgcgc caaggcgggg    840
aaacgcctgg cgtttgttca tttagtcgaa ccacgcgtga cagacccttc tctggttgag    900
ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg gaacaaaaac   1200

<210> SEQ ID NO 200
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 200
```

```
Met Pro Phe Val Lys Asp Phe Lys Pro Gln Ala Leu Gly Asp Thr Asn
1               5                   10                  15

Leu Phe Lys Pro Ile Lys Ile Gly Asn Thr Gln Leu Ala His Arg Ala
                20                  25                  30

Val Met Pro Pro Leu Thr Arg Met Arg Ala Thr His Pro Gly Asn Ile
            35                  40                  45

Pro Asn Lys Glu Trp Ala Ala Val Tyr Tyr Gly Gln Arg Ala Gln Arg
        50                  55                  60

Pro Gly Thr Met Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Lys Lys Ser Phe Ala
                100                 105                 110

Trp Val Gln Leu Trp Ser Leu Gly Trp Ala Ser Phe Pro Asp Val Leu
            115                 120                 125

Ala Arg Asp Gly Leu Arg Tyr Asp Cys Ala Ser Asp Arg Val Tyr Met
        130                 135                 140

Asn Ala Glu Gln Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
        195                 200                 205

Lys Arg Thr Asp Glu Tyr Gly Gly Thr Ile Glu Asn Arg Ala Arg Phe
        210                 215                 220

Thr Leu Glu Val Val Asp Ala Leu Val Glu Ala Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
                260                 265                 270

Leu Glu Lys Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
        290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
        355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 201
<211> LENGTH: 1200
<212> TYPE: DNA
```

```
<213> ORGANISM: Artificial Sequence
<220> FEATURE:
<223> OTHER INFORMATION: chimera of WT OYEs

<400> SEQUENCE: 201
atgcctttcg ttaaggactt caagccgcag gcactgggcg acaccaacct gttcaaacct      60
attaaaattg ggaacacaca gctggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acggagggta cgttcatcag cccgcaggca     240
ggtgggtacg ataacgcgcc tggtatttgg tcagacgaac aggttgccga atggaagaac     300
atcttcctgg ctattcatga ctgtcagtca tttgcgtggg tgcaactgtg gagcctgggc     360
tgggcctcct ttccggatgt gctggcgcgt gatgggttac gttacgattg tgcctccgat     420
cgtgtgtata tgaatgcgac actgcaggaa aaagcgaaag acgctaacaa tctggaacat     480
agcttgacta agacgatat taaacaatat atcaaagatt atattcatgc agctaagaac     540
tcgatcgctg cgggtgcgga cggcgtggaa attcactcag ccaacggtta tctgttaaat     600
cagttcctgg atccgcacag caacaaacgc accgatgagt atgggggcac aattgaaaat     660
cgtgcacgtt ttactctgga agtcgttgac gcgctgattg agaccatcgg cccagaacgc     720
gtgggtttac gtctgagtcc gtacggcact ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caaacccttt tctgactgag     900
ggggagggcg aatactcaga gggcaccaac gattttgctt attccatttg gaaaggtccg     960
attatccgtg ccggcaacta cgcactgcac cctgaagttg tgcgcgaaca agttaaggac    1020
cctcgcaccc tgatcggcta cggccgcttc tttatttcaa atccagacct ggtttaccgc    1080
ttagaagaag gtctgccact gaacaagtat gaccgttcta cgttctacac catgagcgcg    1140
gagggttaca ccgactaccc gacctacgaa gaagccgtag atctgggctg aacaaaaac    1200
```

<210> SEQ ID NO 202
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 202

```
Met Pro Phe Val Lys Asp Phe Lys Pro Gln Ala Leu Gly Asp Thr Asn
1               5                  10                  15

Leu Phe Lys Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
        115                 120                 125
```

```
Ala Arg Asp Gly Leu Arg Tyr Asp Cys Ala Ser Asp Arg Val Tyr Met
    130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Lys Arg Thr Asp Glu Tyr Gly Gly Thr Ile Glu Asn Arg Ala Arg Phe
210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
            275                 280                 285

Val Glu Pro Arg Val Thr Asn Pro Phe Leu Thr Glu Gly Glu Gly Glu
290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
            340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
370                 375                 380

Asp Tyr Pro Thr Tyr Glu Glu Ala Val Asp Leu Gly Trp Asn Lys Asn
385                 390                 395                 400

<210> SEQ ID NO 203
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 203
atgcctttcg ttaagggctt cgagccgatt tcactgcgcg acaccaacct gttcgaacct      60
attaaaattg ggaacacact gctggctcat cgcgcggtaa tgcctccgct gacccgcatg     120
cgcgctcagc atccgggcaa cattccgaac aaggagtggg ctgcggttta ctacggccag     180
cgtgcacagc gtccggggac aatgattatc acggagggta cgttccctag cccgcagtca     240
ggtgggtacg ataacgcgcc tggtatttgg tcagaagaac agattaaaga atggacgaaa     300
atcttcaagg ctattcatga aaataagtca tttgcgtggg tgcaactgtg ggtcctgggc     360
tgggccgcct tccggatac gctggcgcgt gatgggttac gttacgattc tgcctccgat     420
aatgtgtata tgaatgcgga acaggaggaa aaagcgaaaa agctaacaa tccgcaacat     480 agcattacta aagacgaaat taacaatat gtcaaagaat atgttcaggc agctaagaac     540
tcgatcgctg cgggtgcgga cggcgtggaa attcactcag ccaacggtta tctgttaaat     600
```

```
cagttcctgg atccgcacag caacaaacgc accgatgagt atgggggcac aattgaaaat    660
cgtgcacgtt ttactctgga agtcgttgac gcgctgattg agaccatcgg cccagaacgc    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaaccccttt tctggttgag    900 ggggagggcg aatactcaga gggcaccaac gattttgctt attccatttg gaaaggtccg    960
attatccgtg ccggcaacta cgcactgcac cctgaagttg tgcgcgaaca agttaaggac   1020
cctcgcaccc tgatcggcta cggccgcttc tttatttcaa atccagacct ggtttaccgc   1080
ttagaagaag gtctgccact gaacaagtat gaccgttcta cgttctacac catgagcgcg   1140
gagggttaca ccgactaccc gacctacgaa gaagccgtag atctgggctg aacaaaaac    1200
```

<210> SEQ ID NO 204
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 204

```
Met Pro Phe Val Lys Gly Phe Glu Pro Ile Ser Leu Arg Asp Thr Asn
1               5                   10                  15

Leu Phe Glu Pro Ile Lys Ile Gly Asn Thr Leu Leu Ala His Arg Ala
            20                  25                  30

Val Met Pro Pro Leu Thr Arg Met Arg Ala Gln His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Pro Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Lys Arg Thr Asp Glu Tyr Gly Gly Thr Ile Glu Asn Arg Ala Arg Phe
    210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
```

|     |     |     |     | 260 |     |     |     | 265 |     |     |     | 270 |     |     |
| --- | --- | --- | --- | --- | --- | --- | --- | --- | --- | --- | --- | --- | --- | --- |
| Leu | Glu | Arg | Arg | Ala | Lys | Ala | Gly | Lys | Arg | Leu | Ala | Phe | Val | His | Leu |
|     |     | 275 |     |     |     |     | 280 |     |     |     |     | 285 |     |     |     |
| Val | Glu | Pro | Arg | Val | Thr | Asn | Pro | Phe | Leu | Val | Glu | Gly | Glu | Gly | Glu |
|     | 290 |     |     |     |     | 295 |     |     |     |     | 300 |     |     |     |     |
| Tyr | Ser | Glu | Gly | Thr | Asn | Asp | Phe | Ala | Tyr | Ser | Ile | Trp | Lys | Gly | Pro |
| 305 |     |     |     |     | 310 |     |     |     |     | 315 |     |     |     |     | 320 |
| Ile | Ile | Arg | Ala | Gly | Asn | Tyr | Ala | Leu | His | Pro | Glu | Val | Val | Arg | Glu |
|     |     |     |     | 325 |     |     |     |     | 330 |     |     |     |     | 335 |     |
| Gln | Val | Lys | Asp | Pro | Arg | Thr | Leu | Ile | Gly | Tyr | Gly | Arg | Phe | Phe | Ile |
|     |     |     | 340 |     |     |     |     | 345 |     |     |     |     | 350 |     |     |
| Ser | Asn | Pro | Asp | Leu | Val | Tyr | Arg | Leu | Glu | Glu | Gly | Leu | Pro | Leu | Asn |
|     |     | 355 |     |     |     |     | 360 |     |     |     |     | 365 |     |     |     |
| Lys | Tyr | Asp | Arg | Ser | Thr | Phe | Tyr | Thr | Met | Ser | Ala | Glu | Gly | Tyr | Thr |
|     | 370 |     |     |     |     | 375 |     |     |     |     | 380 |     |     |     |     |
| Asp | Tyr | Pro | Thr | Tyr | Glu | Glu | Ala | Val | Asp | Leu | Gly | Trp | Asn | Lys | Asn |
| 385 |     |     |     |     | 390 |     |     |     |     | 395 |     |     |     |     | 400 |

<210> SEQ ID NO 205
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 205

| atgcctttcg | ttaagggctt | cgagccgatt | tcactgcgcg | acaccaacct | gttcgaacct | 60 |
| attaaaattg | ggaacacaca | gctggctcat | cgcgcggtaa | tgcctccgct | gacccgcatg | 120 |
| cgcgctaccc | atccgggcaa | cattccgaac | aaggagtggg | ctgcggttta | ctacggccag | 180 |
| cgtgcacagc | gtccggggac | aatgattatc | acggagggta | cgttcatcag | cccgcaggca | 240 |
| ggtgggtacg | ataacgcgcc | tggtatttgg | tcagacgaac | aggttgccga | atggaagaac | 300 |
| atcttcctgg | ctattcatga | ctgtcagtca | tttgcgtggg | tgcaactgtg | gagcctgggc | 360 |
| tgggcctcct | ttccggatgt | gctggcgcgt | gatgggttac | gttacgattg | tgcctccgat | 420 |
| cgtgtgtata | tgaatgcgac | actgcaggaa | aaagcgaaag | atgctaacaa | tctggaacat | 480 |
| agcttgacta | agacgatat | taaacaatat | atcaaagatt | atattcatgc | agctaagaac | 540 |
| tcgatcgctg | cgggtgcgga | cggcgtggaa | attcactcag | ccaacggtta | tctgttaaat | 600 |
| cagttcctgg | atccgcacag | caacaaacgc | accgatgagt | atggggggcac | aattgaaaat | 660 |
| cgtgcacgtt | ttactctgga | agtcgttgac | gcgctgattg | agaccatcgg | cccagaacgc | 720 |
| gtgggtttac | gtctgagtcc | gtacggcact | ttcaactcta | tgtcgggcgg | cgcggaaccg | 780 |
| ggcattattg | ctcagtatag | ctatgtcctg | ggtgagctgg | agaaacgcgc | caaggcgggg | 840 |
| aaacgcctgg | cgtttgttca | tttagtcgaa | ccacgcgtga | cagacccttc | tctggttgag | 900 |
| ggggagggcg | aatactcaga | gggcaccaac | gattttgctt | attccatttg | gaaaggtccg | 960 |
| attatccgtg | ccggcaactt | cgcactgcac | cctgaagttg | tgcgcgaaga | agttaaggac | 1020 |
| cctcgcaccc | tgatcggcta | cggccgcttc | tttatttcaa | atccagacct | ggttgaccgc | 1080 |
| ttagaaaaag | gtctgccact | gaacaagtat | gaccgtgata | cgttctacaa | aatgagcgcg | 1140 |
| gagggttaca | tcgactaccc | gacctacgaa | gaagccttaa | aactgggctg | gacaaaaaac | 1200 |

<210> SEQ ID NO 206
<211> LENGTH: 400
<212> TYPE: PRT

<213> ORGANISM: Artificial Sequence
<220> FEATURE:
<223> OTHER INFORMATION: chimera of WT OYEs

<400> SEQUENCE: 206

```
Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
        115                 120                 125

Ala Arg Asp Gly Leu Arg Tyr Asp Cys Ala Ser Asp Arg Val Tyr Met
    130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Tyr Ile His
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Lys Arg Thr Asp Glu Tyr Gly Gly Thr Ile Glu Asn Arg Ala Arg Phe
    210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
            260                 265                 270

Leu Glu Lys Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
    290                 295                 300

Tyr Ser Glu Gly Thr Asn Asp Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Asn
385                 390                 395                 400
```

<210> SEQ ID NO 207
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 207

```
atgcctttcg ttaaggactt caagccgcag gcactgggcg acaccaacct gttcaaacct      60
attaaaattg ggaacaacga gctgctgcat cgcgcggtaa ttcctccgct gacccgcatg     120
cgcgctcagc atccgggcaa cattccgaac aaggagtggg ctgcggttta ctacgcccag     180
cgtgcacagc gtccggggac actgattatc acggagggta cgttcatcag cccgcagtca     240
ggtgggtacg ataacgcgcc tggtatttgg tcagaagaac agattaaaga atggacgaaa     300
atcttcaagg ctattcatga aaataagtca tttgcgtggg tgcaactgtg ggtcctgggc     360
tgggccgcct ttccggatac gctggcgcgt gatgggttac gttacgattc tgcctccgat     420
aatgtgtata tgaatgcgga acaggaggaa aaagcgaaaa agctaacaa tccgcaacat      480
agcattacta aagacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat      660
cgtgcacgtt ttactctgga agtcgttgac gcgctgattg agaccatcgg cccagaacgc     720
gtgggtttac gtctgagtcc gtacggcact ttcaactcta tgtcgggcgg cgcggaaccg     780
ggcattgttg ctcagtatgc ctatgtcctg ggtgagctgg agcgtcgcgc caaggcgggg     840
aaacgcctgg cgtttgttca tttagtcgaa ccacgcgtga caaacccttt tctgactgag     900
ggggagggcg aatacaacgg gggcagcaac aaatttgctt attccatttg gaaaggtccg     960
attatccgtg ccggcaactt cgcactgcac cctgaagttg tgcgcgaaga agttaaggac    1020
cctcgcaccc tgatcggcta cggccgcttc tttatttcaa atccagacct ggttgaccgc    1080
ttagaaaaag gtctgccact gaacaagtat gaccgtgata cgttctacaa aatgagcgcg    1140
gagggttaca tcgactaccc gacctacgaa gaagccctaa aactgggctg ggacaaaaac    1200
```

<210> SEQ ID NO 208
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 208

```
Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Lys Glu Trp Ala Ala Val Tyr Tyr Ala Gln Arg Ala Gln Arg
    50                  55                  60

Pro Gly Thr Leu Ile Ile Thr Glu Gly Thr Phe Ile Ser Pro Gln Ser
65                  70                  75                  80

Gly Gly Tyr Asp Asn Ala Pro Gly Ile Trp Ser Glu Glu Gln Ile Lys
                85                  90                  95

Glu Trp Thr Lys Ile Phe Lys Ala Ile His Glu Asn Lys Ser Phe Ala
```

```
                    100                 105                 110
Trp Val Gln Leu Trp Val Leu Gly Trp Ala Ala Phe Pro Asp Thr Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
    195                 200                 205

Asn Arg Thr Asp Glu Tyr Gly Gly Ser Ile Glu Asn Arg Ala Arg Phe
210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
    275                 280                 285

Val Glu Pro Arg Val Thr Asn Pro Phe Leu Thr Glu Gly Glu Gly Glu
290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
    355                 360                 365

Lys Tyr Asp Arg Asp Thr Phe Tyr Lys Met Ser Ala Glu Gly Tyr Ile
370                 375                 380

Asp Tyr Pro Thr Tyr Glu Glu Ala Leu Lys Leu Gly Trp Asp Lys Asn
385                 390                 395                 400

<210> SEQ ID NO 209
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 209
atgcctttcg ttaaggactt cgagccgcag gcactgggcg acaccaacct gttcaaacct      60
attaaaattg gaacacaca gccggctcat cgcgcggtaa tgcctccgct gacccgcatg     120
cgcgctaccc atccgggcaa cattccgaac aaggagtggg ctgcggttta ctacggccag     180
cgtgcacagc gtccggggac aatgattatc acgagggta cgttcatcag cccgcaggca     240
ggtgggtacg ataacgcgcc tggtatttgg tcagacgaac aggttgccga atggaagaac     300
atcttcctgg ctattcatga ctgtcagtca tttgcgtggg tgcaactgtg gagcctgggc     360
tgggcctcct ttccggatgt gctggcgcgt gatgggttac gttacgattc tgcctccgat     420
```

```
aatgtgtata tgaatgcgga acaggaggaa aaagcgaaaa aagctaacaa tccgcaacat    480
agcattacta aagacgaaat taaacaatat gtcaaagaat atgttcaggc agctaagaac    540
tcgatcgctg cgggcgcgga cggcgtggaa attcactcag ccaacggtta tctgttaaat    600
cagttcctgg atccgcacag caacaaacgc accgatgagt atgggggctc aattgaaaat    660
cgtgcacgtt ttactctgga agtcgttgac gcggtggttg atgccatcgg cccagaaaaa    720
gtgggtttac gtctgagtcc gtacggcgtt ttcaactcta tgtcgggcgg cgcggaaacg    780
ggcattgttg ctcagtatgc ctatgtcctg ggtgagctgg agcgtcgcgc caaggcgggg    840
aaacgcctgg cgtttgttca tttagtcgaa ccacgcgtga caaaccctct tctgactgag    900
ggggagggcg aatacaacgg gggcagcaac aaatttgctt attccatttg gaaaggtccg    960
attatccgtg ccggcaactt cgcactgcac cctgaagttg tgcgcgaaga agttaaggac   1020
cctcgcaccc tgatcggcta cggccgcttc tttatttcaa atccagacct ggttgaccgc   1080
ttagaaaaag gtctgccact gaacaagtat gaccgtgata cgttctacaa aatgagcgcg   1140
gagggttaca tcgactaccc gacctacgaa gaagccttaa aactgggctg ggacaaaaac   1200
```

<210> SEQ ID NO 210
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 210

```
Met Pro Phe Val Lys Asp Phe Glu Pro Gln Ala Leu Gly Asp Thr Asn
1               5                   10                  15

Leu Phe Lys Pro Ile Lys Ile Gly Asn Thr Gln Pro Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Lys Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240
```

Val Gly Leu Arg Leu Ser Pro Tyr Gly Val Phe Asn Ser Met Ser Gly
            245                 250                 255

Gly Ala Glu Thr Gly Ile Val Ala Gln Tyr Ala Tyr Val Leu Gly Glu
        260                 265                 270

Leu Glu Arg Arg Ala Lys Ala Gly Lys Arg Leu Ala Phe Val His Leu
            275                 280                 285

Val Glu Pro Arg Val Thr Asn Pro Leu Leu Thr Glu Gly Glu Gly Glu
290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Asn
385                 390                 395                 400

<210> SEQ ID NO 211
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 211
atgcctttcg ttaagggctt cgagccgatt tcactgcgcg acaccaacct gttcgaacct      60
attaaaattg gaacacaca gctggctcat cgcgcggtaa tgcctccgct gacccgcatg     120
cgcgctaccc atccgggcaa cattccgaac aaggagtggg ctgcggttta ctacacccag     180
cgtgcacagc gtccggggac aatgattatc acggagggtg cgttcatcag cccgcaggca     240
ggtgggtacg ataacgcgcc tggtatttgg tcagacgaac aggttgccga atggaagaac     300
atcttcctgg ctattcatga ctgtcagtca tttgcgtggg tgcaactgtg agcctgggc     360 tgggccgcct ttccggatac gctggcgcgt gatgggttac gttacgattc tgcctccgat     420
aatgtgtata tgaatgcgga acaggaggaa aaagcgaaaa agctaacaa tccgcaacat     480 agcattacta agacgaaat taaacaatat gtcaaagaat atgttcaggc agctaagaac     540
tcgatcgctg cgggtgcgga cggcgtggaa attcactcag ccaacggtta tctgttaaat     600
cagttcctgg atccgcacag caacaaccgc accgatgagt atggggctc aattgaaaat     660 cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caaacccttt tctgactgag     900
ggggagggcg aatacaacgg gggcagcaac aaatttgctt attccatttg gaaaggtccg     960
attatccgtg ccggcaactt cgcactgcac cctgaagttg tgcgcgaaga agttaaggac    1020
cctcgcaccc tgatcggcta cggccgcttc tttatttcaa atccagacct ggttgaccgc    1080
ttagaaaaag tctgccact gaacaagtat gaccgtgata cgttctacaa aatgagcgcg    1140
gagggttaca tcgactaccc gacctacgaa gaagccttaa aactgggctg ggacaaaaac    1200

<210> SEQ ID NO 212
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 212

```
Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Thr Gln Arg Ala Gln Arg
    50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365
```

Lys Tyr Asp Arg Asp Thr Phe Tyr Lys Met Ser Ala Glu Gly Tyr Ile
            370                 375                 380

Asp Tyr Pro Thr Tyr Glu Glu Ala Leu Lys Leu Gly Trp Asp Lys Asn
385                 390                 395                 400

<210> SEQ ID NO 213
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 213
atgcctttcg ttaagggctt cgagccgatt tcactgcgcg acaccaacct gttcgaacct      60
attaaaattg gaacacaca gctggctcat cgcgcggtaa tgcctccgct gacccgcatg     120
cgcgctaccc atccgggcaa cattccgaac cgtgattggg ctgtggaata ctacacccag     180
cgtgcacagc gtccggggac aatgattatc acggagggtg cgttcatcag cccgcaggca     240
ggtgggtacg ataacgcgcc tggtgtttgg tcagaagaac agatggtcga atggacgaaa     300
atcttcaacg ctattcatga aaaaagtca tttgtgtggg tgcaactgtg ggtcctgggc     360
tgggccgcct ttccggatac gctggcgcgt gatgggttac gttacgattc tgcctccgat     420
aatgtgtata tgaatgcgga acaggaggaa aaagcgaaaa agctaacaa tccgcaacat     480 agcattacta agacgaaat taacaatat gtcaaagaat atgttcaggc agctaagaac     540
tcgatcgctg cgggtgcgga cggcgtgaa attcactcag ccaacggtta tctgttaaat     600
cagttcctgg atccgcacag caacaaccgc accgatgagt atggggctc aattgaaaat     660 cgtgcacgtt ttactctgga agtcgttgac gcggtggttg atgccatcgg cccagaaaaa     720
gtgggtttac gtctgagtcc gtacggcgtt ttcaactcta tgtcgggcgg cgcggaaacg     780
ggcattgttg ctcagtatgc ctatgtcctg ggtgagctgg agcgtcgcgc caaggcgggg     840
aaacgcctgg cgtttgttca tttagtcgaa ccacgcgtga caaaccctt tctgactgag     900 ggggagggcg aatacaacgg gggcagcaac aaatttgctt attccatttg gaaaggtccg     960
attatccgtg ccggcaactt cgcactgcac cctgaagttg tgcgcgaaga agttaaggac    1020
cctcgcaccc tgatcggcta cggccgcttc tttatttcaa atccagacct ggttgaccgc    1080
ttagaaaaag gtctgccact gaacaagtat gaccgtgata cgttctacaa aatgagcgcg    1140
gagggttaca tcgactaccc gacctacgaa gaagccttaa aactgggctg ggacaaaaaa    1200

<210> SEQ ID NO 214
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 214

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Arg Asp Trp Ala Val Glu Tyr Tyr Thr Gln Arg Ala Gln Arg
    50                  55                  60

Pro Gly Thr Met Ile Ile Thr Glu Gly Ala Phe Ile Ser Pro Gln Ala
65                  70                  75                  80

Gly Gly Tyr Asp Asn Ala Pro Gly Val Trp Ser Glu Glu Gln Met Val
                85                  90                  95

Glu Trp Thr Lys Ile Phe Asn Ala Ile His Glu Lys Lys Ser Phe Val
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Lys
385                 390                 395                 400

<210> SEQ ID NO 215
<211> LENGTH: 1200
<212> TYPE: DNA
<213> ORGANISM: Artificial Sequence
<220> FEATURE:
<223> OTHER INFORMATION: chimera of WT OYEs

<400> SEQUENCE: 215
atgcctttcg ttaaggactt caagccgcag gcactgggcg acaccaacct gttcaaacct     60
attaaaattg gaacacaca gctggctcat cgcgcggtaa tgcctccgct gacccgcatg     120
cgcgctctgc atccgggcaa cattccgaac cgtgattggg ctgtggaata ctacacccag     180
cgtgcacagc gtccggggac aatgattatc acgagggta cgttccctag cccgcagtca     240
ggtgggtacg ataacgcgcc tggtatttgg tcagacgaac aggttgccga atggaagaac     300

```
atcttcctgg ctattcatga ctgtcagtca tttgcgtggg tgcaactgtg ggtcctgggc   360
tgggccgcct ttccggatac gctggcgcgt gatgggttac gttacgattc tgcctccgat   420
aatgtgtata tgaatgcgga acaggaggaa aaagcgaaaa agctaacaa tccgcaacat    480 agcattacta aagacgaaat taaacaatat gtcaaagaat atgttcaggc agctaagaac   540
tcgatcgctg cgggtgcgga cggcgtgaa attcactcag ccaacggtta tctgttaaat    600
cagttcctgg atccgcacag caacaaacgc accgatgagt atggggcac aattgaaaat    660 cgtgcacgtt ttactctgga agtcgttgac gcgctgattg agaccatcgg cccagaacgc   720
gtgggtttac gtctgagtcc gtacggcact ttcaactcta tgtcgggcgg cgcggaaccg   780
ggcattattg ctcagtatag ctatgtcctg ggtgagctgg agaaacgcgc caaggcgggg   840
aaacgcctgg cgtttgttca tttagtcgaa ccacgcgtga cagacccttc tctggttgag   900
ggggagggcg aatactcaga gggcaccaac gattttgctt attccatttg gaaaggtccg   960
attatccgtg ccggcaacta cgcactgcac cctgaagttg tgcgcgaaca agttaaggac  1020
cctcgcaccc tgatcggcta cggccgcttc tttatttcaa atccagacct ggtttaccgc  1080
ttagaagaag gtctgccact gaacaagtat gaccgttcta cgttctacac catgagcgcg  1140
gagggttaca ccgactaccc gacctacgaa gaagccgtag atctgggctg aacaaaaac   1200
```

<210> SEQ ID NO 216
<211> LENGTH: 400
<212> TYPE: PRT
<213> ORGANISM: Artificial Sequence
<220> FEATURE:
<223> OTHER INFORMATION: chimera of WT OYEs

<400> SEQUENCE: 216

```
Met Pro Phe Val Lys Asp Phe Lys Pro Gln Ala Leu Gly Asp Thr Asn
1               5                   10                  15

Leu Phe Lys Pro Ile Lys Ile Gly Asn Thr Gln Leu Ala His Arg Ala
            20                  25                  30

Val Met Pro Pro Leu Thr Arg Met Arg Ala Leu His Pro Gly Asn Ile
        35                  40                  45

Pro Asn Arg Asp Trp Ala Val Glu Tyr Tyr Thr Gln Arg Ala Gln Arg
    50                  55                  60

Pro Gly Thr Met Ile Ile Thr Glu Gly Thr Phe Pro Ser Pro Gln Ser
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Val Leu Gly Trp Ala Ala Phe Pro Asp Thr Leu
        115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205
```

```
Lys Arg Thr Asp Glu Tyr Gly Gly Thr Ile Glu Asn Arg Ala Arg Phe
    210                 215                 220
Thr Leu Glu Val Val Asp Ala Leu Ile Glu Thr Ile Gly Pro Glu Arg
225                 230                 235                 240
Val Gly Leu Arg Leu Ser Pro Tyr Gly Thr Phe Asn Ser Met Ser Gly
                245                 250                 255
Gly Ala Glu Pro Gly Ile Ile Ala Gln Tyr Ser Tyr Val Leu Gly Glu
            260                 265                 270
Leu Glu Lys Arg Ala Lys Ala Gly Lys Arg Leu Ala Phe Val His Leu
        275                 280                 285
Val Glu Pro Arg Val Thr Asp Pro Ser Leu Val Glu Gly Glu Gly Glu
    290                 295                 300
Tyr Ser Glu Gly Thr Asn Asp Phe Ala Tyr Ser Ile Trp Lys Gly Pro
305                 310                 315                 320
Ile Ile Arg Ala Gly Asn Tyr Ala Leu His Pro Glu Val Val Arg Glu
                325                 330                 335
Gln Val Lys Asp Pro Arg Thr Leu Ile Gly Tyr Gly Arg Phe Phe Ile
            340                 345                 350
Ser Asn Pro Asp Leu Val Tyr Arg Leu Glu Glu Gly Leu Pro Leu Asn
        355                 360                 365
Lys Tyr Asp Arg Ser Thr Phe Tyr Thr Met Ser Ala Glu Gly Tyr Thr
    370                 375                 380
Asp Tyr Pro Thr Tyr Glu Glu Ala Val Asp Leu Gly Trp Asn Lys Asn
385                 390                 395                 400

<210> SEQ ID NO 217
<211> LENGTH: 400
<212> TYPE: PRT
<213> ORGANISM: Artificial Sequence
<220> FEATURE:
<223> OTHER INFORMATION: ERED Sequence with chimeric ERED backbone
      Synthetic Construct
<220> FEATURE:
<221> NAME/KEY: MISC_FEATURE
<222> LOCATION: (5)..(5)
<223> OTHER INFORMATION: Xaa is a basic or acidic residue
<220> FEATURE:
<221> NAME/KEY: MISC_FEATURE
<222> LOCATION: (10)..(10)
<223> OTHER INFORMATION: Xaa is a polar or constrained residue
<220> FEATURE:
<221> NAME/KEY: MISC_FEATURE
<222> LOCATION: (28)..(28)
<223> OTHER INFORMATION: Xaa is an aliphatic or constrained residue
<220> FEATURE:
<221> NAME/KEY: MISC_FEATURE
<222> LOCATION: (38)..(38)
<223> OTHER INFORMATION: Xaa is a polar or basic residue
<220> FEATURE:
<221> NAME/KEY: MISC_FEATURE
<222> LOCATION: (40)..(40)
<223> OTHER INFORMATION: Xaa is a non-polar, aliphatic, aromatic, acidic
      or polar residue
<220> FEATURE:
<221> NAME/KEY: MISC_FEATURE
<222> LOCATION: (44)..(44)
<223> OTHER INFORMATION: Xaa is a constrained or aromatic residue
<220> FEATURE:
<221> NAME/KEY: MISC_FEATURE
<222> LOCATION: (75)..(75)
<223> OTHER INFORMATION: Xaa is an aromatic, aliphatic or polar residue
<220> FEATURE:
<221> NAME/KEY: MISC_FEATURE
<222> LOCATION: (83)..(83)
<223> OTHER INFORMATION: Xaa is an aromatic, aliphatic, acidic, or basic
      residue
<220> FEATURE:
<221> NAME/KEY: MISC_FEATURE
```

-continued

```
<222> LOCATION: (117)..(117)
<223> OTHER INFORMATION: Xaa is a cysteine or nonpolar, aliphatic,
      basic, acidic, polar, or aromatic residue
<220> FEATURE:
<221> NAME/KEY: MISC_FEATURE
<222> LOCATION: (119)..(119)
<223> OTHER INFORMATION: Xaa is a constrained or aliphatic residue
<220> FEATURE:
<221> NAME/KEY: MISC_FEATURE
<222> LOCATION: (122)..(122)
<223> OTHER INFORMATION: Xaa is an aliphatic or polar residue
<220> FEATURE:
<221> NAME/KEY: MISC_FEATURE
<222> LOCATION: (124)..(124)
<223> OTHER INFORMATION: Xaa is an aromatic, non-polar or a constrained
      residue
<220> FEATURE:
<221> NAME/KEY: MISC_FEATURE
<222> LOCATION: (147)..(147)
<223> OTHER INFORMATION: Xaa is an acidic or non-polar residue
<220> FEATURE:
<221> NAME/KEY: MISC_FEATURE
<222> LOCATION: (148)..(148)
<223> OTHER INFORMATION: Xaa is a polar or basic residue
<220> FEATURE:
<221> NAME/KEY: MISC_FEATURE
<222> LOCATION: (153)..(153)
<223> OTHER INFORMATION: Xaa is a basic or acidic residue
<220> FEATURE:
<221> NAME/KEY: MISC_FEATURE
<222> LOCATION: (154)..(154)
<223> OTHER INFORMATION: Xaa is a basic residue
<220> FEATURE:
<221> NAME/KEY: MISC_FEATURE
<222> LOCATION: (179)..(179)
<223> OTHER INFORMATION: Xaa is a basic residue
<220> FEATURE:
<221> NAME/KEY: MISC_FEATURE
<222> LOCATION: (209)..(209)
<223> OTHER INFORMATION: Xaa is a polar or acidic residue
<220> FEATURE:
<221> NAME/KEY: MISC_FEATURE
<222> LOCATION: (240)..(240)
<223> OTHER INFORMATION: Xaa is a basic residue
<220> FEATURE:
<221> NAME/KEY: MISC_FEATURE
<222> LOCATION: (248)..(248)
<223> OTHER INFORMATION: Xaa is an aromatic residue or cysteine
<220> FEATURE:
<221> NAME/KEY: MISC_FEATURE
<222> LOCATION: (251)..(251)
<223> OTHER INFORMATION: Xaa is a cysteine, or aromatic, non-polar,
      aliphatic, acidic, basic, or polar residue
<220> FEATURE:
<221> NAME/KEY: MISC_FEATURE
<222> LOCATION: (252)..(252)
<223> OTHER INFORMATION: Xaa is a polar, aromatic or constrained residue
<220> FEATURE:
<221> NAME/KEY: MISC_FEATURE
<222> LOCATION: (255)..(255)
<223> OTHER INFORMATION: Xaa is a polar or constrained residue
<220> FEATURE:
<221> NAME/KEY: MISC_FEATURE
<222> LOCATION: (259)..(259)
<223> OTHER INFORMATION: Xaa is an acidic or non-polar residue
<220> FEATURE:
<221> NAME/KEY: MISC_FEATURE
<222> LOCATION: (294)..(294)
<223> OTHER INFORMATION: Xaa is a polar or aliphatic residue
<220> FEATURE:
<221> NAME/KEY: MISC_FEATURE
<222> LOCATION: (295)..(295)
<223> OTHER INFORMATION: Xaa is an acidic, polar, basic, or non-polar
      residue
<220> FEATURE:
<221> NAME/KEY: MISC_FEATURE
<222> LOCATION: (296)..(296)
<223> OTHER INFORMATION: Xaa is a constrained, aromatic, non-polar,
      aliphatic, basic, acidic, or polar residue
<220> FEATURE:
```

```
<221> NAME/KEY: MISC_FEATURE
<222> LOCATION: (297)..(297)
<223> OTHER INFORMATION: Xaa is a polar, aromatic, non-polar, aliphatic,
      or basic residue
<220> FEATURE:
<221> NAME/KEY: MISC_FEATURE
<222> LOCATION: (302)..(302)
<223> OTHER INFORMATION: Xaa is an acidic or non-polar residue
<220> FEATURE:
<221> NAME/KEY: MISC_FEATURE
<222> LOCATION: (304)..(304)
<223> OTHER INFORMATION: Xaa is an acidic or basic residue
<220> FEATURE:
<221> NAME/KEY: MISC_FEATURE
<222> LOCATION: (305)..(305)
<223> OTHER INFORMATION: Xaa is an aromatic or polar residue
<220> FEATURE:
<221> NAME/KEY: MISC_FEATURE
<222> LOCATION: (311)..(311)
<223> OTHER INFORMATION: Xaa is an acidic residue
<220> FEATURE:
<221> NAME/KEY: MISC_FEATURE
<222> LOCATION: (315)..(315)
<223> OTHER INFORMATION: Xaa is a constrained residue
<220> FEATURE:
<221> NAME/KEY: MISC_FEATURE
<222> LOCATION: (330)..(330)
<223> OTHER INFORMATION: Xaa is a constrained, aromatic or basic residue
<220> FEATURE:
<221> NAME/KEY: MISC_FEATURE
<222> LOCATION: (333)..(333)
<223> OTHER INFORMATION: Xaa is an aliphatic residue
<220> FEATURE:
<221> NAME/KEY: MISC_FEATURE
<222> LOCATION: (339)..(339)
<223> OTHER INFORMATION: Xaa is a basic or polar residue
<220> FEATURE:
<221> NAME/KEY: MISC_FEATURE
<222> LOCATION: (358)..(358)
<223> OTHER INFORMATION: Xaa is an aliphatic residue
<220> FEATURE:
<221> NAME/KEY: MISC_FEATURE
<222> LOCATION: (369)..(369)
<223> OTHER INFORMATION: Xaa is a basic or acidic residue
<220> FEATURE:
<221> NAME/KEY: MISC_FEATURE
<222> LOCATION: (376)..(376)
<223> OTHER INFORMATION: Xaa is an aromatic, non-polar, aliphatic, basic
      or acidic residue
<220> FEATURE:
<221> NAME/KEY: MISC_FEATURE
<222> LOCATION: (379)..(379)
<223> OTHER INFORMATION: Xaa is a polar or nonpolar residue
<220> FEATURE:
<221> NAME/KEY: MISC_FEATURE
<222> LOCATION: (384)..(384)
<223> OTHER INFORMATION: Xaa is a polar or aliphatic residue
<220> FEATURE:
<221> NAME/KEY: MISC_FEATURE
<222> LOCATION: (386)..(386)
<223> OTHER INFORMATION: Xaa is an aromatic or acidic residue
<220> FEATURE:
<221> NAME/KEY: MISC_FEATURE
<222> LOCATION: (397)..(397)
<223> OTHER INFORMATION: Xaa is an aromatic or basic residue
<220> FEATURE:
<221> NAME/KEY: MISC_FEATURE
<222> LOCATION: (399)..(399)
<223> OTHER INFORMATION: Xaa is a basic or acidic residue
<220> FEATURE:
<221> NAME/KEY: MISC_FEATURE
<222> LOCATION: (400)..(400)
<223> OTHER INFORMATION: Xaa is a polar residue

<400> SEQUENCE: 217

Met Ser Phe Val Xaa Asp Phe Lys Pro Xaa Ala Leu Arg Asp Thr Asn
1               5                   10                  15

Leu Phe Glu Pro Ile Lys Ile Gly Asn Thr Gln Xaa Ala His Arg Ala
```

-continued

```
                    20                  25                  30
Val Met Pro Pro Leu Xaa Arg Xaa Arg Ala Thr Xaa Pro Gly Asn Ile
                35                  40                  45
Pro Asn Lys Glu Trp Ala Ala Val Tyr Tyr Gly Gln Arg Ala Gln Arg
            50                  55                  60
Pro Gly Thr Met Ile Ile Thr Glu Gly Thr Xaa Ile Ser Pro Gln Ala
65                  70                  75                  80
Gly Gly Xaa Asp Asn Ala Pro Gly Val Trp Ser Asp Glu Gln Val Ala
                85                  90                  95
Glu Trp Lys Asn Ile Phe Leu Ala Ile His Asp Cys Gln Ser Phe Ala
                100                 105                 110
Trp Val Gln Leu Xaa Val Xaa Gly Trp Xaa Ala Xaa Pro Asp Asn Leu
                115                 120                 125
Ala Arg Asp Gly Leu Arg Tyr Asp Ser Ala Ser Asp Asn Val Tyr Met
            130                 135                 140
Asn Ala Xaa Xaa Glu Glu Lys Ala Xaa Xaa Ala Asn Asn Pro Gln His
145                 150                 155                 160
Ser Ile Thr Lys Asp Glu Ile Lys Gln Tyr Val Lys Glu Tyr Val Gln
                165                 170                 175
Ala Ala Xaa Asn Ser Ile Ala Ala Gly Ala Asp Gly Val Glu Ile His
                180                 185                 190
Ser Ala Asn Gly Tyr Leu Leu Asn Gln Phe Leu Asp Pro His Ser Asn
                195                 200                 205
Xaa Arg Thr Asp Glu Tyr Gly Gly Ser Ile Glu Asn Arg Ala Arg Phe
            210                 215                 220
Thr Leu Glu Val Val Asp Ala Val Val Asp Ala Ile Gly Pro Glu Xaa
225                 230                 235                 240
Val Gly Leu Arg Leu Ser Pro Xaa Gly Val Xaa Xaa Ser Met Xaa Gly
                245                 250                 255
Gly Ala Xaa Thr Gly Ile Val Ala Gln Tyr Ala Tyr Val Leu Gly Glu
            260                 265                 270
Leu Glu Arg Arg Ala Lys Ala Gly Lys Arg Leu Ala Phe Val His Leu
            275                 280                 285
Val Glu Pro Arg Val Xaa Xaa Xaa Xaa Leu Val Glu Gly Xaa Gly Xaa
            290                 295                 300
Xaa Ser Glu Gly Thr Asn Xaa Phe Ala Tyr Xaa Ile Trp Lys Gly Pro
305                 310                 315                 320
Ile Ile Arg Ala Gly Asn Tyr Ala Leu Xaa Pro Glu Xaa Val Arg Glu
                325                 330                 335
Gln Val Xaa Asp Pro Arg Thr Leu Ile Gly Tyr Gly Arg Phe Phe Ile
            340                 345                 350
Ser Asn Pro Asp Leu Xaa Tyr Arg Leu Glu Glu Gly Leu Pro Leu Asn
            355                 360                 365
Xaa Tyr Asp Arg Ser Thr Phe Xaa Thr Met Xaa Ala Glu Gly Tyr Xaa
            370                 375                 380
Asp Xaa Pro Thr Tyr Glu Glu Ala Val Asp Leu Gly Xaa Asn Xaa Xaa
385                 390                 395                 400
```